(12) United States Patent
Ahrens et al.

(10) Patent No.: US 8,153,788 B2
(45) Date of Patent: Apr. 10, 2012

(54) SUBSTITUTED 2,4-DIAMINO-1,3,5-TRIAZINES, PROCESSES FOR THEIR USE AS HERBICIDES AND CROP GROWTH REGULATORS

(76) Inventors: Hartmut Ahrens, Frankfurt (DE); Hansjörg Dietrich, Hofheim (DE); Thomas Auler, Leichlingen (DE); Martin Hills, Idstein (DE); Heinz Kehne, Hofheim (DE); Dieter Feucht, Eschborn (DE); Stefan Herrmann, Langenfeld (DE); Kristian Kather, Langenfeld (DE); Stefan Lehr, Liederbach (DE)

( * ) Notice: Subject to any disclaimer, the term of this patent is extended or adjusted under 35 U.S.C. 154(b) by 769 days.

(21) Appl. No.: 11/957,301

(22) Filed: Dec. 14, 2007

(65) Prior Publication Data
US 2009/0005250 A1    Jan. 1, 2009

(30) Foreign Application Priority Data
Dec. 19, 2006  (DE) .......................... 10 2006 059 941

(51) Int. Cl.
*C07D 251/48* (2006.01)
*C07D 251/50* (2006.01)
*C07D 251/52* (2006.01)
*C07D 251/54* (2006.01)
*A01N 43/68* (2006.01)

(52) U.S. Cl. ........ 544/196; 544/197; 544/204; 544/208; 544/211; 544/212; 504/231; 504/232

(58) Field of Classification Search .................. 544/196, 544/197, 204, 206, 211, 212; 504/231, 232
See application file for complete search history.

(56) References Cited

U.S. PATENT DOCUMENTS

| | | | |
|---|---|---|---|
| 3,830,810 A | 8/1974 | Berrer at al. | |
| 5,250,686 A | 10/1993 | Adachi et al. | |
| 5,286,905 A | 2/1994 | Nakamura et al. | |
| 5,290,754 A | 3/1994 | Nishii et al. | |
| 6,069,114 A | 5/2000 | Lorenz et al. | |
| 6,071,860 A | 6/2000 | Giencke et al. | |
| 6,358,886 B1 | 3/2002 | Riebel et al. | |
| 6,399,541 B1 | 6/2002 | Riebel et al. | |
| 6,440,903 B1 | 8/2002 | Riebel et al. | |
| 6,645,915 B1 * | 11/2003 | Riebel et al. | .................. 504/234 |
| 2001/0011063 A1 | 8/2001 | Giencke et al. | |

FOREIGN PATENT DOCUMENTS

| | | |
|---|---|---|
| DE | 22 58 243 | 6/1973 |
| DE | 196 04 191 | 8/1997 |
| DE | 196 07 450 | 9/1997 |
| DE | 196 41 692 | 4/1998 |
| DE | 197 11 825 | 9/1998 |
| EP | 0 283 522 | 9/1987 |
| EP | 0 411 153 | 2/1990 |
| EP | 0 492 615 | 7/1992 |
| EP | 0 509 544 | 10/1992 |
| EP | 0 864 567 | 9/1998 |
| EP | 1 484 324 | 12/2004 |
| WO | WO 97/19936 | 6/1997 |
| WO | WO 97/31904 | 9/1997 |
| WO | WO 99/46249 | 9/1999 |
| WO | WO 00/32580 | 6/2000 |
| WO | WO 00/69814 | 11/2000 |
| WO | WO 01/44208 | 6/2001 |

* cited by examiner

*Primary Examiner* — Venkataraman Balasubramanian
(74) *Attorney, Agent, or Firm* — Frommer Lawrence & Haug LLP

(57) ABSTRACT

Compounds of the formula (I) or salts thereof, in which

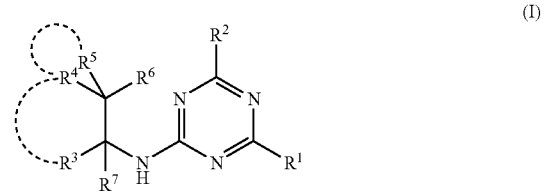

in which $R^1$ is an optionally substituted amino group or analogous group, and $R^2$ to $R^7$ are each as described herein, are suitable as herbicides and crop growth regulators. The compounds (I) can be prepared by the processes described, via intermediates including novel intermediates for example of the formula (III).

11 Claims, No Drawings

SUBSTITUTED 2,4-DIAMINO-1,3,5-TRIAZINES, PROCESSES FOR THEIR USE AS HERBICIDES AND CROP GROWTH REGULATORS

This application claims benefit under 35 U.S.C. 119(a) of German patent application DE 10 2006 059 941.1, filed on 19 Dec. 2006.

Any foregoing applications including German patent application DE 10 2006 059 941.1, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

The invention relates to the technical field of herbicides and crop growth regulators (=plant growth regulators), especially of the herbicides for controlling broadleaf and gramineous weeds in useful plant crops and for general control of undesired growth of plants.

2,4-Diamino-s-triazines with radicals from the group of halogen, alkoxy, alkylthio and other radicals bonded via heteroatoms on the triazine ring are in many cases known as herbicides. These compounds usually have N,N-dialkyl-substituted amino groups; see so-called "triazine-herbicides" such as atrazine, simazine, etc.

It is also known that particular compounds from the group of the alkyl-substituted 2,4-diamino-s-triazines and analogous compounds have herbicidal and crop growth-regulating properties; see, for example, compounds of the 2-amino-4-alkylamino-6-haloalkyl-1,3,5-triazine type WO-A-90/09378 (EP-A-411153) (U.S. Pat. No. 5,290,754), WO-A-88/02368 (EP-A-283522) (U.S. Pat. No. 4,932,998), WO-A-94/24086, (EP-A-509544, EP-A-492,615) (U.S. Pat. No. 5,250,686, U.S. Pat. No. 5,286,905) and of the 2-amino-4-bicyclylamino-1,3,5-triazine type (WO 97/31904, DE-A-1 9607450, (U.S. Pat. No. 6,069,114); WO-A-97/19936; WO-A-2004/069814 (US 2004-157739)). Such compounds generally have an optionally substituted alkyl or cycloalkyl radical on the triazine ring and a (hetero)aromatic group which is bonded via bridged or unbridged aliphatic bridges to an amino group of the 2,4-diamino-s-triazine. These herbicides differ from those of the "triazine herbicides" generally by the efficacy and the application characteristics.

Compared to the latter herbicidal alkyl-substituted 2,4-diamino-s-triazines, analogous 2,4-diamino-s-triazines have also become known, which have purely aliphatic radicals on an amino group; see WO 00/32580 (U.S. Pat. No. 6,645,915) and literature cited there.

However, the use of the derivatives of the latter type as herbicides for controlling harmful plants in various useful plant crops or in uncultivated land is not possible under all desired conditions. For instance, in some cases, the closure of active ingredient gaps requires too high an application rate at which damage to crop plants or plantation crops (including fruit plants) occurs, or the action depends too greatly on environmental conditions such as weather and soil conditions. There is therefore still a need for alternative high-efficacy herbicides for selective use in crop plants or uncultivated land.

Surprisingly, novel herbicidal active ingredients from the latter group of alkyl-substituted 2,4-diamino-1,3,5-triazines have now been found, which, compared to known, structurally similar active ingredients of this group, can be used advantageously as herbicides or crop growth regulators.

The invention provides herbicidal compounds of the formula (I) or salts thereof, in which

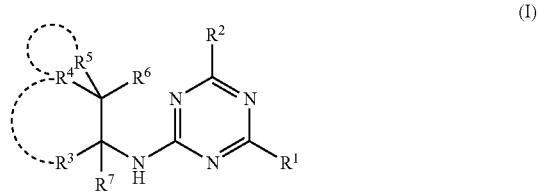

(I)

$R^1$ is a radical of the formula $-NH_2$, $-NH(B^1-D^1)$, or $-N(B^1-D^1)(B^2-D^2)$, in each of which $B^1$, $B^2$, $D^1$ and $D^2$ are each as defined below, or a group of the formula

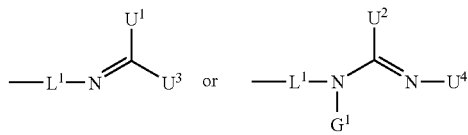

where
$L^1$ is a direct bond, $-O-$, $-S-$ or a group of the formula $-NG^2-$, preferably a direct bond,
$U^1$, $U^2$ are each independently a group of the formula $G^3$, $OG^4$, $SG^5$, $NG^6G^7$, $NG^8NG^9G^{10}$, $NG^{11}OG^{12}$ or $NG^{11}SG^{12}$,
$U^3$ is a group of the formula $G^{13}$, $OG^{14}$, $SG^{15}$, $NG^{16}G^{17}$, $NG^{18}NG^{19}G^{20}$, $NG^{21}OG^{22}$ or $NG^{23}SG^{24}$
$U^4$ is a group of the formula $G^{25}$, $OG^{26}$, $SG^{27}$ or $NG^{28}G^{29}$,
where the $G^1$ to $G^{29}$ radicals are each independently hydrogen, aryl which is unsubstituted or substituted and has from 6 to 30 carbon atoms including substituents, or $(C_3-C_9)$cycloalkyl which is unsubstituted or substituted and has from 3 to 30 carbon atoms including substituents, or heterocyclyl which is substituted or unsubstituted and has from 2 to 30 carbon atoms including substituents,
or
$(C_1-C_6)$alkyl, $(C_2-C_6)$alkenyl or $(C_2-C_6)$alkynyl,
where each of the 3 latter radicals is unsubstituted or substituted by one or more radicals from the group consisting of halogen, hydroxyl, cyano, nitro, thiocyanato, $(C_1-C_4)$alkoxy, $(C_1-C_4)$haloalkoxy, $(C_2-C_4)$alkenyloxy, $(C_2-C_4)$haloalkenyloxy, $(C_1-C_4)$alkylthio, $(C_1-C_4)$haloalkylthio, acyl, $(C_3-C_9)$cycloalkyl, which is unsubstituted or substituted, phenyl which is unsubstituted or substituted, and heterocyclyl which is unsubstituted or substituted and has from 1 to 30 carbon atoms including substituents,
or the $U^1$ and $U^3$ or $U^2$ and $U^4$ or $U^2$ and $G^1$ or $U^4$ and $G^1$ radicals, in pairs with the atoms connecting them, are each a carbocyclic or heterocyclic ring having from 4 to 7 ring atoms, where the ring is unsubstituted or substituted and has up to 30 carbon atoms including substituents,
$B^1$ and $B^2$ are each independently a divalent group of the formulae $-C(=Z^*)-$, $-C(=Z^*)-Z^{**}-$, $-C(=Z^*)-NH-$ or $-C(=Z^*)-NR^*-$, where Z* is an oxygen or sulfur atom, Z** is an oxygen or sulfur atom and R* is $(C_1-C_6)$alkyl, aryl, aryl$(C_1-C_6)$alkyl, $(C_3-C_9)$cycloalkyl or $(C_3-C_8)$cycloalkyl$(C_1-C_6)$alkyl, where each of the 5 latter radicals is unsubstituted or substituted and has up to 30 carbon atoms including substituents, $D^1$ and $D^2$ are each independently hydrogen, $(C_1-C_6)$alkyl, aryl, aryl$(C_1-C_6)$alkyl, $(C_3-C_9)$cycloalkyl or $(C_3-C_9)$cycloalkyl$(C_1-C_6)$alkyl, where each of the 5 latter radicals is unsubstituted or substituted and has up to 30 carbon atoms including substituents, where the group $R^1$ preferably has up to 30 carbon atoms, in particular up to 20 carbon atoms, more especially up to 12 carbon atoms, $R^2$ is hydrogen, $(C_1-C_6)$alkyl, $(C_2-C_6)$alkenyl or $(C_2-C_6)$alkynyl, where each of the three latter groups is unsubstituted or substituted by one or more of the radicals from the group consisting of halogen, hydroxyl, cyano, $(C_1-C_6)$alkoxy, $(C_1-C_6)$alkylthio, $(C_1-C_6)$haloalkoxy, $(C_1-C_4)$alkoxy-$(C_1-C_4)$alkoxy and optionally halogen-, cyano-, $(C_1-C_4)$alkyl- or $(C_1-C_4)$haloalkyl-substituted $(C_3-C_6)$cycloalkyl, or is $(C_3-C_6)$cycloalkyl which is unsubstituted or substituted by one or more radicals from the group consisting of halogen, cyano, $(C_1-C_4)$alkyl and $(C_1-C_4)$haloalkyl, $R^3$ is cyclopropyl or cyclobutyl, where each of the latter two radicals is unsubstituted or substituted by one or more radicals from the group consisting of halogen, $(C_1-C_4)$alkyl, $(C_1-C_4)$haloalkyl, $(C_2-C_4)$alkenyl, $(C_2-C_4)$alkynyl, $(C_1-C_4)$alkoxy, $(C_1-C_4)$haloalkoxy and $(C_1-C_4)$alkylthio, where the cyclic $R^3$ radical, by its carbon atom in the 2 position,
(a) may be connected to the divalent $R^4$ group=methylene and may thus form, with the molecular moiety $R^3$—C—C—$R^4$, a bicycle composed of a five-membered ring and the three- or four-membered ring of $R^3$, or
(b) may be bonded directly or via a methylene group to the carbon atom in the 2 position of the cyclic $CR^4R^5$ radical and thus form a tricycle with the molecular moiety $R^3$—C—$CR^4R^5$, and $R^4$ and $R^5$ are each independently
$(C_1-C_6)$alkyl, $(C_2-C_6)$alkenyl or $(C_2-C_6)$alkynyl, where each of the latter three radicals is unsubstituted or substituted by one or more radicals from the group consisting of halogen, $(C_1-C_4)$alkoxy, $(C_1-C_4)$haloalkoxy and $(C_1-C_4)$alkylthio, or are each independently
cyclopropyl which is unsubstituted or substituted by one or more radicals from the group consisting of halogen, $(C_1-C_4)$alkyl, $(C_1-C_4)$haloalkyl, $(C_2-C_4)$alkenyl, $(C_2-C_4)$alkynyl, $(C_1-C_4)$alkoxy, $(C_1-C_4)$haloalkoxy and $(C_1-C_4)$alkylthio, or $R^4$ and $R^5$, together with the carbon atom bonded to them, are a 3- to 9-membered carbocyclic ring which is unsubstituted or substituted by one or more radicals from the group consisting of halogen, $(C_1-C_4)$alkyl, $(C_1-C_4)$haloalkyl, $(C_1-C_4)$alkoxy-$(C_1-C_4)$alkyl, $(C_1-C_4)$alkoxy, $(C_1-C_4)$haloalkoxy and $(C_1-C_4)$alkylthio,
where a cyclic $CR^4R^5$ radical, by its carbon atom in the 2 position, may be bonded to the carbon atom in the 2 position of the cycle of the $R^3$ group directly or via a methylene group and may thus form a tricycle with the molecular moiety $R^3$—C—$CR^4R^5$, or $R^4$ is a divalent group of the formula —$CH_2$— which is bonded to the carbon atom in the 2 position of the cyclic $R^3$ radical and may thus form, with the molecular moiety $R^3$—C—C—$R^4$, a bicycle composed of a five-membered ring and the three- or four-membered ring of $R^3$, and $R^6$ is hydrogen or $(C_1-C_4)$alkyl which is unsubstituted or substituted by one or more radicals from the group consisting of halogen, $(C_1-C_4)$alkoxy, $(C_1-C_4)$haloalkoxy and $(C_1-C_4)$alkylthio, and $R^7$ is hydrogen, methyl, ethyl or cyclopropyl which is unsubstituted or substituted by one or more radicals from the group consisting of halogen, $(C_1-C_4)$alkyl, $(C_1-C_4)$haloalkyl, $(C_1-C_4)$alkoxy, $(C_1-C_4)$haloalkoxy and $(C_1-C_4)$alkylthio.

The carbon atom in the 2 position of a cycle (see definitions of R3, R4, R5) is a ring carbon atom which is adjacent to the carbon atom in the 1 position, the latter referring to the carbon atom with the "yl position". The "yl position" of an alkyl radical refers to the carbon atom with the free bond.

Unless stated specifically, divalent radicals, for example $B^1$=—C(=Z*)—Z**—, are defined such that, in the combined groups, for example—$B^1$-$D^1$, the bond of the divalent radical which is bonded to the $D^1$ group is that which is written to the right in the formula of the divalent radical, i.e.—$B^1$-$D^1$ is a group of the formula —C(=Z*)—Z**—$D^1$; the same applies to analogous divalent radicals.

The compounds of the formula (I) can form salts by addition of a suitable inorganic or organic acid, for example HCl, HBr, $H_2SO_4$ or $HNO_3$, but also oxalic acid or sulfonic acids, to a basic group, for example amino or alkylamino. Suitable substituents which are present in deprotonated form, for example sulfonic acids or carboxylic acids, may form internal salts with groups which are in turn protonatable, such as amino groups. Salts may likewise be formed by, in the case of suitable substituents, for example sulfonic acids or carboxylic acids, replacing the hydrogen with a cation suitable for agriculture. These salts are, for example, metal salts, especially alkali metal salts or alkaline earth metal salts, especially sodium and potassium salts, or else ammonium salts, salts with organic amines or quaternary ammonium salts.

In the formula (I) and all subsequent formulae, the alkyl, alkoxy, haloalkyl, haloalkoxy, alkylamino and alkylthio radicals, and also the corresponding unsaturated and/or substituted radicals in the carbon skeleton, may each be straight-chain or branched.

The expression "$(C_1-C_4)$alkyl" is a brief notation for alkyl having from 1 to 4 carbon atoms, i.e. encompasses the methyl, ethyl, 1-propyl, 2-propyl, 1-butyl, 2-butyl, 2-methylpropyl or tert-butyl radicals. General alkyl radicals with a larger specified number of carbon atoms, for example "$(C_1-C_6)$alkyl" correspondingly also include straight-chain or branched alkyl radicals having a larger number of carbon atoms, i.e., according to the example, also the alkyl radicals having 5 and 6 carbon atoms. Unless stated specifically, preference is given to the lower carbon skeletons, for example having from 1 to 6 carbon atoms, or having from 2 to 6 carbon atoms in the case of unsaturated groups, in the case of the hydrocarbon radicals such as alkyl, alkenyl and alkynyl radicals, including in combined radicals. Alkyl radicals, including in the combined definitions such as alkoxy, haloalkyl, etc., are, for example, methyl, ethyl, n- or i-propyl, n-, i-, t- or 2-butyl, pentyls, hexyls such as n-hexyl, i-hexyl and 1,3-dimethylbutyl, heptyls such as n-heptyl, 1-methylhexyl and 1,4-dimethylpentyl; alkenyl and alkynyl radicals are defined as the possible unsaturated radicals corresponding to the alkyl radicals; alkenyl is, for example, vinyl, allyl, 1-methyl-2-propenyl, 2-methyl-2-propenyl, 2-butenyl, pentenyl, 2-methylpentenyl or hexenyl group, preferably allyl, 1-methylprop-2-en-1-yl, 2-methyl-prop-2-en-1-yl, but-2-en-1-yl, but-3-en-1-yl, 1-methyl-but-3-en-1-yl or 1-methylbut-2-en-1-yl.

Alkenyl also includes in particular straight-chain or branched hydrocarbon radicals having more than one double bond, such as 1,3-butadienyl and 1,4-pentadienyl, but also allenyl or cumulenyl radicals having one or more cumulated double bonds, for example allenyl (1,2-propadienyl), 1,2-butadienyl and 1,2,3-pentatrienyl.

Alkynyl is, for example, propargyl, but-2-yn-1-yl, but-3-yn-1-yl, 1-methylbut-3-yn-1-yl.

Alkynyl also includes, in particular, straight-chain or branched hydrocarbon radicals having more than one triple bond or else having one or more triple bonds and one or more double bonds, for example 1,3-butatrienyl or 3-penten-1-yn-1-yl.

A 3- to 9-membered carbocyclic ring is $(C_3-C_9)$cycloalkyl or $(C_5-C_9)$cycloalkenyl. $(C_3-C_{10})$Cycloalkyl is a carbocyclic saturated ring system having preferably 3-9 carbon atoms, for example cyclopropyl, cyclobutyl, cyclopentyl, cyclohexyl, cycloheptyl, cyclooctyl or cyclononyl. In the case of substituted cycloalkyl, cyclic systems with substituents are included, where the substituents may also be bonded by a double bond on the cycloalkyl radical, for example an alkylidene group such as methylidene.

$(C_5-C_9)$Cycloalkenyl is a carbocyclic, nonaromatic, partially unsaturated ring system having 5-9 carbon atoms, for example 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl. In the case of substituted cycloalkenyl, the explanations for substituted cycloalkyl apply correspondingly.

Alkylidene, for example also in the form of $(C_1-C_{10})$alkylidene, is the radical of a straight-chain or branched alkane which is bonded via a double bond, the position of the binding site not being fixed. In the case of a branched alkane, of course, only positions at which two hydrogen atoms may be replaced by the double bond are possible; radicals are, for example, $=CH_2$, $=CH-CH_3$, $=C(CH_3)-CH_3$, $=C(CH_3)-C_2H_5$ or $=C(C_2H_5)-C_2H_5$.

Halogen is, for example, fluorine, chlorine, bromine or iodine. Haloalkyl, -alkenyl and -alkynyl are, respectively, alkyl, alkenyl and alkynyl substituted partly or fully by identical or different halogen atoms, preferably from the group of fluorine, chlorine and bromine, in particular from the group of fluorine and chlorine, for example monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example $OCF_3$, $OCHF_2$, $OCH_2F$, $CF_3CF_2O$, $OCH_2CF_3$ and $OCH_2CH_2Cl$; the same applies to haloalkenyl and other halogen-substituted radicals.

Aryl is a mono-, bi- or polycyclic aromatic system, for example phenyl, naphthyl, tetrahydronaphthyl, indenyl, indanyl, pentalenyl, fluorenyl and the like, preferably phenyl.

A heterocyclic radical or ring (heterocyclyl) can be saturated, unsaturated or heteroaromatic; unless defined otherwise, it preferably contains one or more, in particular 1, 2 or 3, heteroatoms in the heterocyclic ring, preferably from the group of N, O and S; it is preferably an aliphatic heterocyclyl radical having from 3 to 7 ring atoms or a heteroaromatic radical having 5 or 6 ring atoms. The heterocyclic radical may, for example, be a heteroaromatic radical or ring (heteroaryl), for example a mono-, bi- or polycyclic aromatic system in which at least one ring contains one or more heteroatoms. It is preferably a heteroaromatic ring having a heteroatom from the group of N, O and S, for example pyridyl, pyrrolyl, thienyl or furyl; it is also preferably a corresponding heteroaromatic ring having 2 or 3 heteroatoms, for example pyrimidinyl, pyridazinyl, pyrazinyl, triazinyl, thiazolyl, thiadiazolyl, oxazolyl, isoxazolyl, pyrazolyl, imidazolyl and triazolyl. It is also preferably a partially or fully hydrogenated heterocyclic radical having one heteroatom from the group of N, O and S, for example oxiranyl, oxetanyl, oxolanyl (=tetrahydrofuryl), oxanyl, pyrrolinyl, pyrrolidyl or piperidyl.

It is also preferably a partially or fully hydrogenated heterocyclic radical having 2 heteroatoms from the group of N, O and S, for example piperazinyl, dioxolanyl, oxazolinyl, isoxazolinyl, oxazolidinyl, isoxazolidinyl and morpholinyl.

Possible substituents for a substituted heterocyclic radical include the substituents specified below, and additionally also oxo. The oxo group may also occur on the ring heteroatoms which may exist in various oxidation states, for example in the case of N and S.

Preferred examples of heterocyclyl are a heterocyclic radical having from 3 to 6 ring atoms from the group of pyridyl, thienyl, furyl, pyrrolyl, oxiranyl, 2-oxetanyl, 3-oxetanyl, oxolanyl (=tetrahydrofuryl), pyrrolidyl, piperidyl, especially oxiranyl, 2-oxetanyl, 3-oxetanyl or oxolanyl, or is a heterocyclic radical having two or three heteroatoms, for example pyrimidinyl, pyridazinyl, pyrazinyl, triazinyl, thienyl, thiazolyl, thiadiazolyl, oxazolyl, isoxazolyl, pyrazolyl, triazolyl, piperazinyl, dioxolanyl, oxazolinyl, isoxazolinyl, oxazolidinyl, isoxazolidinyl or morpholinyl.

When a base structure is substituted "by one or more radicals" from a list of radicals (=group) or a generically defined group of radicals, this in each case includes simultaneous substitution by a plurality of identical and/or structurally different radicals.

Substituted radicals, such as a substituted alkyl, alkenyl, alkynyl, cycloalkyl, aryl, phenyl, benzyl, heterocyclyl and heteroaryl radical, are, for example, a substituted radical derived from the unsubstituted base structure, where the substituents are, for example, one or more, preferably 1, 2 or 3, radicals from the group of halogen, alkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino such as acylamino, mono- and dialkylamino, and alkylsulfinyl, alkylsulfonyl and, in the case of cyclic radicals, also alkyl, haloalkyl, alkylthioalkyl, alkoxyalkyl, optionally substituted mono- and dialkylaminoalkyl and hydroxyalkyl; in the term "substituted radicals", such as substituted alkyl, etc., substituents include, in addition to the saturated hydrocarbon radicals mentioned, corresponding unsaturated and aromatic radicals, such as optionally substituted alkenyl, alkynyl, alkenyloxy, alkynyloxy, phenyl, phenoxy, etc. In the case of substituted cyclic radicals having aliphatic moieties in the ring, cyclic systems with those substituents which are bonded on the ring by a double bond are also included, for example substituted by an alkylidene group such as methylidene or ethylidene.

The substituents mentioned by way of example ("first substituent level") may, when they contain hydrocarbon moieties, optionally be further substituted there ("second substituent level"), for example by one of the substituents as defined for the first substituent level. Corresponding further substituent levels are possible. The term "substituted radical" preferably includes only one or two substituent levels.

Preferred substituents for the substituent levels are, for example, amino, hydroxyl, halogen, nitro, cyano, mercapto, carboxyl, carbonamide, $SF_5$, aminosulfonyl, alkyl, cycloalkyl, alkenyl, cycloalkenyl, alkynyl, monoalkylamino, dialkylamino, N-alkanoylamino, alkoxy, alkenyloxy, alkynyloxy, cycloalkoxy, cycloalkenyloxy, alkoxycarbonyl, alkenyloxycarbonyl, alkynyloxycarbonyl, aryloxycarbonyl, alkanoyl, alkenylcarbonyl, alkynylcarbonyl, arylcarbonyl, alkylthio, cycloalkylthio, alkenylthio, cycloalkenylthio, alkynylthio, alkylsulfinyl, alkylsulfonyl, monoalkylaminosulfonyl, dialkylaminosulfonyl, N-alkylaminocarbonyl, N,N-dialkyl-aminocarbonyl, N-alkanoylaminocarbonyl, N-alkanoyl-N-alkylaminocarbonyl, aryl, aryloxy, benzyl, benzyloxy, benzylthio, arylthio, arylamino and benzylamino.

In the case of radicals with carbon atoms, preference is given to those having from 1 to 6 carbon atoms, preferably from 1 to 4 carbon atoms, in particular 1 or 2 carbon atoms. In general, preferred substituents are those from the group of halogen, e.g. fluorine and chlorine, $(C_1-C_4)$alkyl, preferably methyl or ethyl, $(C_1-C_4)$haloalkyl, preferably trifluoromethyl, $(C_1-C_4)$alkoxy, preferably methoxy or ethoxy, $(C_1-C_4)$haloalkoxy, nitro and cyano. Preference is given to the substituents methyl, methoxy, fluorine and chlorine.

Substituted amino, such as mono- or disubstituted amino, is a radical from the group of the substituted amino radicals which are N-substituted, for example, by one or two identical or different radicals from the group of alkyl, alkoxy, acyl and aryl; preferably mono- and dialkylamino, mono- and diarylamino, acylamino, N-alkyl-N-arylamino, N-alkyl-N-acylamino and N-heterocycles; preference is given to alkyl radicals having from 1 to 4 carbon atoms; aryl is preferably phenyl or substituted phenyl; acyl is as defined below, preferably $(C_1-C_4)$alkanoyl. The same applies to substituted hydroxylamino or hydrazino.

Acyl is a radical of an organic acid which arises in a formal sense by removal of a hydroxyl group on the acid function, and the organic radical in the acid may also be bonded to the acid function via a heteroatom. Examples of acyl are the —CO—R radical of a carboxylic acid HO—CO—R and radicals of acids derived therefrom, such as those of thiocarboxylic acid, optionally N-substituted iminocarboxylic acids or the radical of carbonic monoesters, N-substituted carbamic acid, sulfonic acids, sulfinic acids, N-substituted sulfonamide acids, phosphonic acids or phosphinic acids.

Acyl is, for example, formyl, alkylcarbonyl such as [$(C_1-C_4)$alkyl]carbonyl, phenylcarbonyl, alkyloxycarbonyl, phenyloxycarbonyl, benzyloxycarbonyl, alkylsulfonyl, alkylsulfinyl, N-alkyl-1-iminoalkyl and other radicals of organic acids. The radicals may each be substituted further in the alkyl or phenyl moiety, for example in the alkyl moiety by one or more radicals from the group of halogen, alkoxy, phenyl and phenoxy; examples of substituents in the phenyl moiety are the substituents already mentioned above in general for substituted phenyl. Acyl is preferably an acyl radical in the narrower sense, i.e. a radical of an organic acid in which the acid group is bonded directly to the carbon atom of an organic radical, for example formyl, alkylcarbonyl such as acetyl or [$(C_1-C_4)$alkyl]carbonyl, phenylcarbonyl, alkylsulfonyl, alkylsulfinyl and other radicals of organic acids.

The invention also provides all stereoisomers which are encompassed by formula (I) and mixtures thereof. Such compounds of the formula (I) contain one or more asymmetric carbon atoms or else double bonds which are not stated specifically in the general formulae (I). The possible stereoisomers defined by their specific three-dimensional shape, such as enantiomers, diastereomers, Z- and E-isomers, are all encompassed by the formula (I) and can be obtained from mixtures of the stereoisomers by customary methods or else prepared by stereoselective reactions in combination with the use of stereochemically pure starting materials.

The compounds of formula (I) also includes all crystalline forms including polymorphic forms.

For reasons of higher herbicidal action, better selectivity and/or better preparability in particular, inventive compounds of particular interest are those of the formula (I) mentioned or salts thereof in which individual radicals have one of the preferred definitions already mentioned or mentioned hereinafter, or especially those in which one or more of the preferred definitions already mentioned or mentioned hereinafter occur in combination.

Irrespective of the other radicals from the group of $R^1$, $R^2$, $R^3$, $R^4$, $R^5$, $R^6$, $R^7$ in each case and the subdefinitions corresponding to the general radicals, and preferably in combination with preferred definitions of one or more of these radicals, inventive compounds of particular interest are those with the preferred definitions of the radicals in question listed below.

Preferably, $R^1$ is a radical of the formula —$NH_2$, —$NH(B^1-D^1)$, or —$N(B^1-D^1)(B^2-D^2)$, in each of which $B^1$, $B^2$, $D^1$ and $D^2$ are as defined below, or a group of the formula

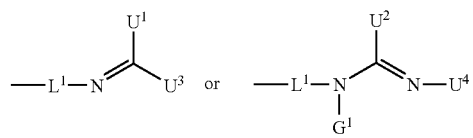

where $L^1$ is a direct bond, —O—, —S— or a group of the formula —$NG^2$-, preferably a direct bond, $U^1$, $U^2$ are each independently a group of the formula $G^3$, $OG^4$, $SG^5$, $NG^6G^7$, $NG^8NG^9G^{10}$, $NG^{11}OG^{12}$ or $NG^{11}SG^{12}$, $U^3$ is a group of the formula $G^{13}$, $OG^{14}$, $SG^{15}$, $NG^{16}G^{17}$, $NG^{18}NG^{19}G^{20}$ $NG^{21}OG^{22}$ or $NG^{23}SG^{24}$ $U^4$ is a group of the formula $G^{25}$, $OG^{26}$, $SG^{27}$ or $NG^{28}G^{29}$, where the $G^1$ to $G^{29}$ radicals are each independently hydrogen or phenyl which is unsubstituted or substituted and has preferably from 6 to 30 carbon atoms including substituents, or $(C_3-C_9)$cycloalkyl which is unsubstituted or substituted and has preferably from 3 to 30 carbon atoms including substituents, or heterocyclyl which is substituted or unsubstituted and has preferably from 2 to 30 carbon atoms including substituents, or $(C_1-C_6)$alkyl, $(C_2-C_6)$alkenyl or $(C_2-C_6)$alkynyl, where each of the 3 latter radicals is unsubstituted or substituted by one or more radicals from the group of halogen, hydroxyl, cyano, nitro, thiocyanato, $(C_1-C_4)$alkoxy, $(C_1-C_4)$haloalkoxy, $(C_2-C_4)$alkenyloxy, $(C_2-C_4)$haloalkenyloxy, $(C_1-C_4)$alkylthio, $(C_1-C_4)$alkylsulfinyl, $(C_1-C_4)$alkylsulfonyl, $(C_1-C_4)$haloalkylthio, $(C_1-C_4)$haloalkylsulfinyl, $(C_1-C_4)$haloalkylsulfonyl, $(C_3-C_8)$cycloalkyl which is unsubstituted or substituted, phenyl which is unsubstituted or substituted, and heterocyclyl which is unsubstituted or substituted, and radicals of the formulae R'—C(=Z')—, R'—C(=Z')—Z—, R'—Z—C(=Z')—, R'R"N—C(=Z')—, R'—Z—C(=Z')—O—, R'R"N—C(=Z')—Z—, R'—Z—C(=Z')—NR"— and R'R"N—C(=Z')—NR'''—, in which R', R" and R''' are each independently $(C_1-C_6)$alkyl, aryl, aryl$(C_1-C_6)$alkyl, $(C_3-C_9)$cycloalkyl or $(C_3-C_9)$cyclo-alkyl$(C_1-C_6)$alkyl, where each of the 5 latter radicals is unsubstituted or substituted, and in which Z and Z' are each independently an oxygen or sulfur atom, or the U$^1$ and U$^3$ or U$^2$ and U$^4$ or U$^2$ and G$^1$ or U$^4$ and G$^1$ radicals, in pairs with the atoms connecting them, are each a carbocyclic or heterocyclic ring having from 4 to 7 ring atoms, where the ring is unsubstituted or substituted, B$^1$ and B$^2$ are each independently a divalent group of the formulae —C(=Z*)—, —C(=Z*)—Z**—, —C(=Z*)—NH— or —C(=Z*)—NR*—, where Z* is an oxygen or sulfur atom, Z** is an oxygen or sulfur atom and R* is (C$_1$-C$_6$)alkyl, phenyl, phenyl(C$_1$-C$_6$)alkyl, (C$_3$-C$_9$)cycloalkyl or (C$_3$-C$_8$)cycloalkyl(C$_1$-C$_6$)alkyl, where each of the 5 latter radicals is unsubstituted or substituted and has preferably up to 20 carbon atoms including substituents, D$^1$ and D$^2$ are each independently hydrogen, (C$_1$-C$_6$)alkyl, phenyl, phenyl(C$_1$-C$_6$)alkyl, (C$_3$-C$_9$)cycloalkyl or (C$_3$-C$_9$)cycloalkyl(C$_1$-C$_6$)alkyl, where each of the 5 latter radicals is unsubstituted or substituted and has preferably up to 20 carbon atoms including substituents, where the radical is preferably an amino group which is preferably unsubstituted or bears one or two substituents which can be eliminated readily under chemical or biological conditions.

The R$^1$ radical generally allows control and influence of the physicochemical properties. The active ingredient can therefore be taken up more rapidly or more slowly by the undesirably growing plants to be controlled. Depending on the use and structure of the R$^1$ radical, the group can be eliminated over a defined period, so that the result is that the active ingredient with the free amino group is released gradually and the active period can be prolonged without needing to use active ingredients of comparable potency with undesirably long active substance degradation from an ecological point of view. This process is advantageous since it allows the amount of active substance required for the application to be made available over a prolonged period. Repeat applications can therefore be avoided. Since the requirements on the activity profile are different in different applications, the profile can be altered by means of suitable leaving groups and thus adjusted to the requirements. The compounds of this series have an advantageous activity profile and good crop plant compatibility.

More preferably,

R$^1$ is a radical of the formula —NH$_2$, —NH(B$^1$-D$^1$), or —N(B$^1$-D$^1$)(B$^2$-D$^2$), in each of which B$^1$, B$^2$, D$^1$ and D$^2$ are as defined below, or a group of the formula

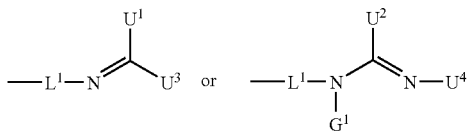

where

L$^1$ is a direct bond, —O—, —S— or a group of the formula —NG$^2$-, preferably a direct bond, U$^1$, U$^2$ are each independently a group of the formula G$^3$, OG$^4$, SG$^5$, NG$^6$G$^7$, NG$^8$NG$^9$G$^{10}$, NG$^{11}$OG$^{12}$ or NG$^{11}$SG$^{12}$, U$^3$ is a group of the formula G$^{13}$, OG$^{14}$, SG$^{15}$, NG$^{16}$G$^{17}$ NG$^{18}$NG$^{19}$G$^{20}$ NG$^{21}$OG$^{22}$ or NG$^{23}$SG$^{24}$ U$^4$ is a group of the formula G$^{25}$, OG$^{26}$, SG$^{27}$ or NG$^{28}$G$^{29}$, where the G$^1$ to G$^{29}$ radicals are each independently hydrogen or phenyl which is unsubstituted or substituted and has preferably from 6 to 30 carbon atoms, in particular from 6 to 22 carbon atoms, including substituents, or (C$_3$-C$_8$)cycloalkyl which is unsubstituted or substituted and has preferably from 3 to 30 carbon atoms, in particular from 6 to 22 carbon atoms, including substituents, or heterocyclyl which is substituted or unsubstituted and has preferably from 2 to 30 carbon atoms, in particular from 2 to 20 carbon atoms, including substituents, or (C$_1$-C$_6$)alkyl, (C$_2$-C$_6$)alkenyl or (C$_2$-C$_6$)alkynyl, where each of the 3 latter radicals is unsubstituted or substituted by one or more radicals from the group of halogen, hydroxyl, cyano, nitro, thiocyanato, (C$_1$-C$_4$)alkoxy, (C$_1$-C$_4$)haloalkoxy, (C$_2$-C$_4$)alkenyloxy, (C$_2$-C$_4$)haloalkenyloxy, (C$_1$-C$_4$)alkylthio, (C$_1$-C$_4$)alkylsulfinyl, (C$_1$-C$_4$)alkylsulfonyl, (C$_1$-C$_4$)haloalkylthio, (C$_1$-C$_4$)haloalkylsulfinyl, (C$_1$-C$_4$)haloalkylsulfonyl, (C$_3$-C$_9$)cycloalkyl which is unsubstituted or substituted, phenyl which is unsubstituted or substituted, and heterocyclyl which is unsubstituted or substituted, and radicals of the formulae R'—C(=Z')—, R'—C(=Z')—Z—, R'—Z—C(=Z')—, R'R"N—C(=Z')—, R'—Z—C(=Z')—O—, R'R"N—C(=Z')—Z—, R'—Z—C(=Z')—NR"— and R'R"N—C(=Z')—NR'"—, in which R', R" and R'" are each independently (C$_1$-C$_6$)alkyl, phenyl, phenyl(C$_1$-C$_6$)alkyl, (C$_3$-C$_9$)cycloalkyl or (C$_3$-C$_9$)cyclo-alkyl(C$_1$-C$_6$)alkyl, where each of the 5 latter radicals is unsubstituted or substituted, and in which Z and Z' are each independently an oxygen or sulfur atom, or the U$^1$ and U$^3$ or U$^2$ and U$^4$ or U$^2$ and G$^1$ or U$^4$ and G$^1$ radicals, in pairs with the atoms connecting them, are each a carbocyclic or heterocyclic ring having from 4 to 7 ring atoms, where the ring is unsubstituted or substituted, B$^1$ and B$^2$ are each independently a divalent group of the formula —C(=Z*)—, —C(=Z*)—Z**—, —C(=Z*)—NH— or —C(=Z*)—NR*—, where Z* is an oxygen or sulfur atom, Z** is an oxygen or sulfur atom and R* is (C$_1$-C$_6$)alkyl, phenyl, phenyl(C$_1$-C$_6$)alkyl, (C$_3$-C$_9$)cycloalkyl or (C$_3$-C$_9$)cycloalkyl(C$_1$-C$_6$)alkyl, where each of the 5 latter radicals is unsubstituted or substituted and has preferably up to 20 carbon atoms including substituents, D$^1$ and D$^2$ are each independently hydrogen, (C$_1$-C$_6$)alkyl, phenyl, phenyl(C$_1$-C$_6$)alkyl, (C$_3$-C$_9$)cycloalkyl or (C$_3$-C$_9$)cycloalkyl(C$_1$-C$_6$)alkyl, where each of the 5 latter radicals is unsubstituted or substituted and has preferably up to 20 carbon atoms including substituents.

In the abovementioned radicals, which are generally unsubstituted or substituted, the possible substituents in acyclic base structures are preferably selected from halogen and (C$_1$-C$_4$)alkoxy; in the case of cyclic base structures, they are preferably selected from halogen, (C$_1$-C$_4$)alkyl and (C$_1$-C$_4$)alkoxy. Preference is additionally given to the unsubstituted base structures in each case.

R$^1$ is, for example, a radical of the formula —NH$_2$, —NH(B$^1$-D$^1$) or —N(B$^1$-D$^1$)(B$^2$-D$^2$), where B$^1$, B$^2$, D$^1$ and D$^2$ are each as already defined or preferably as defined below, or is preferably a radical from the R$^8$ group, where R$^8$ is a radical of the formulae (R$^8$-a) to (R$^8$-d)

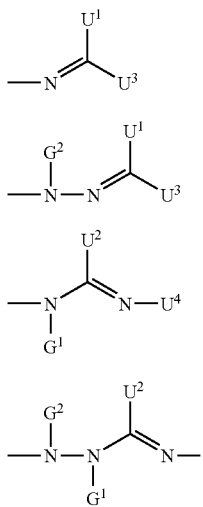

(R8-a)
(R8-b)
(R8-c)
(R8-d)

where the $U^1$, $U^3$, $U^4$, $G^1$ and $G^2$ groups in the formulae are each as defined above for $R^1$. The $R^8$ group corresponds to radicals of the $R^1$ group in which $L^1$=a direct bond or —$NG^2$-. Preference is further given to compounds (I) with radicals which are selected from subgroups from the latter formulae for $R^8$, for example having radicals of the following formulae:

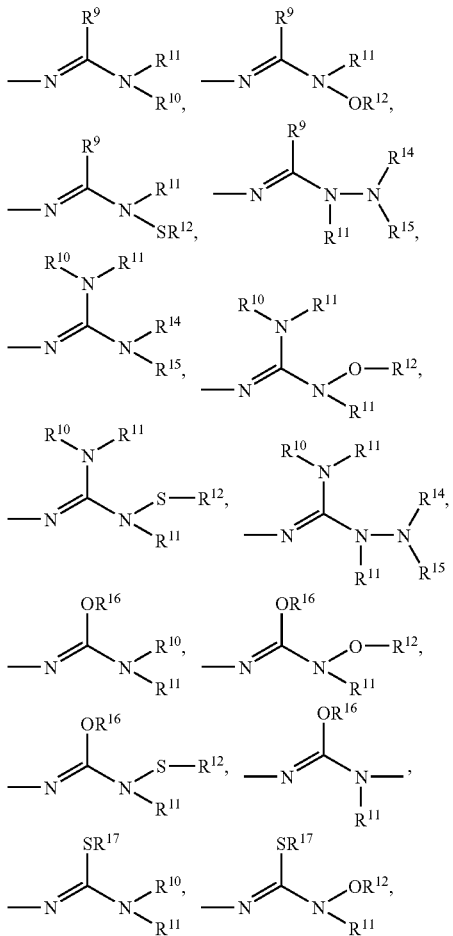

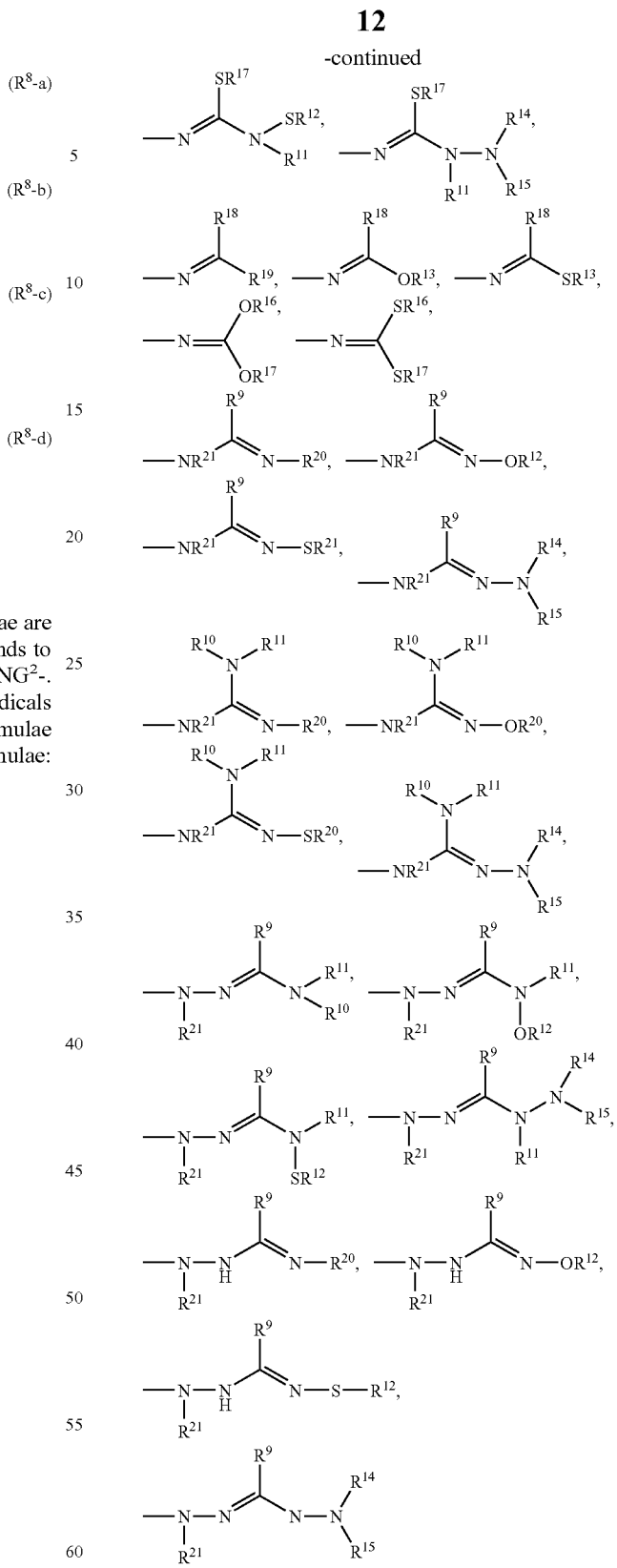

where the $R^9$ to $R^{21}$ radicals are each as defined below.

Compounds of particular interest are also those in which two particular radicals in each case can form a ring with the atoms connecting them in the aforementioned radicals, i.e. in which $R^{10}$ and $R^{11}$ together with the nitrogen atom of the $NR^{10}R^{11}$ group or
$R^{11}$ and $OR^{12}$ together with the nitrogen atom of the $NOR^{12}R^{11}$ group or
$R^{11}$ and $SR^{12}$ together with the nitrogen atom of the $NSR^{12}R^{11}$ group or
$R^{14}$ and $R^{15}$ together with the nitrogen atom of the $NR^{14}R^{15}$ group or
$OR^{16}$ and $OR^{17}$ or $SR^{16}$ and $SR^{17}$ or $OR^{13}$ and $R^{18}$ or $SR^{13}$ and $R^{18}$ or $R^{18}$ and $R^{19}$, together with the carbon atom of the particular atomic moiety of the formula $=C(OR^{16})(OR^{17})$, $=C(SR^{16})(SR^{17})$, $=C(OR^{13})(R^{18})$, $=C(SR^{13})(R^{18})$ or $=C(R^{18})(R^{19})$ in the corresponding radical of the formulae

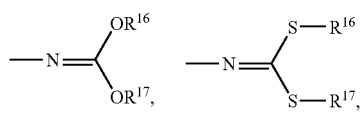

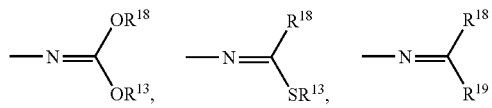

or
$R^9$ and $R^{11}$ together with the atomic moiety

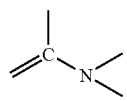

in the radicals of the formulae

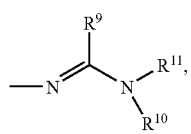

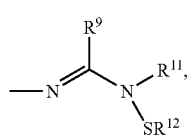

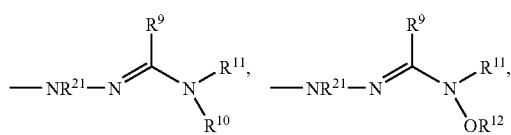

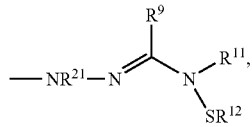

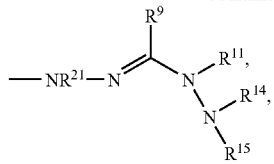

or
$R^9$ and $NR^{21}$ together with the carbon atom of the group of the formula

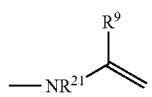

in the particular radicals or
$R^9$ and $R^{20}$ together with the whole radical

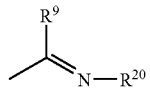

of the groups

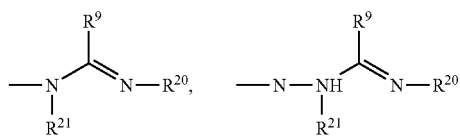

$R^{11}$ and $R^{14}$ together with the atomic moiety

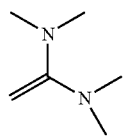

of the groups

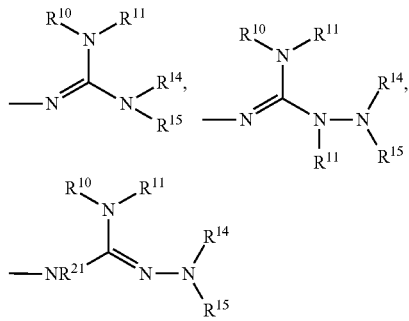

each independently form a carbocyclic ring having from 3 to 9 ring atoms or a heterocyclic ring having from 3 to 7 ring atoms and from 1 to 6 heteroatoms, which comprises the heteroatom mentioned or the atomic moiety mentioned and where any further heteroring atoms are selected from the group of N, O and S and the carbocylic or heterocyclic ring is in each case unsubstituted or substituted, where the $R^9$ to $R^{21}$ radicals are each as defined below.

In the aforementioned atomic moieties, specifically, the double bond "=" bonded at one side indicates the binding site of a double bond or the free double bond (meaning the binding site of an ylidene radical) and not the brief notation for vinyl.

$R^9$, $R^{10}$, $R^{11}$, $R^{12}$, $R^{13}$, $R^{14}$, $R^{15}$, $R^{18}$, $R^{19}$, $R^{20}$, $R^{21}$ in the above formulae are each independently hydrogen, aryl which is unsubstituted or substituted and has preferably from 6 to 30 carbon atoms including substituents, or $(C_3-C_9)$cycloalkyl which is unsubstituted or substituted and has preferably from 3 to 30 carbon atoms including substituents, $(C_4-C_9)$cycloalkenyl which is unsubstituted or substituted and has preferably from 4 to 30 carbon atoms including substituents, or heterocyclyl which is substituted or unsubstituted and has preferably from 2 to 30 carbon atoms including substituents, or $(C_1-C_6)$alkyl, $(C_2-C_6)$alkenyl or $(C_2-C_6)$alkynyl, where each of the 3 latter radicals is unsubstituted or substituted by one or more radicals from the group of halogen, hydroxyl, cyano, nitro, thiocyanato, $(C_1-C_4)$alkoxy, $(C_1-C_4)$haloalkoxy, $(C_2-C_4)$alkenyloxy, $(C_2-C_4)$haloalkenyloxy, $(C_1-C_4)$alkylthio, $(C_1-C_4)$alkylsulfinyl, $(C_1-C_4)$alkylsulfonyl, $(C_1-C_4)$haloalkylsulfinyl, $(C_1-C_4)$haloalkylsulfonyl, $(C_3-C_9)$cycloalkyl which is unsubstituted or substituted, phenyl which is unsubstituted or substituted, heterocyclyl which is unsubstituted or substituted, and radicals of the formulae R'—C(=Z')—, R'—C(=Z')—Z—, R'—Z—C(=Z')—, R'R"N—C(=Z')—, R'—Z—C(=Z')—O—, R'R"N—C(=Z')—Z—, R'—Z—C(=Z')—NR"— and R'R"N—C(=Z')—NR'''—, in which R', R" and R''' are each independently $(C_1-C_6)$alkyl, aryl, aryl$(C_1-C_6)$alkyl, $(C_3-C_9)$cycloalkyl or $(C_3-C_8)$cycloalkyl$(C_1-C_6)$alkyl, where each of the 5 latter radicals is unsubstituted or substituted, and in which Z and Z' are each independently an oxygen or sulfur atom, and has preferably from 1 to 30 carbon atoms including substituents.

$R^{16}$, $R^{17}$ are each independently aryl which is unsubstituted or substituted and has preferably from 6 to 30 carbon atoms including substituents, or $(C_3-C_9)$cycloalkyl which is unsubstituted or substituted and has preferably from 3 to 30 carbon atoms including substituents, or heterocyclyl which is substituted or unsubstituted and has preferably from 2 to 30 carbon atoms including substituents, or $(C_1-C_6)$alkyl, $(C_2-C_6)$alkenyl or $(C_2-C_6)$alkynyl, where each of the 3 latter radicals is unsubstituted or substituted by one or more radicals from the group of halogen, hydroxyl, cyano, nitro, thiocyanato, $(C_1-C_4)$alkoxy, $(C_1-C_4)$haloalkoxy, $(C_2-C_4)$alkenyloxy, $(C_2-C_4)$haloalkenyloxy, $(C_1-C_4)$alkylthio, $(C_1-C_4)$alkylsulfinyl, $(C_1-C_4)$alkylsulfonyl, $(C_1-C_4)$haloalkylsulfinyl, $(C_1-C_4)$haloalkylsulfonyl, $(C_3-C_8)$cycloalkyl which is unsubstituted or substituted, phenyl which is unsubstituted or substituted, heterocyclyl which is unsubstituted or substituted, and radicals of the formulae R'—C(=Z')—, R'—C(=Z')—Z—, R'—Z—C(=Z')—, R'R"N—C(=Z')—, R'—Z—C(=Z')—O—, R'R"N—C(=Z')—Z—, R'—Z—C(=Z')—NR"— and R'R"N—C(=Z')—NR'''—, in which R', R" and R''' are each independently $(C_1-C_6)$alkyl, aryl, aryl$(C_1-C_6)$alkyl, $(C_3-C_9)$cycloalkyl or $(C_3-C_8)$cycloalkyl$(C_1-C_6)$alkyl, where each of the 5 latter radicals is unsubstituted or substituted, and in which Z and Z' are each independently an oxygen or sulfur atom, and has preferably from 1 to 30 carbon atoms including substituents.

The $R^9$, $R^{10}$, $R^{11}$, $R^{12}$, $R^{13}$, $R^{14}$, $R^{15}$, $R^{18}$, $R^{19}$, $R^{20}$, $R^{21}$ radicals are preferably each independently hydrogen.

The $R^9$, $R^{10}$, $R^{11}$, $R^{12}$, $R^{13}$, $R^{14}$, $R^{15}$, $R^{18}$, $R^{19}$, $R^{20}$, $R^{21}$ radicals are preferably each independently also phenyl which is unsubstituted or substituted by one or more radicals from the group of halogen, hydroxyl, amino, nitro, formyl, carboxyl, sulfo, cyano, thiocyanato, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_9)$cycloalkyl, [$(C_1-C_4)$alkyl]carbonyl, [$(C_1-C_4)$alkoxy]carbonyl, aminocarbonyl, mono$(C_1-C_4)$alkylaminocarbonyl, di$(C_1-C_4)$alkylaminocarbonyl, $(C_1-C_4)$alkylsulfonyl and $(C_1-C_4)$haloalkylsulfonyl and has from 6 to 30 carbon atoms, preferably from 6 to 20 carbon atoms, in particular from 6 to 15 carbon atoms, including substituents.

The $R^9$, $R^{10}$, $R^{11}$, $R^{12}$, $R^{13}$, $R^{14}$, $R^{15}$, $R^{18}$, $R^{19}$, $R^{20}$, $R^{21}$ radicals are preferably each independently also $(C_3-C_9)$cycloalkyl which is unsubstituted or substituted by one or more radicals from the group of halogen, hydroxyl, amino, cyano, thiocyanato, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino and di$(C_1-C_4)$alkylamino, and has from 3 to 30 carbon atoms, preferably from 3 to 20 carbon atoms, in particular from 3 to 15 carbon atoms, including substituents.

The $R^9$, $R^{10}$, $R^{11}$, $R^{12}$, $R^{13}$, $R^{14}$, $R^{15}$, $R^{18}$, $R^{19}$, $R^{20}$, $R^{21}$ radicals are preferably each independently also heterocyclyl which is unsubstituted or substituted by one or more radicals from the group of halogen, hydroxyl, amino, nitro, formyl, carboxyl, sulfonyl, cyano, thiocyanato, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_9)$cycloalkyl, [$(C_1-C_4)$alkyl]carbonyl, [$(C_1-C_4)$alkoxy]carbonyl, aminocarbonyl, mono$(C_1-C_4)$alkylaminocarbonyl, di$(C_1-C_4)$alkylaminocarbonyl, $(C_1-C_4)$alkylsulfonyl and $(C_1-C_4)$haloalkylsulfonyl, and has from 2 to 30 carbon atoms, preferably from 2 to 20 carbon atoms, in particular from 2 to 15 carbon atoms, including substituents.

In this case and also in other radicals, heterocyclyl is as defined above in general terms or with preference.

$R^9$, $R^{10}$, $R^{11}$, $R^{12}$, $R^{13}$, $R^{14}$, $R^{15}$, $R^{18}$, $R^{19}$, $R^{20}$, $R^{21}$ are each independently preferably $(C_1-C_4)$alkyl which is unsubstituted or substituted by one or more radicals from the group of halogen, $(C_1-C_4)$alkoxy, $(C_1-C_4)$alkylthio, $(C_1-C_4)$alkylsulfonyl, $(C_3-C_9)$cycloalkyl which is unsubstituted or substituted, and phenyl which is unsubstituted or substituted by one or more radicals from the group of halogen, $(C_1-C_4)$alkyl and $(C_1-C_4)$haloalkyl, $(C_1-C_4)$alkoxy, $(C_1-C_4)$haloalkoxy, $(C_1-C_4)$alkylthio, amino, mono- and di[$(C_1-C_4)$alkyl]amino, $(C_1-C_4)$alkanoylamino, benzoylamino, nitro, cyano, [$(C_1-C_4)$alkyl]carbonyl, formyl, carbamoyl, mono- and di-[$(C_1-C_4)$alkyl]aminocarbonyl and $(C_1-C_4)$alkylsulfonyl, and heterocyclyl having from 3 to 6 ring atoms and from 1 to 3 heteroring atoms from the group of N, O and S, where the ring is unsubstituted or substituted by one or more radicals from the group of halogen, $(C_1-C_4)$alkyl and oxo, or phenyl which is unsubstituted or substituted by one or more radicals from the group of halogen, hydroxyl, amino, nitro, formyl, carboxyl, sulfonyl, cyano, thiocyanato, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-

$C_4$)alkylamino, ($C_3$-$C_9$)cycloalkyl, [($C_1$-$C_4$)alkyl]carbonyl, [($C_1$-$C_4$)alkoxy]carbonyl, aminocarbonyl, mono($C_1$-$C_4$)alkylaminocarbonyl, di($C_1$-$C_4$)alkylaminocarbonyl, ($C_1$-$C_4$)alkylsulfonyl and ($C_1$-$C_4$)haloalkylsulfonyl, and has from 2 to 30 carbon atoms, preferably from 2 to 20 carbon atoms, in particular from 2 to 15 carbon atoms, including substituents.

$R^{16}$, $R^{17}$ are each independently preferably also phenyl which is unsubstituted or substituted by one or more radicals from the group of halogen, hydroxyl, amino, nitro, formyl, carboxyl, sulfo, cyano, thiocyanato, ($C_1$-$C_4$)alkyl, ($C_1$-$C_4$)haloalkyl, ($C_1$-$C_4$)alkoxy, ($C_1$-$C_4$)haloalkoxy, ($C_1$-$C_4$)alkylthio, ($C_1$-$C_4$)haloalkylthio, mono($C_1$-$C_4$)alkylamino, di($C_1$-$C_4$)alkylamino, ($C_3$-$C_9$)cycloalkyl, [($C_1$-$C_4$)alkyl]carbonyl, [($C_1$-$C_4$)alkoxy]carbonyl, aminocarbonyl, mono($C_1$-$C_4$)alkylaminocarbonyl, di($C_1$-$C_4$)alkylaminocarbonyl, ($C_1$-$C_4$)alkylsulfonyl and ($C_1$-$C_4$)haloalkylsulfonyl, and has from 6 to 30 carbon atoms, preferably from 6 to 20 carbon atoms, in particular from 6 to 15 carbon atoms, including substituents.

$R^{16}$, $R^{17}$ are each independently preferably also ($C_3$-$C_9$)cycloalkyl which is unsubstituted or substituted by one or more radicals from the group of halogen, hydroxyl, amino, cyano, thiocyanato, ($C_1$-$C_4$)alkyl, ($C_1$-$C_4$)haloalkyl, ($C_1$-$C_4$)alkoxy, ($C_1$-$C_4$)haloalkoxy, ($C_1$-$C_4$)alkylthio, ($C_1$-$C_4$)haloalkylthio, mono($C_1$-$C_4$)alkylamino and di($C_1$-$C_4$)alkylamino, and has from 3 to 30 carbon atoms, preferably from 3 to 20 carbon atoms, in particular from 3 to 15 carbon atoms, including substituents.

$R^{16}$, $R^{17}$ are each independently preferably also heterocyclyl which is unsubstituted or substituted by one or more radicals from the group of halogen, hydroxyl, amino, nitro, formyl, carboxyl, sulfonyl, cyano, thiocyanato, ($C_1$-$C_4$)alkyl, ($C_1$-$C_4$)haloalkyl, ($C_1$-$C_4$)alkoxy, ($C_1$-$C_4$)haloalkoxy, ($C_1$-$C_4$)alkylthio, ($C_1$-$C_4$)haloalkylthio, mono($C_1$-$C_4$)alkylamino, di($C_1$-$C_4$)alkylamino, ($C_3$-$C_9$)cycloalkyl, [($C_1$-$C_4$)alkyl]carbonyl, [($C_1$-$C_4$)alkoxy]carbonyl, aminocarbonyl, mono($C_1$-$C_4$)alkylaminocarbonyl, di($C_1$-$C_4$)alkylaminocarbonyl, ($C_1$-$C_4$)alkylsulfonyl and ($C_1$-$C_4$)haloalkylsulfonyl, and has from 2 to 30 carbon atoms, preferably from 2 to 20 carbon atoms, in particular from 2 to 15 carbon atoms, including substituents.

In this context, heterocyclyl is as defined above in general or with preference.

$R^{16}$, $R^{17}$ are each independently preferably ($C_1$-$C_4$)alkyl which is unsubstituted or substituted by one or more radicals from the group of halogen, ($C_1$-$C_4$)alkoxy, ($C_1$-$C_4$)alkylthio, ($C_1$-$C_4$)alkylsulfonyl, ($C_3$-$C_9$)cycloalkyl which is unsubstituted or substituted, and phenyl which is unsubstituted or substituted by one or more radicals from the group of halogen, ($C_1$-$C_4$)alkyl and ($C_1$-$C_4$)haloalkyl, ($C_1$-$C_4$)alkoxy, ($C_1$-$C_4$)haloalkoxy, ($C_1$-$C_4$)alkylthio, amino, mono- and di[($C_1$-$C_4$)alkyl]amino, ($C_1$-$C_4$)alkanoylamino, benzoylamino, nitro, cyano, [($C_1$-$C_4$)alkyl]carbonyl, formyl, carbamoyl, mono- and di-[($C_1$-$C_4$)alkyl]aminocarbonyl and ($C_1$-$C_4$)alkylsulfonyl, and heterocyclyl having from 3 to 6 ring atoms and from 1 to 3 heteroring atoms from the group of N, O and S, where the ring is unsubstituted or substituted by one or more radicals from the group of halogen, ($C_1$-$C_4$)alkyl and oxo, or phenyl which is unsubstituted or substituted by one or more radicals from the group of halogen, hydroxyl, amino, nitro, formyl, carboxyl, sulfonyl, cyano, thiocyanato, ($C_1$-$C_4$)alkyl, ($C_1$-$C_4$)haloalkyl, ($C_1$-$C_4$)alkoxy, ($C_1$-$C_4$)haloalkoxy, ($C_1$-$C_4$)alkylthio, ($C_1$-$C_4$)haloalkylthio, mono ($C_1$-$C_4$)alkylamino, di($C_1$-$C_4$)alkylamino, ($C_3$-$C_9$)cycloalkyl, [($C_1$-$C_4$)alkyl]carbonyl, [($C_1$-$C_4$)alkoxy]carbonyl, aminocarbonyl, mono($C_1$-$C_4$)alkylaminocarbonyl, di($C_1$-$C_4$)alkylaminocarbonyl, ($C_1$-$C_4$)alkylsulfonyl and ($C_1$-$C_4$)haloalkylsulfonyl, and has from 2 to 30 carbon atoms, preferably from 2 to 20 carbon atoms, in particular from 2 to 15 carbon atoms, including substituents.

Preferably, $B^1$ and $B^2$ are each independently a divalent group of the formulae —C(=Z*)—, —C(=Z*)—Z**—, —C(=Z*)—NH— or —C(=Z*)—NR*—, where Z*=O or S, Z**=O or S and R*=($C_1$-$C_4$)alkyl, phenyl, phenyl($C_1$-$C_4$)alkyl, ($C_3$-$C_6$)cycloalkyl or ($C_3$-$C_6$)cycloalkyl($C_1$-$C_4$)alkyl, where each of the 5 latter radicals is unsubstituted or substituted by one or more radicals from the group of halogen, hydroxyl, amino, formyl, ($C_1$-$C_4$)alkoxy, ($C_1$-$C_4$)haloalkoxy, ($C_1$-$C_4$)alkylthio, mono($C_1$-$C_4$)alkylamino, di($C_1$-$C_4$)alkylamino, ($C_3$-$C_9$)cycloalkyl, [($C_1$-$C_4$)alkyl]carbonyl, [($C_1$-$C_4$)alkoxy]carbonyl, aminocarbonyl, mono($C_1$-$C_4$)alkylaminocarbonyl, di($C_1$-$C_4$)alkylaminocarbonyl and, in the case of cyclic radicals, also ($C_1$-$C_4$)alkyl and ($C_1$-$C_4$)haloalkyl; in particular, Z* is an oxygen atom and in particular R* is ($C_1$-$C_4$)alkyl, ($C_3$-$C_6$)cycloalkyl, phenyl or phenyl($C_1$-$C_4$)alkyl, where each of the two latter radicals in the phenyl moiety is unsubstituted or substituted by one or more radicals from the group of halogen, ($C_1$-$C_4$)alkyl, ($C_1$-$C_4$)haloalkyl, ($C_1$-$C_4$)alkoxy or ($C_1$-$C_4$)haloalkoxy.

Preferably, $D^1$ and $D^2$ are each independently hydrogen, ($C_1$-$C_4$)alkyl, phenyl, phenyl($C_1$-$C_4$)alkyl, ($C_3$-$C_6$)cycloalkyl or ($C_3$-$C_6$)cycloalkyl($C_1$-$C_4$)alkyl, where each of the 5 latter radicals is unsubstituted or substituted by one or more radicals from the group of halogen, hydroxyl, amino, formyl, ($C_1$-$C_4$)alkoxy, ($C_1$-$C_4$)haloalkoxy, ($C_1$-$C_4$)alkylthio, mono ($C_1$-$C_4$)alkylamino, di($C_1$-$C_4$)alkylamino, ($C_3$-$C_8$)cycloalkyl, [($C_1$-$C_4$)alkyl]carbonyl, [($C_1$-$C_4$)alkoxy]carbonyl, aminocarbonyl, mono($C_1$-$C_4$)alkylaminocarbonyl, di($C_1$-$C_4$)alkylaminocarbonyl and, in the case of cyclic radicals, also ($C_1$-$C_4$)alkyl and ($C_1$-$C_4$)haloalkyl, and are in particular hydrogen, ($C_1$-$C_4$)alkyl or ($C_3$-$C_6$)cycloalkyl or phenyl or phenyl($C_1$-$C_4$)alkyl, where each of the two latter radicals in the phenyl moiety is unsubstituted or substituted by one or more radicals from the group of halogen, ($C_1$-$C_4$)alkyl, ($C_1$-$C_4$)haloalkyl, ($C_1$-$C_4$)alkoxy or ($C_1$-$C_4$)haloalkoxy.

More preferably, $R^1$ is an amino group which is unsubstituted or substituted by one or two groups which can be eliminated readily under physiological conditions in plants.

$R^1$ is preferably amino, acylamino having from 1 to 6 carbon atoms, di($C_1$-$C_4$)alkylamino($C_1$-$C_4$)alkylideneamino or N-heterocyclylamino-($C_1$-$C_4$)alkylideneamino, where the N-heterocycle is a saturated heterocyclic ring having from 1 to 3 ring heteroatoms from the group of N, O and S and at least one nitrogen atom as a ring heteroatom which is bonded to the alkylidene group.

$R^1$ is more preferably amino, ($C_1$-$C_6$)alkanoylamino, which is unsubstituted or substituted by halogen in the alkyl moiety, di-[($C_1$-$C_4$)alkyl]amino-methylideneamino or N-morpholin-4-ylaminomethylideneamino, especially amino.

$R^2$ is preferably hydrogen, ($C_1$-$C_6$)alkyl, ($C_2$-$C_6$)alkenyl or ($C_2$-$C_6$)alkynyl, where each of the three latter groups is unsubstituted or substituted by one or more radicals from the group which consists of halogen, ($C_1$-$C_4$)alkoxy, ($C_1$-$C_4$)alkylthio, ($C_1$-$C_4$)haloalkoxy, ($C_1$-$C_2$)alkoxy($C_1$-$C_2$)alkoxy and optionally halogen- or ($C_1$-$C_4$)alkyl-substituted ($C_3$-$C_6$)cycloalkyl, or is ($C_3$-$C_6$)cycloalkyl which is unsubstituted or substituted by one or more radicals from the group consisting of halogen and ($C_1$-$C_4$)alkyl.

$R^2$ is more preferably $(C_1-C_4)$alkyl which is unsubstituted or substituted by one or more radicals from the group of halogen such as fluorine and chlorine, or is cyclopropyl which is unsubstituted or substituted by one or more radicals from the group consisting of halogen and $(C_1-C_4)$ alkyl.

$R^2$ is very preferably $(C_1-C_4)$alkyl which is unsubstituted or substituted by one or more radicals from the group of fluorine and chlorine in the 1-position of the alkyl radical. Examples of preferred definitions of $R^2$ are the radicals:

methyl, ethyl, n-propyl, i-propyl, cyclopropyl, 1-fluorocyclopropyl, difluoromethyl, trifluoromethyl, 1-fluoroethyl [(R)-, (S)- or (RS)-1-fluoroethyl], 1-fluoro-n-propyl [(R)-, (S)- or (RS)-1-fluoro-n-propyl], 1-fluoroisopropyl, 1-fluorobutyl[(R)-, (S)- or (RS)-1-fluoro-n-butyl].

$R^3$ is preferably cyclopropyl or cyclobutyl, where each of the latter two radicals is unsubstituted or substituted by one or more radicals from the group consisting of halogen, $(C_1-C_4)$alkyl, $(C_2-C_4)$alkenyl and $(C_2-C_4)$alkynyl, where the cyclic $R^3$ radical, by its carbon atom in the 2 position,
  (a) may be connected to the divalent $R^4$ group=methylene and may thus form, with the molecular moiety $R^3$—C—C—$R^4$, a bicycle composed of a five-membered ring and the three- or four-membered ring of $R^3$, or
  (b) may be bonded directly or via a methylene group to the carbon atom in the 2 position of the cyclic $CR^4R^5$ radical and thus form a tricycle with the molecular moiety $R^3$—C—$CR^4R^5$.

$R^3$ is more preferably cyclopropyl or cyclobutyl, where each of the latter two radicals is unsubstituted or substituted by one or more radicals from the group consisting of halogen and $(C_1-C_4)$alkyl, where the cyclic $R^3$ radical, by its carbon atom in the 2 position,
  (a) may be connected to the divalent $R^4$ group=methylene and may thus form, with the molecular moiety $R^3$—C—C—$R^4$, a bicycle composed of a five-membered ring and the three- or four-membered ring of $R^3$, or
  (b) may be bonded directly or via a methylene group to the carbon atom in the 2 position of the cyclic $CR^4R^5$ radical and thus form a tricycle with the molecular moiety $R^3$—C—$CR^4R^5$.

$R^3$ is especially cyclopropyl which is unsubstituted or substituted by one or more radicals from the group consisting of halogen and $(C_1-C_4)$alkyl.

Examples of preferred definitions of $R^3$ are the radicals:
cyclopropyl, 1-methylcyclopropyl, 1-fluorocyclopropyl, 1-chlorocyclopropyl, 2,2-dimethylcyclopropyl, 2,2-dichlorocyclopropyl, cyclobutyl, very particular preference being given to unsubstituted cyclopropyl.

$R^4$ and $R^5$ are preferably each independently
  $(C_1-C_4)$alkyl, $(C_2-C_4)$alkenyl or $(C_2-C_4)$alkynyl, where each of the latter three radicals is unsubstituted or substituted by one or more radicals from the group consisting of halogen, $(C_1-C_4)$alkoxy, $(C_1-C_4)$haloalkoxy and $(C_1-C_4)$alkylthio, or
  cyclopropyl which is unsubstituted or substituted by one or more radicals from the group consisting of halogen and $(C_1-C_4)$alkyl.

$R^4$ and $R^5$ are more preferably each independently
  $(C_1-C_4)$alkyl which is unsubstituted or substituted by one or more radicals from the group consisting of halogen and $(C_1-C_4)$alkoxy, or
  cyclopropyl which is unsubstituted or substituted by one or more radicals from the group consisting of halogen and $(C_1-C_4)$alkyl.

$R^4$ is preferably methyl or cyclopropyl, especially methyl.
$R^5$ is preferably methyl or cyclopropyl, especially methyl.

$R^4$ and $R^5$ are more preferably, together with the carbon atom bonded to them, a 3- to 6-membered carbocyclic ring, preferably cyclopropyl, which is unsubstituted or substituted by one or more radicals from the group consisting of halogen and $(C_1-C_4)$alkyl,
  where the cyclic $CR^4R^5$ radical, by its carbon atom in the 2 position, is bonded to the carbon atom in the 2 position of the cycle of the $R^3$ group directly or via a methylene group and may thus form a tricycle with the molecular moiety $R^3$—C—$CR^4R^5$.

$R^4$ and $R^5$ are especially preferably, together with the carbon atom bonded to them, a 3- to 6-membered carbocyclic ring, preferably cyclopropyl, which is unsubstituted or substituted by one or more radicals from the group consisting of halogen and $(C_1-C_4)$alkyl, particularly preference being given to unsubstituted cyclopropyl.

$R^4$ and $R^5$ are preferably also, together with the carbon atom bonded to them, a 3- to 6-membered carbocyclic ring, preferably cyclopropyl, which is unsubstituted or substituted by one or more radicals from the group consisting of halogen and $(C_1-C_4)$alkyl, where the cyclic $CR^4R^5$ radical, by its carbon atom in the 2 position, is bonded to the carbon atom in the 2 position of the cycle of the $R^3$ group directly or via a methylene group and thus forms a tricycle with the molecular moiety $R^3$—C—$CR^4R^5$.

$R^4$ is preferably also a divalent group of the formula —$CH_2$— which is bonded to the carbon atom in the 2 position of the cyclic $R^3$ radical and thus forms a bicycle composed of a five-membered ring and a three- or four-membered ring of $R^3$ with the molecular moiety $R^3$—C—C—$R^4$.

$R^6$ is preferably hydrogen or $(C_1-C_4)$alkyl which is unsubstituted or substituted by one or more radicals from the group consisting of halogen, $(C_1-C_4)$alkoxy, $(C_1-C_4)$haloalkoxy and $(C_1-C_4)$alkylthio.

$R^6$ is especially hydrogen or methyl, very particularly hydrogen.

$R^7$ is preferably hydrogen, methyl, ethyl or cyclopropyl which is unsubstituted or substituted by one or more radicals from the group consisting of halogen, $(C_1-C_4)$alkyl and $(C_1-C_4)$haloalkyl, $R^7$ is especially hydrogen, methyl, ethyl, cyclopropyl, 1-methylcyclopropyl, 1-fluorocyclopropyl, 1-chlorocyclopropyl, 2,2-dimethylcyclopropyl, 2,2-dichlorocyclopropyl, very particularly hydrogen.

Preference is given to compounds of the formula (I) or salts thereof in which $R^1$ is amino, acylamino having from 1 to 6 carbon atoms, di$(C_1-C_4)$alkylamino-$(C_1-C_4)$alkylideneamino or N-heterocyclylamino-$(C_1-C_4)$alkylideneamino (as already defined above for $R^1$), especially amino, $R^2$ is hydrogen, $(C_1-C_6)$alkyl, $(C_2-C_6)$alkenyl or $(C_2-C_6)$alkynyl, where each of the three latter groups is unsubstituted or substituted by one or more radicals from the group which consists of halogen, $(C_1-C_4)$alkoxy, $(C_1-C_4)$alkylthio, $(C_1-C_4)$haloalkoxy, $(C_1-C_2)$alkoxy$(C_1-C_2)$alkoxy and optionally halogen- or $(C_1-C_4)$alkyl-substituted $(C_3-C_6)$cycloalkyl, or is $(C_3-C_6)$cycloalkyl which is unsubstituted or substituted by one or more radicals from the group consisting of halogen and $(C_1-C_4)$alkyl, $R^3$ is cyclopropyl or cyclobutyl, where each of the two latter radicals is unsubstituted or substituted by one or more radicals from the group consisting of halogen, $(C_1-C_4)$ alkyl, $(C_2-C_4)$alkenyl and $(C_2-C_4)$alkynyl, $R^4$ and $R^5$ are each independently $(C_1-C_4)$alkyl, $(C_2-C_4)$alkenyl or $(C_2-C_4)$alkynyl, where each of the latter three radicals is unsubstituted or substituted by one or more radicals from the group consisting of halogen, $(C_1-C_4)$alkoxy, $(C_1-C_4)$haloalkoxy and $(C_1-C_4)$alkylthio, or cyclopropyl which is unsubstituted or substituted by one or more radicals from the group consisting of halogen and $(C_1-C_4)$alkyl, or $R^4$ and $R^5$, together with the carbon atom bonded to them, is a 3- to 6-membered carbocyclic ring which is unsubstituted or substituted by one or more radicals from the group consisting of halogen and $(C_1-C_4)$alkyl, $R^6$ is hydrogen or $(C_1-C_4)$alkyl which is unsubstituted or substituted by one or more radicals from the group consisting of halogen, $(C_1-C_4)$alkoxy, $(C_1-C_4)$haloalkoxy and $(C_1-C_4)$alkylthio, $R^7$ is hydrogen, methyl, ethyl or cyclopropyl which is unsubstituted or substituted by one or more radicals from the group consisting of halogen, $(C_1-C_4)$alkyl and $(C_1-C_4)$haloalkyl.

Preference is further given to compounds of the formula (I) or salts thereof in which $R^1$ is preferably amino, acylamino having from 1 to 6 carbon atoms, di$(C_1-C_4)$alkylamino$(C_1-C_4)$alkylideneamino or N-heterocyclylamino-$(C_1-C_4)$alkylideneamino (as already defined in detail above for $R^1$), especially amino, $R^2$ is $(C_1-C_4)$alkyl which is unsubstituted or substituted by one or more radicals from the group of halogen, such as fluorine and chlorine, or is cyclopropyl which is unsubstituted or substituted by one or more radicals from the group consisting of halogen and $(C_1-C_4)$alkyl, especially $(C_1-C_4)$alkyl which is unsubstituted or substituted by one or more radicals from the group of fluorine and chlorine in the 1 position of the alkyl radical, $R^3$ is cyclopropyl which is unsubstituted or substituted by one or more radicals from the group consisting of halogen and $(C_1-C_4)$alkyl, $R^4$ and $R^5$ are each independently $(C_1-C_4)$alkyl which is unsubstituted or substituted by one or more radicals from the group consisting of halogen and $(C_1-C_4)$alkoxy, or cyclopropyl which is unsubstituted or substituted by one or more radicals from the group consisting of halogen and $(C_1-C_4)$alkyl, or $R^4$ and $R^5$, together with the carbon atom bonded to them, is a 3- to 6-membered carbocyclic ring, preferably cyclopropyl, which is unsubstituted or substituted by one or more radicals from the group consisting of halogen and $(C_1-C_4)$alkyl, $R^6$ is hydrogen or methyl, very particularly hydrogen, $R^7$ is hydrogen, methyl, ethyl or cyclopropyl which is unsubstituted or substituted by one or more radicals from the group consisting of halogen, $(C_1-C_4)$alkyl and $(C_1-C_4)$haloalkyl, especially hydrogen, methyl, ethyl, cyclopropyl, 1-methylcyclopropyl, 1-fluorocyclopropyl, 1-chlorocyclopropyl, 2,2-dimethylcyclopropyl, 2,2-dichlorocyclopropyl, very particularly hydrogen.

Preference is given to compounds of the formula (I-A) and salts thereof

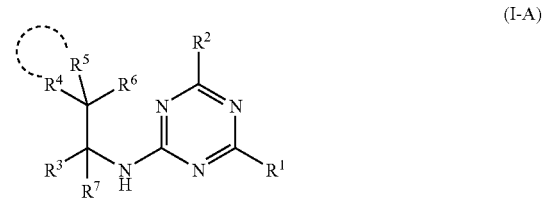

(I-A)

in which $R^1$ to $R^7$ are each as defined or as defined with preference and the $R^4$ and $R^5$ groups may be bonded to form a cyclic structure, but the $R^3$ and $R^4$ groups are not bonded.

Among the compounds (I-A), particular preference is given to the compounds of the formulae (Ia), (Ib), (Ic), (Id), (Ie) and (If) and salts thereof. In these compounds:

compounds of the formula (Ia)=compounds of the formula (I-A) in which $R^1$=amino, compounds of the formula (Ib)=compounds of the formula (I-A) in which $R^1$=acetylamino, compounds of the formula (Ic)=compounds of the formula (I-A) in which $R^1$=propionylamino, compounds of the formula (Id)=compounds of the formula (I-A) in which $R^1$ is the radical of the formula NH—CO—CHCl—CH$_3$ (2-chloropropionylamino), compounds of the formula (Ie)=compounds of the formula (I-A) in which $R^1$ is the dimethylaminomethyleneamino radical, compounds of the formula (If)=compounds of the formula (I-A) in which $R^1$ is the morpholin-4-ylmethyleneamino radical.

Particularly preferred are the compounds of the general formulae (Ia) (Ib), (Ic), (Id), (Ie) and (If) in which the $R^1$ to $R^7$ radicals have the radical definitions used in the example tables.

Preference is also given to bicyclic or tricyclic compounds of the formula (I-B) and salts thereof

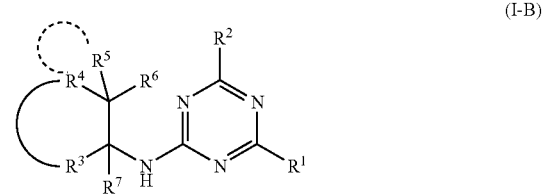

(I-B)

in which $R^1$ to $R^7$ are each as defined or as defined with preference and the $R^3$ and $R^4$ groups are bonded to give a cyclic structure, and $R^4$ and $R^5$ may additionally be bonded to give a cyclic structure.

Particularly preferred are the compounds of the formula (I-B) in which the $R^1$ to $R^7$ radicals each have the radical definitions used in the example tables.

The inventive compounds of the formula (I), (I-A) and (I-B) include all stereoisomers which can occur on the basis of the centers of asymmetry or double bonds in the molecule whose configuration is not designated specifically in the formula or which are not specified explicitly, and a mixture thereof, including the racemic compounds and the mixtures enriched partly with particular stereoisomers.

The invention also encompasses all tautomers, such as keto and enol tautomers, and their mixtures and salts when appropriate functional groups are present.

The invention also provides processes for preparing the compounds of the formula (I) and salts thereof, which comprise a) reacting a compound of the formula (II)

 (II)

in which Fu is a functional group from the group of carboxylic ester, carboxylic orthoester, carbonyl chloride, carboxamide, carboxylic anhydride and trichloromethyl with a compound of the formula (III) or an acid addition salt thereof

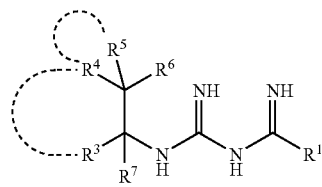 (III)

or b) reacting a compound of the formula (IV)

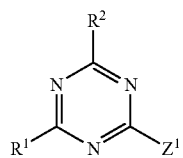 (IV)

in which $Z^1$ is an exchangeable radical or a leaving group, for example chlorine, trichloromethyl, $(C_1-C_4)$alkylsulfonyl, unsubstituted or substituted phenyl-$(C_1-C_4)$alkylsulfonyl or $(C_1-C_4)$alkylphenylsulfonyl with a suitable amine of the formula (V) or an acid addition salt thereof

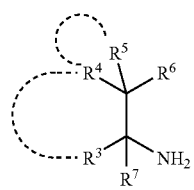 (V)

or c) derivatizing a compound of the formula (I') or salt thereof

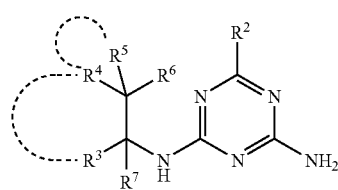 (I')

on the amino group to give the compound of the formula (I), where, in the formulae (II), (III), (IV), (V) and (I'), the $R^1$, $R^2$, $R^3$, $R^4$, $R^5$, $R^6$ and $R^7$ radicals are as defined in the formula (I).

The compounds of the formula (II) and (III) are preferably reacted under base catalysis in an inert organic solvent, for example tetrahydrofuran (THF), dioxane, acetonitrile, dimethylformamide (DMF), methanol and ethanol, at temperatures between −10° C. and the boiling point of the solvent, preferably from 20° C. to 60° C.; if acid addition salts of the formula (III) are used, they are generally liberated in situ with the aid of a base. Suitable bases or basic catalysts include alkali metal hydroxides, alkali metal hydrides, alkali metal carbonates, alkali metal alkoxides, alkaline earth metal hydroxides, alkaline earth metal hydrides, alkaline earth metal carbonates, or organic bases such as triethylamine or 1,8-diazabicyclo[5.4.0]undec-7-ene (DBU). The particular base is used, for example, in the range of from 0.1 to 3 molar equivalents based on the compound of the formula (III). The compound of the formula (II) can be used in relation to the compound of the formula (III), for example, in an equimolar amount or in excess, generally in a molar ratio of (III):(II) of up to 1:4, usually up to 1:3. Analogous processes are known from the literature (cf.: Comprehensive Heterocyclic Chemistry, A. R. Katritzky, C. W. Rees, Pergamon Press, Oxford, N.Y., 1984, Vol. 3; Part 2B; ISBN 0-08-030703-5, p. 290).

The compounds of the formula (IV) and (V) are reacted preferably under base catalysis in an inert organic solvent, for example THF, dioxane, acetonitrile, DMF, methanol and ethanol, at temperatures between −10° C. and the boiling point of the particular solvent or solvent mixture, preferably at from 20° C. to 60° C., and the compound (V), if used as an acid addition salt, is liberated if appropriate in situ with a base. Suitable bases or basic catalysts include alkali metal hydroxides, alkali metal hydrides, alkali metal carbonates, alkali metal alkoxides, alkaline earth metal hydroxides, alkaline earth metal hydrides, alkaline earth metal carbonates or organic bases such as triethylamine or 1,8-diazabicyclo[5.4.0]undec-7-ene (DBU). The particular base is used generally in the range of from 1 to 3 molar equivalents based on the compound of the formula (IV). The compound of the formula (IV) can be used, for example, in an equimolar amount relative to the compound of the formula (V) or with up to 2 molar equivalents of excess. Analogous processes are known from the literature (cf. Comprehensive Heterocyclic Chemistry, A. R. Katritzky, C. W. Rees, Pergamon Press, Oxford, N.Y., 1984, Vol. 3; Part 2B; ISBN 0-08-030703-5, p. 482).

The reactants of the formulae (II), (III), (IV) and (V) are either commercially available or can be prepared by or analogously to literature processes. The compounds of the formula (III) are novel and likewise form part of the subject matter of the invention. The compounds can also be prepared, for example, by one of the processes described below.

The compound of the formula (IV), or a direct precursor thereof, can be prepared, for example, as follows:

1. Reaction of a compound of the formula (II) with an amidinothiourea derivative of the formula (VI)

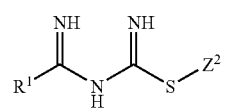 (VI)

in which $Z^2$ is $(C_1-C_4)$alkyl or phenyl$(C_1-C_4)$alkyl and $R^1$ is as defined in formula (I) affords compounds of the formula (IV) in which $Z^1$=—$SZ^2$.

2. Reaction of an amidine of the formula (VII) or of an acid addition salt thereof

$$H_2N-CR^2=NH \qquad (VII)$$

in which $R^2$ is as defined in formula (I)
with an N-cyanodithioiminocarbonate of the formula (VIII)

$$NC-N=C(S-Z^3)_2 \qquad (VIII)$$

in which $Z^3$ is $(C_1\text{-}C_4)$alkyl or phenyl$(C_1\text{-}C_4)$alkyl affords compounds of the formula (IV) in which $Z^1=-S\text{-}Z^3$.

3. Reaction of an alkali metal dicyanamide with a carboxylic acid derivative of the formula (II) mentioned affords compounds of the formula (IV) in which $Z^1=NH_2$, 4. Reaction of trichloroacetonitrile with a nitrile of the formula (IX)

$$R^2-CN \qquad (IX)$$

in which $R^2$ is as defined in formula (I) initially affords compounds of the formula (X)

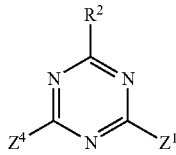

(X)

in which $Z^1$ and $Z^4$ are each $CCl_3$, which can lead by subsequent reaction with compounds of the formula $H-R^2$ ($R^2$ as in formula (I)) to compounds of the formula (IV) in which $Z^1=CCl_3$.

The reaction of the carboxylic acid derivatives of the formula (II) with the amidinothiourea derivatives of the formula (VI) is effected preferably under base catalysis in an organic solvent, for example acetone, THF, dioxane, acetonitrile, DMF, methanol, ethanol, at temperatures of from −10° C. up to the boiling point of the solvent, preferably at from 0° C. to 20° C. However, the reaction can also be effected in water or in aqueous solvents with one or more of the above-mentioned organic solvents. If the compound of the formula (VI) is used as an acid addition salt, it can be liberated if appropriate in situ with a base. Suitable bases or basic catalysts include alkali metal hydroxides, alkali metal hydrides, alkali metal carbonates, alkali metal alkoxides, alkaline earth metal hydroxides, alkaline earth metal hydrides, alkaline earth metal carbonates or organic bases such as triethylamine or 1,8-diazabicyclo[5.4.0]undec-7-ene (DBU). The particular base is used, for example, in the range from 1 to 3 molar equivalents based on the compound of the formula (VI). Compounds of the formula (II) and (VI) can be used, for example, in equimolar amounts or in excess, generally in a molar ratio of (VI):(II) up to 1:4, usually up to 1:3. Analogous processes are known from the literature (cf.: H. Eilingsfeld, H. Scheuermann, Chem. Ber.; 1967, 100, 1874).

The reaction of the amidines of the formula (VII) with the N-cyanodithioiminocarbonates of the formula (VIII) is effected preferably under base catalysis in an inert organic solvent, for example acetonitrile, DMF, dimethylacetamide (DMA), N-methylpyrrolidone (NMP), methanol and ethanol, at temperatures of from −10° C. up to the boiling point of the solvent, preferably at from 20° C. to 80° C. If compound (VII) is used as an acid addition salt, it can be liberated if appropriate in situ with a base. Suitable bases and basic catalysts include alkali metal hydroxides, alkali metal hydrides, alkali metal carbonates, alkali metal alkoxides, alkaline earth metal hydroxides, alkaline earth metal hydrides, alkaline earth metal carbonates or organic bases such as triethylamine or 1,8-diazabicyclo[5.4.0]undec-7-ene (DBU). The particular base is used, for example, in the range from 1 to 3 molar equivalents based on the compound of the formula (VIII); compounds of the formula (VII) and (VIII) may be used generally in equimolar amounts or with 2 molar equivalents of excess of compound of the formula (VII). Analogous processes are known from the literature (cf.: T. A. Riley, W. J. Henney, N. K. Dalley, B. E. Wilson, R. K. Robins; J. Heterocyclic Chem.; 1986, 23 (6), 1706-1714).

The preparation of intermediates of the formula (X) where $Z^1$=chlorine can be effected by reaction of alkali metal dicyanamide with a carboxylic acid derivative of the formula (II), in which case Fu is then preferably the functional group carbonyl chloride (—COCl, chlorocarbonyl) or carboxamide (—CONH$_2$, aminocarbonyl, carbamoyl). The reaction of the reaction components is effected, for example, under acid catalysis in an inert organic solvent, for example toluene, chlorobenzene, chlorinated hydrocarbons, at temperatures between −10° C. and the boiling point of the solvent, preferably at from 20° C. to 80° C., and the resulting intermediates may be chlorinated in situ with a suitable chlorinating reagent, for example phosphorus oxychloride. Suitable acids are, for example, hydrohalic acids such as HCl, or else Lewis acids, for example AlCl$_3$ or BF$_3$ (cf. U.S. Pat. No. 5,095,113, DuPont).

The preparation of intermediates of the formula (X) in which $Z^1$, $Z^4$=trihalomethyl can be effected by reaction of the corresponding trihaloacetonitriles with a carbonitrile of the formula (IX). The reaction of the reaction components is effected, for example, under acid catalysis in an inert organic solvent, for example toluene, chlorobenzene, chlorinated hydrocarbons, at temperatures between −40° C. and the boiling point of the solvent, preferably at from −10° C. to 30° C. Suitable acids are, for example, hydrohalic acids such as HCl, or else Lewis acids, for example AlCl$_3$ or BF$_3$ (cf. EP-A-130939 (U.S. Pat. No. 4,523,947), Ciba Geigy). Intermediates of the formula (IV) in which $Z^1=(C_1\text{-}C_4)$alkylmercapto or unsubstituted phenyl$(C_1\text{-}C_4)$alkylmercapto may be converted in an inert organic solvent, for example toluene, chlorobenzene, chlorinated hydrocarbons or others, at temperatures between −40° C. and the boiling point of the solvent, preferably at from 20° C. to 80° C., with a suitable chlorinating reagent, for example elemental chlorine or phosphorus oxychloride, to give more reactive chlorotriazines of the formula (IV) in which $Z^1$=Cl (cf. J. K. Chakrabarti, D. E. Tupper; Tetrahedron 1975, 31(16), 1879-1882).

Intermediates of the formula (IV), where $Z^1=(C_1\text{-}C_4)$alkylmercapto or unsubstituted or substituted phenyl$(C_1\text{-}C_4)$alkylmercapto or $(C_1\text{-}C_4)$alkylphenylthio may be oxidized in a suitable solvent, for example chlorinated hydrocarbons, acetic acid, water, alcohols, acetone or mixtures thereof, at temperatures between 0° C. and the boiling point of the solvent, preferably from 20° C. to 80° C., with a suitable oxidation reagent, for example m-chloroperbenzoic acid, hydrogen peroxide, potassium peroxomonosulfate (cf.: T. A. Riley, W. J. Henney, N. K. Dailey, B. E. Wilson, R. K. Robins; J. Heterocyclic Chem.; 1986, 23 (6), 1706-1714).

The compounds of the formula (III) can be prepared from compounds of the formula (V) and/or their acid adducts by reacting cyanoguanides ("dicyandiamide") of the formula (XI)

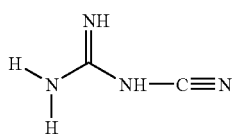
(XI)

optionally in the presence of a reaction assistant, for example hydrochloride, and optionally of a diluent, for example n-decane or 1,2-dichlorobenzene, at temperatures of, for example, between 100° C. and 200° C. (cf. EP-A-492615 (U.S. Pat. No. 5,286,905), preparation examples).

The amines of the formula (V) can be formed from simple structural units as precursors analogously to known methods. The amino group can be obtained, for example, from corresponding ketones by reductive amination (cf. above-mentioned literature, for example on page 1 regarding aminotriazine herbicides).

The preparation of the compounds (I) from compounds (I') and salts thereof by process variant (c) can be effected in different ways, derivatization reactions of amines being possible in principle, for example reactions in which amines are acylated, converted to imines and their derivatives, converted to amidines, ureas or aminals.

The compounds (I) can be prepared, for example, by, analogously to the processes described in WO 00/32580 (U.S. Pat. No. 6,645,915), reacting prepared amino compounds of the formula (I') with reactive carboxylic acid derivatives such as anhydrides, acid halides and activated esters, or else corresponding acid derivatives of sulfonic acids or sulfinic acids under standard conditions. For example, the amino compounds (I') can be reacted with carboxylic anhydrides in an equimolar amount or in an up to twenty-fold excess without solvent or in an inert solvent at from 40 to 150° C., and converted to acylated derivatives of the formula (I). In an analogous manner, it is possible to perform reactions with alkyl- or arylsulfonyl halides or alkyl- or arylsulfinyl halides to give acylated derivatives (I), where the acyl group in the former case is then an alkylsulfonyl or alkylsulfinyl group.

Other derivatization reactions can be performed, for example, with dialkyl acetals, preferably dimethyl or diethyl acetals, in a polar solvent, for example alcohols, preferably methanol or ethanol, at from 10° C. up to the reflux temperature of the solvent, and the reaction of the amine (I') with the acetals can be catalyzed by $H^+$-generating reagents such as p-toluenesulfonic acid. In this way, it is possible to obtain alkyl imide amides of the amines, where the nitrogen of the amine bears the double bond of the imide group.

A further derivatization reaction consists in the preparation of ureas or thioureas with isocyanates or isothiocyanates, optionally with preceding reaction with a base, for example sodium hydride, in a suitable inert solvent such as dimethylformamide at from −20° C. to +60° C., preferably at from 0° C. to +30° C.

A further derivatization reaction leads to addition products in the sense of a Michael reaction with a reactant having a double bond, for example by reaction of acrylonitrile or in an inert solvent, for example acetonitrile, under basic catalysis, for example with potassium hydroxide or Triton B, at temperatures of from 20 to 100° C., to give N-(2-cyanoethyl) compounds which can be eliminated again under physiological conditions.

To prepare the acid addition salts of the compounds of the formula (I), for example, the following acids are possible: hydrohalic acids such as hydrochloric acid or hydrobromic acid, and also phosphoric acid, nitric acid, sulfuric acid, mono- or bifunctional carboxylic acids and hydroxycarboxylic acids such as acetic acid, maleic acid, succinic acid, fumaric acid, tartaric acid, citric acid, salicylic acid, sorbic acid or lactic acid, and also sulfonic acids such as p-toluenesulfonic acid or 1,5-naphthalenedisulfonic acid. The acid addition compounds of the formula (I) can be obtained in a simple manner by the customary salt formation methods, for example by dissolving a compound of the formula (I) in a suitable organic solvent, for example methanol, acetone, methylene chloride or benzine, and adding the acid at temperatures of from 0° C. to 100° C., and can be isolated in a known manner, for example by filtration, and optionally purified by washing with an inert organic solvent.

The base addition salts of the compounds of the formula (I) are preferably prepared in inert polar solvents, for example water, methanol or acetone, at temperatures of from 0° C. to 100° C. Suitable bases for the preparation of the inventive salts are, for example, alkali metal carbonates such as potassium carbonate, alkali metal and alkaline earth metal hydroxides, e.g. NaOH or KOH, alkali metal and alkaline earth metal hydrides, e.g. NaH, alkali metal and alkaline earth metal alkoxides, e.g. sodium methoxide, potassium tert-butoxide, or ammonia or ethanolamine. Quaternary ammonium salts can be prepared, for example, by double decomposition or condensation with quaternary ammonium salts of the formula $[NRR'R''R''']^+X^-$ in which R, R', R'' and R''' are each independently $(C_1-C_4)$alkyl, phenyl or benzyl and $X^-$ is an anion, e.g. $Cl^-$ or $OH^-$.

What is meant by the "inert solvents" (in some cases also referred to as solvents) referred to in the above process variants are in each case solvents which are inert under the particular reaction conditions but need not be inert under all reaction conditions.

A collection of compounds of the formula (I) which can be synthesized by the abovementioned processes can additionally be prepared in a parallelized manner, in which case this can be done in a manual, partly automated or completely automated manner. It is possible to automate the reaction procedure, the workup or the purification of the products or intermediates. Overall, this is understood to mean a procedure as described, for example, by S. H. DeWitt in "Annual Reports in Combinatorial Chemistry and Molecular Diversity: Automated Synthesis", Volume 1, Verlag Escom, 1997, pages 69 to 77. For parallelized reaction procedure and workup, a number of commercially available units can be used, as supplied, for example, by Stem Corporation, Woodrolfe Road, Tollesbury, Essex, CM9 8SE, England or H+P Labortechnik GmbH, Bruckmannring 28, 85764 Oberschleißheim, Germany. For the parallelized purification of compounds (I) or of intermediates which occur in the preparation, available apparatus includes chromatography apparatus, for example from ISCO, Inc., 4700 Superior Street, Lincoln, Nebr. 68504, USA. The apparatus listed enables a modular procedure in which the individual working steps are automated but manual operations have to be performed between the working steps. This can be circumvented by the use of partly or completely integrated automation systems in which the individual automation modules are operated, for example, by robots. Such automation systems can be purchased, for example, from Zymark Corporation, Zymark Center, Hopkinton, Mass. 01748, USA.

In addition to the methods described, compounds (I) can be prepared completely or partially by solid phase-supported methods. For this purpose, individual intermediates or all intermediates of the synthesis or of a synthesis adjusted for the appropriate procedure are bound to a synthetic resin. Solid phase-supported synthesis methods are described adequately in the technical literature, for example: Barry A. Bunin in "The Combinatorial Index", Verlag Academic Press, 1998.

The use of solid phase-supported synthesis methods enables a number of literature procedures, which can again be performed in a manual or automated manner. For example the "teabag method" (Houghten, U.S. Pat. No. 4,631,211; Houghten et al., Proc. Natl. Acad. Sci., 1985, 82, 5131-5135) with products from IRORI, 11149 North Torrey Pines Road, La Jolla, Calif. 92037, USA, can be partly automated. The automation of solid phase-supported parallel synthesis is possible, for example, by means of apparatus from Argonaut Technologies, Inc., 887 Industrial Road, San Carlos, Calif. 94070, USA or MultiSynTech GmbH, Wullener Feld 4, 58454 Witten, Germany.

The preparation by the processes described here affords compounds (I) in the form of substance collections or libraries. The present invention therefore also provides libraries of the compounds of the formula (I) which comprise at least two compounds (I) and precursors thereof.

The inventive compounds of the formula (I) and salts thereof have excellent herbicidal activity against a wide spectrum of economically important monocotyledonous and dicotyledonous harmful plants. The active ingredients also act efficiently on perennial weeds which are difficult to control and give out shoots from rhizomes, root stocks or other perennial organs. It is unimportant whether the substances are applied before sowing, pre-emergence or post-emergence.

A few representatives of the mono- and dicotyledenous weed flora which can be controlled by the inventive compounds will be specified individually by way of example, without any intention that the specification should bring about a restriction to particular species.

Among the monocotyledonous weed species, those on which the active substances act efficiently are, for example, *Agrostis, Alopecurus, Apera, Avena, Brachicaria, Bromus, Dactyloctenium, Digitaria, Echinochloa, Eleocharis, Eleusine, Festuca, Fimbristylis, Ischaemum, Lolium, Monochoria, Panicum, Paspalum, Phalaris, Phleum, Poa, Sagittaria, Scirpus, Setaria, Sphenoclea* and *Cyperus* species from the annual group, and, among the perennial species, *Agropyron, Cynodon, Imperata* and *Sorghum*, and also perennial *Cyperus* species.

In the case of dicotyledonous weed species, the activity spectrum extends to species such as, for example, Galium, Viola, Veronica, Lamium, *Stellaria, Amaranthus, Sinapis, Ipomoea, Matricaria, Abutilon* and *Sida* on the annual side, and also *Convolvulus, Cirsium, Rumex* and *Artemisia* among the perennial weeds. Herbicidal action is also achieved in the case of dicotyledonous harmful plants such as *Ambrosia, Anthemis, Carduus, Centaurea, Chenopodium, Cirsium, Convolvulus, Datura, Emex, Galeopsis, Galinsoga, Kochia, Lepidium, Lindernia, Papaver, Portlaca, Polygonum, Ranunculus, Rorippa, Rotala, Seneceio, Sesbania, Solanum, Sonchus, Taraxacum, Trifolium, Urtica* and *Xanthium*.

Weeds which occur in rice under the specific crop conditions, for example *Sagittaria, Alisma, Eleocharis, Scirpus* and *Cyperus*, are likewise controlled outstandingly by the inventive active ingredients.

When the inventive compounds are applied to the soil surface before germination, the weed seedlings are either prevented completely from emerging or the weeds grow up to the cotyledon stage but then stop growing and finally die off completely after three to four weeks have passed.

When the active substances are applied to the green plant parts post-emergence, a drastic stop in growth likewise occurs very rapidly after the treatment, and the weed plants remain at the stage of growth at the time of application or die off after a certain time, so that weed competition which is harmful to the crop plants is thus eliminated at a very early stage and in a lasting manner.

Even though the inventive compounds have excellent herbicidal activity against mono- and dicotyledonous weeds, crop plants of economically significant crops, for example wheat, barley, rye, rice, maize, sugarbeet, soya, in particular plantation crops such as oil palms, olives, coconut, rubber tree, citrus, pineapple, apple, pear, cherry, cotton, coffee, cocoa, grapes and other comparable fruit and plantation crops, are damaged only insignificantly, if at all. For these reasons, the present compounds are very suitable for the selective control of undesired plant growth in stands of agriculturally useful plants, including ornamental stands. The active ingredients are also suitable, optionally in combination with other active ingredients, for use in uncultivated land, such as on paths, open spaces, beds, lawns, railway embankments, industrial areas, for controlling unwanted plant growth.

In addition, the inventive substances have outstanding growth-regulatory properties in crop plants. They intervene to regulate the plants' metabolism and can thus be used for controlled influence on plant constituents and for easing the harvest, for example by inducing desiccation and stunted growth. Moreover, they are also suitable for the general control and inhibition of undesired vegetative growth without killing the plants. Inhibition of vegetative growth plays a major role in many mono- and dicotyledonous crops, since this allows lodging to be reduced or completely prevented.

Owing to their herbicidal and plant growth-regulatory properties, the active ingredients can also be used to control harmful plants in crops of known genetically modified plants or genetically modified plants which are yet to be developed. The transgenic plants generally feature exceptionally advantageous properties, for example resistances against particular pesticides, especially particular herbicides, resistances toward plant diseases or pathogens of plant diseases, such as particular insects or microorganisms, such as fungi, bacteria or viruses. Other exceptional properties relate, for example, to the harvest with regard to amount, quality, storability, composition and specific constituents. Thus, transgenic plants with increased starch content or altered starch quality or those with different fatty acid composition of the harvest are known.

Preference is given to the use of the inventive compounds of the formula (I) or salts thereof in economically significant transgenic crops of useful and ornamental plants, for example of cereals such as wheat, barley, rye, oats, millet, rice, manioc and maize, or else crops of sugarbeet, cotton, soya, rape, potato, tomato, pea and other vegetable types.

The compounds of the formula (I) can preferably be used as herbicides in useful plant crops which are resistant toward the phytotoxic effects of the herbicides or have been made resistant by genetic engineering.

Conventional routes to the production of novel plants which have modified properties in comparison to existing plants consist, for example, in traditional breeding methods and the generation of mutants. Alternatively, novel plants with altered properties can be obtained with the aid of recombinant methods (see, for example, EP-A-0221044 (U.S. Pat. No. 6,147,278), EP-A-0131624). For example, several cases of the following have been described:
  recombinant modifications of crop plants for the purpose of modification of the starch synthesized in the plants (for example WO 92/11376 (U.S. Pat. Nos. 5,824,798, 6,784,338), WO 92/14827 (U.S. Pat. Nos. 6,215,042, 6,570,066), WO 91/19806 (U.S. Pat. Nos. 5,608,150, 6,538,178, 6,538,179), transgenic crop plants which are resistant toward particular herbicides of the glufosinate type (cf., for example, EP-A-0242236, EP-A-242246 (U.S. Pat. Nos. 5,432,971, 5,561,236, 5,646,024, 5,648,477, 7,112,665) or glyphosate type (WO 92/00377, U.S. Pat. Nos. 5,463,175, 5,776,760, RE 38825) or sulfonylurea type (EP-A-0257993, U.S. Pat. Nos. 5,013,659, 5,141,870, 5,378, 824, 5,605,011), transgenic crop plants, for example cotton, with the ability to produce *Bacillus thuringiensis* toxins (Bt toxins) which make the plants resistant to particular pests (EP-A-0142924, EP-A-0193259 (U.S. Pat. Nos. 5,102,796, 5,380,831, 5,428,147, 5,567,862, 5,578,702, 5,591,605, 5,710,020, 6,013,523, 6,015,891, 6,090,627, 6,111,070, 6,114,138, 6,229,004, 6,251,656, 6,943,282, US 2002-48799), transgenic crop plants with modified fatty acid composition (WO 91/13972, U.S. Pat. Nos. 5,475,099, 5,510, 255, 5,723,595, 6,117,677, 6,348,642, 6,426,447, 6,483, 008, 7,037,692, 7,053,267, US 2003-024011, US 2007-016981).

Numerous molecular biology techniques with which novel transgenic plants with altered properties can be produced are known in principle; see, for example, Sambrook et al., 1989, Molecular Cloning, A Laboratory Manual, 2nd Ed. Cold Spring Harbor Laboratory Press, Cold Spring Harbor, N.Y.; or Winnacker "Gene und Klone" [Genes and Clones], VCH Weinheim 2nd Edition 1996, or Christou, "Trends in Plant Science" 1 (1996) 423-431.

For such recombinant manipulations, nucleic acid molecules can be incorporated into plasmids which allow mutagenesis or a change in sequence through recombination of DNA sequences. With the aid of the abovementioned standard methods, it is possible, for example, to undertake base exchanges, remove part-sequences or add natural or synthetic sequences. For the bonding of the DNA fragments to one another, it is possible to attach adapters or linkers to the fragments.

The production of plant cells with a reduced activity of a gene product can be achieved, for example, by the expression of at least one appropriate antisense RNA, a sense RNA for achieving a cosuppression effect or the expression of at least one correspondingly constructed ribozyme which specifically cleaves transcripts of the abovementioned gene product.

To this end, it is possible firstly to use DNA molecules which include the entire coding sequence of a gene product including any flanking sequences present, or DNA molecules which include only parts of the coding sequence, in which case these parts have to be long enough to bring about an antisense effect in the cells. It is also possible to use DNA sequences which have a high degree of homology to the coding sequences of a gene product but are not completely identical.

In the expression of nucleic acid molecules in plants, the synthesized protein can be localized in any compartment of the plant cell. In order, though, to achieve localization in a particular compartment, it is possible, for example, to link the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated by known techniques to give intact plants. In principle, the transgenic plants may be plants of any desired plant species, i.e. either monocotyledonous or dicotyledonous plants.

It is thus possible to obtain transgenic plants which have altered properties through overexpression, suppression or inhibition of homologous (=natural) genes or gene sequences or expression of heterologous (=foreign) genes or gene sequences.

The inventive compounds (I) may preferably be used in transgenic cultures which are resistant toward herbicides from the group of the imidazolinones, sulfonylureas, glufosinate-ammonium or glyphosate-isopropylammonium and analogous active ingredients.

When the inventive active ingredients are used in transgenic cultures, in addition to the effects on harmful plants observed in other crops, effects specific to the application in the particular transgenic culture often occur, for example an altered or specifically extended weed spectrum which can be controlled, altered application rates which can be used for the application, preferably good combinability with the herbicides toward which the transgenic culture is resistant, and influencing of growth and yield of the transgenic crop plants.

The invention therefore also provides for the use of the inventive compounds (I) as herbicides for controlling harmful plants in transgenic crop plants.

The inventive use for the control of harmful plants or for growth regulation of plants also includes the case in which the active ingredient of the formula (I) or its salt is not formed from a precursor substance ("prodrug") until after application on the plant, in the plant or in the soil. For example, it is assumed that, in most cases, the compounds of the formula (I) in which $R^1$ is different from amino, under the physiological conditions of the plants, are metabolized to compounds of the formula (I'), i.e. compounds of the formula (I) in which $R^1$ is amino. These metabolites are then likewise or even primarily herbicidally active. The former can then be understood as "prodrugs" in the sense described.

The inventive compounds can be used in the form of spray powders, emulsifiable concentrates, sprayable solutions, dusting products or granules in the customary formulations. The invention therefore also provides herbicidal and plant growth-regulating compositions which comprise compounds of the formula (I).

The compounds of the formula (I) can be formulated in various ways according to which biological and/or physico-chemical parameters are required. Possible formulations include, for example: spray powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical technology], Volume 7, C. Hanser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd Ed., Darland Books, Caldwell N.J., H.v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active ethylene oxide adducts], Wiss. Verlagsgesell., Stuttgart 1976; Winnacker-Küchler, "Chemische Technologie", Volume 7, C. Hanser Verlag Munich, 4th Ed. 1986.

Spray powders are preparations which can be dispersed uniformly in water and, as well as the active ingredient, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleylmethyltauride. To prepare the spray powders, the active herbicidal ingredients are ground finely, for example in customary apparatus such as hammer mills, blower mills and air-jet mills and simultaneously or subsequently mixed with the formulation assistants.

Emulsifiable concentrates are prepared by dissolving the active ingredient in an organic solvent, for example butanol, cyclohexanone, dimethylformamide, xylene or else relatively high-boiling aromatics or hydrocarbons or mixtures of the organic solvents with addition of one or more surfactants of the ionic and/or nonionic type (emulsifiers). The emulsifiers used may, for example, be: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active ingredient with finely divided solid substances, for example talc, natural clays such as kaolin, bentonite and pyrophyllite, or diatomaceous earth.

Suspension concentrates may be water- or oil-based. They may be prepared, for example, by wet grinding by means of commercial bead mills and optional addition of surfactants as have, for example, already been listed above for the other formulation types.

Emulsions, for example oil-in-water emulsions (EW), can be prepared, for example, by means of stirrers, colloid mills and/or static mixers using aqueous organic solvents and optionally surfactants, as have, for example, already been listed above for the other formulation types.

Granules can be produced either by spraying the active ingredient onto adsorptive granulated inert material or by applying active ingredient concentrates by means of adhesives, for example polyvinyl alcohol, sodium polyacrylate or else mineral oils, onto the surface of carriers such as sand, kaolinites or of granulated inert material. It is also possible to granulate suitable active ingredients in the manner customary for the production of fertilizer granules—if desired in a mixture with fertilizers.

Water-dispersible granules are prepared generally by the customary processes such as spray-drying, fluidized bed granulation, pan granulation, mixing with high-speed mixers and extrusion without solid inert material.

For the preparation of pan, fluidized bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 ff; "Perry's Chemical Engineer's Handbook", 5th Ed., McGraw-Hill, New York 1973, p. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations contain generally from 0.1 to 99% by weight, in particular from 0.1 to 95% by weight, of active ingredient of the formula (I).

In spray powders, the active ingredient concentration is, for example, from about 10 to 90% by weight; the remainder to 100% by weight consists of customary formulation constituents. In the case of emulsifiable concentrates, the active ingredient concentration may be from about 1 to 90% by weight, preferably from 5 to 80% by weight. Dust-type formulations contain from 1 to 30% by weight of active ingredient, preferably usually from 5 to 20% by weight of active ingredient; sprayable solutions contain from about 0.05 to 80% by weight, preferably from 2 to 50% by weight of active ingredient. In water-dispersible granules, the active ingredient content depends partly on whether the active compound is present in solid or liquid form and which granulation assistants, fillers, etc. are used. In the granules dispersible in water, the content of active ingredient is, for example, between 1 and 95% by weight, preferably between 10 and 80% by weight.

In addition, the active ingredient formulations mentioned optionally comprise the respective customary adhesives, wetting agents, dispersants, emulsifiers, penetrants, preservatives, antifreeze agents and solvents, fillers, carriers and dies, defoamers, evaporation inhibitors and agents which influence the pH and the viscosity. Examples of formulation auxiliaries are described inter alia in "Chemistry and Technology of Agrochemical Formulations", ed. D. A. Knowles, Kluwer Academic Publishers (1998).

The compounds of the formula (I) or salts thereof may be used as such or in the form of their formulations combined with other pesticidally active substances, for example insecticides, acaricides, nematicides, herbicides, fungicides, safeners, fertilizers and/or growth regulators, for example as a finished formulation or as tankmixes. The combination formulations can be prepared on the basis of the abovementioned formulations, while taking account of the physical properties and stabilities of the active ingredients to be combined.

Possible combination partners for the inventive active ingredients, in mixed formulations or in a tankmix, are, for example, known active ingredients which are based on inhibition of, for example, acetolactate synthase, acetyl-coenzyme A carboxylase, PS I, PS II, HPPDO, phytoene desaturase, protoporphyrinogen oxidase, glutamine synthetase, cellulose biosynthesis, 5-enolpyruvylshikimate-3-phosphate synthetase. Such compounds, and also other usable compounds, with a mechanism of action that is, in some cases, unknown or different, are described, for example, in Weed Research 26, 441-445 (1986), or "The Pesticide Manual", 14th edition 2006, published by the British Crop Protection Council (hereinafter also abbreviated to "PM"), and literature cited there. Herbicides, plant growth regulators and herbicide safeners, which are known from the literature and which can be combined with the compounds of the formula (I) include, for example, the following active ingredients (note: the compounds are either referred to by the common name in accordance with the International Organization for Standardization (ISO) or by the chemical names, if appropriate together with a customary code number):

acetochlor; acibenzolar-5-methyl; acifluorfen(-sodium); aclonifen; AD-67; AKH 7088, i.e. [[[1-[5-[2-chloro-4-(trifluoromethyl)-phenoxy]-2-nitrophenyl]-2-methoxyethylidene]amino]oxy]acetic acid and its methyl ester; alachlor; alloxydim(-sodium); ametryn; amicarbazone, amidochlor, amidosulfuron; aminopyralid; amitrol; AMS, i.e. ammonium sulfamate; ancimidol; anilofos; asulam; atrazin; aviglycine; azafenidin, azimsulfuron (DPX-A8947); aziprotryn; barban; BAS 516H, i.e. 5-fluoro-2-phenyl-4H-3,1-benzoxazin-4-one; beflubutamid, benazolin(-ethyl); bencarbzone; benfluralin; benfuresate; benoxacor; bensulfuron(-methyl); bensulide; bentazone; benzfendizone; benzobicyclon, benzofenap; benzofluor; benzoylprop(-ethyl); benzthiazuron; bialaphos; bifenox; bilanafos (bialaphos), bispyribac(-sodium), borax, bromacil; bromobutide; bromofenoxim; bromoxynil; bromuron; buminafos; busoxinone; butachlor; butafenacil, butamifos; butenachlor; buthidazole; butralin; butroxydim, butylate; cafenstrole (CH-900); carbetamide; carfentrazone(-ethyl) (ICI-A0051); caloxydim, CDAA, i.e. 2-chloro-N,N-di-2-propenylacetamide; CDEC, i.e. 2-chlorallyl diethyldithiocarbamate; chlomethoxyfen; chloramben; chlorazifop-butyl, 2-chloro-5-[2,6-dioxo-4-(trifluoromethyl)-3,6-dihydropyrimidin-1(2H)-yl]-4-fluoro-N-[methyl (1-methylethyl)sulfamoyl]benzamide (WO 2001/083459, U.S. Pat. Nos. 6,534,492, 6,689,773, 6,849,618), [[3-[2-chloro-5-[3,6-dihydro-3-methyl-2,6-dioxo-4-(trifluoromethyl)-1(2H)-pyrimidinyl]-4-fluorophenoxy]-2-pyridinyl] oxy]acetic acid ethyl ester (SYN-523) (WO 2006/061562, EP 1122244 (U.S. Pat. No. 6,537,948)), chlorflurenol(-methyl), chlormequat (-chloride), chlormesulon (ICI-A0051); chlorbromuron; chlorbufam; chlorfenac; chloridazon; chlorimuron(-ethyl); chlornitrofen; chlorotoluron; chloroxuron; chlorpropham; chiorsulfuron; chlorthal-dimethyl; chlorthiamid; chlortoluron, cinidon(-methyl and -ethyl), cinmethylin; cinosulfuron; clefoxydim, clethodim; clodinafop and its ester derivatives (e.g. clodinafop-propargyl); clofencet; clomazone; clomeprop; cloprop, cloproxydim; clopyralid; clopyrasulfuron(-methyl), cloquintocet(-mexyl); cloransulam(-methyl), cumyluron (JC 940); cyanamide, cyanazine; cyclanilide, cycloate; cyclosulfamuron (AC 104); cycloxydim; cycluron; cyhalofop and its ester derivatives (e.g. butyl ester, DEH-112); cyperquat; cyprazine; cyprazole; cyprosulfamide; daimuron; 2,4-D, 2,4-DB; 2,4-DB, dalapon; daminozide; dazomet; n-decanol; desmedipham; desmetryn; diallate; dicamba; dichlobenil; dichlormid; dichlorprop(-P) (salts); diclofop and its esters such as diclofop-methyl; diclosulam, diethatyl(-ethyl); difenoxuron; difenzoquat(-metilsulfate); diflufenican; diflufenzopyr, dimefuron; dimepiperate, dimethachlor; dimethametryn; dimethazone; dimethenamid (SAN-582H); dimethenamide-P; dimethylarsinic acid; dimexyflam, dimethipin; dimetrasulfuron, dinitramine; dinoseb; dinoterb; diphenamid; dipropetryn; diquat (salts); dithiopyr; diuron; DNOC; eglinazine-ethyl; EL 77, i.e. 5-cyano-1-(1,1-dimethylethyl)-N-methyl-1H-pyrazole-4-carboxamide; endothal, epoprodan, EPTC, esprocarb; ethalfluralin; ethametsulfuron-methyl; ephephon; ethidimuron; ethiozin; ethofumesate; ethoxyfen and its esters (e.g. ethyl ester, HN-252); ethoxysulfuron, etobenzanid (HW 52); F5231, i.e. N-[2-chloro-4-fluoro-5-[4-(3-fluoropropyl)-4,5-dihydro-5-oxo-1H-tetrazol-1-yl]-phenyl]ethanesulfonamide; fenchlorazole(-ethyl); fenclorim; fenoprop; fenoxan, fenoxapropand fenoxaprop-P and their esters, e.g. fenoxaprop-P-ethyl and fenoxaprop-ethyl; fenoxydim; fentrazamide, fenuron; ferrous sulfate; flamprop(-methyl or -isopropyl or -isopropyl-L); flazasulfuron; floazulate, florasulam, fluazifop and fluazifop-P and their esters, e.g. fluazifop-butyl and fluazifop-P-butyl; fluazolate, flucarbazone(-sodium), flucetosulfuron; fluchloralin; flufenacet; flufenpyr(-ethyl); flumetralin; flumetsulam; flumeturon; flumiclorac(-pentyl), flumioxazin (S-482); flumipropyn; fluometuron, fluorochloridone, fluorodifen; fluoroglycofen(-ethyl); flupoxam (KNW-739); flupropacil (UBIC-4243); flupropanoate; flupyrsulfuron(-methyl)(-sodium); flurazole; flurenol(-butyl); fluridone; fluorochloridone; fluoroxypyr(-meptyl); flurprimidol, flurtamone; fluthiacet(-methyl), fluthiamide, fluxofenim; fomesafen; foramsulfuron, forchlorfenuron; fosamine; furilazole; furyloxyfen; gibberillic acid; glufosinate(-ammonium); glyphosate(-isopropyl-ammonium); halosafen; halosulfuron(-methyl) and its esters (e.g. methyl ester, NC-319); haloxyfop and its esters; haloxyfop-P(=R-haloxyfop) and its esters; HC-252; hexazinone; imazamethabenz(-methyl); imazamox, imazapic, imazapyr; imazaquin and salts such as the ammonium salt; imazamethapyr, imazapic, imazethamethapyr; imazethapyr; imazosulfuron; inabenfide; indanofan; indole-3-ylacetic acid; 4-indol-3-ylbutyric acid; iodosulfuron-methyl(-sodium); ioxynil; isocarbamid; isopropalin; isoproturon; isouron; isoxaben; isoxachlortole, isoxadifen(-ethyl); isoxaflutole, isoxapyrifop; karbutilate; lactofen; lenacil; linuron; maleic hydrazide, MCPA; MCPB; mecoprop(-P); mefenacet; mefenpyr(-diethyl); mefluidid; mepiquat(-chloride), mesotrione, mesosulfuron(-methyl); mesotrione, metam; metamifop; metamitron; metazachlor; methabenzthiazuron; methazole; methoxyphenone; methylarsonic acid; 1-methylcyclopropene; methyldymron; methylisothiocyanate, metobenzuron, metobromuron; (alpha-) metolachlor; metosulam (XRD 511); metoxuron; metribuzin; metsulfuron-methyl; MH; MK-616; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)-phenyl]-2-methylpentanamide; 2-(1-naphthyl) acetamide, 1-naphthylacetic acid, 2-naphthyloxyacetic acid, naproanilide; napropamide; naptalam; NC 310, i.e. 4-(2,4-dichlorbenzoyl)-1-methyl-5-benzyloxypyrazole; neburon; nicosulfuron; nipyraclofen; nitralin; nitrofen; nitrophenolate mixture; nitrofluorfen; nonanoic acid; norflurazon; orbencarb; orthasulfamuron; oryzalin; oxabetrinil; oxadiargyl (RP-020630); oxadiazon; oxasulfuron, oxaziclomefone, oxyfluorfen; paclobutrazol; paraquat(-dichloride); pebulate; pelargonic acid, pendimethalin; penoxulam; pentachlorophenol; pentanochlor; pentoxazone, perfluidone; pethoxamid; phenisopham; phenmedipham; picloram; picolinafen, pinoxaden, piperophos; piributicarb; pirifenop-butyl; pretilachlor; primisulfuron(-methyl); probenazole; procarbazone-(sodium), procyazine, prodiamine; profluralin; profoxydim, prohexadione(-calcium), prohydrojasmon; proglinazine(-ethyl); prometon; prometryn; propachlor; propanil; propaquizafop and its esters; propazine; propham; propisochlor; propoxycarbazone(-sodium); n-propyl-dihydrojasmonate; propyzamide; prosulfalin; prosulfocarb; prosulfuron (CGA-152005); prynachlor; pyraclonil; pyraflufen(-ethyl), pyrasulfotole; pyrazolynate; pyrazon; pyrazosulfuron(-ethyl); pyrazoxyfen; pyribenzoxim, pyributicarb, pyridafol, pyridate; pyriftalid; pyriminobac(-methyl), pyrimisulfan; pyrithiobac (-sodium) (KIH-2031); pyroxasulfone; pyroxofop and its esters (e.g. propargyl ester); pyroxulam; quinclorac; quinmerac; quinoclamine, quinofop and its ester derivatives, quizalofop and quizalofop-P and their ester derivatives, e.g. quizalofop-ethyl; quizalofop(P-tefuryl and -ethyl); renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; sintofen; SN 106279, i.e. 2-[[7-[2-chloro-4-(trifluoromethyl)phenoxy]-2-naphthalenyl]oxy]-propanoic acid and its methyl ester; sulcotrione, sulfentrazone (FMC-97285, F-6285); sulfazuron; sulfometuron(-methyl); sulfosate (ICI-A0224); sulfosulfuron, 2,3,6-TBA, TCA; tebutam (GCP-5544); tebuthiuron; tecnazene, tefurytrione, tembotrione; tepraloxydim, terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiafluamide, thiazafluoron; thiazopyr (Mon-13200); thidiazimin (SN-24085); thidiazuron; thiencarbazone; thifensulfuron(-methyl); thiobencarb; TI-35; tiocarbazil; topramezone, tralkoxydim; tri-allate; triasulfuron; triaziflam, triazofenamide; tribenuron (-methyl); triclopyr; tridiphane; trietazine; trifloxysulfuron (-sodium), trifluralin; triflusulfuron and esters (e.g. methyl ester, DPX-66037); trimeturon; trinexapac(-ethyl); tritosulfuron, tsitodef; uniconazole, vernolate; WL 110547, i.e. 5-phenoxy-1-[3-(trifluormethyl)-phenyl]-1H-tetrazole; BAY MKH 6561, UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023. What is of particular interest is the selective control of harmful plants in crops of useful and ornamental plants. Although the inventive compounds (I) have very good to satisfactory selectivity in a large number of crops, it is possible in principle that phytotoxicity in the crop plants can occur in some crops and, in particular, also in the case of mixtures with other herbicides which are less selective. In this respect, combinations of particular interest are those of inventive compounds (I) which contain the compounds (I), or their combinations with other herbicides or pesticides, and safeners. The safeners, which are used in such amounts that they act as antidotes, reduce the phytotoxic side effects of the herbicides/pesticides used, for example in economically important crops such as cereals (wheat, barley, rye, maize, rice, millet), sugar beet, sugar cane, rape, cotton and soya, preferably cereals. The following groups of compounds are useful, for example, as safeners for the compounds (I) and their combinations with other pesticides:

a) Compounds of the dichlorophenylpyrazoline-3-carboxylic acid type, preferably compounds such as ethyl 1-(2,4-dichlorophenyl)-5-(ethoxycarbonyl)-5-methyl-2-pyrazoline-3-carboxylate (S1-1) ("mefenpyr-diethyl", PM), and related compounds, as described in WO 91/07874 (U.S. Pat. Nos. 5,700,758, 5,703,008), b) Derivatives of dichlorophenylpyrazole carboxylic acid, preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4), ethyl 1-(2,4-dichlorophenyl)-5-phenylpyrazole-3-carboxylate (S1-5) and related compounds, as described in EP-A-333 131 (U.S. Pat. Nos. 5,401,700, 5,945,541) and EP-A-269 806 (U.S. Pat. Nos. 4,891,057, 5,082,949).

c) Compounds of the triazolecarboxylic acid type, preferably compounds such as fenchlorazole(ethyl ester), i.e. ethyl 1-(2,4-dichlorophenyl)-5-trichloromethyl-(1H)-1,2,4-triazole-3-carboxylate (S1-6) and related compounds (EP-A-174 562 (U.S. Pat. No. 4,639,266) and EP-A-346 620);

d) Compounds of the 5-benzyl- or 5-phenyl-2-isoxazoline-3-carboxylic acid type, or the 5,5-diphenyl-2-isoxazoline-3-carboxylic acid type, preferably compounds such as ethyl 5-(2,4-dichlorobenzyl)-2-isoxazoline-3-carboxylate (S1-7) or ethyl 5-phenyl-2-isoxazoline-3-carboxylate (S1-8) and related compounds, as described in WO 91/08202 (U.S. Pat. No. 5,314,863), or ethyl 5,5-diphenyl-2-isoxazolinecarboxylate (S1-9) ("isoxadifen-ethyl") or the-n-propyl ester (S1-10) or ethyl 5-(4-fluorophenyl)-5-phenyl-2-isoxazoline-3-carboxylate (S1-11), as described in patent application WO-A-95/07897 (U.S. Pat. No. 5,516,750).

e) Compounds of the 8-quinolineoxyacetic acid type (S2), preferably 1-methylhex-1-yl (5-chloro-8-quinolineoxy)acetate (common name "cloquintocet-mexyl" (S2-1) (see PM) 1,3-dimethyl but-1-yl (5-chloro-8-quinolineoxy)acetate (S2-2), 4-allyloxybutyl (5-chloro-8-quinolineoxy)acetate (S2-3), 1-allyloxyprop-2-yl (5-chloro-8-quinolineoxy)acetate (S2-4), ethyl (5-chloro-8-quinolineoxy)acetate (S2-5), methyl (5-chloro-8-quinolineoxy)acetate (S2-6), allyl (5-chloro-8-quinolineoxy)acetate (S2-7), 2-(2-propylideneiminoxy)-1-ethyl (5-chloro-8-quinolineoxy)acetate (S2-8), 2-oxoprop-1-yl (5-chloro-8-quinolineoxy)acetate (S2-9) and related compounds, as described in EP-A-86 750 (U.S. Pat. Nos. 4,623,727, 4,758,264, 4,785,105, 4,785,106, 4,822,884, 4,851,033, 5,045,107), EP-A-94 349 (U.S. Pat. Nos. 4,902,340, 5,023,333, 5,102,445) and EP-A-191 736 (U.S. Pat. No. 4,881,966) or EP-A-0 492 366 (U.S. Pat. No. 5,380,852).

f) Compounds of the (5-chloro-8-quinolineoxy)malonic acid type, preferably compounds such as diethyl (5-chloro-8-quinolineoxy)malonate, diallyl (5-chloro-8-quinolineoxy)malonate, methyl ethyl (5-chloro-8-quinolineoxy)malonate and related compounds, as described in EP-A-0 582 198 (U.S. Pat. Nos. 5,739,079, 6,482,947).

g) Active ingredients of the phenoxyacetic or -propionic acid derivative type or the aromatic carboxylic acid type, for example 2,4-dichlorophenoxyacetic acid/esters (2,4-D), 4-chloro-2-methylphenoxypropionic esters (mecoprop), MCPA or 3,6-dichloro-2-methoxybenzoic acid/esters (dicamba).

h) Active ingredients of the pyrimidine type, which are used as soil-acting safeners in rice, for example
"fenclorim" (PM) (=4,6-dichloro-2-phenylpyrimidine), which is known as safener for pretilachlor in sown rice, i) Active ingredients of the dichloroacetamide type, which are frequently used as pre-emergent safeners (soil-acting safeners), for example
"dichlormid" (PM) (=N,N-diallyl-2,2-dichloroacetamide),
"R-29148" (=3-dichloroacetyl-2,2,5-trimethyl-1,3-oxazolidine from Stauffer),
"benoxacor" (PM) (=4-dichloroacetyl-3,4-dihydro-3-methyl-2H-1,4-benzoxazine),
"PPG-1292" (=N-allyl-N-[(1,3-dioxolan-2-yl)methyl]dichloroacetamide from PPG Industries),
"DK-24" (=N-allyl-N-[(allylaminocarbonyl)methyl]dichloroacetamide from Sagro-Chem),
"AD-67" or "MON 4660" (=3-dichloroacetyl-1-oxa-3-aza-spiro[4,5]decane from Nitrokemia or Monsanto),
"diclonon" or "BAS145138" or "LAB145138" (=(=3-dichloroacetyl-2,5,5-trimethyl-1,3-diazabicyclo[4.3.0]nonane from BASF) and
"furilazol" or "MON 13900" (see PM) (=(RS)-3-dichloroacetyl-5-(2-furyl)-2,2-dimethyloxazolidine)

j) Active ingredients of the dichloroacetone derivative type, for example
"MG 191" (CAS-Reg. No. 96420-72-3) (=2-dichloromethyl-2-methyl-1,3-dioxolane from Nitrokemia), which is known as safener for maize,
k) Active ingredients of the oxyimino compound type, which are known as seed dressings, for example
"oxabetrinil" (PM) (=(Z)-1,3-dioxolan-2-ylmethoxyimino(phenyl)acetonitrile), which is known as a seed dressing safener for millet against metolachlor damage,
"fluxofenim" (PM) (=1-(4-chlorophenyl)-2,2,2-trifluoro-1-ethanone O-(1,3-dioxolan-2-ylmethyl) oxime), which is known as a seed dressing safener for millet against metolachlor damage, and
"cyometrinil" or "CGA-43089" (PM) (=(Z)-cyanomethoxy-imino(phenyl)acetonitrile), which is known as a seed dressing safener for millet against metolachlor damage,
l) Active ingredients of the thiazolecarboxylic ester type, which are known as seed dressings, for example
"flurazol" (PM) (=benzyl 2-chloro-4-trifluoromethyl-1,3-thiazole-5-carboxylate), which is known as a seed dressing safener for millet against alachlor and metolachlor damage,
m) Active ingredients of the naphthalenedicarboxylic acid derivative type, which are known as seed dressings, for example
"naphthalic anhydride" (PM) (=1,8-naphthalenedicarboxylic anhydride), which is known as a seed dressing safener for maize against thiocarbamate herbicide damage,
n) Active ingredients of the chromanacetic acid derivative type, for example
"CL 304415" (CAS-Reg. No. 31541-57-8) (=2-(4-carboxychroman-4-yl)acetic acid from American Cyanamid), which is known as safener for maize against imidazolinone damage,
o) Active ingredients which, in addition to a herbidical action against harmful plants, also have safener action in crop plants such as rice, for example
"dimepiperate" or "MY-93" (PM) (=S-1-methyl-1-phenylethyl piperidine-1-thiocarboxylate), which is known as safener for rice against herbicide molinate damage,
"daimuron" or "SK 23" (PM) (=1-(1-methyl-1-phenylethyl)-3-p-tolylurea), which is known as safener for rice against herbicide imazosulfuron damage,
"cumyluron"="JC-940" (=3-(2-chlorophenylmethyl)-1-(1-methyl-1-phenylethyl)urea, see JP-A-60087254), which is known as safener for rice against damage by some herbicides,
"methoxyphenon" or "NK 049" (=3,3'-dimethyl-4-methoxy-benzophenone), which is known as safener for rice against damage by some herbicides,
"CSB" (=1-bromo-4-(chloromethylsulfonyl)benzene) (CAS-Reg. No. 54091-06-4 from Kumiai), which is known as safener against damage by some herbicides in rice,
p) N-Acylsulfonamides of the formula (S3) and salts thereof,

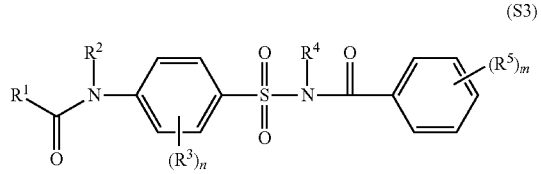

(S3)

as described in WO-A-97/45016 (U.S. Pat. No. 6,235,680), q) Acylsulfamoylbenzoamides of the formula (S4), if appropriate also in salt form,

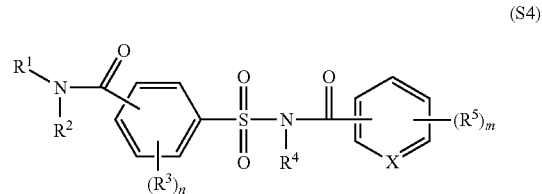

(S4)

as described in the International Application No. PCT/EP98/06097 (U.S. Pat. No. 6,251,827), for example "cyprosulfamides" (S4-1) and
r) compounds of the formula (S5),

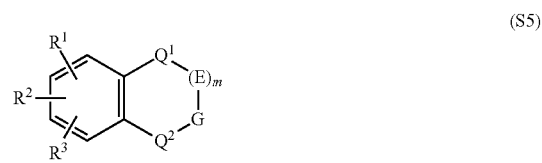

(S5)

as described in WO-A 98/13 361 (U.S. Pat. No. 6,294,504), including the stereoisomers and the salts normally used in agriculture.

Among the safeners mentioned, (S1-1), (S1-9), (S2-1) and (S4-1), are of particular interest.

Some of the safeners are already known as herbicides and consequently also display, in addition to the herbicidal action against harmful plants, protective action in connection with crop plants.

The ratios by weight of herbicide (mixture) to safener generally depend on the application rate of the herbicide and the efficacy of the safener in question and can vary within wide limits, for example in the range from 200:1 to 1:200, preferably from 100:1 to 1:100, in particular from 20:1 to 1:20. Analogously to the compounds (I) or their mixtures, the safeners can be formulated with other herbicides/pesticides and be provided and used as a finished formulation or tankmix with the herbicides.

For use, the herbicide or herbicide/safener formulations which are present in commercially available form are, if appropriate, diluted in the customary manner, for example using water in the case of spray powders, emulsifiable concentrates, dispersions and water-dispersible granules. Preparations in the form of dusts, granules for soil application or broadcasting and sprayable solutions are usually not further diluted with other inert substances prior to use.

The required application rate of the compounds of the formula (I) varies with the external conditions, such as temperature, humidity, the nature of the herbicide used and the like. It can vary within wide limits, for example between 0.001 and 10.0 kg/ha or more of active substance, but is preferably between 0.005 and 5 kg/ha.

In the examples which follow, the quantitative data (including percentages) are based on the weight unless specifically stated otherwise. The designations "R" and "S" used in the context of the description and the examples for the absolute configuration on the particular chiral center of the stereoisomers of the formula (I) follows the RS nomenclature according to the Cahn-Ingold-Prelog rule.

The invention is further described by the following non-limiting examples which further illustrate the invention, and are not intended, nor should they be interpreted to, limit the scope of the invention.

(A) CHEMICAL EXAMPLES

In the formulae in the schemes for examples 1 to 6, the methyl group is abbreviated as "Me".

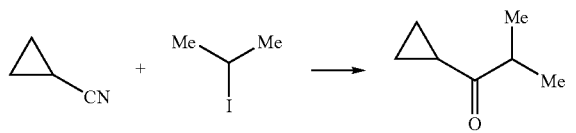

Example 1

Ketone Synthesis (Precursor) Via an Addition of a Grignard Compound to a Nitrile 4.43 g (0.18 mol) of magnesium were initially charged in 10 ml of dry diethyl ether under protective gas. Of a total of 28.15 g (0.17 mol) of 2-iodopropane, a small portion was added; the reaction then started up. The rest of the 2-iodopropane was diluted with 90 ml of dry diethyl ether and then slowly added dropwise such that the reaction mixture attained the boiling temperature. The contents were heated under reflux for one hour and then cooled to 0-4° C. At this temperature, a solution of 10.0 g (0.15 mol) of cyclopropyl cyanide in 100 ml of dry diethyl ether was added dropwise, and then the reaction mixture was heated under reflux for 2 h.

The reaction mixture was cooled in an ice bath, and 80 ml of 10% hydrochloric acid were slowly added dropwise at 5° C. The two phases were separated, the aqueous phase was extracted twice with diethyl ether, the three organic phases were combined and extracted with a saturated sodium chloride solution, and then the organic phases were dried over sodium sulfate and the filtrate was freed of the solvent under reduced pressure.

7.07 g (yield: 42%) of the cyclopropyl isopropyl ketone were isolated; the structure is confirmed by a $^1$H NMR spectrum.

Example 2

Cyclopropanation of Cyclopentenone to a Ketone Precursor

12.28 g (purity 80%, 0.41 mol) of sodium hydride are initially charged in 100 ml of dimethyl sulfoxide under protective gas. Subsequently, 28.0 g (0.34 mol) of cyclopent-2-en-1-one and 90.06 g (0.41 mol) of trimethyloxosulfonium iodide are added. The reaction mixture was stirred at room temperature overnight and finally admixed with water. The mixture was extracted twice with methyl tert-butyl ether and the combined organic phases were extracted with saturated aqueous sodium chloride solution. The organic phase was dried over magnesium sulfate, and the filtrate was concentrated on a rotary evaporator. The residue was rectified under reduced pressure to obtain 10.1 g of the desired ketone as a colorless liquid.

The ketone was converted analogously to the examples which follow first via a reductive amination to the corresponding amine, and the amine was subsequently converted successfully to the desired, correspondingly substituted 2,4-diamino-1,3,5-triazine.

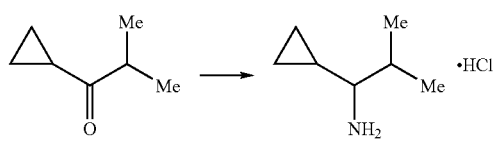

Example 3

Preparation of an Amine by Reductive Amination (Precursor)

A solution of 1.0 g (8.9 mmol) of cyclopropyl isopropyl ketone in 70 ml of methanol was admixed with 17.2 g (0.22 mol) of ammonium acetate and stirred at room temperature for 5 min. Thereafter, 1.7 g (26.7 mmol) of sodium cyanoborohydride were added. The mixture was stirred at room temperature for several days and then admixed with 1M potassium hydroxide solution. The flask contents were stirred for 10 min, then 40 ml of 20% sodium hydroxide solution were added. The mixture was extracted with ethyl acetate. The organic phase was acidified with hydrochloric acid, and the aqueous phase was removed and, after addition of ethyl acetate, alkalized with sodium hydroxide solution with cooling. After extraction with ethyl acetate, the organic phases were dried over magnesium sulfate, and the filtrate was admixed with 15 ml of 1.25M ethanolic HCl solution with cooling. The mixture was stirred for 30 min and then freed of the solvent under reduced pressure. 0.6 g of 1-cyclopropyl-2-methylpropylamine was isolated in the form of its hydrochloride (yield: 45%). A $^1$H NMR spectrum confirms the structure.

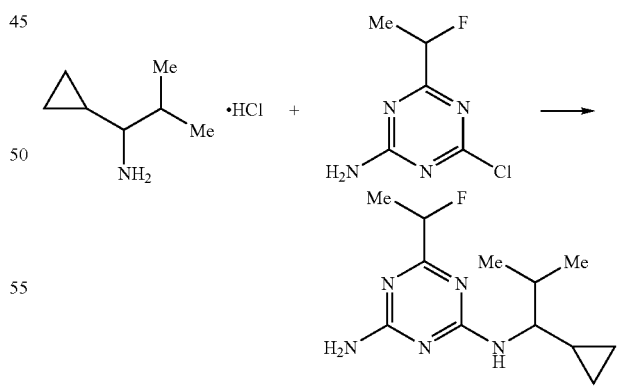

Example 4

Preparation of 4-amino-2-(1-cyclopropyl-2-methyl-propylamino)-6-(R,S-1-fluoroethyl)-1,3,5-triazine 300 mg (2.0 mmol) of 1-cyclopropyl-2-methylpropylamine hydrochloride, 354 mg (2.0 mmol) of 2-amino-4- chloro-6-(1-fluoroethyl)-1,3,5-triazine and 609 mg (4.4 mmol) of potassium carbonate were initially charged in 15 ml of acetonitrile and heated to 80° C. for 16 h. The reaction mixture was filtered with suction through Celite, and the residue was washed with ethyl acetate. The filtrate was freed from the solvent under reduced pressure. The residue was purified by chromatography to obtain 83 mg (yield: 16.4%) of the desired product. A $^1$H NMR and a mass spectrum confirm the structure.

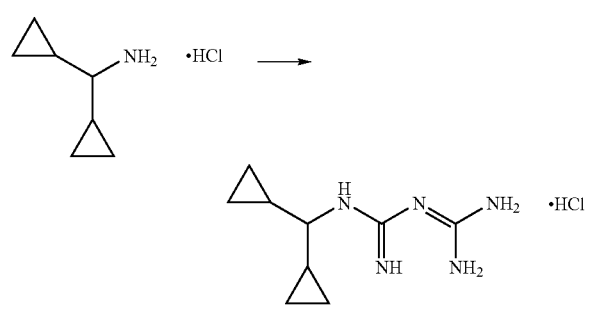

Example 5

Preparation of Dicyclopropylmethylbiguanide 1.6 g (10.8 mmol) of 1,1-dicyclopropylmethylamine hydrochloride were admixed with 0.91 g (10.8 mmol) of cyanoguanidine in a mixture of 6 ml of decane and 20 ml of toluene. The mixture was heated to a temperature of 140° C. for 5 h, in the course of which toluene distilled off. The flask contents were cooled to room temperature, then acetone was added. The precipitate was decanted off and freed of residual solvent under reduced pressure. 1.7 g of the crude product (purity approx. 80%) were obtained, which were used for the next synthesis stage without further purification.

Example 6

4-Amino-2-(dicyclopropylmethylamino)-6-methyl-1,3,5-triazine

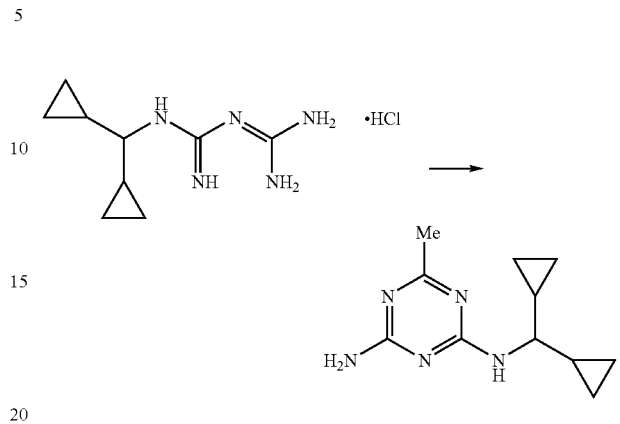

272 mg (80% by weight, 0.94 mmol) of 1,1-dicyclopropylmethylbiguanide hydrochloride were taken up in 4 ml of methanol, admixed with 85 mg (30% by weight, 0.47 mmol) of methanolic sodium methoxide solution and then stirred at room temperature for 10 min. This was followed by successive dropwise addition of 165 mg (1.88 mmol) of ethyl acetate and 84 mg (30% by weight, 0.47 mmol) of methanolic sodium methoxide solution. The mixture was stirred at room temperature overnight. For workup, water was added, then the aqueous phase was extracted twice with ethyl acetate. The combined organic phases were dried and freed of the solvent under reduced pressure. The residue was purified by chromatography to obtain 23 mg (yield: 11.2%) of the desired product. A $^1$H NMR and a mass spectrum confirmed the structure.

The further examples in tables 1 to 7 below are obtained analogously to the processes mentioned.

Example Tables 1 to 7

Table with abbreviations for tables 1-7

| Abbreviation | Chemical name | Chemical formula*) |
|---|---|---|
| Me | Methyl | $CH_3$ |
| Et | Ethyl | $C_2H_5$ |
| c-Pr | Cyclopropyl | |
| c-Bu | Cyclobutyl | |
| 1-Me-c-Pr | 1-Methylcyclopropyl | |
| 1-Cl-c-Pr | 1-Chlorocyclopropyl | |
| 1-F-c-Pr | 1-Fluorocyclopropyl | |

-continued

| Abbreviation | Chemical name | Chemical formula*) |
|---|---|---|
| 2,2-Me$_2$-c-Pr | 2,2-Dimethylcyclopropyl |  |
| 2,2-Cl$_2$-c-Pr | 2,2-Dichlorocyclopropyl |  |
| Ac | Acetyl | —CO—CH$_3$ |
| NHAc | Acetylamino | —NH—CO—CH$_3$ |
| NHCOEt | Propionylamino | —NH—CO—CH$_2$CH$_3$ |
| NHCOCHFMe | 2-Fluoropropionylamino | —NH—CO—CHF—CH$_3$ |
| N=CH—NMe$_2$ | Dimethylaminomethylideneamino | 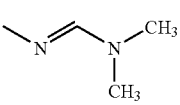 |
| N=CH-morph | Morpholin-4-ylmethylideneamino | 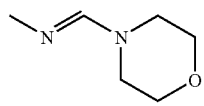 |
| B1 | Bicyclo[3.1.0]hex-2-yl | 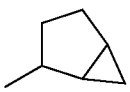 |
| B2 | 3-Methyl-bicyclo[3.1.0]hex-2-yl | 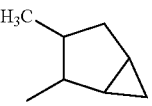 |
| B3 | 3,3-Dimethyl-bicyclo[3.1.0]hex-2-yl | 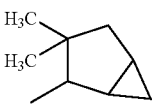 |
| B4 | 3-Cyclopropyl-bicyclo[3.1.0]hex-2-yl | 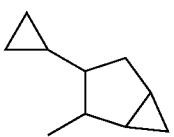 |
| B5 | 3-Cyclopropyl-3-methyl-bicyclo[3.1.0]hex-2-yl | 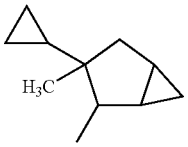 |
| B6 | 3-Methoxymethyl-bicyclo[3.1.0]-hex-2-yl | 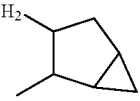 |
| B7 | 3-Methoxymethyl-3-methyl-bicyclo[3.1.0]hex-2-yl | 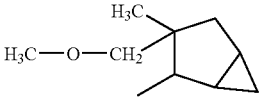 |
| B8 | Tricyclo[4.1.0.0$^{3,5}$]hept-2-yl | 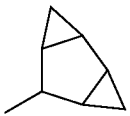 |

-continued

| Abbreviation | Chemical name | Chemical formula*) |
|---|---|---|
| B9 | 4,4,7,7-Tetramethyl-tricyclo[4.1.0.0³,⁵]hept-2-yl | |
| B10 | 4,4,7,7-Tetrachloro-tricyclo[4.1.0.0³,⁵]hept-2-yl | |
| B11 | Tricyclo[5.1.0.0³,⁵]oct-2-yl | |
| B12 | 4,4,8,8-Tetramethyl-tricyclo[5.1.0.0³,⁵]oct-2-yl | |
| B13 | 4,4,8,8-Tetrachloro-tricyclo[5.1.0.0³,⁵]oct-2-yl | |

*)Remark on the preliminary table: in the chemical formula, the dash on a radical denotes its free bond (should not be confused with the notation for a methyl group)

In the column for physical data ("phys. data") of tables 1-7:
"NMR"=data according to $^1$H NMR spectrum ($^1$H nuclear resonance data) are available and are reported at the end of the particular table.
"Resin"=the compound was obtained as a resinous substance ("viscous oil")

TABLE 1

Compounds of the formula (Ia)

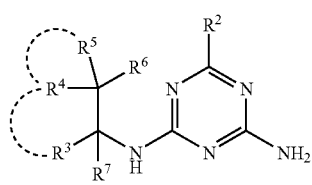

(Ia)

| No. | $R^2$ | $R^3$ | $R^4$ | $R^5$ | $R^6$ | $R^7$ | phys. data |
|---|---|---|---|---|---|---|---|
| 1-1 | H | c-Pr | Me | Me | H | H | |
| 1-2 | H | c-Pr | Me | Me | H | Me | |

TABLE 1-continued

Compounds of the formula (Ia)

$$\text{(Ia)}$$

| No. | R² | R³ | R⁴ | R⁵ | R⁶ | R⁷ | phys. data |
|---|---|---|---|---|---|---|---|
| 1-3 | H | c-Pr | Me | Me | H | c-Pr | |
| 1-4 | H | c-Pr | Me | Me | Me | H | |
| 1-5 | H | c-Pr | Me | Me | Me | Me | |
| 1-6 | H | c-Pr | Me | Me | Me | c-Pr | |
| 1-7 | H | c-Pr | c-Pr | Me | H | H | |
| 1-8 | H | c-Pr | c-Pr | Me | H | Me | |
| 1-9 | H | c-Pr | c-Pr | Me | H | c-Pr | |
| 1-10 | H | c-Pr | c-Pr | Me | Me | H | |
| 1-11 | H | c-Pr | c-Pr | Me | Me | Me | |
| 1-12 | H | c-Pr | c-Pr | Me | Me | c-Pr | |
| 1-13 | H | c-Pr | —CH₂—OMe | Me | H | H | |
| 1-14 | H | c-Pr | —CH₂—OMe | Me | H | Me | |
| 1-15 | H | c-Pr | —CH₂—OMe | Me | H | c-Pr | |
| 1-16 | H | c-Pr | —CH₂—OMe | Me | Me | H | |
| 1-17 | H | c-Pr | —CH₂—OMe | Me | Me | Me | |
| 1-18 | H | c-Pr | —CH₂—OMe | Me | Me | c-Pr | |
| 1-19 | H | c-Pr | —(CH₂)₂— | | H | H | NMR |
| 1-20 | H | c-Pr | —(CH₂)₃— | | H | H | |
| 1-21 | H | c-Pr | —(CH₂)₂— | | H | Me | |
| 1-22 | H | c-Pr | —(CH₂)₃— | | H | Me | |
| 1-23 | H | c-Pr | —(CH₂)₂— | | H | c-Pr | |
| 1-24 | H | c-Pr | —(CH₂)₃— | | H | c-Pr | |
| 1-25 | H | c-Bu | —(CH₂)₃— | | H | H | |
| 1-26 | H | c-Bu | —(CH₂)₃— | | H | Me | |
| 1-27 | H | c-Bu | —(CH₂)₃— | | H | c-Pr | |
| 1-28 | H | 1-Me-c-Pr | Me | Me | H | H | |
| 1-29 | H | 1-Me-c-Pr | Me | Me | Me | H | |
| 1-30 | H | 1-Me-c-Pr | Me | Me | Me | 1-Me-c-Pr | |
| 1-31 | H | 1-Me-c-Pr | c-Pr | Me | H | H | |
| 1-32 | H | 1-Me-c-Pr | c-Pr | Me | Me | H | |
| 1-33 | H | 1-Me-c-Pr | c-Pr | Me | Me | 1-Me-c-Pr | |
| 1-34 | H | 1-Me-c-Pr | —CH₂—OMe | Me | H | H | |
| 1-35 | H | 1-Me-c-Pr | —CH₂—OMe | Me | Me | H | |
| 1-36 | H | 1-Me-c-Pr | —CH₂—OMe | Me | Me | 1-Me-c-Pr | |
| 1-37 | H | 1-Me-c-Pr | —(CH₂)₂— | | H | H | |
| 1-38 | H | 1-Me-c-Pr | —(CH₂)₃— | | H | H | |
| 1-39 | H | 1-Me-c-Pr | —(CH₂)₂— | | Me | H | |
| 1-40 | H | 1-Me-c-Pr | —(CH₂)₂— | | Me | 1-Me-c-Pr | |
| 1-41 | H | 1-Cl-c-Pr | Me | Me | H | H | |
| 1-42 | H | 1-Cl-c-Pr | Me | Me | Me | H | |
| 1-43 | H | 1-Cl-c-Pr | Me | Me | Me | 1-Cl-c-Pr | |
| 1-44 | H | 1-Cl-c-Pr | c-Pr | Me | H | H | |
| 1-45 | H | 1-Cl-c-Pr | c-Pr | Me | Me | H | |
| 1-46 | H | 1-Cl-c-Pr | c-Pr | Me | Me | 1-Cl-c-Pr | |
| 1-47 | H | 1-Cl-c-Pr | —CH₂—OMe | Me | H | H | |
| 1-48 | H | 1-Cl-c-Pr | —CH₂—OMe | Me | Me | H | |
| 1-49 | H | 1-Cl-c-Pr | —CH₂—OMe | Me | Me | 1-Cl-c-Pr | |
| 1-50 | H | 1-Cl-c-Pr | —(CH₂)₂— | | H | H | |
| 1-51 | H | 1-Cl-c-Pr | —(CH₂)₃— | | H | H | |
| 1-52 | H | 1-Cl-c-Pr | —(CH₂)₂— | | Cl | H | |
| 1-53 | H | 1-Cl-c-Pr | —(CH₂)₂— | | Cl | 1-Cl-c-Pr | |
| 1-54 | H | 2,2-Me₂-c-Pr | Me | Me | H | H | |
| 1-55 | H | 2,2-Me₂-c-Pr | Me | Me | Me | H | |
| 1-56 | H | 2,2-Me₂-c-Pr | Me | Me | Me | 2,2-Me₂-c-Pr | |
| 1-57 | H | 2,2-Me₂-c-Pr | c-Pr | Me | H | H | |
| 1-58 | H | 2,2-Me₂-c-Pr | c-Pr | Me | Me | H | |
| 1-59 | H | 2,2-Me₂-c-Pr | c-Pr | Me | Me | 2,2-Me₂-c-Pr | |
| 1-60 | H | 2,2-Me₂-c-Pr | —CH₂—OMe | Me | H | H | |
| 1-61 | H | 2,2-Me₂-c-Pr | —CH₂—OMe | Me | Me | H | |
| 1-62 | H | 2,2-Me₂-c-Pr | —CH₂—OMe | Me | Me | 2,2-Me₂-c-Pr | |
| 1-63 | H | 2,2-Me₂-c-Pr | —(CH₂)₂— | | H | H | |
| 1-64 | H | 2,2-Me₂-c-Pr | —(CH₂)₃— | | H | H | |
| 1-65 | H | 2,2-Me₂-c-Pr | —CH₂—CMe₂— | | H | H | |
| 1-66 | H | 2,2-Me₂-c-Pr | —CH₂—CMe₂— | | H | 2,2-Me₂-c-Pr | |
| 1-67 | H | 2,2-Cl₂-c-Pr | Me | Me | H | H | |

TABLE 1-continued

Compounds of the formula (Ia)

(Ia)

| No. | R² | R³ | R⁴ | R⁵ | R⁶ | R⁷ | phys. data |
|---|---|---|---|---|---|---|---|
| 1-68 | H | 2,2-Cl₂-c-Pr | Me | Me | Me | H | |
| 1-69 | H | 2,2-Cl₂-c-Pr | Me | Me | Me | 2,2-Cl₂-c-Pr | |
| 1-70 | H | 2,2-Cl₂-c-Pr | c-Pr | Me | H | H | |
| 1-71 | H | 2,2-Cl₂-c-Pr | c-Pr | Me | Me | H | |
| 1-72 | H | 2,2-Cl₂-c-Pr | c-Pr | Me | Me | 2,2-Cl₂-c-Pr | |
| 1-73 | H | 2,2-Cl₂-c-Pr | —CH₂—OMe | Me | H | H | |
| 1-74 | H | 2,2-Cl₂-c-Pr | —CH₂—OMe | Me | Me | H | |
| 1-75 | H | 2,2-Cl₂-c-Pr | —CH₂—OMe | Me | Me | 2,2-Cl₂-c-Pr | |
| 1-76 | H | 2,2-Cl₂-c-Pr | —(CH₂)₂— | | H | H | |
| 1-77 | H | 2,2-Cl₂-c-Pr | —(CH₂)₃— | | H | H | |
| 1-78 | H | 2,2-Cl₂-c-Pr | —CH₂—CCl₂— | | H | H | |
| 1-79 | H | 2,2-Cl₂-c-Pr | —CH₂—CCl₂— | | H | 2,2-Cl₂-c-Pr | |
| 1-80 | Me | c-Pr | Me | Me | H | H | |
| 1-81 | Me | c-Pr | Me | Me | H | Me | |
| 1-82 | Me | c-Pr | Me | Me | H | c-Pr | |
| 1-83 | Me | c-Pr | Me | Me | Me | H | |
| 1-84 | Me | c-Pr | Me | Me | Me | Me | |
| 1-85 | Me | c-Pr | Me | Me | Me | c-Pr | |
| 1-86 | Me | c-Pr | c-Pr | Me | H | H | |
| 1-87 | Me | c-Pr | c-Pr | Me | H | Me | |
| 1-88 | Me | c-Pr | c-Pr | Me | H | c-Pr | |
| 1-89 | Me | c-Pr | c-Pr | Me | Me | H | |
| 1-90 | Me | c-Pr | c-Pr | Me | Me | Me | |
| 1-91 | Me | c-Pr | c-Pr | Me | Me | c-Pr | |
| 1-92 | Me | c-Pr | —CH₂—OMe | Me | H | H | |
| 1-93 | Me | c-Pr | —CH₂—OMe | Me | H | Me | |
| 1-94 | Me | c-Pr | —CH₂—OMe | Me | H | c-Pr | |
| 1-95 | Me | c-Pr | —CH₂—OMe | Me | Me | H | |
| 1-96 | Me | c-Pr | —CH₂—OMe | Me | Me | Me | |
| 1-97 | Me | c-Pr | —CH₂—OMe | Me | Me | c-Pr | |
| 1-98 | Me | c-Pr | —(CH₂)₂— | | H | H | NMR |
| 1-99 | Me | c-Pr | —(CH₂)₃— | | H | H | |
| 1-100 | Me | c-Pr | —(CH₂)₂— | | H | Me | |
| 1-101 | Me | c-Pr | —(CH₂)₃— | | H | Me | |
| 1-102 | Me | c-Pr | —(CH₂)₂— | | H | c-Pr | |
| 1-103 | Me | c-Pr | —(CH₂)₃— | | H | c-Pr | |
| 1-104 | Me | c-Bu | —(CH₂)₃— | | H | H | |
| 1-105 | Me | c-Bu | —(CH₂)₃— | | H | Me | |
| 1-106 | Me | c-Bu | —(CH₂)₃— | | H | c-Pr | |
| 1-107 | Me | 1-Me-c-Pr | Me | Me | H | H | |
| 1-108 | Me | 1-Me-c-Pr | Me | Me | Me | H | |
| 1-109 | Me | 1-Me-c-Pr | Me | Me | Me | 1-Me-c-Pr | |
| 1-110 | Me | 1-Me-c-Pr | c-Pr | Me | H | H | |
| 1-111 | Me | 1-Me-c-Pr | c-Pr | Me | Me | H | |
| 1-112 | Me | 1-Me-c-Pr | c-Pr | Me | Me | 1-Me-c-Pr | |
| 1-113 | Me | 1-Me-c-Pr | —CH₂—OMe | Me | H | H | |
| 1-114 | Me | 1-Me-c-Pr | —CH₂—OMe | Me | Me | H | |
| 1-115 | Me | 1-Me-c-Pr | —CH₂—OMe | Me | Me | 1-Me-c-Pr | |
| 1-116 | Me | 1-Me-c-Pr | —(CH₂)₂— | | H | H | |
| 1-117 | Me | 1-Me-c-Pr | —(CH₂)₃— | | H | H | |
| 1-118 | Me | 1-Me-c-Pr | —(CH₂)₂— | | Me | H | |
| 1-119 | Me | 1-Me-c-Pr | —(CH₂)₂— | | Me | 1-Me-c-Pr | |
| 1-120 | Me | 1-Cl-c-Pr | Me | Me | H | H | |
| 1-121 | Me | 1-Cl-c-Pr | Me | Me | Me | H | |
| 1-122 | Me | 1-Cl-c-Pr | Me | Me | Me | 1-Cl-c-Pr | |
| 1-123 | Me | 1-Cl-c-Pr | c-Pr | Me | H | H | |
| 1-124 | Me | 1-Cl-c-Pr | c-Pr | Me | Me | H | |
| 1-125 | Me | 1-Cl-c-Pr | c-Pr | Me | Me | 1-Cl-c-Pr | |
| 1-126 | Me | 1-Cl-c-Pr | —CH₂—OMe | Me | H | H | |
| 1-127 | Me | 1-Cl-c-Pr | —CH₂—OMe | Me | Me | H | |
| 1-128 | Me | 1-Cl-c-Pr | —CH₂—OMe | Me | Me | 1-Cl-c-Pr | |
| 1-129 | Me | 1-Cl-c-Pr | —(CH₂)₂— | | H | H | |
| 1-130 | Me | 1-Cl-c-Pr | —(CH₂)₃— | | H | H | |
| 1-131 | Me | 1-Cl-c-Pr | —(CH₂)₂— | | Cl | H | |
| 1-132 | Me | 1-Cl-c-Pr | —(CH₂)₂— | | Cl | 1-Cl-c-Pr | |

TABLE 1-continued

Compounds of the formula (Ia)

$$\text{(Ia)}$$

| No. | $R^2$ | $R^3$ | $R^4$ | $R^5$ | $R^6$ | $R^7$ | phys. data |
|---|---|---|---|---|---|---|---|
| 1-133 | Me | 2,2-Me$_2$-c-Pr | Me | Me | H | H | |
| 1-134 | Me | 2,2-Me$_2$-c-Pr | Me | Me | Me | H | |
| 1-135 | Me | 2,2-Me$_2$-c-Pr | Me | Me | Me | 2,2-Me$_2$-c-Pr | |
| 1-136 | Me | 2,2-Me$_2$-c-Pr | c-Pr | Me | H | H | |
| 1-137 | Me | 2,2-Me$_2$-c-Pr | c-Pr | Me | Me | H | |
| 1-138 | Me | 2,2-Me$_2$-c-Pr | c-Pr | Me | Me | 2,2-Me$_2$-c-Pr | |
| 1-139 | Me | 2,2-Me$_2$-c-Pr | —CH$_2$—OMe | Me | H | H | |
| 1-140 | Me | 2,2-Me$_2$-c-Pr | —CH$_2$—OMe | Me | Me | H | |
| 1-141 | Me | 2,2-Me$_2$-c-Pr | —CH$_2$—OMe | Me | Me | 2,2-Me$_2$-c-Pr | |
| 1-142 | Me | 2,2-Me$_2$-c-Pr | —(CH$_2$)$_2$— | | H | H | |
| 1-143 | Me | 2,2-Me$_2$-c-Pr | —(CH$_2$)$_3$— | | H | H | |
| 1-144 | Me | 2,2-Me$_2$-c-Pr | —CH$_2$—CMe$_2$— | | H | H | |
| 1-145 | Me | 2,2-Me$_2$-c-Pr | —CH$_2$—CMe$_2$— | | H | 2,2-Me$_2$-c-Pr | |
| 1-146 | Me | 2,2-Cl$_2$-c-Pr | Me | Me | H | H | |
| 1-147 | Me | 2,2-Cl$_2$-c-Pr | Me | Me | Me | H | |
| 1-148 | Me | 2,2-Cl$_2$-c-Pr | Me | Me | Me | 2,2-Cl$_2$-c-Pr | |
| 1-149 | Me | 2,2-Cl$_2$-c-Pr | c-Pr | Me | H | H | |
| 1-150 | Me | 2,2-Cl$_2$-c-Pr | c-Pr | Me | Me | H | |
| 1-151 | Me | 2,2-Cl$_2$-c-Pr | c-Pr | Me | Me | 2,2-Cl$_2$-c-Pr | |
| 1-152 | Me | 2,2-Cl$_2$-c-Pr | —CH$_2$—OMe | Me | H | H | |
| 1-153 | Me | 2,2-Cl$_2$-c-Pr | —CH$_2$—OMe | Me | Me | H | |
| 1-154 | Me | 2,2-Cl$_2$-c-Pr | —CH$_2$—OMe | Me | Me | 2,2-Cl$_2$-c-Pr | |
| 1-155 | Me | 2,2-Cl$_2$-c-Pr | —(CH$_2$)$_2$— | | H | H | |
| 1-156 | Me | 2,2-Cl$_2$-c-Pr | —(CH$_2$)$_3$— | | H | H | |
| 1-157 | Me | 2,2-Cl$_2$-c-Pr | —CH$_2$—CCl$_2$— | | H | H | |
| 1-158 | Me | 2,2-Cl$_2$-c-Pr | —CH$_2$—CCl$_2$— | | H | 2,2-Cl$_2$-c-Pr | |
| 1-159 | Et | c-Pr | Me | Me | H | H | |
| 1-160 | Et | c-Pr | Me | Me | H | Me | |
| 1-161 | Et | c-Pr | Me | Me | H | c-Pr | |
| 1-162 | Et | c-Pr | Me | Me | Me | H | |
| 1-163 | Et | c-Pr | Me | Me | Me | Me | |
| 1-164 | Et | c-Pr | Me | Me | Me | c-Pr | |
| 1-165 | Et | c-Pr | c-Pr | Me | H | H | |
| 1-166 | Et | c-Pr | c-Pr | Me | H | Me | |
| 1-167 | Et | c-Pr | c-Pr | Me | H | c-Pr | |
| 1-168 | Et | c-Pr | c-Pr | Me | Me | H | |
| 1-169 | Et | c-Pr | c-Pr | Me | Me | Me | |
| 1-170 | Et | c-Pr | c-Pr | Me | Me | c-Pr | |
| 1-171 | Et | c-Pr | —CH$_2$—OMe | Me | H | H | |
| 1-172 | Et | c-Pr | —CH$_2$—OMe | Me | H | Me | |
| 1-173 | Et | c-Pr | —CH$_2$—OMe | Me | H | c-Pr | |
| 1-174 | Et | c-Pr | —CH$_2$—OMe | Me | Me | H | |
| 1-175 | Et | c-Pr | —CH$_2$—OMe | Me | Me | Me | |
| 1-176 | Et | c-Pr | —CH$_2$—OMe | Me | Me | c-Pr | |
| 1-177 | Et | c-Pr | —(CH$_2$)$_2$— | | H | H | NMR |
| 1-178 | Et | c-Pr | —(CH$_2$)$_3$— | | H | H | |
| 1-179 | Et | c-Pr | —(CH$_2$)$_2$— | | H | Me | |
| 1-180 | Et | c-Pr | —(CH$_2$)$_3$— | | H | Me | |
| 1-181 | Et | c-Pr | —(CH$_2$)$_2$— | | H | c-Pr | |
| 1-182 | Et | c-Pr | —(CH$_2$)$_3$— | | H | c-Pr | |
| 1-183 | Et | c-Bu | —(CH$_2$)$_3$— | | H | H | NMR |
| 1-184 | Et | c-Bu | —(CH$_2$)$_3$— | | H | Me | |
| 1-185 | Et | c-Bu | —(CH$_2$)$_3$— | | H | c-Pr | |
| 1-186 | Et | 1-Me-c-Pr | Me | Me | H | H | |
| 1-187 | Et | 1-Me-c-Pr | Me | Me | Me | H | |
| 1-188 | Et | 1-Me-c-Pr | Me | Me | Me | 1-Me-c-Pr | |
| 1-189 | Et | 1-Me-c-Pr | c-Pr | Me | H | H | |
| 1-190 | Et | 1-Me-c-Pr | c-Pr | Me | Me | H | |
| 1-191 | Et | 1-Me-c-Pr | c-Pr | Me | Me | 1-Me-c-Pr | |
| 1-192 | Et | 1-Me-c-Pr | —CH$_2$—OMe | Me | H | H | |
| 1-193 | Et | 1-Me-c-Pr | —CH$_2$—OMe | Me | Me | H | |
| 1-194 | Et | 1-Me-c-Pr | —CH$_2$—OMe | Me | Me | 1-Me-c-Pr | |
| 1-195 | Et | 1-Me-c-Pr | —(CH$_2$)$_2$— | | H | H | |
| 1-196 | Et | 1-Me-c-Pr | —(CH$_2$)$_3$— | | H | H | |
| 1-197 | Et | 1-Me-c-Pr | —(CH$_2$)$_2$— | | Me | H | |

TABLE 1-continued

Compounds of the formula (Ia)

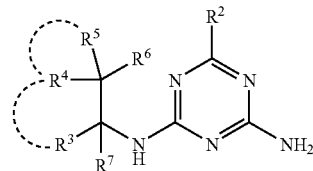

(Ia)

| No. | R² | R³ | R⁴ | R⁵ | R⁶ | R⁷ | phys. data |
|---|---|---|---|---|---|---|---|
| 1-198 | Et | 1-Me-c-Pr | —(CH₂)₂— | | Me | 1-Me-c-Pr | |
| 1-199 | Et | 1-Cl-c-Pr | Me | Me | H | H | |
| 1-200 | Et | 1-Cl-c-Pr | Me | Me | Me | H | |
| 1-201 | Et | 1-Cl-c-Pr | Me | Me | Me | 1-Cl-c-Pr | |
| 1-202 | Et | 1-Cl-c-Pr | c-Pr | Me | H | H | |
| 1-203 | Et | 1-Cl-c-Pr | c-Pr | Me | Me | H | |
| 1-204 | Et | 1-Cl-c-Pr | c-Pr | Me | Me | 1-Cl-c-Pr | |
| 1-205 | Et | 1-Cl-c-Pr | —CH₂—OMe | Me | H | H | |
| 1-206 | Et | 1-Cl-c-Pr | —CH₂—OMe | Me | Me | H | |
| 1-207 | Et | 1-Cl-c-Pr | —CH₂—OMe | Me | Me | 1-Cl-c-Pr | |
| 1-208 | Et | 1-Cl-c-Pr | —(CH₂)₂— | | H | H | |
| 1-209 | Et | 1-Cl-c-Pr | —(CH₂)₃— | | H | H | |
| 1-210 | Et | 1-Cl-c-Pr | —(CH₂)₂— | | Cl | H | |
| 1-211 | Et | 1-Cl-c-Pr | —(CH₂)₂— | | Cl | 1-Cl-c-Pr | |
| 1-212 | Et | 2,2-Me₂-c-Pr | Me | Me | H | H | |
| 1-213 | Et | 2,2-Me₂-c-Pr | Me | Me | Me | H | |
| 1-214 | Et | 2,2-Me₂-c-Pr | Me | Me | Me | 2,2-Me₂-c-Pr | |
| 1-215 | Et | 2,2-Me₂-c-Pr | c-Pr | Me | H | H | |
| 1-216 | Et | 2,2-Me₂-c-Pr | c-Pr | Me | Me | H | |
| 1-217 | Et | 2,2-Me₂-c-Pr | c-Pr | Me | Me | 2,2-Me₂-c-Pr | |
| 1-218 | Et | 2,2-Me₂-c-Pr | —CH₂—OMe | Me | H | H | |
| 1-219 | Et | 2,2-Me₂-c-Pr | —CH₂—OMe | Me | Me | H | |
| 1-220 | Et | 2,2-Me₂-c-Pr | —CH₂—OMe | Me | Me | 2,2-Me₂-c-Pr | |
| 1-221 | Et | 2,2-Me₂-c-Pr | —(CH₂)₂— | | H | H | |
| 1-222 | Et | 2,2-Me₂-c-Pr | —(CH₂)₃— | | H | H | |
| 1-223 | Et | 2,2-Me₂-c-Pr | —CH₂—CMe₂— | | H | H | |
| 1-224 | Et | 2,2-Me₂-c-Pr | —CH₂—CMe₂— | | H | 2,2-Me₂-c-Pr | |
| 1-225 | Et | 2,2-Me₂-c-Pr | Me | Me | H | H | |
| 1-226 | Et | 2,2-Cl₂-c-Pr | Me | Me | Me | H | |
| 1-227 | Et | 2,2-Cl₂-c-Pr | Me | Me | Me | 2,2-Cl₂-c-Pr | |
| 1-228 | Et | 2,2-Cl₂-c-Pr | c-Pr | Me | H | H | |
| 1-229 | Et | 2,2-Cl₂-c-Pr | c-Pr | Me | Me | H | |
| 1-230 | Et | 2,2-Cl₂-c-Pr | c-Pr | Me | Me | 2,2-Cl₂-c-Pr | |
| 1-231 | Et | 2,2-Cl₂-c-Pr | —CH₂—OMe | Me | H | H | |
| 1-232 | Et | 2,2-Cl₂-c-Pr | —CH₂—OMe | Me | Me | H | |
| 1-233 | Et | 2,2-Cl₂-c-Pr | —CH₂—OMe | Me | Me | 2,2-Cl₂-c-Pr | |
| 1-234 | Et | 2,2-Cl₂-c-Pr | —(CH₂)₂— | | H | H | |
| 1-235 | Et | 2,2-Cl₂-c-Pr | —(CH₂)₃— | | H | H | |
| 1-236 | Et | 2,2-Cl₂-c-Pr | —CH₂—CCl₂— | | H | H | |
| 1-237 | Et | 2,2-Cl₂-c-Pr | —CH₂—CCl₂— | | H | 2,2-Cl₂-c-Pr | |
| 1-238 | c-Pr | c-Pr | Me | Me | H | H | |
| 1-239 | c-Pr | c-Pr | Me | Me | H | Me | |
| 1-240 | c-Pr | c-Pr | Me | Me | H | c-Pr | |
| 1-241 | c-Pr | c-Pr | Me | Me | Me | H | |
| 1-242 | c-Pr | c-Pr | Me | Me | Me | Me | |
| 1-243 | c-Pr | c-Pr | Me | Me | Me | c-Pr | |
| 1-244 | c-Pr | c-Pr | c-Pr | Me | H | H | |
| 1-245 | c-Pr | c-Pr | c-Pr | Me | H | Me | |
| 1-246 | c-Pr | c-Pr | c-Pr | Me | H | c-Pr | |
| 1-247 | c-Pr | c-Pr | c-Pr | Me | Me | H | |
| 1-248 | c-Pr | c-Pr | c-Pr | Me | Me | Me | |
| 1-249 | c-Pr | c-Pr | c-Pr | Me | Me | c-Pr | |
| 1-250 | c-Pr | c-Pr | —CH₂—OMe | Me | H | H | |
| 1-251 | c-Pr | c-Pr | —CH₂—OMe | Me | H | Me | |
| 1-252 | c-Pr | c-Pr | —CH₂—OMe | Me | H | c-Pr | |
| 1-253 | c-Pr | c-Pr | —CH₂—OMe | Me | Me | H | |
| 1-254 | c-Pr | c-Pr | —CH₂—OMe | Me | Me | Me | |
| 1-255 | c-Pr | c-Pr | —CH₂—OMe | Me | Me | c-Pr | |
| 1-256 | c-Pr | c-Pr | —(CH₂)₂— | | H | H | NMR |
| 1-257 | c-Pr | c-Pr | —(CH₂)₃— | | H | H | |
| 1-258 | c-Pr | c-Pr | —(CH₂)₂— | | H | Me | |
| 1-259 | c-Pr | c-Pr | —(CH₂)₃— | | H | Me | |
| 1-260 | c-Pr | c-Pr | —(CH₂)₂— | | H | c-Pr | |
| 1-261 | c-Pr | c-Pr | —(CH₂)₃— | | H | c-Pr | |
| 1-262 | c-Pr | c-Bu | —(CH₂)₃— | | H | H | |

TABLE 1-continued

Compounds of the formula (Ia)

(Ia)

| No. | R² | R³ | R⁴ | R⁵ | R⁶ | R⁷ | phys. data |
|---|---|---|---|---|---|---|---|
| 1-263 | c-Pr | c-Bu | —(CH₂)₃— | | H | Me | |
| 1-264 | c-Pr | c-Bu | —(CH₂)₃— | | H | c-Pr | |
| 1-265 | c-Pr | 1-Me-c-Pr | Me | Me | H | H | |
| 1-266 | c-Pr | 1-Me-c-Pr | Me | Me | Me | H | |
| 1-267 | c-Pr | 1-Me-c-Pr | Me | Me | Me | 1-Me-c-Pr | |
| 1-268 | c-Pr | 1-Me-c-Pr | c-Pr | Me | H | H | |
| 1-269 | c-Pr | 1-Me-c-Pr | c-Pr | Me | Me | H | |
| 1-270 | c-Pr | 1-Me-c-Pr | c-Pr | Me | Me | 1-Me-c-Pr | |
| 1-271 | c-Pr | 1-Me-c-Pr | —CH₂—OMe | Me | H | H | |
| 1-272 | c-Pr | 1-Me-c-Pr | —CH₂—OMe | Me | Me | H | |
| 1-273 | c-Pr | 1-Me-c-Pr | —CH₂—OMe | Me | Me | 1-Me-c-Pr | |
| 1-274 | c-Pr | 1-Me-c-Pr | —(CH₂)₂— | | H | H | |
| 1-275 | c-Pr | 1-Me-c-Pr | —(CH₂)₃— | | H | H | |
| 1-276 | c-Pr | 1-Me-c-Pr | —(CH₂)₂— | | Me | H | |
| 1-277 | c-Pr | 1-Me-c-Pr | —(CH₂)₂— | | Me | 1-Me-c-Pr | |
| 1-278 | c-Pr | 1-Cl-c-Pr | Me | Me | H | H | |
| 1-279 | c-Pr | 1-Cl-c-Pr | Me | Me | Me | H | |
| 1-280 | c-Pr | 1-Cl-c-Pr | Me | Me | Me | 1-Cl-c-Pr | |
| 1-281 | c-Pr | 1-Cl-c-Pr | c-Pr | Me | H | H | |
| 1-282 | c-Pr | 1-Cl-c-Pr | c-Pr | Me | Me | H | |
| 1-283 | c-Pr | 1-Cl-c-Pr | c-Pr | Me | Me | 1-Cl-c-Pr | |
| 1-284 | c-Pr | 1-Cl-c-Pr | —CH₂—OMe | Me | H | H | |
| 1-285 | c-Pr | 1-Cl-c-Pr | —CH₂—OMe | Me | Me | H | |
| 1-286 | c-Pr | 1-Cl-c-Pr | —CH₂—OMe | Me | Me | 1-Cl-c-Pr | |
| 1-287 | c-Pr | 1-Cl-c-Pr | —(CH₂)₂— | | H | H | |
| 1-288 | c-Pr | 1-Cl-c-Pr | —(CH₂)₃— | | H | H | |
| 1-289 | c-Pr | 1-Cl-c-Pr | —(CH₂)₂— | | Cl | H | |
| 1-290 | c-Pr | 1-Cl-c-Pr | —(CH₂)₂— | | Cl | 1-Cl-c-Pr | |
| 1-291 | c-Pr | 2,2-Me₂-c-Pr | Me | Me | H | H | |
| 1-292 | c-Pr | 2,2-Me₂-c-Pr | Me | Me | Me | H | |
| 1-293 | c-Pr | 2,2-Me₂-c-Pr | Me | Me | Me | 2,2-Me₂-c-Pr | |
| 1-294 | c-Pr | 2,2-Me₂-c-Pr | c-Pr | Me | H | H | |
| 1-295 | c-Pr | 2,2-Me₂-c-Pr | c-Pr | Me | Me | H | |
| 1-296 | c-Pr | 2,2-Me₂-c-Pr | c-Pr | Me | Me | 2,2-Me₂-c-Pr | |
| 1-297 | c-Pr | 2,2-Me₂-c-Pr | —CH₂—OMe | Me | H | H | |
| 1-298 | c-Pr | 2,2-Me₂-c-Pr | —CH₂—OMe | Me | Me | H | |
| 1-299 | c-Pr | 2,2-Me₂-c-Pr | —CH₂—OMe | Me | Me | 2,2-Me₂-c-Pr | |
| 1-300 | c-Pr | 2,2-Me₂-c-Pr | —(CH₂)₂— | | H | H | |
| 1-301 | c-Pr | 2,2-Me₂-c-Pr | —(CH₂)₃— | | H | H | |
| 1-302 | c-Pr | 2,2-Me₂-c-Pr | —CH₂—CMe₂— | | H | H | |
| 1-303 | c-Pr | 2,2-Me₂-c-Pr | —CH₂—CMe₂— | | H | 2,2-Me₂-c-Pr | |
| 1-304 | c-Pr | 2,2-Cl₂-c-Pr | Me | Me | H | H | |
| 1-305 | c-Pr | 2,2-Cl₂-c-Pr | Me | Me | Me | H | |
| 1-306 | c-Pr | 2,2-Cl₂-c-Pr | Me | Me | Me | 2,2-Cl₂-c-Pr | |
| 1-307 | c-Pr | 2,2-Cl₂-c-Pr | c-Pr | Me | H | H | |
| 1-308 | c-Pr | 2,2-Cl₂-c-Pr | c-Pr | Me | Me | H | |
| 1-309 | c-Pr | 2,2-Cl₂-c-Pr | c-Pr | Me | Me | 2,2-Cl₂-c-Pr | |
| 1-310 | c-Pr | 2,2-Cl₂-c-Pr | —CH₂—OMe | Me | H | H | |
| 1-311 | c-Pr | 2,2-Cl₂-c-Pr | —CH₂—OMe | Me | Me | H | |
| 1-312 | c-Pr | 2,2-Cl₂-c-Pr | —CH₂—OMe | Me | Me | 2,2-Cl₂-c-Pr | |
| 1-313 | c-Pr | 2,2-Cl₂-c-Pr | —(CH₂)₂— | | H | H | |
| 1-314 | c-Pr | 2,2-Cl₂-c-Pr | —(CH₂)₃— | | H | H | |
| 1-315 | c-Pr | 2,2-Cl₂-c-Pr | —CH₂—CCl₂— | | H | H | |
| 1-316 | c-Pr | 2,2-Cl₂-c-Pr | —CH₂—CCl₂— | | H | 2,2-Cl₂-c-Pr | |
| 1-317 | CHFCH₃ | c-Pr | Me | Me | H | H | NMR |
| 1-318 | CHFCH₃ | c-Pr | Me | Me | H | Me | |
| 1-319 | CHFCH₃ | c-Pr | Me | Me | H | c-Pr | |
| 1-320 | CHFCH₃ | c-Pr | Me | Me | Me | H | |
| 1-321 | CHFCH₃ | c-Pr | Me | Me | Me | Me | |
| 1-322 | CHFCH₃ | c-Pr | Me | Me | Me | c-Pr | |
| 1-323 | CHFCH₃ | c-Pr | c-Pr | Me | H | H | |
| 1-324 | CHFCH₃ | c-Pr | c-Pr | Me | H | Me | |
| 1-325 | CHFCH₃ | c-Pr | c-Pr | Me | H | c-Pr | |
| 1-326 | CHFCH₃ | c-Pr | c-Pr | Me | Me | H | |
| 1-327 | CHFCH₃ | c-Pr | c-Pr | Me | Me | Me | |

TABLE 1-continued

Compounds of the formula (Ia)

$$\text{(Ia)}$$

Structure: triazine with $R^2$ at one position, $NH_2$ at another, and NH-C($R^7$)($R^3$)-C($R^4$)($R^6$)($R^5$) side chain with dashed ring closures.

| No. | $R^2$ | $R^3$ | $R^4$ | $R^5$ | $R^6$ | $R^7$ | phys. data |
|---|---|---|---|---|---|---|---|
| 1-328 | CHFCH₃ | c-Pr | c-Pr | Me | Me | c-Pr | |
| 1-329 | CHFCH₃ | c-Pr | —CH₂—OMe | Me | H | H | |
| 1-330 | CHFCH₃ | c-Pr | —CH₂—OMe | Me | H | Me | |
| 1-331 | CHFCH₃ | c-Pr | —CH₂—OMe | Me | H | c-Pr | |
| 1-332 | CHFCH₃ | c-Pr | —CH₂—OMe | Me | Me | H | |
| 1-333 | CHFCH₃ | c-Pr | —CH₂—OMe | Me | Me | Me | |
| 1-334 | CHFCH₃ | c-Pr | —CH₂—OMe | Me | Me | c-Pr | |
| 1-335 | CHFCH₃ | c-Pr | —(CH₂)₂— | | H | H | NMR |
| 1-336 | CHFCH₃ | c-Pr | —(CH₂)₃— | | H | H | |
| 1-337 | CHFCH₃ | c-Pr | —(CH₂)₂— | | H | Me | |
| 1-338 | CHFCH₃ | c-Pr | —(CH₂)₃— | | H | Me | |
| 1-339 | CHFCH₃ | c-Pr | —(CH₂)₂— | | H | c-Pr | |
| 1-340 | CHFCH₃ | c-Pr | —(CH₂)₃— | | H | c-Pr | |
| 1-341 | CHFCH₃ | c-Bu | —(CH₂)₃— | | H | H | NMR |
| 1-342 | CHFCH₃ | c-Bu | —(CH₂)₃— | | H | Me | |
| 1-343 | CHFCH₃ | c-Bu | —(CH₂)₃— | | H | c-Pr | |
| 1-344 | CHFCH₃ | 1-Me-c-Pr | Me | Me | H | H | |
| 1-345 | CHFCH₃ | 1-Me-c-Pr | Me | Me | Me | H | |
| 1-346 | CHFCH₃ | 1-Me-c-Pr | Me | Me | Me | 1-Me-c-Pr | |
| 1-347 | CHFCH₃ | 1-Me-c-Pr | c-Pr | Me | H | H | |
| 1-348 | CHFCH₃ | 1-Me-c-Pr | c-Pr | Me | Me | H | |
| 1-349 | CHFCH₃ | 1-Me-c-Pr | c-Pr | Me | Me | 1-Me-c-Pr | |
| 1-350 | CHFCH₃ | 1-Me-c-Pr | —CH₂—OMe | Me | H | H | |
| 1-351 | CHFCH₃ | 1-Me-c-Pr | —CH₂—OMe | Me | Me | H | |
| 1-352 | CHFCH₃ | 1-Me-c-Pr | —CH₂—OMe | Me | Me | -Me-c-Pr | |
| 1-353 | CHFCH₃ | 1-Me-c-Pr | —(CH₂)₂— | | H | H | |
| 1-354 | CHFCH₃ | 1-Me-c-Pr | —(CH₂)₃— | | H | H | |
| 1-355 | CHFCH₃ | 1-Me-c-Pr | —(CH₂)₂— | | Me | H | |
| 1-356 | CHFCH₃ | 1-Me-c-Pr | —(CH₂)₂— | | Me | 1-Me-c-Pr | |
| 1-357 | CHFCH₃ | 1-Cl-c-Pr | Me | Me | H | H | |
| 1-358 | CHFCH₃ | 1-Cl-c-Pr | Me | Me | Me | H | |
| 1-359 | CHFCH₃ | 1-Cl-c-Pr | Me | Me | Me | 1-Cl-c-Pr | |
| 1-360 | CHFCH₃ | 1-Cl-c-Pr | c-Pr | Me | H | H | |
| 1-361 | CHFCH₃ | 1-Cl-c-Pr | c-Pr | Me | Me | H | |
| 1-362 | CHFCH₃ | 1-Cl-c-Pr | c-Pr | Me | Me | 1-Cl-c-Pr | |
| 1-363 | CHFCH₃ | 1-Cl-c-Pr | —CH₂—OMe | Me | H | H | |
| 1-364 | CHFCH₃ | 1-Cl-c-Pr | —CH₂—OMe | Me | Me | H | |
| 1-365 | CHFCH₃ | 1-Cl-c-Pr | —CH₂—OMe | Me | Me | 1-Cl-c-Pr | |
| 1-366 | CHFCH₃ | 1-Cl-c-Pr | —(CH₂)₂— | | H | H | |
| 1-367 | CHFCH₃ | 1-Cl-c-Pr | —(CH₂)₃— | | H | H | |
| 1-368 | CHFCH₃ | 1-Cl-c-Pr | —(CH₂)₂— | | Cl | H | |
| 1-369 | CHFCH₃ | 1-Cl-c-Pr | —(CH₂)₂— | | Cl | 1-Cl-c-Pr | |
| 1-370 | CHFCH₃ | 2,2-Me₂-c-Pr | Me | Me | H | H | |
| 1-371 | CHFCH₃ | 2,2-Me₂-c-Pr | Me | Me | Me | H | |
| 1-372 | CHFCH₃ | 2,2-Me₂-c-Pr | Me | Me | Me | 2,2-Me₂-c-Pr | |
| 1-373 | CHFCH₃ | 2,2-Me₂-c-Pr | c-Pr | Me | H | H | |
| 1-374 | CHFCH₃ | 2,2-Me₂-c-Pr | c-Pr | Me | Me | H | |
| 1-375 | CHFCH₃ | 2,2-Me₂-c-Pr | c-Pr | Me | Me | 2,2-Me₂-c-Pr | |
| 1-376 | CHFCH₃ | 2,2-Me₂-c-Pr | —CH₂—OMe | Me | H | H | |
| 1-377 | CHFCH₃ | 2,2-Me₂-c-Pr | —CH₂—OMe | Me | Me | H | |
| 1-378 | CHFCH₃ | 2,2-Me₂-c-Pr | —CH₂—OMe | Me | Me | 2,2-Me₂-c-Pr | |
| 1-379 | CHFCH₃ | 2,2-Me₂-c-Pr | —(CH₂)₂— | | H | H | |
| 1-380 | CHFCH₃ | 2,2-Me₂-c-Pr | —(CH₂)₃— | | H | H | |
| 1-381 | CHFCH₃ | 2,2-Me₂-c-Pr | —CH₂—CMe₂— | | H | H | |
| 1-382 | CHFCH₃ | 2,2-Me₂-c-Pr | —CH₂—OMe₂— | | H | 2,2-Me₂-c-Pr | |
| 1-383 | CHFCH₃ | 2,2-Cl₂-c-Pr | Me | Me | H | H | |
| 1-384 | CHFCH₃ | 2,2-Cl₂-c-Pr | Me | Me | Me | H | |
| 1-385 | CHFCH₃ | 2,2-Cl₂-c-Pr | Me | Me | Me | 2,2-Cl₂-c-Pr | |
| 1-386 | CHFCH₃ | 2,2-Cl₂-c-Pr | c-Pr | Me | H | H | |
| 1-387 | CHFCH₃ | 2,2-Cl₂-c-Pr | c-Pr | Me | Me | H | |
| 1-388 | CHFCH₃ | 2,2-Cl₂-c-Pr | c-Pr | Me | Me | 2,2-Cl₂-c-Pr | |
| 1-389 | CHFCH₃ | 2,2-Cl₂-c-Pr | —CH₂—OMe | Me | H | H | |
| 1-390 | CHFCH₃ | 2,2-Cl₂-c-Pr | —CH₂—OMe | Me | Me | H | |
| 1-391 | CHFCH₃ | 2,2-Cl₂-c-Pr | —CH₂—OMe | Me | Me | 2,2-Cl₂-c-Pr | |
| 1-392 | CHFCH₃ | 2,2-Cl₂-c-Pr | —(CH₂)₂— | | H | H | |

TABLE 1-continued

Compounds of the formula (Ia)

$$\text{(Ia)}$$

| No. | R² | R³ | R⁴ | R⁵ | R⁶ | R⁷ | phys. data |
|---|---|---|---|---|---|---|---|
| 1-393 | CHFCH₃ | 2,2-Cl₂-c-Pr | —(CH₂)₃— | | H | H | |
| 1-394 | CHFCH₃ | 2,2-Cl₂-c-Pr | —CH₂—CCl₂— | | H | H | |
| 1-395 | CHFCH₃ | 2,2-Cl₂-c-Pr | —CH₂—CCl₂— | | H | 2,2-Cl₂-c-Pr | |
| 1-396 | CHFC₂H₅ | c-Pr | Me | Me | H | H | |
| 1-397 | CHFC₂H₅ | c-Pr | Me | Me | H | Me | |
| 1-398 | CHFC₂H₅ | c-Pr | Me | Me | H | c-Pr | |
| 1-399 | CHFC₂H₅ | c-Pr | Me | Me | Me | H | |
| 1-400 | CHFC₂H₅ | c-Pr | Me | Me | Me | Me | |
| 1-401 | CHFC₂H₅ | c-Pr | Me | Me | Me | c-Pr | |
| 1-402 | CHFC₂H₅ | c-Pr | c-Pr | Me | H | H | |
| 1-403 | CHFC₂H₅ | c-Pr | c-Pr | Me | H | Me | |
| 1-404 | CHFC₂H₅ | c-Pr | c-Pr | Me | H | c-Pr | |
| 1-405 | CHFC₂H₅ | c-Pr | c-Pr | Me | Me | H | |
| 1-406 | CHFC₂H₅ | c-Pr | c-Pr | Me | Me | Me | |
| 1-407 | CHFC₂H₅ | c-Pr | c-Pr | Me | Me | c-Pr | |
| 1-408 | CHFC₂H₅ | c-Pr | —CH₂—OMe | Me | H | H | |
| 1-409 | CHFC₂H₅ | c-Pr | —CH₂—OMe | Me | H | Me | |
| 1-410 | CHFC₂H₅ | c-Pr | —CH₂—OMe | Me | H | c-Pr | |
| 1-411 | CHFC₂H₅ | c-Pr | —CH₂—OMe | Me | Me | H | |
| 1-412 | CHFC₂H₅ | c-Pr | —CH₂—OMe | Me | Me | Me | |
| 1-413 | CHFC₂H₅ | c-Pr | —CH₂—OMe | Me | Me | c-Pr | |
| 1-414 | CHFC₂H₅ | c-Pr | —(CH₂)₂— | | H | H | NMR |
| 1-415 | CHFC₂H₅ | c-Pr | —(CH₂)₃— | | H | H | |
| 1-416 | CHFC₂H₅ | c-Pr | —(CH₂)₂— | | H | Me | |
| 1-417 | CHFC₂H₅ | c-Pr | —(CH₂)₃— | | H | Me | |
| 1-418 | CHFC₂H₅ | c-Pr | —(CH₂)₂— | | H | c-Pr | |
| 1-419 | CHFC₂H₅ | c-Pr | —(CH₂)₃— | | H | c-Pr | |
| 1-420 | CHFC₂H₅ | c-Bu | —(CH₂)₃— | | H | H | NMR |
| 1-421 | CHFC₂H₅ | c-Bu | —(CH₂)₃— | | H | Me | |
| 1-422 | CHFC₂H₅ | c-Bu | —(CH₂)₃— | | H | c-Pr | |
| 1-423 | CHFC₂H₅ | 1-Me-c-Pr | Me | Me | H | H | |
| 1-424 | CHFC₂H₅ | 1-Me-c-Pr | Me | Me | Me | H | |
| 1-425 | CHFC₂H₅ | 1-Me-c-Pr | Me | Me | Me | 1-Me-c-Pr | |
| 1-426 | CHFC₂H₅ | 1-Me-c-Pr | c-Pr | Me | H | H | |
| 1-427 | CHFC₂H₅ | 1-Me-c-Pr | c-Pr | Me | Me | H | |
| 1-428 | CHFC₂H₅ | 1-Me-c-Pr | c-Pr | Me | Me | 1-Me-c-Pr | |
| 1-429 | CHFC₂H₅ | 1-Me-c-Pr | —CH₂—OMe | Me | H | H | |
| 1-430 | CHFC₂H₅ | 1-Me-c-Pr | —CH₂—OMe | Me | Me | H | |
| 1-431 | CHFC₂H₅ | 1-Me-c-Pr | —CH₂—OMe | Me | Me | 1-Me-c-Pr | |
| 1-432 | CHFC₂H₅ | 1-Me-c-Pr | —(CH₂)₂— | | H | H | |
| 1-433 | CHFC₂H₅ | 1-Me-c-Pr | —(CH₂)₃— | | H | H | |
| 1-434 | CHFC₂H₅ | 1-Me-c-Pr | —(CH₂)₂— | | Me | H | |
| 1-435 | CHFC₂H₅ | 1-Me-c-Pr | —(CH₂)₂— | | Me | 1-Me-c-Pr | |
| 1-436 | CHFC₂H₅ | 1-Cl-c-Pr | Me | Me | H | H | |
| 1-437 | CHFC₂H₅ | 1-Cl-c-Pr | Me | Me | Me | H | |
| 1-438 | CHFC₂H₅ | 1-Cl-c-Pr | Me | Me | Me | 1-Cl-c-Pr | |
| 1-439 | CHFC₂H₅ | 1-Cl-c-Pr | c-Pr | Me | H | H | |
| 1-440 | CHFC₂H₅ | 1-Cl-c-Pr | c-Pr | Me | Me | H | |
| 1-441 | CHFC₂H₅ | 1-Cl-c-Pr | c-Pr | Me | Me | 1-Cl-c-Pr | |
| 1-442 | CHFC₂H₅ | 1-Cl-c-Pr | —CH₂—OMe | Me | H | H | |
| 1-443 | CHFC₂H₅ | 1-Cl-c-Pr | —CH₂—OMe | Me | Me | H | |
| 1-444 | CHFC₂H₅ | 1-Cl-c-Pr | —CH₂—OMe | Me | Me | 1-Cl-c-Pr | |
| 1-445 | CHFC₂H₅ | 1-Cl-c-Pr | —(CH₂)₂— | | H | H | |
| 1-446 | CHFC₂H₅ | 1-Cl-c-Pr | —(CH₂)₃— | | H | H | |
| 1-447 | CHFC₂H₅ | 1-Cl-c-Pr | —(CH₂)₂— | | Cl | H | |
| 1-448 | CHFC₂H₅ | 1-Cl-c-Pr | —(CH₂)₂— | | Cl | 1-Cl-c-Pr | |
| 1-449 | CHFC₂H₅ | 2,2-Me₂-c-Pr | Me | Me | H | H | |
| 1-450 | CHFC₂H₅ | 2,2-Me₂-c-Pr | Me | Me | Me | H | |
| 1-451 | CHFC₂H₅ | 2,2-Me₂-c-Pr | Me | Me | Me | 2,2-Me₂-c-Pr | |
| 1-452 | CHFC₂H₅ | 2,2-Me₂-c-Pr | c-Pr | Me | H | H | |
| 1-453 | CHFC₂H₅ | 2,2-Me₂-c-Pr | c-Pr | Me | Me | H | |
| 1-454 | CHFC₂H₅ | 2,2-Me₂-c-Pr | c-Pr | Me | Me | 2,2-Me₂-c-Pr | |
| 1-455 | CHFC₂H₅ | 2,2-Me₂-c-Pr | —CH₂—OMe | Me | H | H | |
| 1-456 | CHFC₂H₅ | 2,2-Me₂-c-Pr | —CH₂—OMe | Me | Me | H | |
| 1-457 | CHFC₂H₅ | 2,2-Me₂-c-Pr | —CH₂—OMe | Me | Me | 2,2-Me₂-c-Pr | |

TABLE 1-continued

Compounds of the formula (Ia)

$$\text{(Ia)}$$

[Structure of formula (Ia): a 1,3,5-triazine ring bearing R² at one position, NH₂ at another, and NH-C(R³)(R⁷)-C(R⁴)(R⁶)- with R⁵ shown as dashed bonds indicating optional ring formation]

| No. | R² | R³ | R⁴ | R⁵ | R⁶ | R⁷ | phys. data |
|---|---|---|---|---|---|---|---|
| 1-458 | CHFC₂H₅ | 2,2-Me₂-c-Pr | —(CH₂)₂— | | H | H | |
| 1-459 | CHFC₂H₅ | 2,2-Me₂-c-Pr | —(CH₂)₃— | | H | H | |
| 1-460 | CHFC₂H₅ | 2,2-Me₂-c-Pr | —CH₂—CMe₂— | | H | H | |
| 1-461 | CHFC₂H₅ | 2,2-Me₂-c-Pr | —CH₂—CMe₂— | | H | 2,2-Me₂-c-Pr | |
| 1-462 | CHFC₂H₅ | 2,2-Cl₂-c-Pr | Me | Me | H | H | |
| 1-463 | CHFC₂H₅ | 2,2-Cl₂-c-Pr | Me | Me | Me | H | |
| 1-464 | CHFC₂H₅ | 2,2-Cl₂-c-Pr | Me | Me | Me | 2,2-Cl₂-c-Pr | |
| 1-465 | CHFC₂H₅ | 2,2-Cl₂-c-Pr | c-Pr | Me | H | H | |
| 1-466 | CHFC₂H₅ | 2,2-Cl₂-c-Pr | c-Pr | Me | Me | H | |
| 1-467 | CHFC₂H₅ | 2,2-Cl₂-c-Pr | c-Pr | Me | Me | 2,2-Cl₂-c-Pr | |
| 1-468 | CHFC₂H₅ | 2,2-Cl₂-c-Pr | —CH₂—OMe | Me | H | H | |
| 1-469 | CHFC₂H₅ | 2,2-Cl₂-c-Pr | —CH₂—OMe | Me | Me | H | |
| 1-470 | CHFC₂H₅ | 2,2-Cl₂-c-Pr | —CH₂—OMe | Me | Me | 2,2-Cl₂-c-Pr | |
| 1-471 | CHFC₂H₅ | 2,2-Cl₂-c-Pr | —(CH₂)₂— | | H | H | |
| 1-472 | CHFC₂H₅ | 2,2-Cl₂-c-Pr | —(CH₂)₃— | | H | H | |
| 1-473 | CHFC₂H₅ | 2,2-Cl₂-c-Pr | —CH₂—CCl₂— | | H | H | |
| 1-474 | CHFC₂H₅ | 2,2-Cl₂-c-Pr | —CH₂—CCl₂— | | H | 2,2-Cl₂-c-Pr | |
| 1-475 | CF(CH₃)₂ | c-Pr | Me | Me | H | H | NMR |
| 1-476 | CF(CH₃)₂ | c-Pr | Me | Me | H | Me | |
| 1-477 | CF(CH₃)₂ | c-Pr | Me | Me | H | c-Pr | |
| 1-478 | CF(CH₃)₂ | c-Pr | Me | Me | Me | H | |
| 1-479 | CF(CH₃)₂ | c-Pr | Me | Me | Me | Me | |
| 1-480 | CF(CH₃)₂ | c-Pr | Me | Me | Me | c-Pr | |
| 1-481 | CF(CH₃)₂ | c-Pr | c-Pr | Me | H | H | |
| 1-482 | CF(CH₃)₂ | c-Pr | c-Pr | Me | H | Me | |
| 1-483 | CF(CH₃)₂ | c-Pr | c-Pr | Me | H | c-Pr | |
| 1-484 | CF(CH₃)₂ | c-Pr | c-Pr | Me | Me | H | |
| 1-485 | CF(CH₃)₂ | c-Pr | c-Pr | Me | Me | Me | |
| 1-486 | CF(CH₃)₂ | c-Pr | c-Pr | Me | Me | c-Pr | |
| 1-487 | CF(CH₃)₂ | c-Pr | —CH₂—OMe | Me | H | H | |
| 1-488 | CF(CH₃)₂ | c-Pr | —CH₂—OMe | Me | H | Me | |
| 1-489 | CF(CH₃)₂ | c-Pr | —CH₂—OMe | Me | H | c-Pr | |
| 1-490 | CF(CH₃)₂ | c-Pr | —CH₂—OMe | Me | Me | H | |
| 1-491 | CF(CH₃)₂ | c-Pr | —CH₂—OMe | Me | Me | Me | |
| 1-492 | CF(CH₃)₂ | c-Pr | —CH₂—OMe | Me | Me | c-Pr | |
| 1-493 | CF(CH₃)₂ | c-Pr | —(CH₂)₂— | | H | H | NMR |
| 1-494 | CF(CH₃)₂ | c-Pr | —(CH₂)₃— | | H | H | |
| 1-495 | CF(CH₃)₂ | c-Pr | —(CH₂)₂— | | H | Me | |
| 1-496 | CF(CH₃)₂ | c-Pr | —(CH₂)₃— | | H | Me | |
| 1-497 | CF(CH₃)₂ | c-Pr | —(CH₂)₂— | | H | c-Pr | |
| 1-498 | CF(CH₃)₂ | c-Pr | —(CH₂)₃— | | H | c-Pr | |
| 1-499 | CF(CH₃)₂ | c-Bu | —(CH₂)₃— | | H | H | NMR |
| 1-500 | CF(CH₃)₂ | c-Bu | —(CH₂)₃— | | H | Me | |
| 1-501 | CF(CH₃)₂ | c-Bu | —(CH₂)₃— | | H | c-Pr | |
| 1-502 | CF(CH₃)₂ | 1-Me-c-Pr | Me | Me | H | H | |
| 1-503 | CF(CH₃)₂ | 1-Me-c-Pr | Me | Me | Me | H | |
| 1-504 | CF(CH₃)₂ | 1-Me-c-Pr | Me | Me | Me | 1-Me-c-Pr | |
| 1-505 | CF(CH₃)₂ | 1-Me-c-Pr | c-Pr | Me | H | H | |
| 1-506 | CF(CH₃)₂ | 1-Me-c-Pr | c-Pr | Me | Me | H | |
| 1-507 | CF(CH₃)₂ | 1-Me-c-Pr | c-Pr | Me | Me | 1-Me-c-Pr | |
| 1-508 | CF(CH₃)₂ | 1-Me-c-Pr | —CH₂—OMe | Me | H | H | |
| 1-509 | CF(CH₃)₂ | 1-Me-c-Pr | —CH₂—OMe | Me | Me | H | |
| 1-510 | CF(CH₃)₂ | 1-Me-c-Pr | —CH₂—OMe | Me | Me | 1-Me-c-Pr | |
| 1-511 | CF(CH₃)₂ | 1-Me-c-Pr | —(CH₂)₂— | | H | H | |
| 1-512 | CF(CH₃)₂ | 1-Me-c-Pr | —(CH₂)₃— | | H | H | |
| 1-513 | CF(CH₃)₂ | 1-Me-c-Pr | —(CH₂)₂— | | Me | H | |
| 1-514 | CF(CH₃)₂ | 1-Me-c-Pr | —(CH₂)₂— | | Me | 1-Me-c-Pr | |
| 1-515 | CF(CH₃)₂ | 1-Cl-c-Pr | Me | Me | H | H | |
| 1-516 | CF(CH₃)₂ | 1-Cl-c-Pr | Me | Me | Me | H | |
| 1-517 | CF(CH₃)₂ | 1-Cl-c-Pr | Me | Me | Me | 1-Cl-c-Pr | |
| 1-518 | CF(CH₃)₂ | 1-Cl-c-Pr | c-Pr | Me | H | H | |
| 1-519 | CF(CH₃)₂ | 1-Cl-c-Pr | c-Pr | Me | Me | H | |
| 1-520 | CF(CH₃)₂ | 1-Cl-c-Pr | c-Pr | Me | Me | 1-Cl-c-Pr | |
| 1-521 | CF(CH₃)₂ | 1-Cl-c-Pr | —CH₂—OMe | Me | H | H | |
| 1-522 | CF(CH₃)₂ | 1-Cl-c-Pr | —CH₂—OMe | Me | Me | H | |

TABLE 1-continued

Compounds of the formula (Ia)

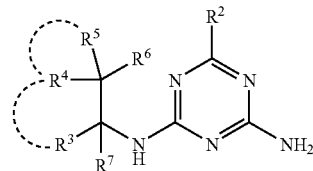

(Ia)

| No. | $R^2$ | $R^3$ | $R^4$ | $R^5$ | $R^6$ | $R^7$ | phys. data |
|---|---|---|---|---|---|---|---|
| 1-523 | $CF(CH_3)_2$ | 1-Cl-c-Pr | —$CH_2$—OMe | Me | Me | 1-Cl-c-Pr | |
| 1-524 | $CF(CH_3)_2$ | 1-Cl-c-Pr | —$(CH_2)_2$— | | H | H | |
| 1-525 | $CF(CH_3)_2$ | 1-Cl-c-Pr | —$(CH_2)_3$— | | H | H | |
| 1-526 | $CF(CH_3)_2$ | 1-Cl-c-Pr | —$(CH_2)_2$— | | Cl | H | |
| 1-527 | $CF(CH_3)_2$ | 1-Cl-c-Pr | —$(CH_2)_2$— | | Cl | 1-Cl-c-Pr | |
| 1-528 | $CF(CH_3)_2$ | 2,2-$Me_2$-c-Pr | Me | Me | H | H | |
| 1-529 | $CF(CH_3)_2$ | 2,2-$Me_2$-c-Pr | Me | Me | Me | H | |
| 1-530 | $CF(CH_3)_2$ | 2,2-$Me_2$-c-Pr | Me | Me | Me | 2,2-$Me_2$-c-Pr | |
| 1-531 | $CF(CH_3)_2$ | 2,2-$Me_2$-c-Pr | c-Pr | Me | H | H | |
| 1-532 | $CF(CH_3)_2$ | 2,2-$Me_2$-c-Pr | c-Pr | Me | Me | H | |
| 1-533 | $CF(CH_3)_2$ | 2,2-$Me_2$-c-Pr | c-Pr | Me | Me | 2,2-$Me_2$-c-Pr | |
| 1-534 | $CF(CH_3)_2$ | 2,2-$Me_2$-c-Pr | —$CH_2$—OMe | Me | H | H | |
| 1-535 | $CF(CH_3)_2$ | 2,2-$Me_2$-c-Pr | —$CH_2$—OMe | Me | Me | H | |
| 1-536 | $CF(CH_3)_2$ | 2,2-$Me_2$-c-Pr | —$CH_2$—OMe | Me | Me | 2,2-$Me_2$-c-Pr | |
| 1-537 | $CF(CH_3)_2$ | 2,2-$Me_2$-c-Pr | —$(CH_2)_2$— | | H | H | |
| 1-538 | $CF(CH_3)_2$ | 2,2-$Me_2$-c-Pr | —$(CH_2)_3$— | | H | H | |
| 1-539 | $CF(CH_3)_2$ | 2,2-$Me_2$-c-Pr | —$CH_2$—$CMe_2$— | | H | H | |
| 1-540 | $CF(CH_3)_2$ | 2,2-$Me_2$-c-Pr | —$CH_2$—$CMe_2$— | | H | 2,2-$Me_2$-c-Pr | |
| 1-541 | $CF(CH_3)_2$ | 2,2-$Cl_2$-c-Pr | Me | Me | H | H | |
| 1-542 | $CF(CH_3)_2$ | 2,2-$Cl_2$-c-Pr | Me | Me | Me | H | |
| 1-543 | $CF(CH_3)_2$ | 2,2-$Cl_2$-c-Pr | Me | Me | Me | 2,2-$Cl_2$-c-Pr | |
| 1-544 | $CF(CH_3)_2$ | 2,2-$Cl_2$-c-Pr | c-Pr | Me | H | H | |
| 1-545 | $CF(CH_3)_2$ | 2,2-$Cl_2$-c-Pr | c-Pr | Me | Me | H | |
| 1-546 | $CF(CH_3)_2$ | 2,2-$Cl_2$-c-Pr | c-Pr | Me | Me | 2,2-$Cl_2$-c-Pr | |
| 1-547 | $CF(CH_3)_2$ | 2,2-$Cl_2$-c-Pr | —$CH_2$—OMe | Me | H | H | |
| 1-548 | $CF(CH_3)_2$ | 2,2-$Cl_2$-c-Pr | —$CH_2$—OMe | Me | Me | H | |
| 1-549 | $CF(CH_3)_2$ | 2,2-$Cl_2$-c-Pr | —$CH_2$—OMe | Me | Me | 2,2-$Cl_2$-c-Pr | |
| 1-550 | $CF(CH_3)_2$ | 2,2-$Cl_2$-c-Pr | —$(CH_2)_2$— | | H | H | |
| 1-551 | $CF(CH_3)_2$ | 2,2-$Cl_2$-c-Pr | —$(CH_2)_3$— | | H | H | |
| 1-552 | $CF(CH_3)_2$ | 2,2-$Cl_2$-c-Pr | —$CH_2$—$CCl_2$— | | H | H | |
| 1-553 | $CF(CH_3)_2$ | 2,2-$Cl_2$-c-Pr | —$CH_2$—$CCl_2$— | | H | 2,2-$Cl_2$-c-Pr | |
| 1-554 | 1-F-c-Pr | c-Pr | Me | Me | H | H | |
| 1-555 | 1-F-c-Pr | c-Pr | Me | Me | H | Me | |
| 1-556 | 1-F-c-Pr | c-Pr | Me | Me | H | c-Pr | |
| 1-557 | 1-F-c-Pr | c-Pr | Me | Me | Me | H | |
| 1-558 | 1-F-c-Pr | c-Pr | Me | Me | Me | Me | |
| 1-559 | 1-F-c-Pr | c-Pr | Me | Me | Me | c-Pr | |
| 1-560 | 1-F-c-Pr | c-Pr | c-Pr | Me | H | H | |
| 1-561 | 1-F-c-Pr | c-Pr | c-Pr | Me | H | Me | |
| 1-562 | 1-F-c-Pr | c-Pr | c-Pr | Me | H | c-Pr | |
| 1-563 | 1-F-c-Pr | c-Pr | c-Pr | Me | Me | H | |
| 1-564 | 1-F-c-Pr | c-Pr | c-Pr | Me | Me | Me | |
| 1-565 | 1-F-c-Pr | c-Pr | c-Pr | Me | Me | c-Pr | |
| 1-566 | 1-F-c-Pr | c-Pr | —$CH_2$—OMe | Me | H | H | |
| 1-567 | 1-F-c-Pr | c-Pr | —$CH_2$—OMe | Me | H | Me | |
| 1-568 | 1-F-c-Pr | c-Pr | —$CH_2$—OMe | Me | H | c-Pr | |
| 1-569 | 1-F-c-Pr | c-Pr | —$CH_2$—OMe | Me | Me | H | |
| 1-570 | 1-F-c-Pr | c-Pr | —$CH_2$—OMe | Me | Me | Me | |
| 1-571 | 1-F-c-Pr | c-Pr | —$CH_2$—OMe | Me | Me | c-Pr | |
| 1-572 | 1-F-c-Pr | c-Pr | —$(CH_2)_2$— | | H | H | NMR |
| 1-573 | 1-F-c-Pr | c-Pr | —$(CH_2)_3$— | | H | H | |
| 1-574 | 1-F-c-Pr | c-Pr | —$(CH_2)_2$— | | H | Me | |
| 1-575 | 1-F-c-Pr | c-Pr | —$(CH_2)_3$— | | H | Me | |
| 1-576 | 1-F-c-Pr | c-Pr | —$(CH_2)_2$— | | H | c-Pr | |
| 1-577 | 1-F-c-Pr | c-Pr | —$(CH_2)_3$— | | H | c-Pr | |
| 1-578 | 1-F-c-Pr | c-Bu | —$(CH_2)_3$— | | H | H | |
| 1-579 | 1-F-c-Pr | c-Bu | —$(CH_2)_3$— | | H | Me | |
| 1-580 | 1-F-c-Pr | c-Bu | —$(CH_2)_3$— | | H | c-Pr | |
| 1-581 | 1-F-c-Pr | 1-Me-c-Pr | Me | Me | H | H | |
| 1-582 | 1-F-c-Pr | 1-Me-c-Pr | Me | Me | Me | H | |
| 1-583 | 1-F-c-Pr | 1-Me-c-Pr | Me | Me | Me | 1-Me-c-Pr | |
| 1-584 | 1-F-c-Pr | 1-Me-c-Pr | c-Pr | Me | H | H | |
| 1-585 | 1-F-c-Pr | 1-Me-c-Pr | c-Pr | Me | Me | H | |
| 1-586 | 1-F-c-Pr | 1-Me-c-Pr | c-Pr | Me | Me | 1-Me-c-Pr | |
| 1-587 | 1-F-c-Pr | 1-Me-c-Pr | —$CH_2$—OMe | Me | H | H | |

TABLE 1-continued

Compounds of the formula (Ia)

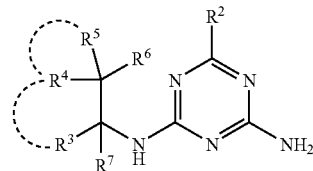

(Ia)

| No. | $R^2$ | $R^3$ | $R^4$ | $R^5$ | $R^6$ | $R^7$ | phys. data |
|---|---|---|---|---|---|---|---|
| 1-588 | 1-F-c-Pr | 1-Me-c-Pr | —CH$_2$—OMe | Me | Me | H | |
| 1-589 | 1-F-c-Pr | 1-Me-c-Pr | —CH$_2$—OMe | Me | Me | 1-Me-c-Pr | |
| 1-590 | 1-F-c-Pr | 1-Me-c-Pr | —(CH$_2$)$_2$— | | H | H | |
| 1-591 | 1-F-c-Pr | 1-Me-c-Pr | —(CH$_2$)$_3$— | | H | H | |
| 1-592 | 1-F-c-Pr | 1-Me-c-Pr | —(CH$_2$)$_2$— | | Me | H | |
| 1-593 | 1-F-c-Pr | 1-Me-c-Pr | —(CH$_2$)$_2$— | | Me | 1-Me-c-Pr | |
| 1-594 | 1-F-c-Pr | 1-Cl-c-Pr | Me | Me | H | H | |
| 1-595 | 1-F-c-Pr | 1-Cl-c-Pr | Me | Me | Me | H | |
| 1-596 | 1-F-c-Pr | 1-Cl-c-Pr | Me | Me | Me | 1-Cl-c-Pr | |
| 1-597 | 1-F-c-Pr | 1-Cl-c-Pr | c-Pr | Me | H | H | |
| 1-598 | 1-F-c-Pr | 1-Cl-c-Pr | c-Pr | Me | Me | H | |
| 1-599 | 1-F-c-Pr | 1-Cl-c-Pr | c-Pr | Me | Me | 1-Cl-c-Pr | |
| 1-600 | 1-F-c-Pr | 1-Cl-c-Pr | —CH$_2$—OMe | Me | H | H | |
| 1-601 | 1-F-c-Pr | 1-Cl-c-Pr | —CH$_2$—OMe | Me | Me | H | |
| 1-602 | 1-F-c-Pr | 1-Cl-c-Pr | —CH$_2$—OMe | Me | Me | 1-Cl-c-Pr | |
| 1-603 | 1-F-c-Pr | 1-Cl-c-Pr | —(CH$_2$)$_2$— | | H | H | |
| 1-604 | 1-F-c-Pr | 1-Cl-c-Pr | —(CH$_2$)$_3$— | | H | H | |
| 1-605 | 1-F-c-Pr | 1-Cl-c-Pr | —(CH$_2$)$_2$— | | Cl | H | |
| 1-606 | 1-F-c-Pr | 1-Cl-c-Pr | —(CH$_2$)$_2$— | | Cl | 1-Cl-c-Pr | |
| 1-607 | 1-F-c-Pr | 2,2-Me$_2$-c-Pr | Me | Me | H | H | |
| 1-608 | 1-F-c-Pr | 2,2-Me$_2$-c-Pr | Me | Me | Me | H | |
| 1-609 | 1-F-c-Pr | 2,2-Me$_2$-c-Pr | Me | Me | Me | 2,2-Me$_2$-c-Pr | |
| 1-610 | 1-F-c-Pr | 2,2-Me$_2$-c-Pr | c-Pr | Me | H | H | |
| 1-611 | 1-F-c-Pr | 2,2-Me$_2$-c-Pr | c-Pr | Me | Me | H | |
| 1-612 | 1-F-c-Pr | 2,2-Me$_2$-c-Pr | c-Pr | Me | Me | 2,2-Me$_2$-c-Pr | |
| 1-613 | 1-F-c-Pr | 2,2-Me$_2$-c-Pr | —CH$_2$—OMe | Me | H | H | |
| 1-614 | 1-F-c-Pr | 2,2-Me$_2$-c-Pr | —CH$_2$—OMe | Me | Me | H | |
| 1-615 | 1-F-c-Pr | 2,2-Me$_2$-c-Pr | —CH$_2$—OMe | Me | Me | 2,2-Me$_2$-c-Pr | |
| 1-616 | 1-F-c-Pr | 2,2-Me$_2$-c-Pr | —(CH$_2$)$_2$— | | H | H | |
| 1-617 | 1-F-c-Pr | 2,2-Me$_2$-c-Pr | —(CH$_2$)$_3$— | | H | H | |
| 1-618 | 1-F-c-Pr | 2,2-Me$_2$-c-Pr | —CH$_2$—CMe$_2$— | | H | H | |
| 1-619 | 1-F-c-Pr | 2,2-Me$_2$-c-Pr | —CH$_2$—CMe$_2$— | | H | 2,2-Me$_2$-c-Pr | |
| 1-620 | 1-F-c-Pr | 2,2-Cl$_2$-c-Pr | Me | Me | H | H | |
| 1-621 | 1-F-c-Pr | 2,2-Cl$_2$-c-Pr | Me | Me | Me | H | |
| 1-622 | 1-F-c-Pr | 2,2-Cl$_2$-c-Pr | Me | Me | Me | 2,2-Cl$_2$-c-Pr | |
| 1-623 | 1-F-c-Pr | 2,2-Me$_2$-c-Pr | c-Pr | Me | H | H | |
| 1-624 | 1-F-c-Pr | 2,2-Cl$_2$-c-Pr | c-Pr | Me | Me | H | |
| 1-625 | 1-F-c-Pr | 2,2-Cl$_2$-c-Pr | c-Pr | Me | Me | 2,2-Cl$_2$-c-Pr | |
| 1-626 | 1-F-c-Pr | 2,2-Cl$_2$-c-Pr | —CH$_2$—OMe | Me | H | H | |
| 1-627 | 1-F-c-Pr | 2,2-Cl$_2$-c-Pr | —CH$_2$—OMe | Me | Me | H | |
| 1-628 | 1-F-c-Pr | 2,2-Cl$_2$-c-Pr | —CH$_2$—OMe | Me | Me | 2,2-Cl$_2$-c-Pr | |
| 1-629 | 1-F-c-Pr | 2,2-Cl$_2$-c-Pr | —(CH$_2$)$_2$— | | H | H | |
| 1-630 | 1-F-c-Pr | 2,2-Cl$_2$-c-Pr | —(CH$_2$)$_3$— | | H | H | |
| 1-631 | 1-F-c-Pr | 2,2-Cl$_2$-c-Pr | —CH$_2$—CCl$_2$— | | H | H | |
| 1-632 | 1-F-c-Pr | 2,2-Cl$_2$-c-Pr | —CH$_2$—CCl$_2$— | | H | 2,2-Cl$_2$-c-Pr | |
| 1-633 | CHF2 | c-Pr | Me | Me | H | H | |
| 1-634 | CHF2 | c-Pr | Me | Me | H | Me | |
| 1-635 | CHF2 | c-Pr | Me | Me | H | c-Pr | |
| 1-636 | CHF2 | c-Pr | Me | Me | Me | H | |
| 1-637 | CHF2 | c-Pr | Me | Me | Me | Me | |
| 1-638 | CHF2 | c-Pr | Me | Me | Me | c-Pr | |
| 1-639 | CHF2 | c-Pr | c-Pr | Me | H | H | |
| 1-640 | CHF2 | c-Pr | c-Pr | Me | H | Me | |
| 1-641 | CHF2 | c-Pr | c-Pr | Me | H | c-Pr | |
| 1-642 | CHF2 | c-Pr | c-Pr | Me | Me | H | |
| 1-643 | CHF2 | c-Pr | c-Pr | Me | Me | Me | |
| 1-644 | CHF2 | c-Pr | c-Pr | Me | Me | c-Pr | |
| 1-645 | CHF2 | c-Pr | —CH$_2$—OMe | Me | H | H | |
| 1-646 | CHF2 | c-Pr | —CH$_2$—OMe | Me | H | Me | |
| 1-647 | CHF2 | c-Pr | —CH$_2$—OMe | Me | H | c-Pr | |
| 1-648 | CHF2 | c-Pr | —CH$_2$—OMe | Me | Me | H | |
| 1-649 | CHF2 | c-Pr | —CH$_2$—OMe | Me | Me | Me | |
| 1-650 | CHF2 | c-Pr | —CH$_2$—OMe | Me | Me | c-Pr | |
| 1-651 | CHF2 | c-Pr | —(CH$_2$)$_2$— | | H | H | NMR |
| 1-652 | CHF2 | c-Pr | —(CH$_2$)$_3$— | | H | H | |

TABLE 1-continued

Compounds of the formula (Ia)

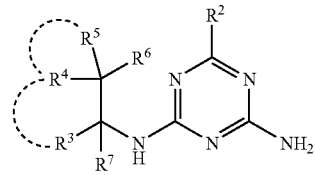

| No. | R² | R³ | R⁴ | R⁵ | R⁶ | R⁷ | phys. data |
|---|---|---|---|---|---|---|---|
| 1-653 | CHF2 | c-Pr | —(CH₂)₂— | | H | Me | |
| 1-654 | CHF2 | c-Pr | —(CH₂)₃— | | H | Me | |
| 1-655 | CHF2 | c-Pr | —(CH₂)₂— | | H | c-Pr | |
| 1-656 | CHF2 | c-Pr | —(CH₂)₃— | | H | c-Pr | |
| 1-657 | CHF2 | c-Bu | —(CH₂)₃— | | H | H | |
| 1-658 | CHF2 | c-Bu | —(CH₂)₃— | | H | Me | |
| 1-659 | CHF2 | c-Bu | —(CH₂)₃— | | H | c-Pr | |
| 1-660 | CHF2 | 1-Me-c-Pr | Me | Me | H | H | |
| 1-661 | CHF2 | 1-Me-c-Pr | Me | Me | Me | H | |
| 1-662 | CHF2 | 1-Me-c-Pr | Me | Me | Me | 1-Me-c-Pr | |
| 1-663 | CHF2 | 1-Me-c-Pr | c-Pr | Me | H | H | |
| 1-664 | CHF2 | 1-Me-c-Pr | c-Pr | Me | Me | H | |
| 1-665 | CHF2 | 1-Me-c-Pr | c-Pr | Me | Me | 1-Me-c-Pr | |
| 1-666 | CHF2 | 1-Me-c-Pr | —CH₂—OMe | Me | H | H | |
| 1-667 | CHF2 | 1-Me-c-Pr | —CH₂—OMe | Me | Me | H | |
| 1-668 | CHF2 | 1-Me-c-Pr | —CH₂—OMe | Me | Me | 1-Me-c-Pr | |
| 1-669 | CHF2 | 1-Me-c-Pr | —(CH₂)₂— | | H | H | |
| 1-670 | CHF2 | 1-Me-c-Pr | —(CH₂)₃— | | H | H | |
| 1-671 | CHF2 | 1-Me-c-Pr | —(CH₂)₂— | | Me | H | |
| 1-672 | CHF2 | 1-Me-c-Pr | —(CH₂)₂— | | Me | 1-Me-c-Pr | |
| 1-673 | CHF2 | 1-Cl-c-Pr | Me | Me | H | H | |
| 1-674 | CHF2 | 1-Cl-c-Pr | Me | Me | Me | H | |
| 1-675 | CHF2 | 1-Cl-c-Pr | Me | Me | Me | 1-Cl-c-Pr | |
| 1-676 | CHF2 | 1-Cl-c-Pr | c-Pr | Me | H | H | |
| 1-677 | CHF2 | 1-Cl-c-Pr | c-Pr | Me | Me | H | |
| 1-678 | CHF2 | 1-Cl-c-Pr | c-Pr | Me | Me | 1-Cl-c-Pr | |
| 1-679 | CHF2 | 1-Cl-c-Pr | —CH₂—OMe | Me | H | H | |
| 1-680 | CHF2 | 1-Cl-c-Pr | —CH₂—OMe | Me | Me | H | |
| 1-681 | CHF2 | 1-Cl-c-Pr | —CH₂—OMe | Me | Me | 1-Cl-c-Pr | |
| 1-682 | CHF2 | 1-Cl-c-Pr | —(CH₂)₂— | | H | H | |
| 1-683 | CHF2 | 1-Cl-c-Pr | —(CH₂)₃— | | H | H | |
| 1-684 | CHF2 | 1-Cl-c-Pr | —(CH₂)₂— | | Cl | H | |
| 1-685 | CHF2 | 1-Cl-c-Pr | —(CH₂)₂— | | Cl | 1-Cl-c-Pr | |
| 1-686 | CHF2 | 2,2-Me₂-c-Pr | Me | Me | H | H | |
| 1-687 | CHF2 | 2,2-Me₂-c-Pr | Me | Me | Me | H | |
| 1-688 | CHF2 | 2,2-Me₂-c-Pr | Me | Me | Me | 2,2-Me₂-c-Pr | |
| 1-689 | CHF2 | 2,2-Me₂-c-Pr | c-Pr | Me | H | H | |
| 1-690 | CHF2 | 2,2-Me₂-c-Pr | c-Pr | Me | Me | H | |
| 1-691 | CHF2 | 2,2-Me₂-c-Pr | c-Pr | Me | Me | 2,2-Me₂-c-Pr | |
| 1-692 | CHF2 | 2,2-Me₂-c-Pr | —CH₂—OMe | Me | H | H | |
| 1-693 | CHF2 | 2,2-Me₂-c-Pr | —CH₂—OMe | Me | Me | H | |
| 1-694 | CHF2 | 2,2-Me₂-c-Pr | —CH₂—OMe | Me | Me | 2,2-Me₂-c-Pr | |
| 1-695 | CHF2 | 2,2-Me₂-c-Pr | —(CH₂)₂— | | H | H | |
| 1-696 | CHF2 | 2,2-Me₂-c-Pr | —(CH₂)₃— | | H | H | |
| 1-697 | CHF2 | 2,2-Me₂-c-Pr | —CH₂—CMe₂— | | H | H | |
| 1-698 | CHF2 | 2,2-Me₂-c-Pr | —CH₂—CMe₂— | | H | 2,2-Me₂-c-Pr | |
| 1-699 | CHF2 | 2,2-Cl₂-c-Pr | Me | Me | H | H | |
| 1-700 | CHF2 | 2,2-Cl₂-c-Pr | Me | Me | Me | H | |
| 1-701 | CHF2 | 2,2-Cl₂-c-Pr | Me | Me | Me | 2,2-Cl₂-c-Pr | |
| 1-702 | CHF2 | 2,2-Me₂-c-Pr | c-Pr | Me | H | H | |
| 1-703 | CHF2 | 2,2-Cl₂-c-Pr | c-Pr | Me | Me | H | |
| 1-704 | CHF2 | 2,2-Cl₂-c-Pr | c-Pr | Me | Me | 2,2-Cl₂-c-Pr | |
| 1-705 | CHF2 | 2,2-Cl₂-c-Pr | —CH₂—OMe | Me | H | H | |
| 1-706 | CHF2 | 2,2-Cl₂-c-Pr | —CH₂—OMe | Me | Me | H | |
| 1-707 | CHF2 | 2,2-Cl₂-c-Pr | —CH₂—OMe | Me | Me | 2,2-Cl₂-c-Pr | |
| 1-708 | CHF2 | 2,2-Cl₂-c-Pr | —(CH₂)₂— | | H | H | |
| 1-709 | CHF2 | 2,2-Cl₂-c-Pr | —(CH₂)₃— | | H | H | |

TABLE 1-continued

Compounds of the formula (Ia)

(Ia)

| No. | R² | R³ | R⁴ | R⁵ | R⁶ | R⁷ | phys. data |
|---|---|---|---|---|---|---|---|
| 1-710 | CHF2 | 2,2-Cl₂-c-Pr | —CH₂—CCl₂— | | H | H | |
| 1-711 | CHF2 | 2,2-Cl₂-c-Pr | —CH₂—CCl₂— | | H | 2,2-Cl₂-c-Pr | |

Explanations for table 1:

"NMR" of the example compounds were, unless stated otherwise, in each case measured as a ¹H NMR spectrum at 300 MHz (CDCl₃) (¹H nuclear resonance data). Characteristic chemical shifts δ (ppm) are reported below for some example compounds:

Ex. No.   δ (ppm) =

1-19:   8.10 (s, 1 H), 3.30 (m, 1 H), 0.95 (m, 2 H), 0.55-0.25 (m, 8 H);
1-98:   3.35 (m, 1 H), 2.25 (s, 3 H), 0.95 (m, 2 H), 0.55-0.25 (m, 8 H);
1-177:  3.35 (q, 1 H), 2.50 (q, 2 H), 1.25 (t, 3 H), 0.95 (m, 2 H), 0.55-0.25 (m, 8 H);
1-183:  4.00 (q, 1 H), 2.45 (m, 2 H), 2.30 (m, 2 H), 1.90-1.65 (m, 12 H), 1.20 (t, 3 H);
1-256:  3.20 (q, 1 H), 1.65 (m, 1 H), 1.00-0.95 (m, 2 H), 0.90-0.80 (m, 4 H), 0.45-0.20 (m, 8 H);
1-317:  5.40-5.10 (m, 1 H), 3.35 (m, 1 H), 2.00-1.80 (m, 1 H), 1.60 (dd, 3 H), 0.95 (m, 7 H), 0.55-0.25 (m, 4 H);
1-335:  5.25 (dq, 1 H), 3.30 (q, 1 H), 1.60 (dd, 3 H), 1.00-0.85 (m, 2 H), 0.55-0.25 (m, 8 H);
1-341:  5.30-5.00 (m, 1 H), 4.10-3.90 (m, 1 H), 2.30 (m, 2 H), 1.90-1.50 (m, 15 H);
1-414:  5.15-4.90 (ddd, 1 H), 3.35 (m, 1 H), 2.05-1.85 (m, 2 H), 1.05 (dd, 3 H), 0.95 (m, 2 H), 0.55-0.25 (m, 8 H);
1-420:  5.10-4.80 (m, 1 H), 3.95 (m, 1 H), 2.25 (m, 2 H), 2.00-1.30 (m, 14 H), 0.95 (dd, 3 H);
1-475:  3.30 (m, 1 H), 1.95 (m, 1 H), 1.60 (d, 6 H), 0.95 (d, 6 H), 0.85 (m, 1 H), 0.60-0.25 (m, 4 H);
1-493:  3.30 (m, 1 H), 1.65 (d, 6 H), 0.90 (m, 2 H), 0.55-0.25 (m, 8 H);
1-499:  4.00 (m, 1 H), 2.25 (m, 2 H), 1.90-1.50 (m, 18 H);
1-572:  3.30-2.80 (m, 1 H), 1.40-1.25 (d, 4 H), 0.80 (m, 2 H), 0.45-0.15 (m, 8 H)
1-651:  6.12 (t, 1 H), 3.30 (m, 1 H), 0.95 (m, 2 H), 0.60-0.30 (m, 8 H)
        1-651 was analyzed as a ¹H NMR spectrum at 400 MHz (CDCl₃).

TABLE 2

Compounds of the formula (Ib)

(Ib)

| No. | R² | R³ | R⁴ | R⁵ | R⁶ | R⁷ | phys. data |
|---|---|---|---|---|---|---|---|
| 2-1 | H | c-Pr | Me | Me | H | H | |
| 2-2 | H | c-Pr | Me | Me | Me | H | |
| 2-3 | H | c-Pr | c-Pr | Me | H | H | |
| 2-4 | H | c-Pr | c-Pr | Me | Me | H | |
| 2-5 | H | c-Pr | —CH₂—OMe | Me | H | H | |
| 2-6 | H | c-Pr | —CH₂—OMe | Me | Me | H | |
| 2-7 | H | c-Pr | —(CH₂)₂— | | H | H | |
| 2-8 | H | c-Pr | —(CH₂)₂— | | H | Me | |
| 2-9 | H | c-Pr | —(CH₂)₂— | | H | c-Pr | |
| 2-10 | H | c-Bu | —(CH₂)₃— | | H | H | |
| 2-11 | H | c-Bu | —(CH₂)₃— | | H | Me | |
| 2-12 | H | c-Bu | —(CH₂)₃— | | H | c-Pr | |

TABLE 2-continued

Compounds of the formula (Ib)

(Ib)

| No. | R² | R³ | R⁴ | R⁵ | R⁶ | R⁷ | phys. data |
|---|---|---|---|---|---|---|---|
| 2-13 | Me | c-Pr | Me | Me | H | H | |
| 2-14 | Me | c-Pr | Me | Me | Me | H | |
| 2-15 | Me | c-Pr | c-Pr | Me | H | H | |
| 2-16 | Me | c-Pr | c-Pr | Me | Me | H | |
| 2-17 | Me | c-Pr | —CH₂—OMe | Me | H | H | |
| 2-18 | Me | c-Pr | —CH₂—OMe | Me | Me | H | |
| 2-19 | Me | c-Pr | —(CH₂)₂— | | H | H | |
| 2-20 | Me | c-Pr | —(CH₂)₂— | | H | Me | |
| 2-21 | Me | c-Pr | —(CH₂)₂— | | H | c-Pr | |
| 2-22 | Me | c-Bu | —(CH₂)₃— | | H | H | |
| 2-23 | Me | c-Bu | —(CH₂)₃— | | H | Me | |
| 2-24 | Me | c-Bu | —(CH₂)₃— | | H | c-Pr | |
| 2-25 | Me | 1-Me-c-Pr | Me | Me | H | H | |
| 2-26 | Me | 1-Me-c-Pr | Me | Me | Me | H | |
| 2-27 | Me | 1-Me-c-Pr | c-Pr | Me | H | H | |
| 2-28 | Me | 1-Me-c-Pr | c-Pr | Me | Me | H | |
| 2-29 | Me | 1-Me-c-Pr | —(CH₂)₂— | | H | H | |
| 2-30 | Me | 1-Me-c-Pr | —(CH₂)₂— | | Me | H | |
| 2-31 | Me | 1-Cl-c-Pr | Me | Me | H | H | |
| 2-32 | Me | 1-Cl-c-Pr | Me | Me | Me | H | |
| 2-33 | Me | 1-Cl-c-Pr | c-Pr | Me | H | H | |
| 2-34 | Me | 1-Cl-c-Pr | c-Pr | Me | Me | H | |
| 2-35 | Me | 1-Cl-c-Pr | —(CH₂)₂— | | H | H | |
| 2-36 | Me | 1-Cl-c-Pr | —(CH₂)₂— | | Me | H | |
| 2-37 | Me | 2,2-Me₂-c-Pr | Me | Me | H | H | |
| 2-38 | Me | 2,2-Me₂-c-Pr | Me | Me | Me | H | |
| 2-39 | Me | 2,2-Me₂-c-Pr | c-Pr | Me | H | H | |
| 2-40 | Me | 2,2-Me₂-c-Pr | c-Pr | Me | Me | H | |
| 2-41 | Me | 2,2-Me₂-c-Pr | —(CH₂)₂— | | H | H | |
| 2-42 | Me | 2,2-Me₂-c-Pr | —CH₂—CMe₂— | | H | H | |
| 2-43 | Me | 2,2-Cl₂-c-Pr | Me | Me | H | H | |
| 2-44 | Me | 2,2-Cl₂-c-Pr | Me | Me | Me | H | |
| 2-45 | Me | 2,2-Cl₂-c-Pr | c-Pr | Me | H | H | |
| 2-46 | Me | 2,2-Cl₂-c-Pr | c-Pr | Me | Me | H | |
| 2-47 | Me | 2,2-Cl₂-c-Pr | —(CH₂)₂— | | H | H | |
| 2-48 | Me | 2,2-Cl₂-c-Pr | —CH₂—CCl₂— | | H | H | |
| 2-49 | Et | c-Pr | Me | Me | H | H | |
| 2-50 | Et | c-Pr | Me | Me | Me | H | |
| 2-51 | Et | c-Pr | c-Pr | Me | H | H | |
| 2-52 | Et | c-Pr | c-Pr | Me | Me | H | |
| 2-53 | Et | c-Pr | —CH₂—OMe | Me | H | H | |
| 2-54 | Et | c-Pr | —CH₂—OMe | Me | Me | H | |
| 2-55 | Et | c-Pr | —(CH₂)₂— | | H | H | |
| 2-56 | Et | c-Pr | —(CH₂)₂— | | H | Me | |
| 2-57 | Et | c-Pr | —(CH₂)₂— | | H | c-Pr | |
| 2-58 | Et | c-Bu | —(CH₂)₃— | | H | H | |
| 2-59 | Et | c-Bu | —(CH₂)₃— | | H | Me | |
| 2-60 | Et | c-Bu | —(CH₂)₃— | | H | c-Pr | |
| 2-61 | Et | 1-Me-c-Pr | Me | Me | H | H | |
| 2-62 | Et | 1-Me-c-Pr | Me | Me | Me | H | |
| 2-63 | Et | 1-Me-c-Pr | c-Pr | Me | H | H | |
| 2-64 | Et | 1-Me-c-Pr | c-Pr | Me | Me | H | |
| 2-65 | Et | 1-Me-c-Pr | —(CH₂)₂— | | H | H | |
| 2-66 | Et | 1-Me-c-Pr | —(CH₂)₂— | | Me | H | |
| 2-67 | Et | 1-Cl-c-Pr | Me | Me | H | H | |
| 2-68 | Et | 1-Cl-c-Pr | Me | Me | Me | H | |
| 2-69 | Et | 1-Cl-c-Pr | c-Pr | Me | H | H | |
| 2-70 | Et | 1-Cl-c-Pr | c-Pr | Me | Me | H | |

TABLE 2-continued

Compounds of the formula (Ib)

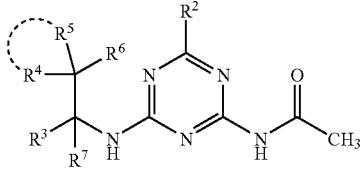

(Ib)

| No. | $R^2$ | $R^3$ | $R^4$ | $R^5$ | $R^6$ | $R^7$ | phys. data |
|---|---|---|---|---|---|---|---|
| 2-71 | Et | 1-Cl-c-Pr | —(CH$_2$)$_2$— | | H | H | |
| 2-72 | Et | 1-Cl-c-Pr | —(CH$_2$)$_2$— | | Me | H | |
| 2-73 | Et | 2,2-Me$_2$-c-Pr | Me | Me | H | H | |
| 2-74 | Et | 2,2-Me$_2$-c-Pr | Me | Me | Me | H | |
| 2-75 | Et | 2,2-Me$_2$-c-Pr | c-Pr | Me | H | H | |
| 2-76 | Et | 2,2-Me$_2$-c-Pr | c-Pr | Me | Me | H | |
| 2-77 | Et | 2,2-Me$_2$-c-Pr | —(CH$_2$)$_2$— | | H | H | |
| 2-78 | Et | 2,2-Me$_2$-c-Pr | —CH$_2$—CMe$_2$— | | H | H | |
| 2-79 | Et | 2,2-Cl$_2$-c-Pr | Me | Me | H | H | |
| 2-80 | Et | 2,2-Cl$_2$-c-Pr | Me | Me | Me | H | |
| 2-81 | Et | 2,2-Cl$_2$-c-Pr | c-Pr | Me | H | H | |
| 2-82 | Et | 2,2-Cl$_2$-c-Pr | c-Pr | Me | Me | H | |
| 2-83 | Et | 2,2-Cl$_2$-c-Pr | —(CH$_2$)$_2$— | | H | H | |
| 2-84 | Et | 2,2-Cl$_2$-c-Pr | —CH$_2$—CCl$_2$— | | H | H | |
| 2-85 | c-Pr | c-Pr | Me | Me | H | H | |
| 2-86 | c-Pr | c-Pr | Me | Me | Me | H | |
| 2-87 | c-Pr | c-Pr | c-Pr | Me | H | H | |
| 2-88 | c-Pr | c-Pr | c-Pr | Me | Me | H | |
| 2-89 | c-Pr | c-Pr | —CH$_2$—OMe | Me | H | H | |
| 2-90 | c-Pr | c-Pr | —CH$_2$—OMe | Me | Me | H | |
| 2-91 | c-Pr | c-Pr | —(CH$_2$)$_2$— | | H | H | |
| 2-92 | c-Pr | c-Pr | —(CH$_2$)$_2$— | | H | Me | |
| 2-93 | c-Pr | c-Pr | —(CH$_2$)$_2$— | | H | c-Pr | |
| 2-94 | c-Pr | c-Bu | —(CH$_2$)$_3$— | | H | H | |
| 2-95 | c-Pr | c-Bu | —(CH$_2$)$_3$— | | H | Me | |
| 2-96 | c-Pr | c-Bu | —(CH$_2$)$_3$— | | H | c-Pr | |
| 2-97 | c-Pr | 1-Me-c-Pr | Me | Me | H | H | |
| 2-98 | c-Pr | 1-Me-c-Pr | Me | Me | Me | H | |
| 2-99 | c-Pr | 1-Me-c-Pr | c-Pr | Me | H | H | |
| 2-100 | c-Pr | 1-Me-c-Pr | c-Pr | Me | Me | H | |
| 2-101 | c-Pr | 1-Me-c-Pr | —(CH$_2$)$_2$— | | H | H | |
| 2-102 | c-Pr | 1-Me-c-Pr | —(CH$_2$)$_2$— | | Me | H | |
| 2-103 | c-Pr | 1-Cl-c-Pr | Me | Me | H | H | |
| 2-104 | c-Pr | 1-Cl-c-Pr | Me | Me | Me | H | |
| 2-105 | c-Pr | 1-Cl-c-Pr | c-Pr | Me | H | H | |
| 2-106 | c-Pr | 1-Cl-c-Pr | c-Pr | Me | Me | H | |
| 2-107 | c-Pr | 1-Cl-c-Pr | —(CH$_2$)$_2$— | | H | H | |
| 2-108 | c-Pr | 1-Cl-c-Pr | —(CH$_2$)$_2$— | | Me | H | |
| 2-109 | c-Pr | 2,2-Me$_2$-c-Pr | Me | Me | H | H | |
| 2-110 | c-Pr | 2,2-Me$_2$-c-Pr | Me | Me | Me | H | |
| 2-111 | c-Pr | 2,2-Me$_2$-c-Pr | c-Pr | Me | H | H | |
| 2-112 | c-Pr | 2,2-Me$_2$-c-Pr | c-Pr | Me | Me | H | |
| 2-113 | c-Pr | 2,2-Me$_2$-c-Pr | —(CH$_2$)$_2$— | | H | H | |
| 2-114 | c-Pr | 2,2-Me$_2$-c-Pr | —CH$_2$—CMe$_2$— | | H | H | |
| 2-115 | c-Pr | 2,2-Cl$_2$-c-Pr | Me | Me | H | H | |
| 2-116 | c-Pr | 2,2-Cl$_2$-c-Pr | Me | Me | Me | H | |
| 2-117 | c-Pr | 2,2-Cl$_2$-c-Pr | c-Pr | Me | H | H | |
| 2-118 | c-Pr | 2,2-Cl$_2$-c-Pr | c-Pr | Me | Me | H | |
| 2-119 | c-Pr | 2,2-Cl$_2$-c-Pr | —(CH$_2$)$_2$— | | H | H | |
| 2-120 | c-Pr | 2,2-Cl$_2$-c-Pr | —CH$_2$—CCl$_2$— | | H | H | |
| 2-121 | CHFCH$_3$ | c-Pr | Me | Me | H | H | |
| 2-122 | CHFCH$_3$ | c-Pr | Me | Me | Me | H | |

TABLE 2-continued

Compounds of the formula (Ib)

(Ib)

| No. | R² | R³ | R⁴ | R⁵ | R⁶ | R⁷ | phys. data |
|---|---|---|---|---|---|---|---|
| 2-123 | CHFCH₃ | c-Pr | c-Pr | Me | H | H | |
| 2-124 | CHFCH₃ | c-Pr | c-Pr | Me | Me | H | |
| 2-125 | CHFCH₃ | c-Pr | —CH₂—OMe | Me | H | H | |
| 2-126 | CHFCH₃ | c-Pr | —CH₂—OMe | Me | Me | H | |
| 2-127 | CHFCH₃ | c-Pr | —(CH₂)₂— | | H | H | |
| 2-128 | CHFCH₃ | c-Pr | —(CH₂)₂— | | H | Me | |
| 2-129 | CHFCH₃ | c-Pr | —(CH₂)₂— | | H | c-Pr | |
| 2-130 | CHFCH₃ | c-Bu | —(CH₂)₃— | | H | H | |
| 2-131 | CHFCH₃ | c-Bu | —(CH₂)₃— | | H | Me | |
| 2-132 | CHFCH₃ | c-Bu | —(CH₂)₃— | | H | c-Pr | |
| 2-133 | CHFCH₃ | 1-Me-c-Pr | Me | Me | H | H | |
| 2-134 | CHFCH₃ | 1-Me-c-Pr | Me | Me | Me | H | |
| 2-135 | CHFCH₃ | 1-Me-c-Pr | c-Pr | Me | H | H | |
| 2-136 | CHFCH₃ | 1-Me-c-Pr | c-Pr | Me | Me | H | |
| 2-137 | CHFCH₃ | 1-Me-c-Pr | —(CH₂)₂— | | H | H | |
| 2-138 | CHFCH₃ | 1-Me-c-Pr | —(CH₂)₂— | | Me | H | |
| 2-139 | CHFCH₃ | 1-Cl-c-Pr | Me | Me | H | H | |
| 2-140 | CHFCH₃ | 1-Cl-c-Pr | Me | Me | Me | H | |
| 2-141 | CHFCH₃ | 1-Cl-c-Pr | c-Pr | Me | H | H | |
| 2-142 | CHFCH₃ | 1-Cl-c-Pr | c-Pr | Me | Me | H | |
| 2-143 | CHFCH₃ | 1-Cl-c-Pr | —(CH₂)₂— | | H | H | |
| 2-144 | CHFCH₃ | 1-Cl-c-Pr | —(CH₂)₂— | | Me | H | |
| 2-145 | CHFCH₃ | 2,2-Me₂-c-Pr | Me | Me | H | H | |
| 2-146 | CHFCH₃ | 2,2-Me₂-c-Pr | Me | Me | Me | H | |
| 2-147 | CHFCH₃ | 2,2-Me₂-c-Pr | c-Pr | Me | H | H | |
| 2-148 | CHFCH₃ | 2,2-Me₂-c-Pr | c-Pr | Me | Me | H | |
| 2-149 | CHFCH₃ | 2,2-Me₂-c-Pr | —(CH₂)₂— | | H | H | |
| 2-150 | CHFCH₃ | 2,2-Me₂-c-Pr | —CH₂—CMe₂— | | H | H | |
| 2-151 | CHFCH₃ | 2,2-Cl₂-c-Pr | Me | Me | H | H | |
| 2-152 | CHFCH₃ | 2,2-Cl₂-c-Pr | Me | Me | Me | H | |
| 2-153 | CHFCH₃ | 2,2-Cl₂-c-Pr | c-Pr | Me | H | H | |
| 2-154 | CHFCH₃ | 2,2-Cl₂-c-Pr | c-Pr | Me | Me | H | |
| 2-155 | CHFCH₃ | 2,2-Cl₂-c-Pr | —(CH₂)₂— | | H | H | |
| 2-156 | CHFCH₃ | 2,2-Cl₂-c-Pr | —CH₂—CCl₂— | | H | H | |
| 2-157 | CHFC₂H₅ | c-Pr | Me | Me | H | H | |
| 2-158 | CHFC₂H₅ | c-Pr | Me | Me | Me | H | |
| 2-159 | CHFC₂H₅ | c-Pr | c-Pr | Me | H | H | |
| 2-160 | CHFC₂H₅ | c-Pr | c-Pr | Me | Me | H | |
| 2-161 | CHFC₂H₅ | c-Pr | —CH₂—OMe | Me | H | H | |
| 2-162 | CHFC₂H₅ | c-Pr | —CH₂—OMe | Me | Me | H | |
| 2-163 | CHFC₂H₅ | c-Pr | —(CH₂)₂— | | H | H | |
| 2-164 | CHFC₂H₅ | c-Pr | —(CH₂)₂— | | H | Me | |
| 2-165 | CHFC₂H₅ | c-Pr | —(CH₂)₂— | | H | c-Pr | |
| 2-166 | CHFC₂H₅ | c-Bu | —(CH₂)₃— | | H | H | |
| 2-167 | CHFC₂H₅ | c-Bu | —(CH₂)₃— | | H | Me | |
| 2-168 | CHFC₂H₅ | c-Bu | —(CH₂)₃— | | H | c-Pr | |
| 2-169 | CHFC₂H₅ | 1-Me-c-Pr | Me | Me | H | H | |
| 2-170 | CHFC₂H₅ | 1-Me-c-Pr | Me | Me | Me | H | |
| 2-171 | CHFC₂H₅ | 1-Me-c-Pr | c-Pr | Me | H | H | |
| 2-172 | CHFC₂H₅ | 1-Me-c-Pr | c-Pr | Me | Me | H | |
| 2-173 | CHFC₂H₅ | 1-Me-c-Pr | —(CH₂)₂— | | H | H | |
| 2-174 | CHFC₂H₅ | 1-Me-c-Pr | —(CH₂)₂— | | Me | H | |
| 2-175 | CHFC₂H₅ | 1-Cl-c-Pr | Me | Me | H | H | |
| 2-176 | CHFC₂H₅ | 1-Cl-c-Pr | Me | Me | Me | H | |
| 2-177 | CHFC₂H₅ | 1-Cl-c-Pr | c-Pr | Me | H | H | |
| 2-178 | CHFC₂H₅ | 1-Cl-c-Pr | c-Pr | Me | Me | H | |
| 2-179 | CHFC₂H₅ | 1-Cl-c-Pr | —(CH₂)₂— | | H | H | |
| 2-180 | CHFC₂H₅ | 1-Cl-c-Pr | —(CH₂)₂— | | Me | H | |

TABLE 2-continued

Compounds of the formula (Ib)

(Ib)

| No. | R² | R³ | R⁴ | R⁵ | R⁶ | R⁷ | phys. data |
|---|---|---|---|---|---|---|---|
| 2-181 | CHFC₂H₅ | 2,2-Me₂-c-Pr | Me | Me | H | H | |
| 2-182 | CHFC₂H₅ | 2,2-Me₂-c-Pr | Me | Me | Me | H | |
| 2-183 | CHFC₂H₅ | 2,2-Me₂-c-Pr | c-Pr | Me | H | H | |
| 2-184 | CHFC₂H₅ | 2,2-Me₂-c-Pr | c-Pr | Me | Me | H | |
| 2-185 | CHFC₂H₅ | 2,2-Me₂-c-Pr | —(CH₂)₂— | | H | H | |
| 2-186 | CHFC₂H₅ | 2,2-Me₂-c-Pr | —CH₂—CMe₂— | | H | H | |
| 2-187 | CHFC₂H₅ | 2,2-Cl₂-c-Pr | Me | Me | H | H | |
| 2-188 | CHFC₂H₅ | 2,2-Cl₂-c-Pr | Me | Me | Me | H | |
| 2-189 | CHFC₂H₅ | 2,2-Cl₂-c-Pr | c-Pr | Me | H | H | |
| 2-190 | CHFC₂H₅ | 2,2-Cl₂-c-Pr | c-Pr | Me | Me | H | |
| 2-191 | CHFC₂H₅ | 2,2-Cl₂-c-Pr | —(CH₂)₂— | | H | H | |
| 2-192 | CHFC₂H₅ | 2,2-Cl₂-c-Pr | —CH₂—CCl₂— | | H | H | |
| 2-193 | CF(CH₃)₂ | c-Pr | Me | Me | H | H | resin |
| 2-194 | CF(CH₃)₂ | c-Pr | Me | Me | Me | H | |
| 2-195 | CF(CH₃)₂ | c-Pr | c-Pr | Me | H | H | |
| 2-196 | CF(CH₃)₂ | c-Pr | c-Pr | Me | Me | H | |
| 2-197 | CF(CH₃)₂ | c-Pr | —CH₂—OMe | Me | H | H | |
| 2-198 | CF(CH₃)₂ | c-Pr | —CH₂—OMe | Me | Me | H | |
| 2-199 | CF(CH₃)₂ | c-Pr | —(CH₂)₂— | | H | H | NMR |
| 2-200 | CF(CH₃)₂ | c-Pr | —(CH₂)₂— | | H | Me | |
| 2-201 | CF(CH₃)₂ | c-Pr | —(CH₂)₂— | | H | c-Pr | |
| 2-202 | CF(CH₃)₂ | c-Bu | —(CH₂)₃— | | H | H | resin |
| 2-203 | CF(CH₃)₂ | c-Bu | —(CH₂)₃— | | H | Me | |
| 2-204 | CF(CH₃)₂ | c-Bu | —(CH₂)₃— | | H | c-Pr | |
| 2-205 | CF(CH₃)₂ | 1-Me-c-Pr | Me | Me | H | H | |
| 2-206 | CF(CH₃)₂ | 1-Me-c-Pr | Me | Me | Me | H | |
| 2-207 | CF(CH₃)₂ | 1-Me-c-Pr | c-Pr | Me | H | H | |
| 2-208 | CF(CH₃)₂ | 1-Me-c-Pr | c-Pr | Me | Me | H | |
| 2-209 | CF(CH₃)₂ | 1-Me-c-Pr | —(CH₂)₂— | | H | H | |
| 2-210 | CF(CH₃)₂ | 1-Me-c-Pr | —(CH₂)₂— | | Me | H | |
| 2-211 | CF(CH₃)₂ | 1-Cl-c-Pr | Me | Me | H | H | |
| 2-212 | CF(CH₃)₂ | 1-Cl-c-Pr | Me | Me | Me | H | |
| 2-213 | CF(CH₃)₂ | 1-Cl-c-Pr | c-Pr | Me | H | H | |
| 2-214 | CF(CH₃)₂ | 1-Cl-c-Pr | c-Pr | Me | Me | H | |
| 2-215 | CF(CH₃)₂ | 1-Cl-c-Pr | —(CH₂)₂— | | H | H | |
| 2-216 | CF(CH₃)₂ | 1-Cl-c-Pr | —(CH₂)₂— | | Me | H | |
| 2-217 | CF(CH₃)₂ | 2,2-Me₂-c-Pr | Me | Me | H | H | |
| 2-218 | CF(CH₃)₂ | 2,2-Me₂-c-Pr | Me | Me | Me | H | |
| 2-219 | CF(CH₃)₂ | 2,2-Me₂-c-Pr | c-Pr | Me | H | H | |
| 2-220 | CF(CH₃)₂ | 2,2-Me₂-c-Pr | c-Pr | Me | Me | H | |
| 2-221 | CF(CH₃)₂ | 2,2-Me₂-c-Pr | —(CH₂)₂— | | H | H | |
| 2-222 | CF(CH₃)₂ | 2,2-Me₂-c-Pr | —CH₂—CMe₂— | | H | H | |
| 2-223 | CF(CH₃)₂ | 2,2-Cl₂-c-Pr | Me | Me | H | H | |
| 2-224 | CF(CH₃)₂ | 2,2-Cl₂-c-Pr | Me | Me | Me | H | |
| 2-225 | CF(CH₃)₂ | 2,2-Cl₂-c-Pr | c-Pr | Me | H | H | |
| 2-226 | CF(CH₃)₂ | 2,2-Cl₂-c-Pr | c-Pr | Me | Me | H | |
| 2-227 | CF(CH₃)₂ | 2,2-Cl₂-c-Pr | —(CH₂)₂— | | H | H | |
| 2-228 | CF(CH₃)₂ | 2,2-Cl₂-c-Pr | —CH₂—CCl₂— | | H | H | |
| 2-229 | 1-F-c-Pr | c-Pr | Me | Me | H | H | |
| 2-230 | 1-F-c-Pr | c-Pr | Me | Me | Me | H | |
| 2-231 | 1-F-c-Pr | c-Pr | c-Pr | Me | H | H | |
| 2-232 | 1-F-c-Pr | c-Pr | c-Pr | Me | Me | H | |

TABLE 2-continued

Compounds of the formula (Ib)

| No. | R² | R³ | R⁴ | R⁵ | R⁶ | R⁷ | phys. data |
|---|---|---|---|---|---|---|---|
| 2-233 | 1-F-c-Pr | c-Pr | —CH₂—OMe | Me | H | H | |
| 2-234 | 1-F-c-Pr | c-Pr | —CH₂—OMe | Me | Me | H | |
| 2-235 | 1-F-c-Pr | c-Pr | —(CH₂)₂— | | H | H | |
| 2-236 | 1-F-c-Pr | c-Pr | —(CH₂)₂— | | H | Me | |
| 2-237 | 1-F-c-Pr | c-Pr | —(CH₂)₂— | | H | c-Pr | |
| 2-238 | 1-F-c-Pr | c-Bu | —(CH₂)₃— | | H | H | |
| 2-239 | 1-F-c-Pr | c-Bu | —(CH₂)₃— | | H | Me | |
| 2-240 | 1-F-c-Pr | c-Bu | —(CH₂)₃— | | H | c-Pr | |
| 2-241 | 1-F-c-Pr | 1-Me-c-Pr | Me | Me | H | H | |
| 2-242 | 1-F-c-Pr | 1-Me-c-Pr | Me | Me | Me | H | |
| 2-243 | 1-F-c-Pr | 1-Me-c-Pr | c-Pr | Me | H | H | |
| 2-244 | 1-F-c-Pr | 1-Me-c-Pr | c-Pr | Me | Me | H | |
| 2-245 | 1-F-c-Pr | 1-Me-c-Pr | —(CH₂)₂— | | H | H | |
| 2-246 | 1-F-c-Pr | 1-Me-c-Pr | —(CH₂)₂— | | Me | H | |
| 2-247 | 1-F-c-Pr | 1-Cl-c-Pr | Me | Me | H | H | |
| 2-248 | 1-F-c-Pr | 1-Cl-c-Pr | Me | Me | Me | H | |
| 2-249 | 1-F-c-Pr | 1-Cl-c-Pr | c-Pr | Me | H | H | |
| 2-250 | 1-F-c-Pr | 1-Cl-c-Pr | c-Pr | Me | Me | H | |
| 2-251 | 1-F-c-Pr | 1-Cl-c-Pr | —(CH₂)₂— | | H | H | |
| 2-252 | 1-F-c-Pr | 1-Cl-c-Pr | —(CH₂)₂— | | Me | H | |
| 2-253 | 1-F-c-Pr | 2,2-Me₂-c-Pr | Me | Me | H | H | |
| 2-254 | 1-F-c-Pr | 2,2-Me₂-c-Pr | Me | Me | Me | H | |
| 2-255 | 1-F-c-Pr | 2,2-Me₂-c-Pr | c-Pr | Me | H | H | |
| 2-256 | 1-F-c-Pr | 2,2-Me₂-c-Pr | c-Pr | Me | Me | H | |
| 2-257 | 1-F-c-Pr | 2,2-Me₂-c-Pr | —(CH₂)₂— | | H | H | |
| 2-258 | 1-F-c-Pr | 2,2-Me₂-c-Pr | —CH₂—CMe₂— | | H | H | |
| 2-259 | 1-F-c-Pr | 2,2-Cl₂-c-Pr | Me | Me | H | H | |
| 2-260 | 1-F-c-Pr | 2,2-Cl₂-c-Pr | Me | Me | Me | H | |
| 2-261 | 1-F-c-Pr | 2,2-Cl₂-c-Pr | c-Pr | Me | H | H | |
| 2-262 | 1-F-c-Pr | 2,2-Cl₂-c-Pr | c-Pr | Me | Me | H | |
| 2-263 | 1-F-c-Pr | 2,2-Cl₂-c-Pr | —(CH₂)₂— | | H | H | |
| 2-264 | 1-F-c-Pr | 2,2-Cl₂-c-Pr | —CH₂—CCl₂— | | H | H | |
| 2-265 | CHF2 | c-Pr | Me | Me | H | H | |
| 2-266 | CHF2 | c-Pr | Me | Me | Me | H | |
| 2-267 | CHF2 | c-Pr | c-Pr | Me | H | H | |
| 2-268 | CHF2 | c-Pr | c-Pr | Me | Me | H | |
| 2-269 | CHF2 | c-Pr | —CH₂—OMe | Me | H | H | |
| 2-270 | CHF2 | c-Pr | —CH₂—OMe | Me | Me | H | |
| 2-271 | CHF2 | c-Pr | —(CH₂)₂— | | H | H | |
| 2-272 | CHF2 | c-Pr | —(CH₂)₂— | | H | Me | |
| 2-273 | CHF2 | c-Pr | —(CH₂)₂— | | H | c-Pr | |
| 2-274 | CHF2 | c-Bu | —(CH₂)₃— | | H | H | |
| 2-275 | CHF2 | c-Bu | —(CH₂)₃— | | H | Me | |
| 2-276 | CHF2 | c-Bu | —(CH₂)₃— | | H | c-Pr | |

Explanations for table 2:
"NMR" of the example compounds were in each case measured as a ¹H NMR spectrum at 400 MHz (CDCl₃) (¹H nuclear resonance data). Characteristic chemical shifts δ (ppm) for example compounds are listed below:
Ex. No.  δ (ppm) =
2-199:  3.30 (m, 1 H), 2.60 and 2.55 (each s, together 3 H), 1.70-1.60 (twice d, together 6 H), 1.10-0.90 (m, 2 H), 0.55-0.25 (m, 8 H)

TABLE 3

Compounds of the formula (Ic)

$$\text{(Ic)}$$

| No. | R² | R³ | R⁴ | R⁵ | R⁶ | R⁷ | phys. data |
|---|---|---|---|---|---|---|---|
| 3-1 | H | c-Pr | Me | Me | H | H | |
| 3-2 | H | c-Pr | Me | Me | Me | H | |
| 3-3 | H | c-Pr | c-Pr | Me | H | H | |
| 3-4 | H | c-Pr | c-Pr | Me | Me | H | |
| 3-5 | H | c-Pr | —CH₂—OMe | Me | H | H | |
| 3-6 | H | c-Pr | —CH₂—OMe | Me | Me | H | |
| 3-7 | H | c-Pr | —(CH₂)₂— | | H | H | |
| 3-8 | H | c-Pr | —(CH₂)₂— | | H | Me | |
| 3-9 | H | c-Pr | —(CH₂)₂— | | H | c-Pr | |
| 3-10 | H | c-Bu | —(CH₂)₃— | | H | H | |
| 3-11 | H | c-Bu | —(CH₂)₃— | | H | Me | |
| 3-12 | H | c-Bu | —(CH₂)₃— | | H | c-Pr | |
| 3-13 | H | 1-Me-c-Pr | Me | Me | H | H | |
| 3-14 | H | 1-Me-c-Pr | Me | Me | Me | H | |
| 3-15 | H | 1-Me-c-Pr | c-Pr | Me | H | H | |
| 3-16 | H | 1-Me-c-Pr | c-Pr | Me | Me | H | |
| 3-17 | Me | c-Pr | Me | Me | H | H | |
| 3-18 | Me | c-Pr | Me | Me | Me | H | |
| 3-19 | Me | c-Pr | c-Pr | Me | H | H | |
| 3-20 | Me | c-Pr | c-Pr | Me | Me | H | |
| 3-21 | Me | c-Pr | —CH₂—OMe | Me | H | H | |
| 3-22 | Me | c-Pr | —CH₂—OMe | Me | Me | H | |
| 3-23 | Me | c-Pr | —(CH₂)₂— | | H | H | |
| 3-24 | Me | c-Pr | —(CH₂)₂— | | H | Me | |
| 3-25 | Me | c-Pr | —(CH₂)₂— | | H | c-Pr | |
| 3-26 | Me | c-Bu | —(CH₂)₃— | | H | H | |
| 3-27 | Me | c-Bu | —(CH₂)₃— | | H | Me | |
| 3-28 | Me | c-Bu | —(CH₂)₃— | | H | c-Pr | |
| 3-29 | Me | 1-Me-c-Pr | Me | Me | H | H | |
| 3-30 | Me | 1-Me-c-Pr | Me | Me | Me | H | |
| 3-31 | Me | 1-Me-c-Pr | c-Pr | Me | H | H | |
| 3-32 | Me | 1-Me-c-Pr | c-Pr | Me | Me | H | |
| 3-33 | Me | 1-Me-c-Pr | —(CH₂)₂— | | H | H | |
| 3-34 | Me | 1-Me-c-Pr | —(CH₂)₂— | | Me | H | |
| 3-35 | Me | 1-Cl-c-Pr | Me | Me | H | H | |
| 3-36 | Me | 1-Cl-c-Pr | Me | Me | Me | H | |
| 3-37 | Me | 1-Cl-c-Pr | c-Pr | Me | H | H | |
| 3-38 | Me | 1-Cl-c-Pr | c-Pr | Me | Me | H | |
| 3-39 | Me | 1-Cl-c-Pr | —(CH₂)₂— | | H | H | |
| 3-40 | Me | 1-Cl-c-Pr | —(CH₂)₂— | | Me | H | |
| 3-41 | Me | 2,2-Me₂-c-Pr | Me | Me | H | H | |
| 3-42 | Me | 2,2-Me₂-c-Pr | Me | Me | Me | H | |
| 3-43 | Me | 2,2-Me₂-c-Pr | c-Pr | Me | H | H | |
| 3-44 | Me | 2,2-Me₂-c-Pr | c-Pr | Me | Me | H | |
| 3-45 | Me | 2,2-Me₂-c-Pr | —(CH₂)₂— | | H | H | |
| 3-46 | Me | 2,2-Me₂-c-Pr | —CH₂—CMe₂— | | H | H | |
| 3-47 | Me | 2,2-Cl₂-c-Pr | Me | Me | H | H | |
| 3-48 | Me | 2,2-Cl₂-c-Pr | Me | Me | Me | H | |
| 3-49 | Me | 2,2-Cl₂-c-Pr | c-Pr | Me | H | H | |
| 3-50 | Me | 2,2-Cl₂-c-Pr | c-Pr | Me | Me | H | |
| 3-51 | Me | 2,2-Cl₂-c-Pr | —(CH₂)₂— | | H | H | |
| 3-52 | Me | 2,2-Cl₂-c-Pr | —CH₂—CCl₂— | | H | H | |
| 3-53 | Et | c-Pr | Me | Me | H | H | |
| 3-54 | Et | c-Pr | Me | Me | Me | H | |
| 3-55 | Et | c-Pr | c-Pr | Me | H | H | |
| 3-56 | Et | c-Pr | c-Pr | Me | Me | H | |
| 3-57 | Et | c-Pr | —CH₂—OMe | Me | H | H | |
| 3-58 | Et | c-Pr | —CH₂—OMe | Me | Me | H | |
| 3-59 | Et | c-Pr | —(CH₂)₂— | | H | H | |
| 3-60 | Et | c-Pr | —(CH₂)₂— | | H | Me | |
| 3-61 | Et | c-Pr | —(CH₂)₂— | | H | c-Pr | |
| 3-62 | Et | c-Bu | —(CH₂)₃— | | H | H | |
| 3-63 | Et | c-Bu | —(CH₂)₃— | | H | Me | |
| 3-64 | Et | c-Bu | —(CH₂)₃— | | H | c-Pr | |

TABLE 3-continued

Compounds of the formula (Ic)

(Ic)

| No. | R² | R³ | R⁴ | R⁵ | R⁶ | R⁷ | phys. data |
|---|---|---|---|---|---|---|---|
| 3-65 | Et | 1-Me-c-Pr | Me | Me | H | H | |
| 3-66 | Et | 1-Me-c-Pr | Me | Me | Me | H | |
| 3-67 | Et | 1-Me-c-Pr | c-Pr | Me | H | H | |
| 3-68 | Et | 1-Me-c-Pr | c-Pr | Me | Me | H | |
| 3-69 | Et | 1-Me-c-Pr | —(CH₂)₂— | | H | H | |
| 3-70 | Et | 1-Me-c-Pr | —(CH₂)₂— | | Me | H | |
| 3-71 | Et | 1-Cl-c-Pr | Me | Me | H | H | |
| 3-72 | Et | 1-Cl-c-Pr | Me | Me | Me | H | |
| 3-73 | Et | 1-Cl-c-Pr | c-Pr | Me | H | H | |
| 3-74 | Et | 1-Cl-c-Pr | c-Pr | Me | Me | H | |
| 3-75 | Et | 1-Cl-c-Pr | —(CH₂)₂— | | H | H | |
| 3-76 | Et | 1-Cl-c-Pr | —(CH₂)₂— | | Me | H | |
| 3-77 | Et | 2,2-Me₂-c-Pr | Me | Me | H | H | |
| 3-78 | Et | 2,2-Me₂-c-Pr | Me | Me | Me | H | |
| 3-79 | Et | 2,2-Me₂-c-Pr | c-Pr | Me | H | H | |
| 3-80 | Et | 2,2-Me₂-c-Pr | c-Pr | Me | Me | H | |
| 3-81 | Et | 2,2-Me₂-c-Pr | —(CH₂)₂— | | H | H | |
| 3-82 | Et | 2,2-Me₂-c-Pr | —CH₂—CMe₂— | | H | H | |
| 3-83 | Et | 2,2-Cl₂-c-Pr | Me | Me | H | H | |
| 3-84 | Et | 2,2-Cl₂-c-Pr | Me | Me | Me | H | |
| 3-85 | Et | 2,2-Cl₂-c-Pr | c-Pr | Me | H | H | |
| 3-86 | Et | 2,2-Cl₂-c-Pr | c-Pr | Me | Me | H | |
| 3-87 | Et | 2,2-Cl₂-c-Pr | —(CH₂)₂— | | H | H | |
| 3-88 | Et | 2,2-Cl₂-c-Pr | —CH₂—CCl₂— | | H | H | |
| 3-89 | c-Pr | c-Pr | Me | Me | H | H | |
| 3-90 | c-Pr | c-Pr | Me | Me | Me | H | |
| 3-91 | c-Pr | c-Pr | c-Pr | Me | H | H | |
| 3-92 | c-Pr | c-Pr | c-Pr | Me | Me | H | |
| 3-93 | c-Pr | c-Pr | —CH₂—OMe | Me | H | H | |
| 3-94 | c-Pr | c-Pr | —CH₂—OMe | Me | Me | H | |
| 3-95 | c-Pr | c-Pr | —(CH₂)₂— | | H | H | |
| 3-96 | c-Pr | c-Pr | —(CH₂)₂— | | H | Me | |
| 3-97 | c-Pr | c-Pr | —(CH₂)₂— | | H | c-Pr | |
| 3-98 | c-Pr | c-Bu | —(CH₂)₃— | | H | H | |
| 3-99 | c-Pr | c-Bu | —(CH₂)₃— | | H | Me | |
| 3-100 | c-Pr | c-Bu | —(CH₂)₃— | | H | c-Pr | |
| 3-101 | c-Pr | 1-Me-c-Pr | Me | Me | H | H | |
| 3-102 | c-Pr | 1-Me-c-Pr | Me | Me | Me | H | |
| 3-103 | c-Pr | 1-Me-c-Pr | c-Pr | Me | H | H | |
| 3-104 | c-Pr | 1-Me-c-Pr | c-Pr | Me | Me | H | |
| 3-105 | c-Pr | 1-Me-c-Pr | —(CH₂)₂— | | H | H | |
| 3-106 | c-Pr | 1-Me-c-Pr | —(CH₂)₂— | | Me | H | |
| 3-107 | c-Pr | 1-Cl-c-Pr | Me | Me | H | H | |
| 3-108 | c-Pr | 1-Cl-c-Pr | Me | Me | Me | H | |
| 3-109 | c-Pr | 1-Cl-c-Pr | c-Pr | Me | H | H | |
| 3-110 | c-Pr | 1-Cl-c-Pr | c-Pr | Me | Me | H | |
| 3-111 | c-Pr | 1-Cl-c-Pr | —(CH₂)₂— | | H | H | |
| 3-112 | c-Pr | 1-Cl-c-Pr | —(CH₂)₂— | | Me | H | |
| 3-113 | c-Pr | 2,2-Me₂-c-Pr | Me | Me | H | H | |
| 3-114 | c-Pr | 2,2-Me₂-c-Pr | Me | Me | Me | H | |
| 3-115 | c-Pr | 2,2-Me₂-c-Pr | c-Pr | Me | H | H | |
| 3-116 | c-Pr | 2,2-Me₂-c-Pr | c-Pr | Me | Me | H | |
| 3-117 | c-Pr | 2,2-Me₂-c-Pr | —(CH₂)₂— | | H | H | |
| 3-118 | c-Pr | 2,2-Me₂-c-Pr | —CH₂—CMe₂— | | H | H | |
| 3-119 | c-Pr | 2,2-Cl₂-c-Pr | Me | Me | H | H | |
| 3-120 | c-Pr | 2,2-Cl₂-c-Pr | Me | Me | Me | H | |
| 3-121 | c-Pr | 2,2-Cl₂-c-Pr | c-Pr | Me | H | H | |
| 3-122 | c-Pr | 2,2-Cl₂-c-Pr | c-Pr | Me | Me | H | |
| 3-123 | c-Pr | 2,2-Cl₂-c-Pr | —(CH₂)₂— | | H | H | |
| 3-124 | c-Pr | 2,2-Cl₂-c-Pr | —CH₂—CCl₂— | | H | H | |
| 3-125 | CHFCH₃ | c-Pr | Me | Me | H | H | |
| 3-126 | CHFCH₃ | c-Pr | Me | Me | Me | H | |
| 3-127 | CHFCH₃ | c-Pr | c-Pr | Me | H | H | |
| 3-128 | CHFCH₃ | c-Pr | c-Pr | Me | Me | H | |

TABLE 3-continued

Compounds of the formula (Ic)

(Ic)

| No. | $R^2$ | $R^3$ | $R^4$ | $R^5$ | $R^6$ | $R^7$ | phys. data |
|---|---|---|---|---|---|---|---|
| 3-129 | CHFCH$_3$ | c-Pr | —CH$_2$—OMe | Me | H | H | |
| 3-130 | CHFCH$_3$ | c-Pr | —CH$_2$—OMe | Me | Me | H | |
| 3-131 | CHFCH$_3$ | c-Pr | —(CH$_2$)$_2$— | | H | H | |
| 3-132 | CHFCH$_3$ | c-Pr | —(CH$_2$)$_2$— | | H | Me | |
| 3-133 | CHFCH$_3$ | c-Pr | —(CH$_2$)$_2$— | | H | c-Pr | |
| 3-134 | CHFCH$_3$ | c-Bu | —(CH$_2$)$_3$— | | H | H | |
| 3-135 | CHFCH$_3$ | c-Bu | —(CH$_2$)$_3$— | | H | Me | |
| 3-136 | CHFCH$_3$ | c-Bu | —(CH$_2$)$_3$— | | H | c-Pr | |
| 3-137 | CHFCH$_3$ | 1-Me-c-Pr | Me | Me | H | H | |
| 3-138 | CHFCH$_3$ | 1-Me-c-Pr | Me | Me | Me | H | |
| 3-139 | CHFCH$_3$ | 1-Me-c-Pr | c-Pr | Me | H | H | |
| 3-140 | CHFCH$_3$ | 1-Me-c-Pr | c-Pr | Me | Me | H | |
| 3-141 | CHFCH$_3$ | 1-Me-c-Pr | —(CH$_2$)$_2$— | | H | H | |
| 3-142 | CHFCH$_3$ | 1-Me-c-Pr | —(CH$_2$)$_2$— | | Me | H | |
| 3-143 | CHFCH$_3$ | 1-Cl-c-Pr | Me | Me | H | H | |
| 3-144 | CHFCH$_3$ | 1-Cl-c-Pr | Me | Me | Me | H | |
| 3-145 | CHFCH$_3$ | 1-Cl-c-Pr | c-Pr | Me | H | H | |
| 3-146 | CHFCH$_3$ | 1-Cl-c-Pr | c-Pr | Me | Me | H | |
| 3-147 | CHFCH$_3$ | 1-Cl-c-Pr | —(CH$_2$)$_2$— | | H | H | |
| 3-148 | CHFCH$_3$ | 1-Cl-c-Pr | —(CH$_2$)$_2$— | | Me | H | |
| 3-149 | CHFCH$_3$ | 2,2-Me$_2$-c-Pr | Me | Me | H | H | |
| 3-150 | CHFCH$_3$ | 2,2-Me$_2$-c-Pr | Me | Me | Me | H | |
| 3-151 | CHFCH$_3$ | 2,2-Me$_2$-c-Pr | c-Pr | Me | H | H | |
| 3-152 | CHFCH$_3$ | 2,2-Me$_2$-c-Pr | c-Pr | Me | Me | H | |
| 3-153 | CHFCH$_3$ | 2,2-Me$_2$-c-Pr | —(CH$_2$)$_2$— | | H | H | |
| 3-154 | CHFCH$_3$ | 2,2-Me$_2$-c-Pr | —CH$_2$—CMe$_2$— | | H | H | |
| 3-155 | CHFCH$_3$ | 2,2-Cl$_2$-c-Pr | Me | Me | H | H | |
| 3-156 | CHFCH$_3$ | 2,2-Cl$_2$-c-Pr | Me | Me | Me | H | |
| 3-157 | CHFCH$_3$ | 2,2-Cl$_2$-c-Pr | c-Pr | Me | H | H | |
| 3-158 | CHFCH$_3$ | 2,2-Cl$_2$-c-Pr | c-Pr | Me | Me | H | |
| 3-159 | CHFCH$_3$ | 2,2-Cl$_2$-c-Pr | —(CH$_2$)$_2$— | | H | H | |
| 3-160 | CHFCH$_3$ | 2,2-Cl$_2$-c-Pr | —CH$_2$—CCl$_2$— | | H | H | |
| 3-161 | CHFC$_2$H$_5$ | c-Pr | Me | Me | H | H | |
| 3-162 | CHFC$_2$H$_5$ | c-Pr | Me | Me | Me | H | |
| 3-163 | CHFC$_2$H$_5$ | c-Pr | c-Pr | Me | H | H | |
| 3-164 | CHFC$_2$H$_5$ | c-Pr | c-Pr | Me | Me | H | |
| 3-165 | CHFC$_2$H$_5$ | c-Pr | —CH$_2$—OMe | Me | H | H | |
| 3-166 | CHFC$_2$H$_5$ | c-Pr | —CH$_2$—OMe | Me | Me | H | |
| 3-167 | CHFC$_2$H$_5$ | c-Pr | —(CH$_2$)$_2$— | | H | Me | |
| 3-168 | CHFC$_2$H$_5$ | c-Pr | —(CH$_2$)$_2$— | | H | Me | |
| 3-169 | CHFC$_2$H$_5$ | c-Pr | —(CH$_2$)$_2$— | | H | c-Pr | |
| 3-170 | CHFC$_2$H$_5$ | c-Bu | —(CH$_2$)$_3$— | | H | H | |
| 3-171 | CHFC$_2$H$_5$ | c-Bu | —(CH$_2$)$_3$— | | H | Me | |
| 3-172 | CHFC$_2$H$_5$ | c-Bu | —(CH$_2$)$_3$— | | H | c-Pr | |
| 3-173 | CHFC$_2$H$_5$ | 1-Me-c-Pr | Me | Me | H | H | |
| 3-174 | CHFC$_2$H$_5$ | 1-Me-c-Pr | Me | Me | Me | H | |
| 3-175 | CHFC$_2$H$_5$ | 1-Me-c-Pr | c-Pr | Me | H | H | |
| 3-176 | CHFC$_2$H$_5$ | 1-Me-c-Pr | c-Pr | Me | Me | H | |
| 3-177 | CHFC$_2$H$_5$ | 1-Me-c-Pr | —(CH$_2$)$_2$— | | H | H | |
| 3-178 | CHFC$_2$H$_5$ | 1-Me-c-Pr | —(CH$_2$)$_2$— | | Me | H | |
| 3-179 | CHFC$_2$H$_5$ | 1-Cl-c-Pr | Me | Me | H | H | |
| 3-180 | CHFC$_2$H$_5$ | 1-Cl-c-Pr | Me | Me | Me | H | |
| 3-181 | CHFC$_2$H$_5$ | 1-Cl-c-Pr | c-Pr | Me | H | H | |
| 3-182 | CHFC$_2$H$_5$ | 1-Cl-c-Pr | c-Pr | Me | Me | H | |
| 3-183 | CHFC$_2$H$_5$ | 1-Cl-c-Pr | —(CH$_2$)$_2$— | | H | H | |
| 3-184 | CHFC$_2$H$_5$ | 1-Cl-c-Pr | —(CH$_2$)$_2$— | | Me | H | |
| 3-185 | CHFC$_2$H$_5$ | 2,2-Me$_2$-c-Pr | Me | Me | H | H | |
| 3-186 | CHFC$_2$H$_5$ | 2,2-Me$_2$-c-Pr | Me | Me | Me | H | |
| 3-187 | CHFC$_2$H$_5$ | 2,2-Me$_2$-c-Pr | c-Pr | Me | H | H | |
| 3-188 | CHFC$_2$H$_5$ | 2,2-Me$_2$-c-Pr | c-Pr | Me | Me | H | |
| 3-189 | CHFC$_2$H$_5$ | 2,2-Me$_2$-c-Pr | —(CH$_2$)$_2$— | | H | H | |
| 3-190 | CHFC$_2$H$_5$ | 2,2-Me$_2$-c-Pr | —CH$_2$—CMe$_2$— | | H | H | |
| 3-191 | CHFC$_2$H$_5$ | 2,2-Cl$_2$-c-Pr | Me | Me | H | H | |
| 3-192 | CHFC$_2$H$_5$ | 2,2-Cl$_2$-c-Pr | Me | Me | Me | H | |

TABLE 3-continued

Compounds of the formula (Ic)

(Ic)

| No. | R² | R³ | R⁴ | R⁵ | R⁶ | R⁷ | phys. data |
|---|---|---|---|---|---|---|---|
| 3-193 | CHFC₂H₅ | 2,2-Cl₂-c-Pr | c-Pr | Me | H | H | |
| 3-194 | CHFC₂H₅ | 2,2-Cl₂-c-Pr | c-Pr | Me | Me | H | |
| 3-195 | CHFC₂H₅ | 2,2-Cl₂-c-Pr | —(CH₂)₂— | | H | H | |
| 3-196 | CHFC₂H₅ | 2,2-Cl₂-c-Pr | —CH₂—CCl₂— | | H | H | |
| 3-197 | CF(CH₃)₂ | c-Pr | Me | Me | H | H | resin |
| 3-198 | CF(CH₃)₂ | c-Pr | Me | Me | Me | H | |
| 3-199 | CF(CH₃)₂ | c-Pr | c-Pr | Me | H | H | |
| 3-200 | CF(CH₃)₂ | c-Pr | c-Pr | Me | Me | H | |
| 3-201 | CF(CH₃)₂ | c-Pr | —CH₂—OMe | Me | H | H | |
| 3-202 | CF(CH₃)₂ | c-Pr | —CH₂—OMe | Me | Me | H | |
| 3-203 | CF(CH₃)₂ | c-Pr | —(CH₂)₂— | | H | H | resin |
| 3-204 | CF(CH₃)₂ | c-Pr | —(CH₂)₂— | | H | Me | |
| 3-205 | CF(CH₃)₂ | c-Pr | —(CH₂)₂— | | H | c-Pr | |
| 3-206 | CF(CH₃)₂ | c-Bu | —(CH₂)₃— | | H | H | resin |
| 3-207 | CF(CH₃)₂ | c-Bu | —(CH₂)₃— | | H | Me | |
| 3-208 | CF(CH₃)₂ | c-Bu | —(CH₂)₃— | | H | c-Pr | |
| 3-209 | CF(CH₃)₂ | 1-Me-c-Pr | Me | Me | H | H | |
| 3-210 | CF(CH₃)₂ | 1-Me-c-Pr | Me | Me | Me | H | |
| 3-211 | CF(CH₃)₂ | 1-Me-c-Pr | c-Pr | Me | H | H | |
| 3-212 | CF(CH₃)₂ | 1-Me-c-Pr | c-Pr | Me | Me | H | |
| 3-213 | CF(CH₃)₂ | 1-Me-c-Pr | —(CH₂)₂— | | H | H | |
| 3-214 | CF(CH₃)₂ | 1-Me-c-Pr | —(CH₂)₂— | | Me | H | |
| 3-215 | CF(CH₃)₂ | 1-Cl-c-Pr | Me | Me | H | H | |
| 3-216 | CF(CH₃)₂ | 1-Cl-c-Pr | Me | Me | Me | H | |
| 3-217 | CF(CH₃)₂ | 1-Cl-c-Pr | c-Pr | Me | H | H | |
| 3-218 | CF(CH₃)₂ | 1-Cl-c-Pr | c-Pr | Me | Me | H | |
| 3-219 | CF(CH₃)₂ | 1-Cl-c-Pr | —(CH₂)₂— | | H | H | |
| 3-220 | CF(CH₃)₂ | 1-Cl-c-Pr | —(CH₂)₂— | | Me | H | |
| 3-221 | CF(CH₃)₂ | 2,2-Me₂-c-Pr | Me | Me | H | H | |
| 3-222 | CF(CH₃)₂ | 2,2-Me₂-c-Pr | Me | Me | Me | H | |
| 3-223 | CF(CH₃)₂ | 2,2-Me₂-c-Pr | c-Pr | Me | H | H | |
| 3-224 | CF(CH₃)₂ | 2,2-Me₂-c-Pr | c-Pr | Me | Me | H | |
| 3-225 | CF(CH₃)₂ | 2,2-Me₂-c-Pr | —(CH₂)₂— | | H | H | |
| 3-226 | CF(CH₃)₂ | 2,2-Me₂-c-Pr | —CH₂—CMe₂— | | H | H | |
| 3-227 | CF(CH₃)₂ | 2,2-Cl₂-c-Pr | Me | Me | H | H | |
| 3-228 | CF(CH₃)₂ | 2,2-Cl₂-c-Pr | Me | Me | Me | H | |
| 3-229 | CF(CH₃)₂ | 2,2-Cl₂-c-Pr | c-Pr | Me | H | H | |
| 3-230 | CF(CH₃)₂ | 2,2-Cl₂-c-Pr | c-Pr | Me | Me | H | |
| 3-231 | CF(CH₃)₂ | 2,2-Cl₂-c-Pr | —(CH₂)₂— | | H | H | |
| 3-232 | CF(CH₃)₂ | 2,2-Cl₂-c-Pr | —CH₂—CCl₂— | | H | H | |
| 3-233 | 1-F-c-Pr | c-Pr | Me | Me | H | H | |
| 3-234 | 1-F-c-Pr | c-Pr | Me | Me | Me | H | |
| 3-235 | 1-F-c-Pr | c-Pr | c-Pr | Me | H | H | |
| 3-236 | 1-F-c-Pr | c-Pr | c-Pr | Me | Me | H | |
| 3-237 | 1-F-c-Pr | c-Pr | —CH₂—OMe | Me | H | H | |
| 3-238 | 1-F-c-Pr | c-Pr | —CH₂—OMe | Me | Me | H | |
| 3-239 | 1-F-c-Pr | c-Pr | —(CH₂)₂— | | H | H | |
| 3-240 | 1-F-c-Pr | c-Pr | —(CH₂)₂— | | H | Me | |
| 3-241 | 1-F-c-Pr | c-Pr | —(CH₂)₂— | | H | c-Pr | |
| 3-242 | 1-F-c-Pr | c-Bu | —(CH₂)₃— | | H | H | |
| 3-243 | 1-F-c-Pr | c-Bu | —(CH₂)₃— | | H | Me | |
| 3-244 | 1-F-c-Pr | c-Bu | —(CH₂)₃— | | H | c-Pr | |
| 3-245 | 1-F-c-Pr | 1-Me-c-Pr | Me | Me | H | H | |
| 3-246 | 1-F-c-Pr | 1-Me-c-Pr | Me | Me | Me | H | |
| 3-247 | 1-F-c-Pr | 1-Me-c-Pr | c-Pr | Me | H | H | |
| 3-248 | 1-F-c-Pr | 1-Me-c-Pr | c-Pr | Me | Me | H | |
| 3-249 | 1-F-c-Pr | 1-Me-c-Pr | —(CH₂)₂— | | H | H | |
| 3-250 | 1-F-c-Pr | 1-Me-c-Pr | —(CH₂)₂— | | Me | H | |
| 3-251 | 1-F-c-Pr | 1-Cl-c-Pr | Me | Me | H | H | |
| 3-252 | 1-F-c-Pr | 1-Cl-c-Pr | Me | Me | Me | H | |
| 3-253 | 1-F-c-Pr | 1-Cl-c-Pr | c-Pr | Me | H | H | |
| 3-254 | 1-F-c-Pr | 1-Cl-c-Pr | c-Pr | Me | Me | H | |
| 3-255 | 1-F-c-Pr | 1-Cl-c-Pr | —(CH₂)₂— | | H | H | |
| 3-256 | 1-F-c-Pr | 1-Cl-c-Pr | —(CH₂)₂— | | Me | H | |

TABLE 3-continued

Compounds of the formula (Ic)

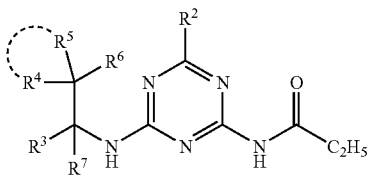
(Ic)

| No. | $R^2$ | $R^3$ | $R^4$ | $R^5$ | $R^6$ | $R^7$ | phys. data |
|---|---|---|---|---|---|---|---|
| 3-257 | 1-F-c-Pr | 2,2-Me$_2$-c-Pr | Me | Me | H | H | |
| 3-258 | 1-F-c-Pr | 2,2-Me$_2$-c-Pr | Me | Me | Me | H | |
| 3-259 | 1-F-c-Pr | 2,2-Me$_2$-c-Pr | c-Pr | Me | H | H | |
| 3-260 | 1-F-c-Pr | 2,2-Me$_2$-c-Pr | c-Pr | Me | Me | H | |
| 3-261 | 1-F-c-Pr | 2,2-Me$_2$-c-Pr | —(CH$_2$)$_2$— | | H | H | |
| 3-262 | 1-F-c-Pr | 2,2-Me$_2$-c-Pr | —CH$_2$—CMe$_2$— | | H | H | |
| 3-263 | 1-F-c-Pr | 2,2-Cl$_2$-c-Pr | Me | Me | H | H | |
| 3-264 | 1-F-c-Pr | 2,2-Cl$_2$-c-Pr | Me | Me | Me | H | |
| 3-265 | 1-F-c-Pr | 2,2-Cl$_2$-c-Pr | c-Pr | Me | H | H | |
| 3-266 | 1-F-c-Pr | 2,2-Cl$_2$-c-Pr | c-Pr | Me | Me | H | |
| 3-267 | 1-F-c-Pr | 2,2-Cl$_2$-c-Pr | —(CH$_2$)$_2$— | | H | H | |
| 3-268 | 1-F-c-Pr | 2,2-Cl$_2$-c-Pr | —CH$_2$—CCl$_2$— | | H | H | |
| 3-269 | CHF2 | c-Pr | Me | Me | H | H | |
| 3-270 | CHF2 | c-Pr | Me | Me | Me | H | |
| 3-271 | CHF2 | c-Pr | c-Pr | Me | H | H | |
| 3-272 | CHF2 | c-Pr | c-Pr | Me | Me | H | |
| 3-273 | CHF2 | c-Pr | —CH$_2$—OMe | Me | H | H | |
| 3-274 | CHF2 | c-Pr | —CH$_2$—OMe | Me | Me | H | |
| 3-275 | CHF2 | c-Pr | —(CH$_2$)$_2$— | | H | H | |
| 3-276 | CHF2 | c-Pr | —(CH$_2$)$_2$— | | H | Me | |
| 3-277 | CHF2 | c-Pr | —(CH$_2$)$_2$— | | H | c-Pr | |
| 3-278 | CHF2 | c-Bu | —(CH$_2$)$_3$— | | H | H | |
| 3-279 | CHF2 | c-Bu | —(CH$_2$)$_3$— | | H | Me | |
| 3-280 | CHF2 | c-Bu | —(CH$_2$)$_3$— | | H | c-Pr | |

TABLE 4

Compounds of the formula (Id)

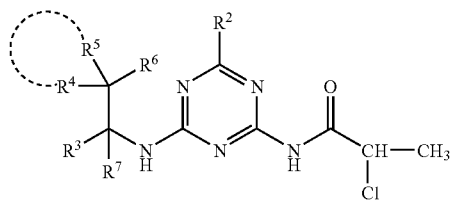
(Id)

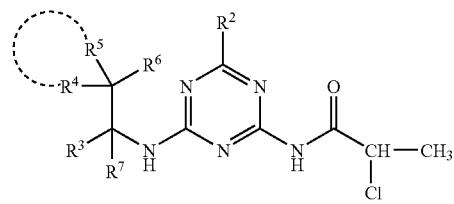
(Id)

| No. | $R^2$ | $R^3$ | $R^4$ | $R^5$ | $R^6$ | $R^7$ | phys. data |
|---|---|---|---|---|---|---|---|
| 4-1 | H | c-Pr | Me | Me | H | H | |
| 4-2 | H | c-Pr | Me | Me | Me | H | |
| 4-3 | H | c-Pr | c-Pr | Me | H | H | |
| 4-4 | H | c-Pr | c-Pr | Me | Me | H | |
| 4-5 | H | c-Pr | —CH$_2$—OMe | Me | H | H | |
| 4-6 | H | c-Pr | —CH$_2$—OMe | Me | Me | H | |
| 4-7 | H | c-Pr | —(CH$_2$)$_2$— | | H | H | |
| 4-8 | H | c-Pr | —(CH$_2$)$_2$— | | H | Me | |
| 4-9 | H | c-Pr | —(CH$_2$)$_2$— | | H | c-Pr | |
| 4-10 | H | c-Bu | —(CH$_2$)$_3$— | | H | H | |
| 4-11 | H | c-Bu | —(CH$_2$)$_3$— | | H | Me | |
| 4-12 | H | c-Bu | —(CH$_2$)$_3$— | | H | c-Pr | |
| 4-13 | H | 1-Me-c-Pr | Me | Me | H | H | |
| 4-14 | H | 1-Me-c-Pr | Me | Me | Me | H | |
| 4-15 | Me | c-Pr | Me | Me | H | H | |
| 4-16 | Me | c-Pr | Me | Me | Me | H | |
| 4-17 | Me | c-Pr | c-Pr | Me | H | H | |
| 4-18 | Me | c-Pr | c-Pr | Me | Me | H | |
| 4-19 | Me | c-Pr | —CH$_2$—OMe | Me | H | H | |
| 4-20 | Me | c-Pr | —CH$_2$—OMe | Me | Me | H | |
| 4-21 | Me | c-Pr | —(CH$_2$)$_2$— | | H | H | |
| 4-22 | Me | c-Pr | —(CH$_2$)$_2$— | | H | Me | |
| 4-23 | Me | c-Pr | —(CH$_2$)$_2$— | | H | c-Pr | |
| 4-24 | Me | c-Bu | —(CH$_2$)$_3$— | | H | H | |
| 4-25 | Me | c-Bu | —(CH$_2$)$_3$— | | H | Me | |
| 4-26 | Me | c-Bu | —(CH$_2$)$_3$— | | H | c-Pr | |
| 4-27 | Me | 1-Me-c-Pr | Me | Me | H | H | |
| 4-28 | Me | 1-Me-c-Pr | Me | Me | Me | H | |
| 4-29 | Me | 1-Me-c-Pr | c-Pr | Me | H | H | |
| 4-30 | Me | 1-Me-c-Pr | c-Pr | Me | Me | H | |
| 4-31 | Me | 1-Me-c-Pr | —(CH$_2$)$_2$— | | H | H | |
| 4-32 | Me | 1-Me-c-Pr | —(CH$_2$)$_2$— | | Me | | |
| 4-33 | Me | 1-Cl-c-Pr | Me | Me | H | H | |
| 4-34 | Me | 1-Cl-c-Pr | Me | Me | Me | H | |

TABLE 4-continued

Compounds of the formula (Id)

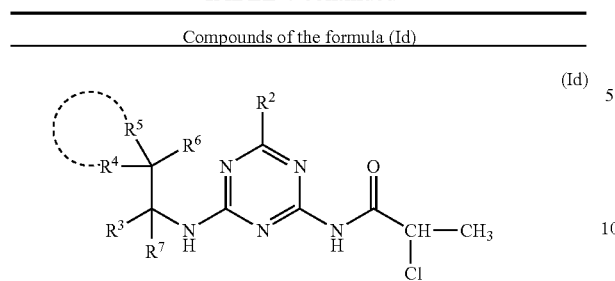

| No. | R² | R³ | R⁴ | R⁵ | R⁶ | R⁷ | phys. data |
|---|---|---|---|---|---|---|---|
| 4-35 | Me | 1-Cl-c-Pr | c-Pr | Me | H | H | |
| 4-36 | Me | 1-Cl-c-Pr | c-Pr | Me | Me | H | |
| 4-37 | Me | 1-Cl-c-Pr | —(CH₂)₂— | | H | H | |
| 4-38 | Me | 1-Cl-c-Pr | —(CH₂)₂— | | Me | H | |
| 4-39 | Me | 2,2-Me₂-c-Pr | Me | Me | H | H | |
| 4-40 | Me | 2,2-Me₂-c-Pr | Me | Me | Me | H | |
| 4-41 | Me | 2,2-Me₂-c-Pr | c-Pr | Me | H | H | |
| 4-42 | Me | 2,2-Me₂-c-Pr | c-Pr | Me | Me | H | |
| 4-43 | Me | 2,2-Me₂-c-Pr | —(CH₂)₂— | | H | H | |
| 4-44 | Me | 2,2-Me₂-c-Pr | —CH₂—CMe₂— | | H | H | |
| 4-45 | Me | 2,2-Cl₂-c-Pr | Me | Me | H | H | |
| 4-46 | Me | 2,2-Cl₂-c-Pr | Me | Me | Me | H | |
| 4-47 | Me | 2,2-Cl₂-c-Pr | c-Pr | Me | H | H | |
| 4-48 | Me | 2,2-Cl₂-c-Pr | c-Pr | Me | Me | H | |
| 4-49 | Me | 2,2-Cl₂-c-Pr | —(CH₂)₂— | | H | H | |
| 4-50 | Me | 2,2-Cl₂-c-Pr | —CH₂—CCl₂— | | H | H | |
| 4-51 | Et | c-Pr | Me | Me | H | H | |
| 4-52 | Et | c-Pr | Me | Me | Me | H | |
| 4-53 | Et | c-Pr | c-Pr | Me | H | H | |
| 4-54 | Et | c-Pr | c-Pr | Me | Me | H | |
| 4-55 | Et | c-Pr | —CH₂—OMe | Me | H | H | |
| 4-56 | Et | c-Pr | —CH₂—OMe | Me | Me | H | |
| 4-57 | Et | c-Pr | —(CH₂)₂— | | H | H | |
| 4-58 | Et | c-Pr | —(CH₂)₂— | | H | Me | |
| 4-59 | Et | c-Pr | —(CH₂)₂— | | H | c-Pr | |
| 4-60 | Et | c-Bu | —(CH₂)₃— | | H | H | |
| 4-61 | Et | c-Bu | —(CH₂)₃— | | H | Me | |
| 4-62 | Et | c-Bu | —(CH₂)₃— | | H | c-Pr | |
| 4-63 | Et | 1-Me-c-Pr | Me | Me | H | H | |
| 4-64 | Et | 1-Me-c-Pr | Me | Me | Me | H | |
| 4-65 | Et | 1-Me-c-Pr | c-Pr | Me | H | H | |
| 4-66 | Et | 1-Me-c-Pr | c-Pr | Me | Me | H | |
| 4-67 | Et | 1-Me-c-Pr | —(CH₂)₂— | | H | H | |
| 4-68 | Et | 1-Me-c-Pr | —(CH₂)₂— | | Me | H | |
| 4-69 | Et | 1-Cl-c-Pr | Me | Me | H | H | |
| 4-70 | Et | 1-Cl-c-Pr | Me | Me | Me | H | |
| 4-71 | Et | 1-Cl-c-Pr | c-Pr | Me | H | H | |
| 4-72 | Et | 1-Cl-c-Pr | c-Pr | Me | Me | H | |
| 4-73 | Et | 1-Cl-c-Pr | —(CH₂)₂— | | H | H | |
| 4-74 | Et | 1-Cl-c-Pr | —(CH₂)₂— | | Me | H | |
| 4-75 | Et | 2,2-Me₂-c-Pr | Me | Me | H | H | |
| 4-76 | Et | 2,2-Me₂-c-Pr | Me | Me | Me | H | |
| 4-77 | Et | 2,2-Me₂-c-Pr | c-Pr | Me | H | H | |
| 4-78 | Et | 2,2-Me₂-c-Pr | c-Pr | Me | Me | H | |
| 4-79 | Et | 2,2-Me₂-c-Pr | —(CH₂)₂— | | H | H | |
| 4-80 | Et | 2,2-Me₂-c-Pr | —CH₂—CMe₂— | | H | H | |
| 4-81 | Et | 2,2-Cl₂-c-Pr | Me | Me | H | H | |
| 4-82 | Et | 2,2-Cl₂-c-Pr | Me | Me | Me | H | |
| 4-83 | Et | 2,2-Cl₂-c-Pr | c-Pr | Me | H | H | |
| 4-84 | Et | 2,2-Cl₂-c-Pr | c-Pr | Me | Me | H | |
| 4-85 | Et | 2,2-Cl₂-c-Pr | —(CH₂)₂— | | H | H | |
| 4-86 | Et | 2,2-Cl₂-c-Pr | —CH₂—CCl₂— | | H | H | |
| 4-87 | c-Pr | c-Pr | Me | Me | H | H | |
| 4-88 | c-Pr | c-Pr | Me | Me | Me | H | |
| 4-89 | c-Pr | c-Pr | c-Pr | Me | H | H | |
| 4-90 | c-Pr | c-Pr | c-Pr | Me | Me | H | |
| 4-91 | c-Pr | c-Pr | —CH₂—OMe | Me | H | H | |
| 4-92 | c-Pr | c-Pr | —CH₂—OMe | Me | Me | H | |
| 4-93 | c-Pr | c-Pr | —(CH₂)₂— | | H | H | |
| 4-94 | c-Pr | c-Pr | —(CH₂)₂— | | H | Me | |
| 4-95 | c-Pr | c-Pr | —(CH₂)₂— | | H | c-Pr | |
| 4-96 | c-Pr | c-Bu | —(CH₂)₃— | | H | H | |
| 4-97 | c-Pr | c-Bu | —(CH₂)₃— | | H | Me | |
| 4-98 | c-Pr | c-Bu | —(CH₂)₃— | | H | c-Pr | |
| 4-99 | c-Pr | 1-Me-c-Pr | Me | Me | H | H | |
| 4-100 | c-Pr | 1-Me-c-Pr | Me | Me | Me | H | |
| 4-101 | c-Pr | 1-Me-c-Pr | c-Pr | Me | H | H | |
| 4-102 | c-Pr | 1-Me-c-Pr | c-Pr | Me | Me | H | |
| 4-103 | c-Pr | 1-Me-c-Pr | —(CH₂)₂— | | H | H | |
| 4-104 | c-Pr | 1-Me-c-Pr | —(CH₂)₂— | | Me | H | |
| 4-105 | c-Pr | 1-Cl-c-Pr | Me | Me | H | H | |
| 4-106 | c-Pr | 1-Cl-c-Pr | Me | Me | Me | H | |
| 4-107 | c-Pr | 1-Cl-c-Pr | c-Pr | Me | H | H | |
| 4-108 | c-Pr | 1-Cl-c-Pr | c-Pr | Me | Me | H | |
| 4-109 | c-Pr | 1-Cl-c-Pr | —(CH₂)₂— | | H | H | |
| 4-110 | c-Pr | 1-Cl-c-Pr | —(CH₂)₂— | | Me | H | |
| 4-111 | c-Pr | 2,2-Me₂-c-Pr | Me | Me | H | H | |
| 4-112 | c-Pr | 2,2-Me₂-c-Pr | Me | Me | Me | H | |
| 4-113 | c-Pr | 2,2-Me₂-c-Pr | c-Pr | Me | H | H | |
| 4-114 | c-Pr | 2,2-Me₂-c-Pr | c-Pr | Me | Me | H | |
| 4-115 | c-Pr | 2,2-Me₂-c-Pr | —(CH₂)₂— | | H | H | |
| 4-116 | c-Pr | 2,2-Me₂-c-Pr | —CH₂—CMe₂— | | H | H | |
| 4-117 | c-Pr | 2,2-Cl₂-c-Pr | Me | Me | H | H | |
| 4-118 | c-Pr | 2,2-Cl₂-c-Pr | Me | Me | Me | H | |
| 4-119 | c-Pr | 2,2-Cl₂-c-Pr | c-Pr | Me | H | H | |
| 4-120 | c-Pr | 2,2-Cl₂-c-Pr | c-Pr | Me | Me | H | |
| 4-121 | c-Pr | 2,2-Cl₂-c-Pr | —(CH₂)₂— | | H | H | |
| 4-122 | c-Pr | 2,2-Cl₂-c-Pr | —CH₂—CCl₂— | | H | H | |
| 4-123 | CHFCH₃ | c-Pr | Me | Me | H | H | |
| 4-124 | CHFCH₃ | c-Pr | Me | Me | Me | H | |
| 4-125 | CHFCH₃ | c-Pr | c-Pr | Me | H | H | |
| 4-126 | CHFCH₃ | c-Pr | c-Pr | Me | Me | H | |
| 4-127 | CHFCH₃ | c-Pr | —CH₂—OMe | Me | H | H | |
| 4-128 | CHFCH₃ | c-Pr | —CH₂—OMe | Me | Me | H | |
| 4-129 | CHFCH₃ | c-Pr | —(CH₂)₂— | | H | H | |
| 4-130 | CHFCH₃ | c-Pr | —(CH₂)₂— | | H | Me | |
| 4-131 | CHFCH₃ | c-Pr | —(CH₂)₂— | | H | c-Pr | |
| 4-132 | CHFCH₃ | c-Bu | —(CH₂)₃— | | H | H | |
| 4-133 | CHFCH₃ | c-Bu | —(CH₂)₃— | | H | Me | |
| 4-134 | CHFCH₃ | c-Bu | —(CH₂)₃— | | H | c-Pr | |
| 4-135 | CHFCH₃ | 1-Me-c-Pr | Me | Me | H | H | |
| 4-136 | CHFCH₃ | 1-Me-c-Pr | Me | Me | Me | H | |
| 4-137 | CHFCH₃ | 1-Me-c-Pr | c-Pr | Me | H | H | |
| 4-138 | CHFCH₃ | 1-Me-c-Pr | c-Pr | Me | Me | H | |
| 4-139 | CHFCH₃ | 1-Me-c-Pr | —(CH₂)₂— | | H | H | |
| 4-140 | CHFCH₃ | 1-Me-c-Pr | —(CH₂)₂— | | Me | H | |
| 4-141 | CHFCH₃ | 1-Cl-c-Pr | Me | Me | H | H | |
| 4-142 | CHFCH₃ | 1-Cl-c-Pr | Me | Me | Me | H | |
| 4-143 | CHFCH₃ | 1-Cl-c-Pr | c-Pr | Me | H | H | |
| 4-144 | CHFCH₃ | 1-Cl-c-Pr | c-Pr | Me | Me | H | |
| 4-145 | CHFCH₃ | 1-Cl-c-Pr | —(CH₂)₂— | | H | H | |
| 4-146 | CHFCH₃ | 1-Cl-c-Pr | —(CH₂)₂— | | Me | H | |
| 4-147 | CHFCH₃ | 2,2-Me₂-c-Pr | Me | Me | H | H | |
| 4-148 | CHFCH₃ | 2,2-Me₂-c-Pr | Me | Me | Me | H | |
| 4-149 | CHFCH₃ | 2,2-Me₂-c-Pr | c-Pr | Me | H | H | |
| 4-150 | CHFCH₃ | 2,2-Me₂-c-Pr | c-Pr | Me | Me | H | |
| 4-151 | CHFCH₃ | 2,2-Me₂-c-Pr | —(CH₂)₂— | | H | H | |
| 4-152 | CHFCH₃ | 2,2-Me₂-c-Pr | —CH₂—CMe₂— | | H | H | |
| 4-153 | CHFCH₃ | 2,2-Cl₂-c-Pr | Me | Me | H | H | |
| 4-154 | CHFCH₃ | 2,2-Cl₂-c-Pr | Me | Me | Me | H | |
| 4-155 | CHFCH₃ | 2,2-Cl₂-c-Pr | c-Pr | Me | H | H | |

TABLE 4-continued

Compounds of the formula (Id)

| No. | R² | R³ | R⁴ | R⁵ | R⁶ | R⁷ | phys. data |
|---|---|---|---|---|---|---|---|
| 4-156 | CHFCH₃ | 2,2-Cl₂-c-Pr | c-Pr | Me | Me | H | |
| 4-157 | CHFCH₃ | 2,2-Cl₂-c-Pr | —(CH₂)₂— | | H | H | |
| 4-158 | CHFCH₃ | 2,2-Cl₂-c-Pr | —CH₂—CCl₂— | | H | H | |
| 4-159 | CHFC₂H₅ | c-Pr | Me | Me | H | H | |
| 4-160 | CHFC₂H₅ | c-Pr | Me | Me | Me | H | |
| 4-161 | CHFC₂H₅ | c-Pr | c-Pr | Me | H | H | |
| 4-162 | CHFC₂H₅ | c-Pr | c-Pr | Me | Me | H | |
| 4-163 | CHFC₂H₅ | c-Pr | —CH₂—OMe | Me | H | H | |
| 4-164 | CHFC₂H₅ | c-Pr | —CH₂—OMe | Me | Me | H | |
| 4-165 | CHFC₂H₅ | c-Pr | —(CH₂)₂— | | H | H | |
| 4-166 | CHFC₂H₅ | c-Pr | —(CH₂)₂— | | H | Me | |
| 4-167 | CHFC₂H₅ | c-Pr | —(CH₂)₂— | | H | c-Pr | |
| 4-168 | CHFC₂H₅ | c-Bu | —(CH₂)₃— | | H | H | |
| 4-169 | CHFC₂H₅ | c-Bu | —(CH₂)₃— | | H | Me | |
| 4-170 | CHFC₂H₅ | c-Bu | —(CH₂)₃— | | H | c-Pr | |
| 4-171 | CHFC₂H₅ | 1-Me-c-Pr | Me | Me | H | H | |
| 4-172 | CHFC₂H₅ | 1-Me-c-Pr | Me | Me | Me | H | |
| 4-173 | CHFC₂H₅ | 1-Me-c-Pr | c-Pr | Me | H | H | |
| 4-174 | CHFC₂H₅ | 1-Me-c-Pr | c-Pr | Me | Me | H | |
| 4-175 | CHFC₂H₅ | 1-Me-c-Pr | —(CH₂)₂— | | H | H | |
| 4-176 | CHFC₂H₅ | 1-Me-c-Pr | —(CH₂)₂— | | Me | H | |
| 4-177 | CHFC₂H₅ | 1-Cl-c-Pr | Me | Me | H | H | |
| 4-178 | CHFC₂H₅ | 1-Cl-c-Pr | Me | Me | Me | H | |
| 4-179 | CHFC₂H₅ | 1-Cl-c-Pr | c-Pr | Me | H | H | |
| 4-180 | CHFC₂H₅ | 1-Cl-c-Pr | c-Pr | Me | Me | H | |
| 4-181 | CHFC₂H₅ | 1-Cl-c-Pr | —(CH₂)₂— | | H | H | |
| 4-182 | CHFC₂H₅ | 1-Cl-c-Pr | —(CH₂)₂— | | Me | H | |
| 4-183 | CHFC₂H₅ | 2,2-Me₂-c-Pr | Me | Me | H | H | |
| 4-184 | CHFC₂H₅ | 2,2-Me₂-c-Pr | Me | Me | Me | H | |
| 4-185 | CHFC₂H₅ | 2,2-Me₂-c-Pr | c-Pr | Me | H | H | |
| 4-186 | CHFC₂H₅ | 2,2-Me₂-c-Pr | c-Pr | Me | Me | H | |
| 4-187 | CHFC₂H₅ | 2,2-Me₂-c-Pr | —(CH₂)₂— | | H | H | |
| 4-188 | CHFC₂H₅ | 2,2-Me₂-c-Pr | —CH₂—CMe₂— | | H | H | |
| 4-189 | CHFC₂H₅ | 2,2-Cl₂-c-Pr | Me | Me | H | H | |
| 4-190 | CHFC₂H₅ | 2,2-Cl₂-c-Pr | Me | Me | Me | H | |
| 4-191 | CHFC₂H₅ | 2,2-Cl₂-c-Pr | c-Pr | Me | H | H | |
| 4-192 | CHFC₂H₅ | 2,2-Cl₂-c-Pr | c-Pr | Me | Me | H | |
| 4-193 | CHFC₂H₅ | 2,2-Cl₂-c-Pr | —(CH₂)₂— | | H | H | |
| 4-194 | CHFC₂H₅ | 2,2-Cl₂-c-Pr | —CH₂—CCl₂— | | H | H | |
| 4-195 | CF(CH₃)₂ | c-Pr | Me | Me | H | H | resin |
| 4-196 | CF(CH₃)₂ | c-Pr | Me | Me | Me | H | |
| 4-197 | CF(CH₃)₂ | c-Pr | c-Pr | Me | H | H | |
| 4-198 | CF(CH₃)₂ | c-Pr | c-Pr | Me | Me | H | |
| 4-199 | CF(CH₃)₂ | c-Pr | —CH₂—OMe | Me | H | H | |
| 4-200 | CF(CH₃)₂ | c-Pr | —CH₂—OMe | Me | Me | H | |
| 4-201 | CF(CH₃)₂ | c-Pr | —(CH₂)₂— | | H | H | resin |
| 4-202 | CF(CH₃)₂ | c-Pr | —(CH₂)₂— | | H | Me | |
| 4-203 | CF(CH₃)₂ | c-Pr | —(CH₂)₂— | | H | c-Pr | |
| 4-204 | CF(CH₃)₂ | c-Bu | —(CH₂)₃— | | H | H | resin |
| 4-205 | CF(CH₃)₂ | c-Bu | —(CH₂)₃— | | H | Me | |
| 4-206 | CF(CH₃)₂ | c-Bu | —(CH₂)₃— | | H | c-Pr | |
| 4-207 | CF(CH₃)₂ | 1-Me-c-Pr | Me | Me | H | H | |
| 4-208 | CF(CH₃)₂ | 1-Me-c-Pr | Me | Me | Me | H | |
| 4-209 | CF(CH₃)₂ | 1-Me-c-Pr | c-Pr | Me | H | H | |
| 4-210 | CF(CH₃)₂ | 1-Me-c-Pr | c-Pr | Me | Me | H | |
| 4-211 | CF(CH₃)₂ | 1-Me-c-Pr | —(CH₂)₂— | | H | H | |
| 4-212 | CF(CH₃)₂ | 1-Me-c-Pr | —(CH₂)₂— | | Me | H | |
| 4-213 | CF(CH₃)₂ | 1-Cl-c-Pr | Me | Me | H | H | |
| 4-214 | CF(CH₃)₂ | 1-Cl-c-Pr | Me | Me | Me | H | |
| 4-215 | CF(CH₃)₂ | 1-Cl-c-Pr | c-Pr | Me | H | H | |
| 4-216 | CF(CH₃)₂ | 1-Cl-c-Pr | c-Pr | Me | Me | H | |
| 4-217 | CF(CH₃)₂ | 1-Cl-c-Pr | —(CH₂)₂— | | H | H | |
| 4-218 | CF(CH₃)₂ | 1-Cl-c-Pr | —(CH₂)₂— | | Me | H | |
| 4-219 | CF(CH₃)₂ | 2,2-Me₂-c-Pr | Me | Me | H | H | |
| 4-220 | CF(CH₃)₂ | 2,2-Me₂-c-Pr | Me | Me | Me | H | |
| 4-221 | CF(CH₃)₂ | 2,2-Me₂-c-Pr | c-Pr | Me | H | H | |
| 4-222 | CF(CH₃)₂ | 2,2-Me₂-c-Pr | c-Pr | Me | Me | H | |
| 4-223 | CF(CH₃)₂ | 2,2-Me₂-c-Pr | —(CH₂)₂— | | H | H | |
| 4-224 | CF(CH₃)₂ | 2,2-Me₂-c-Pr | —CH₂—CMe₂— | | H | H | |
| 4-225 | CF(CH₃)₂ | 2,2-Cl₂-c-Pr | Me | Me | H | H | |
| 4-226 | CF(CH₃)₂ | 2,2-Cl₂-c-Pr | Me | Me | Me | H | |
| 4-227 | CF(CH₃)₂ | 2,2-Cl₂-c-Pr | c-Pr | Me | H | H | |
| 4-228 | CF(CH₃)₂ | 2,2-Cl₂-c-Pr | c-Pr | Me | Me | H | |
| 4-229 | CF(CH₃)₂ | 2,2-Cl₂-c-Pr | —(CH₂)₂— | | H | H | |
| 4-230 | CF(CH₃)₂ | 2,2-Cl₂-c-Pr | —CH₂—CCl₂— | | H | H | |
| 4-231 | 1-F-c-Pr | c-Pr | Me | Me | H | H | |
| 4-232 | 1-F-c-Pr | c-Pr | Me | Me | Me | H | |
| 4-233 | 1-F-c-Pr | c-Pr | c-Pr | Me | H | H | |
| 4-234 | 1-F-c-Pr | c-Pr | c-Pr | Me | Me | H | |
| 4-235 | 1-F-c-Pr | c-Pr | —CH₂—OMe | Me | H | H | |
| 4-236 | 1-F-c-Pr | c-Pr | —CH₂—OMe | Me | Me | H | |
| 4-237 | 1-F-c-Pr | c-Pr | —(CH₂)₂— | | H | H | |
| 4-238 | 1-F-c-Pr | c-Pr | —(CH₂)₂— | | H | Me | |
| 4-239 | 1-F-c-Pr | c-Pr | —(CH₂)₂— | | H | c-Pr | |
| 4-240 | 1-F-c-Pr | c-Bu | —(CH₂)₃— | | H | H | |
| 4-241 | 1-F-c-Pr | c-Bu | —(CH₂)₃— | | H | Me | |
| 4-242 | 1-F-c-Pr | c-Bu | —(CH₂)₃— | | H | c-Pr | |
| 4-243 | 1-F-c-Pr | 1-Me-c-Pr | Me | Me | H | H | |
| 4-244 | 1-F-c-Pr | 1-Me-c-Pr | Me | Me | Me | H | |
| 4-245 | 1-F-c-Pr | 1-Me-c-Pr | c-Pr | Me | H | H | |
| 4-246 | 1-F-c-Pr | 1-Me-c-Pr | c-Pr | Me | Me | H | |
| 4-247 | 1-F-c-Pr | 1-Me-c-Pr | —(CH₂)₂— | | H | H | |
| 4-248 | 1-F-c-Pr | 1-Me-c-Pr | —(CH₂)₂— | | Me | H | |
| 4-249 | 1-F-c-Pr | 1-Cl-c-Pr | Me | Me | H | H | |
| 4-250 | 1-F-c-Pr | 1-Cl-c-Pr | Me | Me | Me | H | |
| 4-251 | 1-F-c-Pr | 1-Cl-c-Pr | c-Pr | Me | H | H | |
| 4-252 | 1-F-c-Pr | 1-Cl-c-Pr | c-Pr | Me | Me | H | |
| 4-253 | 1-F-c-Pr | 1-Cl-c-Pr | —(CH₂)₂— | | H | H | |
| 4-254 | 1-F-c-Pr | 1-Cl-c-Pr | —(CH₂)₂— | | Me | H | |
| 4-255 | 1-F-c-Pr | 2,2-Me₂-c-Pr | Me | Me | H | H | |
| 4-256 | 1-F-c-Pr | 2,2-Me₂-c-Pr | Me | Me | Me | H | |
| 4-257 | 1-F-c-Pr | 2,2-Me₂-c-Pr | c-Pr | Me | H | H | |
| 4-258 | 1-F-c-Pr | 2,2-Me₂-c-Pr | c-Pr | Me | Me | H | |
| 4-259 | 1-F-c-Pr | 2,2-Me₂-c-Pr | —(CH₂)₂— | | H | H | |
| 4-260 | 1-F-c-Pr | 2,2-Me₂-c-Pr | —CH₂—CMe₂— | | H | H | |
| 4-261 | 1-F-c-Pr | 2,2-Cl₂-c-Pr | Me | Me | H | H | |
| 4-262 | 1-F-c-Pr | 2,2-Cl₂-c-Pr | Me | Me | Me | H | |
| 4-263 | 1-F-c-Pr | 2,2-Cl₂-c-Pr | c-Pr | Me | H | H | |
| 4-264 | 1-F-c-Pr | 2,2-Cl₂-c-Pr | c-Pr | Me | Me | H | |
| 4-265 | 1-F-c-Pr | 2,2-Cl₂-c-Pr | —(CH₂)₂— | | H | H | |
| 4-266 | 1-F-c-Pr | 2,2-Cl₂-c-Pr | —CH₂—CCl₂— | | H | H | |
| 4-267 | CHF2 | c-Pr | Me | Me | H | H | |
| 4-268 | CHF2 | c-Pr | Me | Me | Me | H | |
| 4-269 | CHF2 | c-Pr | c-Pr | Me | H | H | |
| 4-270 | CHF2 | c-Pr | c-Pr | Me | Me | H | |
| 4-271 | CHF2 | c-Pr | —CH₂—OMe | Me | H | H | |
| 4-272 | CHF2 | c-Pr | —CH₂—OMe | Me | Me | H | |
| 4-273 | CHF2 | c-Pr | —(CH₂)₂— | | H | H | |
| 4-274 | CHF2 | c-Pr | —(CH₂)₂— | | H | Me | |
| 4-275 | CHF2 | c-Pr | —(CH₂)₂— | | H | c-Pr | |
| 4-276 | CHF2 | c-Bu | —(CH₂)₃— | | H | H | |
| 4-277 | CHF2 | c-Bu | —(CH₂)₃— | | H | Me | |
| 4-278 | CHF2 | c-Bu | —(CH₂)₃— | | H | c-Pr | |

TABLE 5

Compounds of the formula (Ie)

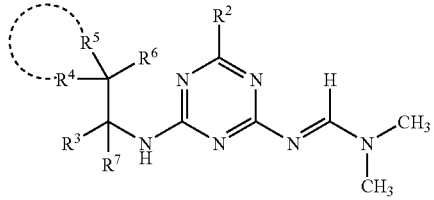
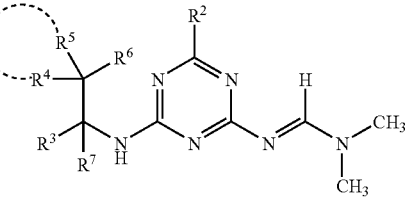

| No. | $R^2$ | $R^3$ | $R^4$ | $R^5$ | $R^6$ | $R^7$ | phys. data |
|---|---|---|---|---|---|---|---|
| 5-1 | H | c-Pr | Me | Me | H | H | |
| 5-2 | H | c-Pr | Me | Me | Me | H | |
| 5-3 | H | c-Pr | c-Pr | Me | H | H | |
| 5-4 | H | c-Pr | c-Pr | Me | Me | H | |
| 5-5 | H | c-Pr | —CH$_2$—OMe | Me | H | H | |
| 5-6 | H | c-Pr | —CH$_2$—OMe | Me | Me | H | |
| 5-7 | H | c-Pr | —(CH$_2$)$_2$— | | H | H | |
| 5-8 | H | c-Pr | —(CH$_2$)$_2$— | | H | Me | |
| 5-9 | H | c-Pr | —(CH$_2$)$_2$— | | H | c-Pr | |
| 5-10 | H | c-Bu | —(CH$_2$)$_3$— | | H | H | |
| 5-11 | H | c-Bu | —(CH$_2$)$_3$— | | H | Me | |
| 5-12 | H | c-Bu | —(CH$_2$)$_3$— | | H | c-Pr | |
| 5-13 | H | 1-Me-c-Pr | Me | Me | H | H | |
| 5-14 | H | 1-Me-c-Pr | Me | Me | Me | H | |
| 5-15 | Me | c-Pr | Me | Me | H | H | |
| 5-16 | Me | c-Pr | Me | Me | Me | H | |
| 5-17 | Me | c-Pr | c-Pr | Me | H | H | |
| 5-18 | Me | c-Pr | c-Pr | Me | Me | H | |
| 5-19 | Me | c-Pr | —CH$_2$—OMe | Me | H | H | |
| 5-20 | Me | c-Pr | —CH$_2$—OMe | Me | Me | H | |
| 5-21 | Me | c-Pr | —(CH$_2$)$_2$— | | H | H | |
| 5-22 | Me | c-Pr | —(CH$_2$)$_2$— | | H | Me | |
| 5-23 | Me | c-Pr | —(CH$_2$)$_2$— | | H | c-Pr | |
| 5-24 | Me | c-Bu | —(CH$_2$)$_3$— | | H | H | |
| 5-25 | Me | c-Bu | —(CH$_2$)$_3$— | | H | Me | |
| 5-26 | Me | c-Bu | —(CH$_2$)$_3$— | | H | c-Pr | |
| 5-27 | Me | 1-Me-c-Pr | Me | Me | H | H | |
| 5-28 | Me | 1-Me-c-Pr | Me | Me | Me | H | |
| 5-29 | Me | 1-Me-c-Pr | c-Pr | Me | H | H | |
| 5-30 | Me | 1-Me-c-Pr | c-Pr | Me | Me | H | |
| 5-31 | Me | 1-Me-c-Pr | —(CH$_2$)$_2$— | | H | H | |
| 5-32 | Me | 1-Me-c-Pr | —(CH$_2$)$_2$— | | Me | H | |
| 5-33 | Me | 1-Cl-c-Pr | Me | Me | H | H | |
| 5-34 | Me | 1-Cl-c-Pr | Me | Me | Me | H | |
| 5-35 | Me | 1-Cl-c-Pr | c-Pr | Me | H | H | |
| 5-36 | Me | 1-Cl-c-Pr | c-Pr | Me | Me | H | |
| 5-37 | Me | 1-Cl-c-Pr | —(CH$_2$)$_2$— | | H | H | |
| 5-38 | Me | 1-Cl-c-Pr | —(CH$_2$)$_2$— | | Me | H | |
| 5-39 | Me | 2,2-Me$_2$-c-Pr | Me | Me | H | H | |
| 5-40 | Me | 2,2-Me$_2$-c-Pr | Me | Me | Me | H | |
| 5-41 | Me | 2,2-Me$_2$-c-Pr | c-Pr | Me | H | H | |
| 5-42 | Me | 2,2-Me$_2$-c-Pr | c-Pr | Me | Me | H | |
| 5-43 | Me | 2,2-Me$_2$-c-Pr | —(CH$_2$)$_2$— | | H | H | |
| 5-44 | Me | 2,2-Me$_2$-c-Pr | —CH$_2$—CMe$_2$— | | H | H | |
| 5-45 | Me | 2,2-Cl$_2$-c-Pr | Me | Me | H | H | |
| 5-46 | Me | 2,2-Cl$_2$-c-Pr | Me | Me | Me | H | |
| 5-47 | Me | 2,2-Cl$_2$-c-Pr | c-Pr | Me | H | H | |
| 5-48 | Me | 2,2-Cl$_2$-c-Pr | c-Pr | Me | Me | H | |
| 5-49 | Me | 2,2-Cl$_2$-c-Pr | —(CH$_2$)$_2$— | | H | H | |
| 5-50 | Me | 2,2-Cl$_2$-c-Pr | —CH$_2$—CCl$_2$— | | H | H | |
| 5-51 | Et | c-Pr | Me | Me | H | H | |
| 5-52 | Et | c-Pr | Me | Me | Me | H | |
| 5-53 | Et | c-Pr | c-Pr | Me | H | H | |
| 5-54 | Et | c-Pr | c-Pr | Me | Me | H | |
| 5-55 | Et | c-Pr | —CH$_2$—OMe | Me | H | H | |
| 5-56 | Et | c-Pr | —CH$_2$—OMe | Me | Me | H | |
| 5-57 | Et | c-Pr | —(CH$_2$)$_2$— | | H | H | |
| 5-58 | Et | c-Pr | —(CH$_2$)$_2$— | | H | Me | |
| 5-59 | Et | c-Pr | —(CH$_2$)$_2$— | | H | c-Pr | |
| 5-60 | Et | c-Bu | —(CH$_2$)$_3$— | | H | H | |
| 5-61 | Et | c-Bu | —(CH$_2$)$_3$— | | H | Me | |
| 5-62 | Et | c-Bu | —(CH$_2$)$_3$— | | H | c-Pr | |
| 5-63 | Et | 1-Me-c-Pr | Me | Me | H | H | |
| 5-64 | Et | 1-Me-c-Pr | Me | Me | Me | H | |
| 5-65 | Et | 1-Me-c-Pr | c-Pr | Me | H | H | |
| 5-66 | Et | 1-Me-c-Pr | c-Pr | Me | Me | H | |
| 5-67 | Et | 1-Me-c-Pr | —(CH$_2$)$_2$— | | H | H | |
| 5-68 | Et | 1-Me-c-Pr | —(CH$_2$)$_2$— | | Me | H | |
| 5-69 | Et | 1-Cl-c-Pr | Me | Me | H | H | |
| 5-70 | Et | 1-Cl-c-Pr | Me | Me | Me | H | |
| 5-71 | Et | 1-Cl-c-Pr | c-Pr | Me | H | H | |
| 5-72 | Et | 1-Cl-c-Pr | c-Pr | Me | Me | H | |
| 5-73 | Et | 1-Cl-c-Pr | —(CH$_2$)$_2$— | | H | H | |
| 5-74 | Et | 1-Cl-c-Pr | —(CH$_2$)$_2$— | | Me | H | |
| 5-75 | Et | 2,2-Me$_2$-c-Pr | Me | Me | H | H | |
| 5-76 | Et | 2,2-Me$_2$-c-Pr | Me | Me | Me | H | |
| 5-77 | Et | 2,2-Me$_2$-c-Pr | c-Pr | Me | H | H | |
| 5-78 | Et | 2,2-Me$_2$-c-Pr | c-Pr | Me | Me | H | |
| 5-79 | Et | 2,2-Me$_2$-c-Pr | —(CH$_2$)$_2$— | | H | H | |
| 5-80 | Et | 2,2-Me$_2$-c-Pr | —CH$_2$—CMe$_2$— | | H | H | |
| 5-81 | Et | 2,2-Cl$_2$-c-Pr | Me | Me | H | H | |
| 5-82 | Et | 2,2-Cl$_2$-c-Pr | Me | Me | Me | H | |
| 5-83 | Et | 2,2-Cl$_2$-c-Pr | c-Pr | Me | H | H | |
| 5-84 | Et | 2,2-Cl$_2$-c-Pr | c-Pr | Me | Me | H | |
| 5-85 | Et | 2,2-Cl$_2$-c-Pr | —(CH$_2$)$_2$— | | H | H | |
| 5-86 | Et | 2,2-Cl$_2$-c-Pr | —CH$_2$—CCl$_2$— | | H | H | |
| 5-87 | c-Pr | c-Pr | Me | Me | H | H | |
| 5-88 | c-Pr | c-Pr | Me | Me | Me | H | |
| 5-89 | c-Pr | c-Pr | c-Pr | Me | H | H | |
| 5-90 | c-Pr | c-Pr | c-Pr | Me | Me | H | |
| 5-91 | c-Pr | c-Pr | —CH$_2$—OMe | Me | H | H | |
| 5-92 | c-Pr | c-Pr | —CH$_2$—OMe | Me | Me | H | |
| 5-93 | c-Pr | c-Pr | —(CH$_2$)$_2$— | | H | H | |
| 5-94 | c-Pr | c-Pr | —(CH$_2$)$_2$— | | H | Me | |
| 5-95 | c-Pr | c-Pr | —(CH$_2$)$_2$— | | H | c-Pr | |
| 5-96 | c-Pr | c-Bu | —(CH$_2$)$_3$— | | H | H | |
| 5-97 | c-Pr | c-Bu | —(CH$_2$)$_3$— | | H | Me | |
| 5-98 | c-Pr | c-Bu | —(CH$_2$)$_3$— | | H | c-Pr | |
| 5-99 | c-Pr | 1-Me-c-Pr | Me | Me | H | H | |
| 5-100 | c-Pr | 1-Me-c-Pr | Me | Me | Me | H | |
| 5-101 | c-Pr | 1-Me-c-Pr | c-Pr | Me | H | H | |
| 5-102 | c-Pr | 1-Me-c-Pr | c-Pr | Me | Me | H | |
| 5-103 | c-Pr | 1-Me-c-Pr | —(CH$_2$)$_2$— | | H | H | |
| 5-104 | c-Pr | 1-Me-c-Pr | —(CH$_2$)$_2$— | | Me | H | |
| 5-105 | c-Pr | 1-Cl-c-Pr | Me | Me | H | H | |
| 5-106 | c-Pr | 1-Cl-c-Pr | Me | Me | Me | H | |
| 5-107 | c-Pr | 1-Cl-c-Pr | c-Pr | Me | H | H | |
| 5-108 | c-Pr | 1-Cl-c-Pr | c-Pr | Me | Me | H | |
| 5-109 | c-Pr | 1-Cl-c-Pr | —(CH$_2$)$_2$— | | H | H | |
| 5-110 | c-Pr | 1-Cl-c-Pr | —(CH$_2$)$_2$— | | Me | H | |
| 5-111 | c-Pr | 2,2-Me$_2$-c-Pr | Me | Me | H | H | |
| 5-112 | c-Pr | 2,2-Me$_2$-c-Pr | Me | Me | Me | H | |
| 5-113 | c-Pr | 2,2-Me$_2$-c-Pr | c-Pr | Me | H | H | |
| 5-114 | c-Pr | 2,2-Me$_2$-c-Pr | c-Pr | Me | Me | H | |
| 5-115 | c-Pr | 2,2-Me$_2$-c-Pr | —(CH$_2$)$_2$— | | H | H | |
| 5-116 | c-Pr | 2,2-Me$_2$-c-Pr | —CH$_2$—CMe$_2$— | | H | H | |
| 5-117 | c-Pr | 2,2-Cl$_2$-c-Pr | Me | Me | H | H | |
| 5-118 | c-Pr | 2,2-Cl$_2$-c-Pr | Me | Me | Me | H | |
| 5-119 | c-Pr | 2,2-Cl$_2$-c-Pr | c-Pr | Me | H | H | |
| 5-120 | c-Pr | 2,2-Cl$_2$-c-Pr | c-Pr | Me | Me | H | |
| 5-121 | c-Pr | 2,2-Cl$_2$-c-Pr | —(CH$_2$)$_2$— | | H | H | |
| 5-122 | c-Pr | 2,2-Cl$_2$-c-Pr | —CH$_2$—CCl$_2$— | | H | H | |
| 5-123 | CHFCH$_3$ | c-Pr | Me | Me | H | H | |
| 5-124 | CHFCH$_3$ | c-Pr | Me | Me | Me | H | |
| 5-125 | CHFCH$_3$ | c-Pr | c-Pr | Me | H | H | |
| 5-126 | CHFCH$_3$ | c-Pr | c-Pr | Me | Me | H | |

TABLE 5-continued

Compounds of the formula (Ie)

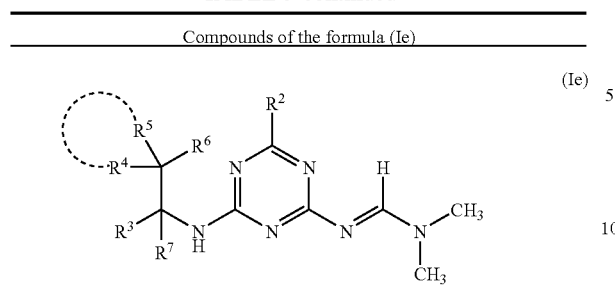

| No. | $R^2$ | $R^3$ | $R^4$ | $R^5$ | $R^6$ | $R^7$ | phys. data |
|---|---|---|---|---|---|---|---|
| 5-127 | CHFCH$_3$ | c-Pr | —CH$_2$—OMe | Me | H | H | |
| 5-128 | CHFCH$_3$ | c-Pr | —CH$_2$—OMe | Me | Me | H | |
| 5-129 | CHFCH$_3$ | c-Pr | —(CH$_2$)$_2$— | | H | H | |
| 5-130 | CHFCH$_3$ | c-Pr | —(CH$_2$)$_2$— | | H | Me | |
| 5-131 | CHFCH$_3$ | c-Pr | —(CH$_2$)$_2$— | | H | c-Pr | |
| 5-132 | CHFCH$_3$ | c-Bu | —(CH$_2$)$_3$— | | H | H | |
| 5-133 | CHFCH$_3$ | c-Bu | —(CH$_2$)$_3$— | | H | Me | |
| 5-134 | CHFCH$_3$ | c-Bu | —(CH$_2$)$_3$— | | H | c-Pr | |
| 5-135 | CHFCH$_3$ | 1-Me-c-Pr | Me | Me | H | H | |
| 5-136 | CHFCH$_3$ | 1-Me-c-Pr | Me | Me | Me | H | |
| 5-137 | CHFCH$_3$ | 1-Me-c-Pr | c-Pr | Me | H | H | |
| 5-138 | CHFCH$_3$ | 1-Me-c-Pr | c-Pr | Me | Me | H | |
| 5-139 | CHFCH$_3$ | 1-Me-c-Pr | —(CH$_2$)$_2$— | | H | H | |
| 5-140 | CHFCH$_3$ | 1-Me-c-Pr | —(CH$_2$)$_2$— | | Me | H | |
| 5-141 | CHFCH$_3$ | 1-Cl-c-Pr | Me | Me | H | H | |
| 5-142 | CHFCH$_3$ | 1-Cl-c-Pr | Me | Me | Me | H | |
| 5-143 | CHFCH$_3$ | 1-Cl-c-Pr | c-Pr | Me | H | H | |
| 5-144 | CHFCH$_3$ | 1-Cl-c-Pr | c-Pr | Me | Me | H | |
| 5-145 | CHFCH$_3$ | 1-Cl-c-Pr | —(CH$_2$)$_2$— | | H | H | |
| 5-146 | CHFCH$_3$ | 1-Cl-c-Pr | —(CH$_2$)$_2$— | | Me | H | |
| 5-147 | CHFCH$_3$ | 2,2-Me$_2$-c-Pr | Me | Me | H | H | |
| 5-148 | CHFCH$_3$ | 2,2-Me$_2$-c-Pr | Me | Me | Me | H | |
| 5-149 | CHFCH$_3$ | 2,2-Me$_2$-c-Pr | c-Pr | Me | H | H | |
| 5-150 | CHFCH$_3$ | 2,2-Me$_2$-c-Pr | c-Pr | Me | Me | H | |
| 5-151 | CHFCH$_3$ | 2,2-Me$_2$-c-Pr | —(CH$_2$)$_2$— | | H | H | |
| 5-152 | CHFCH$_3$ | 2,2-Me$_2$-c-Pr | —CH$_2$—CMe$_2$— | | H | H | |
| 5-153 | CHFCH$_3$ | 2,2-Cl$_2$-c-Pr | Me | Me | H | H | |
| 5-154 | CHFCH$_3$ | 2,2-Cl$_2$-c-Pr | Me | Me | Me | H | |
| 5-155 | CHFCH$_3$ | 2,2-Cl$_2$-c-Pr | c-Pr | Me | H | H | |
| 5-156 | CHFCH$_3$ | 2,2-Cl$_2$-c-Pr | c-Pr | Me | Me | H | |
| 5-157 | CHFCH$_3$ | 2,2-Cl$_2$-c-Pr | —(CH$_2$)$_2$— | | H | H | |
| 5-158 | CHFCH$_3$ | 2,2-Cl$_2$-c-Pr | —CH$_2$—CCl$_2$— | | H | H | |
| 5-159 | CHFC$_2$H$_5$ | c-Pr | Me | Me | H | H | |
| 5-160 | CHFC$_2$H$_5$ | c-Pr | Me | Me | Me | H | |
| 5-161 | CHFC$_2$H$_5$ | c-Pr | c-Pr | Me | H | H | |
| 5-162 | CHFC$_2$H$_5$ | c-Pr | c-Pr | Me | Me | H | |
| 5-163 | CHFC$_2$H$_5$ | c-Pr | —CH$_2$—OMe | Me | H | H | |
| 5-164 | CHFC$_2$H$_5$ | c-Pr | —CH$_2$—OMe | Me | Me | H | |
| 5-165 | CHFC$_2$H$_5$ | c-Pr | —(CH$_2$)$_2$— | | H | H | |
| 5-166 | CHFC$_2$H$_5$ | c-Pr | —(CH$_2$)$_2$— | | H | Me | |
| 5-167 | CHFC$_2$H$_5$ | c-Pr | —(CH$_2$)$_2$— | | H | c-Pr | |
| 5-168 | CHFC$_2$H$_5$ | c-Bu | —(CH$_2$)$_3$— | | H | H | |
| 5-169 | CHFC$_2$H$_5$ | c-Bu | —(CH$_2$)$_3$— | | H | Me | |
| 5-170 | CHFC$_2$H$_5$ | c-Bu | —(CH$_2$)$_3$— | | H | c-Pr | |
| 5-171 | CHFC$_2$H$_5$ | 1-Me-c-Pr | Me | Me | H | H | |
| 5-172 | CHFC$_2$H$_5$ | 1-Me-c-Pr | Me | Me | Me | H | |
| 5-173 | CHFC$_2$H$_5$ | 1-Me-c-Pr | c-Pr | Me | H | H | |
| 5-174 | CHFC$_2$H$_5$ | 1-Me-c-Pr | c-Pr | Me | Me | H | |
| 5-175 | CHFC$_2$H$_5$ | 1-Me-c-Pr | —(CH$_2$)$_2$— | | H | H | |
| 5-176 | CHFC$_2$H$_5$ | 1-Me-c-Pr | —(CH$_2$)$_2$— | | Me | H | |
| 5-177 | CHFC$_2$H$_5$ | 1-Cl-c-Pr | Me | Me | H | H | |
| 5-178 | CHFC$_2$H$_5$ | 1-Cl-c-Pr | Me | Me | Me | H | |
| 5-179 | CHFC$_2$H$_5$ | 1-Cl-c-Pr | c-Pr | Me | H | H | |
| 5-180 | CHFC$_2$H$_5$ | 1-Cl-c-Pr | c-Pr | Me | Me | H | |
| 5-181 | CHFC$_2$H$_5$ | 1-Cl-c-Pr | —(CH$_2$)$_2$— | | H | H | |
| 5-182 | CHFC$_2$H$_5$ | 1-Cl-c-Pr | —(CH$_2$)$_2$— | | Me | H | |
| 5-183 | CHFC$_2$H$_5$ | 2,2-Me$_2$-c-Pr | Me | Me | H | H | |
| 5-184 | CHFC$_2$H$_5$ | 2,2-Me$_2$-c-Pr | Me | Me | Me | H | |
| 5-185 | CHFC$_2$H$_5$ | 2,2-Me$_2$-c-Pr | c-Pr | Me | H | H | |
| 5-186 | CHFC$_2$H$_5$ | 2,2-Me$_2$-c-Pr | c-Pr | Me | Me | H | |
| 5-187 | CHFC$_2$H$_5$ | 2,2-Me$_2$-c-Pr | —(CH$_2$)$_2$— | | H | H | |
| 5-188 | CHFC$_2$H$_5$ | 2,2-Me$_2$-c-Pr | —CH$_2$—CMe$_2$— | | H | H | |
| 5-189 | CHFC$_2$H$_5$ | 2,2-Cl$_2$-c-Pr | Me | Me | H | H | |
| 5-190 | CHFC$_2$H$_5$ | 2,2-Cl$_2$-c-Pr | Me | Me | Me | H | |
| 5-191 | CHFC$_2$H$_5$ | 2,2-Cl$_2$-c-Pr | c-Pr | Me | H | H | |
| 5-192 | CHFC$_2$H$_5$ | 2,2-Cl$_2$-c-Pr | c-Pr | Me | Me | H | |
| 5-193 | CHFC$_2$H$_5$ | 2,2-Cl$_2$-c-Pr | —(CH$_2$)$_2$— | | H | H | |
| 5-194 | CHFC$_2$H$_5$ | 2,2-Cl$_2$-c-Pr | —CH$_2$—CCl$_2$— | | H | H | |
| 5-195 | CF(CH$_3$)$_2$ | c-Pr | Me | Me | H | H | resin |
| 5-196 | CF(CH$_3$)$_2$ | c-Pr | Me | Me | Me | H | |
| 5-197 | CF(CH$_3$)$_2$ | c-Pr | c-Pr | Me | H | H | |
| 5-198 | CF(CH$_3$)$_2$ | c-Pr | c-Pr | Me | Me | H | |
| 5-199 | CF(CH$_3$)$_2$ | c-Pr | —CH$_2$—OMe | Me | H | H | |
| 5-200 | CF(CH$_3$)$_2$ | c-Pr | —CH$_2$—OMe | Me | Me | H | |
| 5-201 | CF(CH$_3$)$_2$ | c-Pr | —(CH$_2$)$_2$— | | H | H | NMR |
| 5-202 | CF(CH$_3$)$_2$ | c-Pr | —(CH$_2$)$_2$— | | H | Me | |
| 5-203 | CF(CH$_3$)$_2$ | c-Pr | —(CH$_2$)$_2$— | | H | c-Pr | |
| 5-204 | CF(CH$_3$)$_2$ | c-Bu | —(CH$_2$)$_3$— | | H | H | resin |
| 5-205 | CF(CH$_3$)$_2$ | c-Bu | —(CH$_2$)$_3$— | | H | Me | |
| 5-206 | CF(CH$_3$)$_2$ | c-Bu | —(CH$_2$)$_3$— | | H | c-Pr | |
| 5-207 | CF(CH$_3$)$_2$ | 1-Me-c-Pr | Me | Me | H | H | |
| 5-208 | CF(CH$_3$)$_2$ | 1-Me-c-Pr | Me | Me | Me | H | |
| 5-209 | CF(CH$_3$)$_2$ | 1-Me-c-Pr | c-Pr | Me | H | H | |
| 5-210 | CF(CH$_3$)$_2$ | 1-Me-c-Pr | c-Pr | Me | Me | H | |
| 5-211 | CF(CH$_3$)$_2$ | 1-Me-c-Pr | —(CH$_2$)$_2$— | | H | H | |
| 5-212 | CF(CH$_3$)$_2$ | 1-Me-c-Pr | —(CH$_2$)$_2$— | | Me | H | |
| 5-213 | CF(CH$_3$)$_2$ | 1-Cl-c-Pr | Me | Me | H | H | |
| 5-214 | CF(CH$_3$)$_2$ | 1-Cl-c-Pr | Me | Me | Me | H | |
| 5-215 | CF(CH$_3$)$_2$ | 1-Cl-c-Pr | c-Pr | Me | H | H | |
| 5-216 | CF(CH$_3$)$_2$ | 1-Cl-c-Pr | c-Pr | Me | Me | H | |
| 5-217 | CF(CH$_3$)$_2$ | 1-Cl-c-Pr | —(CH$_2$)$_2$— | | H | H | |
| 5-218 | CF(CH$_3$)$_2$ | 1-Cl-c-Pr | —(CH$_2$)$_2$— | | Me | H | |
| 5-219 | CF(CH$_3$)$_2$ | 2,2-Me$_2$-c-Pr | Me | Me | H | H | |
| 5-220 | CF(CH$_3$)$_2$ | 2,2-Me$_2$-c-Pr | Me | Me | Me | H | |
| 5-221 | CF(CH$_3$)$_2$ | 2,2-Me$_2$-c-Pr | c-Pr | Me | H | H | |
| 5-222 | CF(CH$_3$)$_2$ | 2,2-Me$_2$-c-Pr | c-Pr | Me | Me | H | |
| 5-223 | CF(CH$_3$)$_2$ | 2,2-Me$_2$-c-Pr | —(CH$_2$)$_2$— | | H | H | |
| 5-224 | CF(CH$_3$)$_2$ | 2,2-Me$_2$-c-Pr | —CH$_2$—CMe$_2$— | | H | H | |
| 5-225 | CF(CH$_3$)$_2$ | 2,2-Cl$_2$-c-Pr | Me | Me | H | H | |
| 5-226 | CF(CH$_3$)$_2$ | 2,2-Cl$_2$-c-Pr | Me | Me | Me | H | |
| 5-227 | CF(CH$_3$)$_2$ | 2,2-Cl$_2$-c-Pr | c-Pr | Me | H | H | |
| 5-228 | CF(CH$_3$)$_2$ | 2,2-Cl$_2$-c-Pr | c-Pr | Me | Me | H | |
| 5-229 | CF(CH$_3$)$_2$ | 2,2-Cl$_2$-c-Pr | —(CH$_2$)$_2$— | | H | H | |
| 5-230 | CF(CH$_3$)$_2$ | 2,2-Cl$_2$-c-Pr | —CH$_2$—CCl$_2$— | | H | H | |
| 5-231 | 1-F-c-Pr | c-Pr | Me | Me | H | H | |
| 5-232 | 1-F-c-Pr | c-Pr | Me | Me | Me | H | |
| 5-233 | 1-F-c-Pr | c-Pr | c-Pr | Me | H | H | |
| 5-234 | 1-F-c-Pr | c-Pr | c-Pr | Me | Me | H | |
| 5-235 | 1-F-c-Pr | c-Pr | —CH$_2$—OMe | Me | H | H | |
| 5-236 | 1-F-c-Pr | c-Pr | —CH$_2$—OMe | Me | Me | H | |
| 5-237 | 1-F-c-Pr | c-Pr | —(CH$_2$)$_2$— | | H | H | |
| 5-238 | 1-F-c-Pr | c-Pr | —(CH$_2$)$_2$— | | H | Me | |
| 5-239 | 1-F-c-Pr | c-Pr | —(CH$_2$)$_2$— | | H | c-Pr | |
| 5-240 | 1-F-c-Pr | c-Bu | —(CH$_2$)$_3$— | | H | H | |
| 5-241 | 1-F-c-Pr | c-Bu | —(CH$_2$)$_3$— | | H | Me | |
| 5-242 | 1-F-c-Pr | c-Bu | —(CH$_2$)$_3$— | | H | c-Pr | |
| 5-243 | 1-F-c-Pr | 1-Me-c-Pr | Me | Me | H | H | |
| 5-244 | 1-F-c-Pr | 1-Me-c-Pr | Me | Me | Me | H | |
| 5-245 | 1-F-c-Pr | 1-Me-c-Pr | c-Pr | Me | H | H | |
| 5-246 | 1-F-c-Pr | 1-Me-c-Pr | c-Pr | Me | Me | H | |
| 5-247 | 1-F-c-Pr | 1-Me-c-Pr | —(CH$_2$)$_2$— | | H | H | |
| 5-248 | 1-F-c-Pr | 1-Me-c-Pr | —(CH$_2$)$_2$— | | Me | H | |
| 5-249 | 1-F-c-Pr | 1-Cl-c-Pr | Me | Me | H | H | |
| 5-250 | 1-F-c-Pr | 1-Cl-c-Pr | Me | Me | Me | H | |
| 5-251 | 1-F-c-Pr | 1-Cl-c-Pr | c-Pr | Me | H | H | |
| 5-252 | 1-F-c-Pr | 1-Cl-c-Pr | c-Pr | Me | Me | H | |

TABLE 5-continued

Compounds of the formula (Ie)

| No. | R² | R³ | R⁴ | R⁵ | R⁶ | R⁷ | phys. data |
|---|---|---|---|---|---|---|---|
| 5-253 | 1-F-c-Pr | 1-Cl-c-Pr | —(CH₂)₂— | | H | H | |
| 5-254 | 1-F-c-Pr | 1-Cl-c-Pr | —(CH₂)₂— | | Me | | |
| 5-255 | 1-F-c-Pr | 2,2-Me₂-c-Pr | Me | Me | H | H | |
| 5-256 | 1-F-c-Pr | 2,2-Me₂-c-Pr | Me | Me | Me | H | |
| 5-257 | 1-F-c-Pr | 2,2-Me₂-c-Pr | c-Pr | Me | H | H | |
| 5-258 | 1-F-c-Pr | 2,2-Me₂-c-Pr | c-Pr | Me | Me | H | |
| 5-259 | 1-F-c-Pr | 2,2-Me₂-c-Pr | —(CH₂)₂— | | H | H | |
| 5-260 | 1-F-c-Pr | 2,2-Me₂-c-Pr | —CH₂—CMe₂— | | H | H | |
| 5-261 | 1-F-c-Pr | 2,2-Cl₂-c-Pr | Me | Me | H | H | |
| 5-262 | 1-F-c-Pr | 2,2-Cl₂-c-Pr | Me | Me | Me | H | |
| 5-263 | 1-F-c-Pr | 2,2-Cl₂-c-Pr | c-Pr | Me | H | H | |
| 5-264 | 1-F-c-Pr | 2,2-Cl₂-c-Pr | c-Pr | Me | Me | H | |
| 5-265 | 1-F-c-Pr | 2,2-Cl₂-c-Pr | —(CH₂)₂— | | H | H | |
| 5-266 | 1-F-c-Pr | 2,2-Cl₂-c-Pr | —CH₂—CCl₂— | | H | H | |
| 5-267 | CHF2 | c-Pr | Me | Me | H | H | |
| 5-268 | CHF2 | c-Pr | Me | Me | Me | H | |
| 5-269 | CHF2 | c-Pr | c-Pr | Me | H | H | |
| 5-270 | CHF2 | c-Pr | c-Pr | Me | Me | H | |
| 5-271 | CHF2 | c-Pr | —CH₂—OMe | Me | H | H | |
| 5-272 | CHF2 | c-Pr | —CH₂—OMe | Me | Me | H | |
| 5-273 | CHF2 | c-Pr | —(CH₂)₂— | | H | H | |
| 5-274 | CHF2 | c-Pr | —(CH₂)₂— | | H | Me | |
| 5-275 | CHF2 | c-Pr | —(CH₂)₂— | | H | c-Pr | |
| 5-276 | CHF2 | c-Bu | —(CH₂)₃— | | H | H | |
| 5-277 | CHF2 | c-Bu | —(CH₂)₃— | | H | Me | |
| 5-278 | CHF2 | c-Bu | —(CH₂)₃— | | H | c-Pr | |

Explanations for table 5:
"NMR" of the example compounds were in each case measured as a ¹H NMR spectrum at 400 MHz (CDCl₃) (¹H nuclear resonance data). Characteristic chemical shifts δ (ppm) for example compounds are listed below:
Ex. No. 5-201: δ (ppm) = 8.75 (m, 1 H), 3.60-3.25 (m, 1 H), 3.15 (s, 6 H), 1.70 (m, 6 H), 0.95 (m, 2 H), 0.55-0.25 (m, 8 H)

TABLE 6

Compounds of the formula (If)

| No. | R² | R³ | R⁴ | R⁵ | R⁶ | R⁷ | phys. data |
|---|---|---|---|---|---|---|---|
| 6-1 | H | c-Pr | Me | Me | H | H | |
| 6-2 | H | c-Pr | Me | Me | Me | H | |
| 6-3 | H | c-Pr | c-Pr | Me | H | H | |
| 6-4 | H | c-Pr | c-Pr | Me | Me | H | |
| 6-5 | H | c-Pr | —CH₂—OMe | Me | H | H | |
| 6-6 | H | c-Pr | —CH₂—OMe | Me | Me | H | |
| 6-7 | H | c-Pr | —(CH₂)₂— | | H | H | |
| 6-8 | H | c-Pr | —(CH₂)₂— | | H | Me | |
| 6-9 | H | c-Pr | —(CH₂)₂— | | H | c-Pr | |
| 6-10 | H | c-Bu | —(CH₂)₃— | | H | H | |
| 6-11 | H | c-Bu | —(CH₂)₃— | | H | Me | |
| 6-12 | H | c-Bu | —(CH₂)₃— | | H | c-Pr | |
| 6-13 | Me | c-Pr | Me | Me | H | H | |
| 6-14 | Me | c-Pr | Me | Me | Me | H | |
| 6-15 | Me | c-Pr | c-Pr | Me | H | H | |
| 6-16 | Me | c-Pr | c-Pr | Me | Me | H | |
| 6-17 | Me | c-Pr | —CH₂—OMe | Me | H | H | |
| 6-18 | Me | c-Pr | —CH₂—OMe | Me | Me | H | |
| 6-19 | Me | c-Pr | —(CH₂)₂— | | H | H | |
| 6-20 | Me | c-Pr | —(CH₂)₂— | | H | Me | |
| 6-21 | Me | c-Pr | —(CH₂)₂— | | H | c-Pr | |
| 6-22 | Me | c-Bu | —(CH₂)₃— | | H | H | |
| 6-23 | Me | c-Bu | —(CH₂)₃— | | H | Me | |
| 6-24 | Me | c-Bu | —(CH₂)₃— | | H | c-Pr | |
| 6-25 | Me | 1-Me-c-Pr | Me | Me | H | H | |
| 6-26 | Me | 1-Me-c-Pr | Me | Me | Me | H | |
| 6-27 | Me | 1-Me-c-Pr | c-Pr | Me | H | H | |
| 6-28 | Me | 1-Me-c-Pr | c-Pr | Me | Me | H | |
| 6-29 | Me | 1-Me-c-Pr | —(CH₂)₂— | | H | H | |
| 6-30 | Me | 1-Me-c-Pr | —(CH₂)₂— | | Me | H | |
| 6-31 | Me | 1-Cl-c-Pr | Me | Me | H | H | |
| 6-32 | Me | 1-Cl-c-Pr | Me | Me | Me | H | |
| 6-33 | Me | 1-Cl-c-Pr | c-Pr | Me | H | H | |
| 6-34 | Me | 1-Cl-c-Pr | c-Pr | Me | Me | H | |
| 6-35 | Me | 1-Cl-c-Pr | —(CH₂)₂— | | H | H | |
| 6-36 | Me | 1-Cl-c-Pr | —(CH₂)₂— | | Me | H | |
| 6-37 | Me | 2,2-Me₂-c-Pr | Me | Me | H | H | |
| 6-38 | Me | 2,2-Me₂-c-Pr | Me | Me | Me | H | |
| 6-39 | Me | 2,2-Me₂-c-Pr | c-Pr | Me | H | H | |
| 6-40 | Me | 2,2-Me₂-c-Pr | c-Pr | Me | Me | H | |
| 6-41 | Me | 2,2-Me₂-c-Pr | —(CH₂)₂— | | H | H | |
| 6-42 | Me | 2,2-Me₂-c-Pr | —CH₂—CMe₂— | | H | H | |
| 6-43 | Me | 2,2-Cl₂-c-Pr | Me | Me | H | H | |
| 6-44 | Me | 2,2-Cl₂-c-Pr | Me | Me | Me | H | |
| 6-45 | Me | 2,2-Cl₂-c-Pr | c-Pr | Me | H | H | |
| 6-46 | Me | 2,2-Cl₂-c-Pr | c-Pr | Me | Me | H | |
| 6-47 | Me | 2,2-Cl₂-c-Pr | —(CH₂)₂— | | H | H | |
| 6-48 | Me | 2,2-Cl₂-c-Pr | —CH₂—CCl₂— | | H | H | |
| 6-49 | Et | c-Pr | Me | Me | H | H | |
| 6-50 | Et | c-Pr | Me | Me | Me | H | |
| 6-51 | Et | c-Pr | c-Pr | Me | H | H | |
| 6-52 | Et | c-Pr | c-Pr | Me | Me | H | |
| 6-53 | Et | c-Pr | —CH₂—OMe | Me | H | H | |
| 6-54 | Et | c-Pr | —CH₂—OMe | Me | Me | H | |
| 6-55 | Et | c-Pr | —(CH₂)₂— | | H | H | |
| 6-56 | Et | c-Pr | —(CH₂)₂— | | H | Me | |
| 6-57 | Et | c-Pr | —(CH₂)₂— | | H | c-Pr | |
| 6-58 | Et | c-Bu | —(CH₂)₃— | | H | H | |
| 6-59 | Et | c-Bu | —(CH₂)₃— | | H | Me | |
| 6-60 | Et | c-Bu | —(CH₂)₃— | | H | c-Pr | |
| 6-61 | Et | 1-Me-c-Pr | Me | Me | H | H | |
| 6-62 | Et | 1-Me-c-Pr | Me | Me | Me | H | |
| 6-63 | Et | 1-Me-c-Pr | c-Pr | Me | H | H | |
| 6-64 | Et | 1-Me-c-Pr | c-Pr | Me | Me | H | |
| 6-65 | Et | 1-Me-c-Pr | —(CH₂)₂— | | H | H | |
| 6-66 | Et | 1-Me-c-Pr | —(CH₂)₂— | | Me | H | |
| 6-67 | Et | 1-Cl-c-Pr | Me | Me | H | H | |
| 6-68 | Et | 1-Cl-c-Pr | Me | Me | Me | H | |
| 6-69 | Et | 1-Cl-c-Pr | c-Pr | Me | H | H | |
| 6-70 | Et | 1-Cl-c-Pr | c-Pr | Me | Me | H | |
| 6-71 | Et | 1-Cl-c-Pr | —(CH₂)₂— | | H | H | |
| 6-72 | Et | 1-Cl-c-Pr | —(CH₂)₂— | | Me | H | |
| 6-73 | Et | 2,2-Me₂-c-Pr | Me | Me | H | H | |

TABLE 6-continued

Compounds of the formula (If)

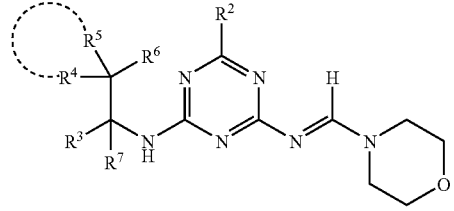

| No. | R² | R³ | R⁴ | R⁵ | R⁶ | R⁷ | phys. data |
|---|---|---|---|---|---|---|---|
| 6-74 | Et | 2,2-Me₂-c-Pr | Me | Me | Me | H | |
| 6-75 | Et | 2,2-Me₂-c-Pr | c-Pr | Me | H | H | |
| 6-76 | Et | 2,2-Me₂-c-Pr | c-Pr | Me | Me | H | |
| 6-77 | Et | 2,2-Me₂-c-Pr | —(CH₂)₂— | | H | H | |
| 6-78 | Et | 2,2-Me₂-c-Pr | —CH₂—CMe₂— | | H | H | |
| 6-79 | Et | 2,2-Cl₂-c-Pr | Me | Me | H | H | |
| 6-80 | Et | 2,2-Cl₂-c-Pr | Me | Me | Me | H | |
| 6-81 | Et | 2,2-Cl₂-c-Pr | c-Pr | Me | H | H | |
| 6-82 | Et | 2,2-Cl₂-c-Pr | c-Pr | Me | Me | H | |
| 6-83 | Et | 2,2-Cl₂-c-Pr | —(CH₂)₂— | | H | H | |
| 6-84 | Et | 2,2-Cl₂-c-Pr | —CH₂—CCl₂— | | H | H | |
| 6-85 | c-Pr | c-Pr | Me | Me | H | H | |
| 6-86 | c-Pr | c-Pr | Me | Me | Me | H | |
| 6-87 | c-Pr | c-Pr | c-Pr | Me | H | H | |
| 6-88 | c-Pr | c-Pr | c-Pr | Me | Me | H | |
| 6-89 | c-Pr | c-Pr | —CH₂—OMe | Me | H | H | |
| 6-90 | c-Pr | c-Pr | —CH₂—OMe | Me | Me | H | |
| 6-91 | c-Pr | c-Pr | —(CH₂)₂— | | H | H | |
| 6-92 | c-Pr | c-Pr | —(CH₂)₂— | | H | Me | |
| 6-93 | c-Pr | c-Pr | —(CH₂)₂— | | H | c-Pr | |
| 6-94 | c-Pr | c-Bu | —(CH₂)₃— | | H | H | |
| 6-95 | c-Pr | c-Bu | —(CH₂)₃— | | H | Me | |
| 6-96 | c-Pr | c-Bu | —(CH₂)₃— | | H | c-Pr | |
| 6-97 | c-Pr | 1-Me-c-Pr | Me | Me | H | H | |
| 6-98 | c-Pr | 1-Me-c-Pr | Me | Me | Me | H | |
| 6-99 | c-Pr | 1-Me-c-Pr | c-Pr | Me | H | H | |
| 6-100 | c-Pr | 1-Me-c-Pr | c-Pr | Me | Me | H | |
| 6-101 | c-Pr | 1-Me-c-Pr | —(CH₂)₂— | | H | H | |
| 6-102 | c-Pr | 1-Me-c-Pr | —(CH₂)₂— | | Me | H | |
| 6-103 | c-Pr | 1-Cl-c-Pr | Me | Me | H | H | |
| 6-104 | c-Pr | 1-Cl-c-Pr | Me | Me | Me | H | |
| 6-105 | c-Pr | 1-Cl-c-Pr | c-Pr | Me | H | H | |
| 6-106 | c-Pr | 1-Cl-c-Pr | c-Pr | Me | Me | H | |
| 6-107 | c-Pr | 1-Cl-c-Pr | —(CH₂)₂— | | H | H | |
| 6-108 | c-Pr | 1-Cl-c-Pr | —(CH₂)₂— | | Me | H | |
| 6-109 | c-Pr | 2,2-Me₂-c-Pr | Me | Me | H | H | |
| 6-110 | c-Pr | 2,2-Me₂-c-Pr | Me | Me | Me | H | |
| 6-111 | c-Pr | 2,2-Me₂-c-Pr | c-Pr | Me | H | H | |
| 6-112 | c-Pr | 2,2-Me₂-c-Pr | c-Pr | Me | Me | H | |
| 6-113 | c-Pr | 2,2-Me₂-c-Pr | —(CH₂)₂— | | H | H | |
| 6-114 | c-Pr | 2,2-Me₂-c-Pr | —CH₂—CMe₂— | | H | H | |
| 6-115 | c-Pr | 2,2-Cl₂-c-Pr | Me | Me | H | H | |
| 6-116 | c-Pr | 2,2-Cl₂-c-Pr | Me | Me | Me | H | |
| 6-117 | c-Pr | 2,2-Cl₂-c-Pr | c-Pr | Me | H | H | |
| 6-118 | c-Pr | 2,2-Cl₂-c-Pr | c-Pr | Me | Me | H | |
| 6-119 | c-Pr | 2,2-Cl₂-c-Pr | —(CH₂)₂— | | H | H | |
| 6-120 | c-Pr | 2,2-Cl₂-c-Pr | —CH₂—CCl₂— | | H | H | |
| 6-121 | CHFCH₃ | c-Pr | Me | Me | H | H | |
| 6-122 | CHFCH₃ | c-Pr | Me | Me | Me | H | |
| 6-123 | CHFCH₃ | c-Pr | c-Pr | Me | H | H | |
| 6-124 | CHFCH₃ | c-Pr | c-Pr | Me | Me | H | |
| 6-125 | CHFCH₃ | c-Pr | —CH₂—OMe | Me | H | H | |
| 6-126 | CHFCH₃ | c-Pr | —CH₂—OMe | Me | Me | H | |
| 6-127 | CHFCH₃ | c-Pr | —(CH₂)₂— | | H | H | |
| 6-128 | CHFCH₃ | c-Pr | —(CH₂)₂— | | H | Me | |
| 6-129 | CHFCH₃ | c-Pr | —(CH₂)₂— | | H | c-Pr | |
| 6-130 | CHFCH₃ | c-Bu | —(CH₂)₃— | | H | H | |
| 6-131 | CHFCH₃ | c-Bu | —(CH₂)₃— | | H | Me | |
| 6-132 | CHFCH₃ | c-Bu | —(CH₂)₃— | | H | c-Pr | |
| 6-133 | CHFCH₃ | 1-Me-c-Pr | Me | Me | H | H | |
| 6-134 | CHFCH₃ | 1-Me-c-Pr | Me | Me | Me | H | |
| 6-135 | CHFCH₃ | 1-Me-c-Pr | c-Pr | Me | H | H | |
| 6-136 | CHFCH₃ | 1-Me-c-Pr | c-Pr | Me | Me | H | |
| 6-137 | CHFCH₃ | 1-Me-c-Pr | —(CH₂)₂— | | H | H | |
| 6-138 | CHFCH₃ | 1-Me-c-Pr | —(CH₂)₂— | | Me | H | |
| 6-139 | CHFCH₃ | 1-Cl-c-Pr | Me | Me | H | H | |
| 6-140 | CHFCH₃ | 1-Cl-c-Pr | Me | Me | Me | H | |
| 6-141 | CHFCH₃ | 1-Cl-c-Pr | c-Pr | Me | H | H | |
| 6-142 | CHFCH₃ | 1-Cl-c-Pr | c-Pr | Me | Me | H | |
| 6-143 | CHFCH₃ | 1-Cl-c-Pr | —(CH₂)₂— | | H | H | |
| 6-144 | CHFCH₃ | 1-Cl-c-Pr | —(CH₂)₂— | | Me | H | |
| 6-145 | CHFCH₃ | 2,2-Me₂-c-Pr | Me | Me | H | H | |
| 6-146 | CHFCH₃ | 2,2-Me₂-c-Pr | Me | Me | Me | H | |
| 6-147 | CHFCH₃ | 2,2-Me₂-c-Pr | c-Pr | Me | H | H | |
| 6-148 | CHFCH₃ | 2,2-Me₂-c-Pr | c-Pr | Me | Me | H | |
| 6-149 | CHFCH₃ | 2,2-Me₂-c-Pr | —(CH₂)₂— | | H | H | |
| 6-150 | CHFCH₃ | 2,2-Me₂-c-Pr | —CH₂—CMe₂— | | H | H | |
| 6-151 | CHFCH₃ | 2,2-Cl₂-c-Pr | Me | Me | H | H | |
| 6-152 | CHFCH₃ | 2,2-Cl₂-c-Pr | Me | Me | Me | H | |
| 6-153 | CHFCH₃ | 2,2-Cl₂-c-Pr | c-Pr | Me | H | H | |
| 6-154 | CHFCH₃ | 2,2-Cl₂-c-Pr | c-Pr | Me | Me | H | |
| 6-155 | CHFCH₃ | 2,2-Cl₂-c-Pr | —(CH₂)₂— | | H | H | |
| 6-156 | CHFCH₃ | 2,2-Cl₂-c-Pr | —CH₂—CCl₂— | | H | H | |
| 6-157 | CHFC₂H₅ | c-Pr | Me | Me | H | H | |
| 6-158 | CHFC₂H₅ | c-Pr | Me | Me | Me | H | |
| 6-159 | CHFC₂H₅ | c-Pr | c-Pr | Me | H | H | |
| 6-160 | CHFC₂H₅ | c-Pr | c-Pr | Me | Me | H | |
| 6-161 | CHFC₂H₅ | c-Pr | —CH₂—OMe | Me | H | H | |
| 6-162 | CHFC₂H₅ | c-Pr | —CH₂—OMe | Me | Me | H | |
| 6-163 | CHFC₂H₅ | c-Pr | —(CH₂)₂— | | H | H | |
| 6-164 | CHFC₂H₅ | c-Pr | —(CH₂)₂— | | H | Me | |
| 6-165 | CHFC₂H₅ | c-Pr | —(CH₂)₂— | | H | c-Pr | |
| 6-166 | CHFC₂H₅ | c-Bu | —(CH₂)₃— | | H | H | |
| 6-167 | CHFC₂H₅ | c-Bu | —(CH₂)₃— | | H | Me | |
| 6-168 | CHFC₂H₅ | c-Bu | —(CH₂)₃— | | H | c-Pr | |
| 6-169 | CHFC₂H₅ | 1-Me-c-Pr | Me | Me | H | H | |
| 6-170 | CHFC₂H₅ | 1-Me-c-Pr | Me | Me | Me | H | |
| 6-171 | CHFC₂H₅ | 1-Me-c-Pr | c-Pr | Me | H | H | |
| 6-172 | CHFC₂H₅ | 1-Me-c-Pr | c-Pr | Me | Me | H | |
| 6-173 | CHFC₂H₅ | 1-Me-c-Pr | —(CH₂)₂— | | H | H | |
| 6-174 | CHFC₂H₅ | 1-Me-c-Pr | —(CH₂)₂— | | Me | H | |
| 6-175 | CHFC₂H₅ | 1-Cl-c-Pr | Me | Me | H | H | |
| 6-176 | CHFC₂H₅ | 1-Cl-c-Pr | Me | Me | Me | H | |
| 6-177 | CHFC₂H₅ | 1-Cl-c-Pr | c-Pr | Me | H | H | |
| 6-178 | CHFC₂H₅ | 1-Cl-c-Pr | c-Pr | Me | Me | H | |
| 6-179 | CHFC₂H₅ | 1-Cl-c-Pr | —(CH₂)₂— | | H | H | |
| 6-180 | CHFC₂H₅ | 1-Cl-c-Pr | —(CH₂)₂— | | Me | H | |
| 6-181 | CHFC₂H₅ | 2,2-Me₂-c-Pr | Me | Me | H | H | |
| 6-182 | CHFC₂H₅ | 2,2-Me₂-c-Pr | Me | Me | Me | H | |
| 6-183 | CHFC₂H₅ | 2,2-Me₂-c-Pr | c-Pr | Me | H | H | |
| 6-184 | CHFC₂H₅ | 2,2-Me₂-c-Pr | c-Pr | Me | Me | H | |
| 6-185 | CHFC₂H₅ | 2,2-Me₂-c-Pr | —(CH₂)₂— | | H | H | |
| 6-186 | CHFC₂H₅ | 2,2-Me₂-c-Pr | —CH₂—CMe₂— | | H | H | |
| 6-187 | CHFC₂H₅ | 2,2-Cl₂-c-Pr | Me | Me | H | H | |
| 6-188 | CHFC₂H₅ | 2,2-Cl₂-c-Pr | Me | Me | Me | H | |
| 6-189 | CHFC₂H₅ | 2,2-Cl₂-c-Pr | c-Pr | Me | H | H | |
| 6-190 | CHFC₂H₅ | 2,2-Cl₂-c-Pr | c-Pr | Me | Me | H | |
| 6-191 | CHFC₂H₅ | 2,2-Cl₂-c-Pr | —(CH₂)₂— | | H | H | |
| 6-192 | CHFC₂H₅ | 2,2-Cl₂-c-Pr | —CH₂—CCl₂— | | H | H | |
| 6-193 | CF(CH₃)₂ | c-Pr | Me | Me | H | H | resin |
| 6-194 | CF(CH₃)₂ | c-Pr | Me | Me | Me | H | |
| 6-195 | CF(CH₃)₂ | c-Pr | c-Pr | Me | H | H | |
| 6-196 | CF(CH₃)₂ | c-Pr | c-Pr | Me | Me | H | |
| 6-197 | CF(CH₃)₂ | c-Pr | —CH₂—OMe | Me | H | H | |
| 6-198 | CF(CH₃)₂ | c-Pr | —CH₂—OMe | Me | Me | H | |
| 6-199 | CF(CH₃)₂ | c-Pr | —(CH₂)₂— | | H | H | NMR |

TABLE 6-continued

Compounds of the formula (If)

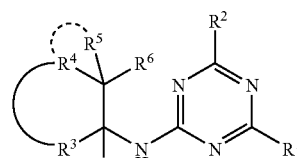

(If)

| No. | R² | R³ | R⁴ | R⁵ | R⁶ | R⁷ | phys. data |
|---|---|---|---|---|---|---|---|
| 6-200 | CF(CH₃)₂ | c-Pr | —(CH₂)₂— | | H | Me | |
| 6-201 | CF(CH₃)₂ | c-Pr | —(CH₂)₂— | | H | c-Pr | |
| 6-202 | CF(CH₃)₂ | c-Bu | —(CH₂)₃— | | H | H | resin |
| 6-203 | CF(CH₃)₂ | c-Bu | —(CH₂)₃— | | H | Me | |
| 6-204 | CF(CH₃)₂ | c-Bu | —(CH₂)₃— | | H | c-Pr | |
| 6-205 | CF(CH₃)₂ | 1-Me-c-Pr | Me | Me | H | H | |
| 6-206 | CF(CH₃)₂ | 1-Me-c-Pr | Me | Me | Me | H | |
| 6-207 | CF(CH₃)₂ | 1-Me-c-Pr | c-Pr | Me | H | H | |
| 6-208 | CF(CH₃)₂ | 1-Me-c-Pr | c-Pr | Me | Me | H | |
| 6-209 | CF(CH₃)₂ | 1-Me-c-Pr | —(CH₂)₂— | | H | H | |
| 6-210 | CF(CH₃)₂ | 1-Me-c-Pr | —(CH₂)₂— | | Me | H | |
| 6-211 | CF(CH₃)₂ | 1-Cl-c-Pr | Me | Me | H | H | |
| 6-212 | CF(CH₃)₂ | 1-Cl-c-Pr | Me | Me | Me | H | |
| 6-213 | CF(CH₃)₂ | 1-Cl-c-Pr | c-Pr | Me | H | H | |
| 6-214 | CF(CH₃)₂ | 1-Cl-c-Pr | c-Pr | Me | Me | H | |
| 6-215 | CF(CH₃)₂ | 1-Cl-c-Pr | —(CH₂)₂— | | H | H | |
| 6-216 | CF(CH₃)₂ | 1-Cl-c-Pr | —(CH₂)₂— | | Me | H | |
| 6-217 | CF(CH₃)₂ | 2,2-Me₂-c-Pr | Me | Me | H | H | |
| 6-218 | CF(CH₃)₂ | 2,2-Me₂-c-Pr | Me | Me | Me | H | |
| 6-219 | CF(CH₃)₂ | 2,2-Me₂-c-Pr | c-Pr | Me | H | H | |
| 6-220 | CF(CH₃)₂ | 2,2-Me₂-c-Pr | c-Pr | Me | Me | H | |
| 6-221 | CF(CH₃)₂ | 2,2-Me₂-c-Pr | —(CH₂)₂— | | H | H | |
| 6-222 | CF(CH₃)₂ | 2,2-Me₂-c-Pr | —CH₂—CMe₂— | | H | H | |
| 6-223 | CF(CH₃)₂ | 2,2-Cl₂-c-Pr | Me | Me | H | H | |
| 6-224 | CF(CH₃)₂ | 2,2-Cl₂-c-Pr | Me | Me | Me | H | |
| 6-225 | CF(CH₃)₂ | 2,2-Cl₂-c-Pr | c-Pr | Me | H | H | |
| 6-226 | CF(CH₃)₂ | 2,2-Cl₂-c-Pr | c-Pr | Me | Me | H | |
| 6-227 | CF(CH₃)₂ | 2,2-Cl₂-c-Pr | —(CH₂)₂— | | H | H | |
| 6-228 | CF(CH₃)₂ | 2,2-Cl₂-c-Pr | —CH₂—CCl₂— | | H | H | |
| 6-229 | 1-F-c-Pr | c-Pr | Me | Me | H | H | |
| 6-230 | 1-F-c-Pr | c-Pr | Me | Me | Me | H | |
| 6-231 | 1-F-c-Pr | c-Pr | c-Pr | Me | H | H | |
| 6-232 | 1-F-c-Pr | c-Pr | c-Pr | Me | Me | H | |
| 6-233 | 1-F-c-Pr | c-Pr | —CH₂—OMe | Me | H | H | |
| 6-234 | 1-F-c-Pr | c-Pr | —CH₂—OMe | Me | Me | H | |
| 6-235 | 1-F-c-Pr | c-Pr | —(CH₂)₂— | | H | H | |
| 6-236 | 1-F-c-Pr | c-Pr | —(CH₂)₂— | | H | Me | |
| 6-237 | 1-F-c-Pr | c-Pr | —(CH₂)₂— | | H | c-Pr | |
| 6-238 | 1-F-c-Pr | c-Bu | —(CH₂)₃— | | H | H | |
| 6-239 | 1-F-c-Pr | c-Bu | —(CH₂)₃— | | H | Me | |
| 6-240 | 1-F-c-Pr | c-Bu | —(CH₂)₃— | | H | c-Pr | |
| 6-241 | 1-F-c-Pr | 1-Me-c-Pr | Me | Me | H | H | |
| 6-242 | 1-F-c-Pr | 1-Me-c-Pr | Me | Me | Me | H | |
| 6-243 | 1-F-c-Pr | 1-Me-c-Pr | c-Pr | Me | H | H | |
| 6-244 | 1-F-c-Pr | 1-Me-c-Pr | c-Pr | Me | Me | H | |
| 6-245 | 1-F-c-Pr | 1-Me-c-Pr | —(CH₂)₂— | | H | H | |
| 6-246 | 1-F-c-Pr | 1-Me-c-Pr | —(CH₂)₂— | | Me | H | |
| 6-247 | 1-F-c-Pr | 1-Cl-c-Pr | Me | Me | H | H | |
| 6-248 | 1-F-c-Pr | 1-Cl-c-Pr | Me | Me | Me | H | |
| 6-249 | 1-F-c-Pr | 1-Cl-c-Pr | c-Pr | Me | H | H | |
| 6-250 | 1-F-c-Pr | 1-Cl-c-Pr | c-Pr | Me | Me | H | |
| 6-251 | 1-F-c-Pr | 1-Cl-c-Pr | —(CH₂)₂— | | H | H | |
| 6-252 | 1-F-c-Pr | 1-Cl-c-Pr | —(CH₂)₂— | | Me | H | |
| 6-253 | 1-F-c-Pr | 2,2-Me₂-c-Pr | Me | Me | H | H | |
| 6-254 | 1-F-c-Pr | 2,2-Me₂-c-Pr | Me | Me | Me | H | |
| 6-255 | 1-F-c-Pr | 2,2-Me₂-c-Pr | c-Pr | Me | H | H | |
| 6-256 | 1-F-c-Pr | 2,2-Me₂-c-Pr | c-Pr | Me | Me | H | |
| 6-257 | 1-F-c-Pr | 2,2-Me₂-c-Pr | —(CH₂)₂— | | H | H | |
| 6-258 | 1-F-c-Pr | 2,2-Me₂-c-Pr | —CH₂—CMe₂— | | H | H | |
| 6-259 | 1-F-c-Pr | 2,2-Cl₂-c-Pr | Me | Me | H | H | |
| 6-260 | 1-F-c-Pr | 2,2-Cl₂-c-Pr | Me | Me | Me | H | |
| 6-261 | 1-F-c-Pr | 2,2-Cl₂-c-Pr | c-Pr | Me | H | H | |
| 6-262 | 1-F-c-Pr | 2,2-Cl₂-c-Pr | c-Pr | Me | Me | H | |
| 6-263 | 1-F-c-Pr | 2,2-Cl₂-c-Pr | —(CH₂)₂— | | H | H | |
| 6-264 | 1-F-c-Pr | 2,2-Cl₂-c-Pr | —CH₂—CCl₂— | | H | H | |
| 6-265 | CHF2 | c-Pr | Me | Me | H | H | |
| 6-266 | CHF2 | c-Pr | Me | Me | Me | H | |
| 6-267 | CHF2 | c-Pr | c-Pr | Me | H | H | |
| 6-268 | CHF2 | c-Pr | c-Pr | Me | Me | H | |
| 6-269 | CHF2 | c-Pr | —CH₂—OMe | Me | H | H | |
| 6-270 | CHF2 | c-Pr | —CH₂—OMe | Me | Me | H | |
| 6-271 | CHF2 | c-Pr | —(CH₂)₂— | | H | H | |
| 6-272 | CHF2 | c-Pr | —(CH₂)₂— | | H | Me | |
| 6-273 | CHF2 | c-Pr | —(CH₂)₂— | | H | c-Pr | |
| 6-274 | CHF2 | c-Bu | —(CH₂)₃— | | H | H | |
| 6-275 | CHF2 | c-Bu | —(CH₂)₃— | | H | Me | |
| 6-276 | CHF2 | c-Bu | —(CH₂)₃— | | H | c-Pr | |

Explanations for table 6:
"NMR" of the example compounds were in each case measured as a ¹H NMR spectrum at 400 MHz (CDCl₃) (¹H nuclear resonance data). Characteristic chemical shifts δ (ppm) for example compounds are listed below:
Ex. No. 6-199: δ (ppm) = 8.80 (m, 1 H), 3.90-3.40 (m, 8H), 2.65 (m, 1 H), 1.70 (m, 6 H), 0.95 (m, 2 H), 0.55-0.25 (m, 8 H)

TABLE 7

Compounds of the formula (I-B),

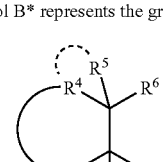

(I-B)

where, in the table which follows, the symbol B* represents the group of the formula (B*)

(abbreviations B1 to B13 inter alia, see table of abbreviations before table 1):

| No. | R¹ | R² | B* | phys. data |
|---|---|---|---|---|
| 7-1 | NH₂ | H | B1 | resin |
| 7-2 | NH₂ | H | B2 | resin |
| 7-3 | NH₂ | H | B3 | |
| 7-4 | NH₂ | H | B4 | |
| 7-5 | NH₂ | H | B5 | |
| 7-6 | NH₂ | H | B6 | |
| 7-7 | NH₂ | H | B7 | |
| 7-8 | NH₂ | H | B8 | resin |
| 7-9 | NH₂ | H | B9 | resin |
| 7-10 | NH₂ | H | B10 | resin |
| 7-11 | NH₂ | H | B11 | |
| 7-12 | NH₂ | H | B12 | |

TABLE 7-continued

Compounds of the formula (I-B),

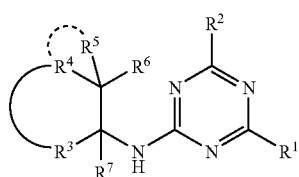

(I-B)

where, in the table which follows,
the symbol B* represents the group of the formula

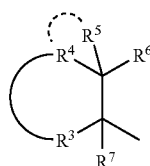

(B*)

(abbreviations B1 to B13 inter alia,
see table of abbreviations before table 1):

| No. | R¹ | R² | B* | phys. data |
|---|---|---|---|---|
| 7-13 | NH₂ | H | B13 | |
| 7-14 | NH₂ | Me | B1 | resin |
| 7-15 | NH₂ | Me | B2 | resin |
| 7-16 | NH₂ | Me | B3 | |
| 7-17 | NH₂ | Me | B4 | |
| 7-18 | NH₂ | Me | B5 | |
| 7-19 | NH₂ | Me | B6 | |
| 7-20 | NH₂ | Me | B7 | |
| 7-21 | NH₂ | Me | B8 | resin |
| 7-22 | NH₂ | Me | B9 | resin |
| 7-23 | NH₂ | Me | B10 | resin |
| 7-24 | NH₂ | Me | B11 | |
| 7-25 | NH₂ | Me | B12 | |
| 7-26 | NH₂ | Me | B13 | |
| 7-27 | NH₂ | Et | B1 | resin |
| 7-28 | NH₂ | Et | B2 | resin |
| 7-29 | NH₂ | Et | B3 | |
| 7-30 | NH₂ | Et | B4 | |
| 7-31 | NH₂ | Et | B5 | |
| 7-32 | NH₂ | Et | B6 | |
| 7-33 | NH₂ | Et | B7 | |
| 7-34 | NH₂ | Et | B8 | resin |
| 7-35 | NH₂ | Et | B9 | resin |
| 7-36 | NH₂ | Et | B10 | resin |
| 7-37 | NH₂ | Et | B11 | |
| 7-38 | NH₂ | Et | B12 | |
| 7-39 | NH₂ | Et | B13 | |
| 7-40 | NH₂ | c-Pr | B1 | resin |
| 7-41 | NH₂ | c-Pr | B2 | resin |
| 7-42 | NH₂ | c-Pr | B3 | |
| 7-43 | NH₂ | c-Pr | B4 | |
| 7-44 | NH₂ | c-Pr | B5 | |
| 7-45 | NH₂ | c-Pr | B6 | |
| 7-46 | NH₂ | c-Pr | B7 | |
| 7-47 | NH₂ | c-Pr | B8 | resin |
| 7-48 | NH₂ | c-Pr | B9 | resin |
| 7-49 | NH₂ | c-Pr | B10 | resin |
| 7-50 | NH₂ | c-Pr | B11 | |
| 7-51 | NH₂ | c-Pr | B12 | |
| 7-52 | NH₂ | c-Pr | B13 | |
| 7-53 | NH₂ | CHFCH₃ | B1 | resin |
| 7-54 | NH₂ | CHFCH₃ | B2 | resin |
| 7-55 | NH₂ | CHFCH₃ | B3 | |
| 7-56 | NH₂ | CHFCH₃ | B4 | |
| 7-57 | NH₂ | CHFCH₃ | B5 | |
| 7-58 | NH₂ | CHFCH₃ | B6 | |
| 7-59 | NH₂ | CHFCH₃ | B7 | |
| 7-60 | NH₂ | CHFCH₃ | B8 | resin |
| 7-61 | NH₂ | CHFCH₃ | B9 | resin |
| 7-62 | NH₂ | CHFCH₃ | B10 | resin |
| 7-63 | NH₂ | CHFCH₃ | B11 | |
| 7-64 | NH₂ | CHFCH₃ | B12 | |
| 7-65 | NH₂ | CHFCH₃ | B13 | |
| 7-66 | NH₂ | CHFC₂H₅ | B1 | resin |
| 7-67 | NH₂ | CHFC₂H₅ | B2 | resin |
| 7-68 | NH₂ | CHFC₂H₅ | B3 | |
| 7-69 | NH₂ | CHFC₂H₅ | B4 | |
| 7-70 | NH₂ | CHFC₂H₅ | B5 | |
| 7-71 | NH₂ | CHFC₂H₅ | B6 | |
| 7-72 | NH₂ | CHFC₂H₅ | B7 | |
| 7-73 | NH₂ | CHFC₂H₅ | B8 | resin |
| 7-74 | NH₂ | CHFC₂H₅ | B9 | resin |
| 7-75 | NH₂ | CHFC₂H₅ | B10 | resin |
| 7-76 | NH₂ | CHFC₂H₅ | B11 | |
| 7-77 | NH₂ | CHFC₂H₅ | B12 | |
| 7-78 | NH₂ | CHFC₂H₅ | B13 | |
| 7-79 | NH₂ | CF(CH₃)₂ | B1 | NMR |
| 7-80 | NH₂ | CF(CH₃)₂ | B2 | resin |
| 7-81 | NH₂ | CF(CH₃)₂ | B3 | |
| 7-82 | NH₂ | CF(CH₃)₂ | B4 | |
| 7-83 | NH₂ | CF(CH₃)₂ | B5 | |
| 7-84 | NH₂ | CF(CH₃)₂ | B6 | |
| 7-85 | NH₂ | CF(CH₃)₂ | B7 | |
| 7-86 | NH₂ | CF(CH₃)₂ | B8 | resin |
| 7-87 | NH₂ | CF(CH₃)₂ | B9 | resin |
| 7-88 | NH₂ | CF(CH₃)₂ | B10 | resin |
| 7-89 | NH₂ | CF(CH₃)₂ | B11 | |
| 7-90 | NH₂ | CF(CH₃)₂ | B12 | |
| 7-91 | NH₂ | CF(CH₃)₂ | B13 | |
| 7-92 | NH₂ | 1-F-c-Pr | B1 | resin |
| 7-93 | NH₂ | 1-F-c-Pr | B2 | resin |
| 7-94 | NH₂ | 1-F-c-Pr | B3 | |
| 7-95 | NH₂ | 1-F-c-Pr | B4 | |
| 7-96 | NH₂ | 1-F-c-Pr | B5 | |
| 7-97 | NH₂ | 1-F-c-Pr | B6 | |
| 7-98 | NH₂ | 1-F-c-Pr | B7 | |
| 7-99 | NH₂ | 1-F-c-Pr | B8 | resin |
| 7-100 | NH₂ | 1-F-c-Pr | B9 | resin |
| 7-101 | NH₂ | 1-F-c-Pr | B10 | resin |
| 7-102 | NH₂ | 1-F-c-Pr | B11 | |
| 7-103 | NH₂ | 1-F-c-Pr | B12 | |
| 7-104 | NH₂ | 1-F-c-Pr | B13 | |
| 7-105 | NH₂ | CHF2 | B1 | resin |
| 7-106 | NH₂ | CHF2 | B2 | resin |
| 7-107 | NH₂ | CHF2 | B3 | |
| 7-108 | NH₂ | CHF2 | B4 | |
| 7-109 | NH₂ | CHF2 | B5 | |
| 7-110 | NH₂ | CHF2 | B6 | |
| 7-111 | NH₂ | CHF2 | B7 | |
| 7-112 | NH₂ | CHF2 | B8 | resin |
| 7-113 | NH₂ | CHF2 | B9 | resin |
| 7-114 | NH₂ | CHF2 | B10 | resin |
| 7-115 | NH₂ | CHF2 | B11 | |
| 7-116 | NH₂ | CHF2 | B12 | |
| 7-117 | NH₂ | CHF2 | B13 | |
| 7-118 | NHAc | H | B1 | resin |

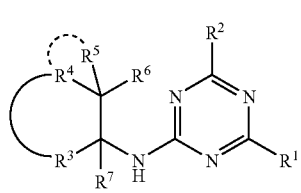

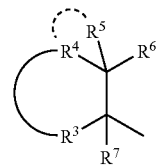

TABLE 7-continued

Compounds of the formula (I-B),

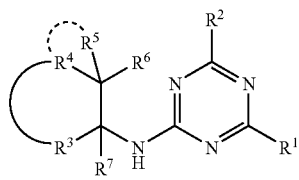
(I-B)

where, in the table which follows,
the symbol B* represents the group of the formula

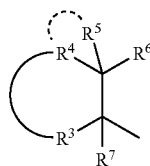
(B*)

(abbreviations B1 to B13 inter alia,
see table of abbreviations before table 1):

| No. | R¹ | R² | B* | phys. data |
|---|---|---|---|---|
| 7-119 | NHAc | H | B2 | resin |
| 7-120 | NHAc | H | B3 | |
| 7-121 | NHAc | H | B4 | |
| 7-122 | NHAc | H | B5 | |
| 7-123 | NHAc | H | B6 | |
| 7-124 | NHAc | H | B7 | |
| 7-125 | NHAc | H | B8 | resin |
| 7-126 | NHAc | H | B9 | resin |
| 7-127 | NHAc | H | B10 | resin |
| 7-128 | NHAc | H | B11 | |
| 7-129 | NHAc | H | B12 | |
| 7-130 | NHAc | H | B13 | |
| 7-131 | NHAc | Me | B1 | resin |
| 7-132 | NHAc | Me | B2 | resin |
| 7-133 | NHAc | Me | B3 | |
| 7-134 | NHAc | Me | B4 | |
| 7-135 | NHAc | Me | B5 | |
| 7-136 | NHAc | Me | B6 | |
| 7-137 | NHAc | Me | B7 | |
| 7-138 | NHAc | Me | B8 | resin |
| 7-139 | NHAc | Me | B9 | resin |
| 7-140 | NHAc | Me | B10 | resin |
| 7-141 | NHAc | Me | B11 | |
| 7-142 | NHAc | Me | B12 | |
| 7-143 | NHAc | Me | B13 | |
| 7-144 | NHAc | Et | B1 | resin |
| 7-145 | NHAc | Et | B2 | resin |
| 7-146 | NHAc | Et | B3 | |
| 7-147 | NHAc | Et | B4 | |
| 7-148 | NHAc | Et | B5 | |
| 7-149 | NHAc | Et | B6 | |
| 7-150 | NHAc | Et | B7 | |
| 7-151 | NHAc | Et | B8 | resin |
| 7-152 | NHAc | Et | B9 | resin |
| 7-153 | NHAc | Et | B10 | resin |
| 7-154 | NHAc | Et | B11 | |
| 7-155 | NHAc | Et | B12 | |
| 7-156 | NHAc | Et | B13 | |
| 7-157 | NHAc | c-Pr | B1 | resin |
| 7-158 | NHAc | c-Pr | B2 | resin |
| 7-159 | NHAc | c-Pr | B3 | |
| 7-160 | NHAc | c-Pr | B4 | |
| 7-161 | NHAc | c-Pr | B5 | |
| 7-162 | NHAc | c-Pr | B6 | |
| 7-163 | NHAc | c-Pr | B7 | |
| 7-164 | NHAc | c-Pr | B8 | resin |
| 7-165 | NHAc | c-Pr | B9 | resin |
| 7-166 | NHAc | c-Pr | B10 | resin |
| 7-167 | NHAc | c-Pr | B11 | |
| 7-168 | NHAc | c-Pr | B12 | |
| 7-169 | NHAc | c-Pr | B13 | |
| 7-170 | NHAc | CHFCH₃ | B1 | resin |
| 7-171 | NHAc | CHFCH₃ | B2 | resin |
| 7-172 | NHAc | CHFCH₃ | B3 | |
| 7-173 | NHAc | CHFCH₃ | B4 | |
| 7-174 | NHAc | CHFCH₃ | B5 | |
| 7-175 | NHAc | CHFCH₃ | B6 | |
| 7-176 | NHAc | CHFCH₃ | B7 | |
| 7-177 | NHAc | CHFCH₃ | B8 | resin |
| 7-178 | NHAc | CHFCH₃ | B9 | resin |
| 7-179 | NHAc | CHFCH₃ | B10 | resin |
| 7-180 | NHAo | CHFCH₃ | B11 | |
| 7-181 | NHAc | CHFCH₃ | B12 | |
| 7-182 | NHAc | CHFCH₃ | B13 | |
| 7-183 | NHAc | CHFC₂H₅ | B1 | resin |
| 7-184 | NHAc | CHFC₂H₅ | B2 | resin |
| 7-185 | NHAc | CHFC₂H₅ | B3 | |
| 7-186 | NHAc | CHFC₂H₅ | B4 | |
| 7-187 | NHAc | CHFC₂H₅ | B5 | |
| 7-188 | NHAc | CHFC₂H₅ | B6 | |
| 7-189 | NHAc | CHFC₂H₅ | B7 | |
| 7-190 | NHAc | CHFC₂H₅ | B8 | resin |
| 7-191 | NHAc | CHFC₂H₅ | B9 | resin |
| 7-192 | NHAc | CHFC₂H₅ | B10 | resin |
| 7-193 | NHAc | CHFC₂H₅ | B11 | |
| 7-194 | NHAc | CHFC₂H₅ | B12 | |
| 7-195 | NHAc | CHFC₂H₅ | B13 | |
| 7-196 | NHAc | CF(CH₃)₂ | B1 | resin |
| 7-197 | NHAc | CF(CH₃)₂ | B2 | resin |
| 7-198 | NHAc | CF(CH₃)₂ | B3 | |
| 7-199 | NHAc | CF(CH₃)₂ | B4 | |
| 7-200 | NHAc | CF(CH₃)₂ | B5 | |
| 7-201 | NHAc | CF(CH₃)₂ | B6 | |
| 7-202 | NHAc | CF(CH₃)₂ | B7 | |
| 7-203 | NHAc | CF(CH₃)₂ | B8 | resin |
| 7-204 | NHAc | CF(CH₃)₂ | B9 | resin |
| 7-205 | NHAc | CF(CH₃)₂ | B10 | resin |
| 7-206 | NHAc | CF(CH₃)₂ | B11 | |
| 7-207 | NHAc | CF(CH₃)₂ | B12 | |
| 7-208 | NHAc | CF(CH₃)₂ | B13 | |
| 7-209 | NHAc | 1-F-c-Pr | B1 | resin |
| 7-210 | NHAc | 1-F-c-Pr | B2 | resin |
| 7-211 | NHAc | 1-F-c-Pr | B3 | |
| 7-212 | NHAc | 1-F-c-Pr | B4 | |
| 7-213 | NHAc | 1-F-c-Pr | B5 | |
| 7-214 | NHAc | 1-F-c-Pr | B6 | |
| 7-215 | NHAc | 1-F-c-Pr | B7 | |
| 7-216 | NHAc | 1-F-c-Pr | B8 | resin |
| 7-217 | NHAc | 1-F-c-Pr | B9 | resin |
| 7-218 | NHAc | 1-F-c-Pr | B10 | resin |
| 7-219 | NHAc | 1-F-c-Pr | B11 | |
| 7-220 | NHAc | 1-F-c-Pr | B12 | |
| 7-221 | NHAc | 1-F-c-Pr | B13 | |
| 7-222 | NHAc | CHF2 | B1 | resin |
| 7-223 | NHAc | CHF2 | B2 | resin |
| 7-224 | NHAc | CHF2 | B3 | |

TABLE 7-continued

Compounds of the formula (I-B),

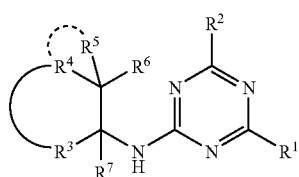

(I-B)

where, in the table which follows,
the symbol B* represents the group of the formula

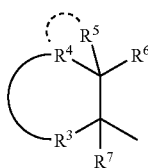

(B*)

(abbreviations B1 to B13 inter alia,
see table of abbreviations before table 1):

| No. | R¹ | R² | B* | phys. data |
|---|---|---|---|---|
| 7-225 | NHAc | CHF2 | B4 | |
| 7-226 | NHAc | CHF2 | B5 | |
| 7-227 | NHAc | CHF2 | B6 | |
| 7-228 | NHAc | CHF2 | B7 | |
| 7-229 | NHAc | CHF2 | B8 | resin |
| 7-230 | NHAc | CHF2 | B9 | resin |
| 7-231 | NHAc | CHF2 | B10 | resin |
| 7-232 | NHAc | CHF2 | B11 | |
| 7-233 | NHAc | CHF2 | B12 | |
| 7-234 | NHAc | CHF2 | B13 | |
| 7-235 | NHCOEt | H | B1 | resin |
| 7-236 | NHCOEt | H | B2 | resin |
| 7-237 | NHCOEt | H | B3 | |
| 7-238 | NHCOEt | H | B4 | |
| 7-239 | NHCOEt | H | B5 | |
| 7-240 | NHCOEt | H | B6 | |
| 7-241 | NHCOEt | H | B7 | |
| 7-242 | NHCOEt | H | B8 | resin |
| 7-243 | NHCOEt | H | B9 | resin |
| 7-244 | NHCOEt | H | B10 | resin |
| 7-245 | NHCOEt | H | B11 | |
| 7-246 | NHCOEt | H | B12 | |
| 7-247 | NHCOEt | H | B13 | |
| 7-248 | NHCOEt | Me | B1 | resin |
| 7-249 | NHCOEt | Me | B2 | resin |
| 7-250 | NHCOEt | Me | B3 | |
| 7-251 | NHCOEt | Me | B4 | |
| 7-252 | NHCOEt | Me | B5 | |
| 7-253 | NHCOEt | Me | B6 | |
| 7-254 | NHCOEt | Me | B7 | |
| 7-255 | NHCOEt | Me | B8 | resin |
| 7-256 | NHCOEt | Me | B9 | resin |
| 7-257 | NHCOEt | Me | B10 | resin |
| 7-258 | NHCOEt | Me | B11 | |
| 7-259 | NHCOEt | Me | B12 | |
| 7-260 | NHCOEt | Me | B13 | |
| 7-261 | NHCOEt | Et | B1 | resin |
| 7-262 | NHCOEt | Et | B2 | resin |
| 7-263 | NHCOEt | Et | B3 | |
| 7-264 | NHCOEt | Et | B4 | |
| 7-265 | NHCOEt | Et | B5 | |
| 7-266 | NHCOEt | Et | B6 | |
| 7-267 | NHCOEt | Et | B7 | |
| 7-268 | NHCOEt | Et | B8 | resin |
| 7-269 | NHCOEt | Et | B9 | resin |
| 7-270 | NHCOEt | Et | B10 | resin |
| 7-271 | NHCOEt | Et | B11 | |
| 7-272 | NHCOEt | Et | B12 | |
| 7-273 | NHCOEt | Et | B13 | |
| 7-274 | NHCOEt | c-Pr | B1 | resin |
| 7-275 | NHCOEt | c-Pr | B2 | resin |
| 7-276 | NHCOEt | c-Pr | B3 | |
| 7-277 | NHCOEt | c-Pr | B4 | |
| 7-278 | NHCOEt | c-Pr | B5 | |
| 7-279 | NHCOEt | c-Pr | B6 | |
| 7-280 | NHCOEt | c-Pr | B7 | |
| 7-281 | NHCOEt | c-Pr | B8 | resin |
| 7-282 | NHCOEt | c-Pr | B9 | resin |
| 7-283 | NHCOEt | c-Pr | B10 | resin |
| 7-284 | NHCOEt | c-Pr | B11 | |
| 7-285 | NHCOEt | c-Pr | B12 | |
| 7-286 | NHCOEt | c-Pr | B13 | |
| 7-287 | NHCOEt | CHFCH₃ | B1 | resin |
| 7-288 | NHCOEt | CHFCH₃ | B2 | resin |
| 7-289 | NHCOEt | CHFCH₃ | B3 | |
| 7-290 | NHCOEt | CHFCH₃ | B4 | |
| 7-291 | NHCOEt | CHFCH₃ | B5 | |
| 7-292 | NHCOEt | CHFCH₃ | B6 | |
| 7-293 | NHCOEt | CHFCH₃ | B7 | |
| 7-294 | NHCOEt | CHFCH₃ | B8 | resin |
| 7-295 | NHCOEt | CHFCH₃ | B9 | resin |
| 7-296 | NHCOEt | CHFCH₃ | B10 | resin |
| 7-297 | NHCOEt | CHFCH₃ | B11 | |
| 7-298 | NHCOEt | CHFCH₃ | B12 | |
| 7-299 | NHCOEt | CHFCH₃ | B13 | |
| 7-300 | NHCOEt | CHFC₂H₅ | B1 | resin |
| 7-301 | NHCOEt | CHFC₂H₅ | B2 | resin |
| 7-302 | NHCOEt | CHFC₂H₅ | B3 | |
| 7-303 | NHCOEt | CHFC₂H₅ | B4 | |
| 7-304 | NHCOEt | CHFC₂H₅ | B5 | |
| 7-305 | NHCOEt | CHFC₂H₅ | B6 | |
| 7-306 | NHCOEt | CHFC₂H₅ | B7 | |
| 7-307 | NHCOEt | CHFC₂H₅ | B8 | resin |
| 7-308 | NHCOEt | CHFC₂H₅ | B9 | resin |
| 7-309 | NHCOEt | CHFC₂H₅ | B10 | resin |
| 7-310 | NHCOEt | CHFC₂H₅ | B11 | |
| 7-311 | NHCOEt | CHFC₂H₅ | B12 | |
| 7-312 | NHCOEt | CHFC₂H₅ | B13 | |
| 7-313 | NHCOEt | CF(CH₃)₂ | B1 | resin |
| 7-314 | NHCOEt | CF(CH₃)₂ | B2 | resin |
| 7-315 | NHCOEt | CF(CH₃)₂ | B3 | |
| 7-316 | NHCOEt | CF(CH₃)₂ | B4 | |
| 7-317 | NHCOEt | CF(CH₃)₂ | B5 | |
| 7-318 | NHCOEt | CF(CH₃)₂ | B6 | |
| 7-319 | NHCOEt | CF(CH₃)₂ | B7 | |
| 7-320 | NHCOEt | CF(CH₃)₂ | B8 | resin |
| 7-321 | NHCOEt | CF(CH₃)₂ | B9 | resin |
| 7-322 | NHCOEt | CF(CH₃)₂ | B10 | resin |
| 7-323 | NHCOEt | CF(CH₃)₂ | B11 | |
| 7-324 | NHCOEt | CF(CH₃)₂ | B12 | |
| 7-325 | NHCOEt | CF(CH₃)₂ | B13 | |
| 7-326 | NHCOEt | 1-F-c-Pr | B1 | resin |
| 7-327 | NHCOEt | 1-F-c-Pr | B2 | resin |
| 7-328 | NHCOEt | 1-F-c-Pr | B3 | |
| 7-329 | NHCOEt | 1-F-c-Pr | B4 | |
| 7-330 | NHCOEt | 1-F-c-Pr | B5 | |

TABLE 7-continued

Compounds of the formula (I-B),

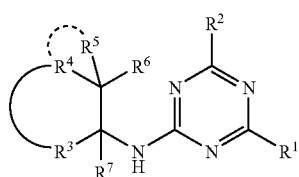

where, in the table which follows,
the symbol B* represents the group of the formula

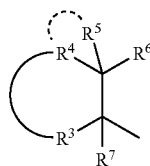

(abbreviations B1 to B13 inter alia,
see table of abbreviations before table 1):

| No. | R¹ | R² | B* | phys. data |
|---|---|---|---|---|
| 7-331 | NHCOEt | 1-F-c-Pr | B6 | |
| 7-332 | NHCOEt | 1-F-c-Pr | B7 | |
| 7-333 | NHCOEt | 1-F-c-Pr | B8 | resin |
| 7-334 | NHCOEt | 1-F-c-Pr | B9 | resin |
| 7-335 | NHCOEt | 1-F-c-Pr | B10 | resin |
| 7-336 | NHCOEt | 1-F-c-Pr | B11 | |
| 7-337 | NHCOEt | 1-F-c-Pr | B12 | |
| 7-338 | NHCOEt | 1-F-c-Pr | B13 | |
| 7-339 | NHCOEt | CHF2 | B1 | resin |
| 7-340 | NHCOEt | CHF2 | B2 | resin |
| 7-341 | NHCOEt | CHF2 | B3 | |
| 7-342 | NHCOEt | CHF2 | B4 | |
| 7-343 | NHCOEt | CHF2 | B5 | |
| 7-344 | NHCOEt | CHF2 | B6 | |
| 7-345 | NHCOEt | CHF2 | B7 | |
| 7-346 | NHCOEt | CHF2 | B8 | resin |
| 7-347 | NHCOEt | CHF2 | B9 | resin |
| 7-348 | NHCOEt | CHF2 | B10 | resin |
| 7-349 | NHCOEt | CHF2 | B11 | |
| 7-350 | NHCOEt | CHF2 | B12 | |
| 7-351 | NHCOEt | CHF2 | B13 | |
| 7-352 | NHCOCHFMe | H | B1 | resin |
| 7-353 | NHCOCHFMe | H | B2 | resin |
| 7-354 | NHCOCHFMe | H | B3 | |
| 7-355 | NHCOCHFMe | H | B4 | |
| 7-356 | NHCOCHFMe | H | B5 | |
| 7-357 | NHCOCHFMe | H | B6 | |
| 7-358 | NHCOCHFMe | H | B7 | |
| 7-359 | NHCOCHFMe | H | B8 | resin |
| 7-360 | NHCOCHFMe | H | B9 | resin |
| 7-361 | NHCOCHFMe | H | B10 | resin |
| 7-362 | NHCOCHFMe | H | B11 | |
| 7-363 | NHCOCHFMe | H | B12 | |
| 7-364 | NHCOCHFMe | H | B13 | |
| 7-365 | NHCOCHFMe | Me | B1 | resin |
| 7-366 | NHCOCHFMe | Me | B2 | resin |
| 7-367 | NHCOCHFMe | Me | B3 | |
| 7-368 | NHCOCHFMe | Me | B4 | |
| 7-369 | NHCOCHFMe | Me | B5 | |
| 7-370 | NHCOCHFMe | Me | B6 | |
| 7-371 | NHCOCHFMe | Me | B7 | |
| 7-372 | NHCOCHFMe | Me | B8 | resin |
| 7-373 | NHCOCHFMe | Me | B9 | resin |
| 7-374 | NHCOCHFMe | Me | B10 | resin |
| 7-375 | NHCOCHFMe | Me | B11 | |
| 7-376 | NHCOCHFMe | Me | B12 | |
| 7-377 | NHCOCHFMe | Me | B13 | |
| 7-378 | NHCOCHFMe | Et | B1 | resin |
| 7-379 | NHCOCHFMe | Et | B2 | resin |
| 7-380 | NHCOCHFMe | Et | B3 | |
| 7-381 | NHCOCHFMe | Et | B4 | |
| 7-382 | NHCOCHFMe | Et | B5 | |
| 7-383 | NHCOCHFMe | Et | B6 | |
| 7-384 | NHCOCHFMe | Et | B7 | |
| 7-385 | NHCOCHFMe | Et | B8 | resin |
| 7-386 | NHCOCHFMe | Et | B9 | resin |
| 7-387 | NHCOCHFMe | Et | B10 | resin |
| 7-388 | NHCOCHFMe | Et | B11 | |
| 7-389 | NHCOCHFMe | Et | B12 | |
| 7-390 | NHCOCHFMe | Et | B13 | |
| 7-391 | NHCOCHFMe | c-Pr | B1 | resin |
| 7-392 | NHCOCHFMe | c-Pr | B2 | resin |
| 7-393 | NHCOCHFMe | c-Pr | B3 | |
| 7-394 | NHCOCHFMe | c-Pr | B4 | |
| 7-395 | NHCOCHFMe | c-Pr | B5 | |
| 7-396 | NHCOCHFMe | c-Pr | B6 | |
| 7-397 | NHCOCHFMe | c-Pr | B7 | |
| 7-398 | NHCOCHFMe | c-Pr | B8 | resin |
| 7-399 | NHCOCHFMe | c-Pr | B9 | resin |
| 7-400 | NHCOCHFMe | c-Pr | B10 | resin |
| 7-401 | NHCOCHFMe | c-Pr | B11 | |
| 7-402 | NHCOCHFMe | c-Pr | B12 | |
| 7-403 | NHCOCHFMe | c-Pr | B13 | |
| 7-404 | NHCOCHFMe | CHFCH₃ | B1 | resin |
| 7-405 | NHCOCHFMe | CHFCH₃ | B2 | resin |
| 7-406 | NHCOCHFMe | CHFCH₃ | B3 | |
| 7-407 | NHCOCHFMe | CHFCH₃ | B4 | |
| 7-408 | NHCOCHFMe | CHFCH₃ | B5 | |
| 7-409 | NHCOCHFMe | CHFCH₃ | B6 | |
| 7-410 | NHCOCHFMe | CHFCH₃ | B7 | |
| 7-411 | NHCOCHFMe | CHFCH₃ | B8 | resin |
| 7-412 | NHCOCHFMe | CHFCH₃ | B9 | resin |
| 7-413 | NHCOCHFMe | CHFCH₃ | B10 | resin |
| 7-414 | NHCOCHFMe | CHFCH₃ | B11 | |
| 7-415 | NHCOCHFMe | CHFCH₃ | B12 | |
| 7-416 | NHCOCHFMe | CHFCH₃ | B13 | |
| 7-417 | NHCOCHFMe | CHFC₂H₅ | B1 | resin |
| 7-418 | NHCOCHFMe | CHFC₂H₅ | B2 | resin |
| 7-419 | NHCOCHFMe | CHFC₂H₅ | B3 | |
| 7-420 | NHCOCHFMe | CHFC₂H₅ | B4 | |
| 7-421 | NHCOCHFMe | CHFC₂H₅ | B5 | |
| 7-422 | NHCOCHFMe | CHFC₂H₅ | B6 | |
| 7-423 | NHCOCHFMe | CHFC₂H₅ | B7 | |
| 7-424 | NHCOCHFMe | CHFC₂H₅ | B8 | resin |
| 7-425 | NHCOCHFMe | CHFC₂H₅ | B9 | resin |
| 7-426 | NHCOCHFMe | CHFC₂H₅ | B10 | resin |
| 7-427 | NHCOCHFMe | CHFC₂H₅ | B11 | |
| 7-428 | NHCOCHFMe | CHFC₂H₅ | B12 | |
| 7-429 | NHCOCHFMe | CHFC₂H₅ | B13 | |
| 7-430 | NHCOCHFMe | CF(CH₃)₂ | B1 | resin |
| 7-431 | NHCOCHFMe | CF(CH₃)₂ | B2 | resin |
| 7-432 | NHCOCHFMe | CF(CH₃)₂ | B3 | |
| 7-433 | NHCOCHFMe | CF(CH₃)₂ | B4 | |
| 7-434 | NHCOCHFMe | CF(CH₃)₂ | B5 | |
| 7-435 | NHCOCHFMe | CF(CH₃)₂ | B6 | |
| 7-436 | NHCOCHFMe | CF(CH₃)₂ | B7 | |

TABLE 7-continued

Compounds of the formula (I-B),

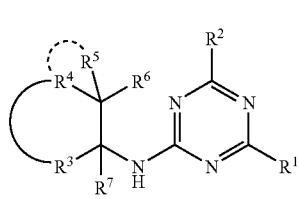
(I-B)

where, in the table which follows,
the symbol B* represents the group of the formula

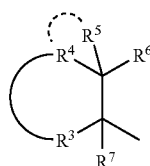
(B*)

(abbreviations B1 to B13 inter alia,
see table of abbreviations before table 1):

| No. | R¹ | R² | B* | phys. data |
|---|---|---|---|---|
| 7-437 | NHCOCHFMe | CF(CH₃)₂ | B8 | resin |
| 7-438 | NHCOCHFMe | CF(CH₃)₂ | B9 | resin |
| 7-439 | NHCOCHFMe | CF(CH₃)₂ | B10 | resin |
| 7-440 | NHCOCHFMe | CF(CH₃)₂ | B11 | |
| 7-441 | NHCOCHFMe | CF(CH₃)₂ | B12 | |
| 7-442 | NHCOCHFMe | CF(CH₃)₂ | B13 | |
| 7-443 | NHCOCHFMe | 1-F-c-Pr | B1 | resin |
| 7-444 | NHCOCHFMe | 1-F-c-Pr | B2 | resin |
| 7-445 | NHCOCHFMe | 1-F-c-Pr | B3 | |
| 7-446 | NHCOCHFMe | 1-F-c-Pr | B4 | |
| 7-447 | NHCOCHFMe | 1-F-c-Pr | B5 | |
| 7-448 | NHCOCHFMe | 1-F-c-Pr | B6 | |
| 7-449 | NHCOCHFMe | 1-F-c-Pr | B7 | |
| 7-450 | NHCOCHFMe | 1-F-c-Pr | B8 | resin |
| 7-451 | NHCOCHFMe | 1-F-c-Pr | B9 | resin |
| 7-452 | NHCOCHFMe | 1-F-c-Pr | B10 | resin |
| 7-453 | NHCOCHFMe | 1-F-c-Pr | B11 | |
| 7-454 | NHCOCHFMe | 1-F-c-Pr | B12 | |
| 7-455 | NHCOCHFMe | 1-F-c-Pr | B13 | |
| 7-456 | NHCOCHFMe | CHF2 | B1 | resin |
| 7-457 | NHCOCHFMe | CHF2 | B2 | resin |
| 7-458 | NHCOCHFMe | CHF2 | B3 | |
| 7-459 | NHCOCHFMe | CHF2 | B4 | |
| 7-460 | NHCOCHFMe | CHF2 | B5 | |
| 7-461 | NHCOCHFMe | CHF2 | B6 | |
| 7-462 | NHCOCHFMe | CHF2 | B7 | |
| 7-463 | NHCOCHFMe | CHF2 | B8 | resin |
| 7-464 | NHCOCHFMe | CHF2 | B9 | resin |
| 7-465 | NHCOCHFMe | CHF2 | B10 | resin |
| 7-466 | NHCOCHFMe | CHF2 | B11 | |
| 7-467 | NHCOCHFMe | CHF2 | B12 | |
| 7-468 | NHCOCHFMe | CHF2 | B13 | |
| 7-469 | N=CH—NMe₂ | H | B1 | resin |
| 7-470 | N=CH—NMe₂ | H | B2 | resin |
| 7-471 | N=CH—NMe₂ | H | B3 | |
| 7-472 | N=CH—NMe₂ | H | B4 | |
| 7-473 | N=CH—NMe₂ | H | B5 | |
| 7-474 | N=CH—NMe₂ | H | B6 | |
| 7-475 | N=CH—NMe₂ | H | B7 | |
| 7-476 | N=CH—NMe₂ | H | B8 | resin |
| 7-477 | N=CH—NMe₂ | H | B9 | resin |
| 7-478 | N=CH—NMe₂ | H | B10 | resin |
| 7-479 | N=CH—NMe₂ | H | B11 | |
| 7-480 | N=CH—NMe₂ | H | B12 | |
| 7-481 | N=CH—NMe₂ | H | B13 | |
| 7-482 | N=CH—NMe₂ | Me | B1 | resin |
| 7-483 | N=CH—NMe₂ | Me | B2 | resin |
| 7-484 | N=CH—NMe₂ | Me | B3 | |
| 7-485 | N=CH—NMe₂ | Me | B4 | |
| 7-486 | N=CH—NMe₂ | Me | B5 | |
| 7-487 | N=CH—NMe₂ | Me | B6 | |
| 7-488 | N=CH—NMe₂ | Me | B7 | |
| 7-489 | N=CH—NMe₂ | Me | B8 | resin |

TABLE 7-continued

Compounds of the formula (I-B),

(I-B)

where, in the table which follows,
the symbol B* represents the group of the formula

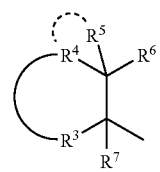
(B*)

(abbreviations B1 to B13 inter alia,
see table of abbreviations before table 1):

| No. | R¹ | R² | B* | phys. data |
|---|---|---|---|---|
| 7-490 | N=CH—NMe₂ | Me | B9 | resin |
| 7-491 | N=CH—NMe₂ | Me | B10 | resin |
| 7-492 | N=CH—NMe₂ | Me | B11 | |
| 7-493 | N=CH—NMe₂ | Me | B12 | |
| 7-494 | N=CH—NMe₂ | Me | B13 | |
| 7-495 | N=CH—NMe₂ | Et | B1 | resin |
| 7-496 | N=CH—NMe₂ | Et | B2 | resin |
| 7-497 | N=CH—NMe₂ | Et | B3 | |
| 7-498 | N=CH—NMe₂ | Et | B4 | |
| 7-499 | N=CH—NMe₂ | Et | B5 | |
| 7-500 | N=CH—NMe₂ | Et | B6 | |
| 7-501 | N=CH—NMe₂ | Et | B7 | |
| 7-502 | N=CH—NMe₂ | Et | B8 | resin |
| 7-503 | N=CH—NMe₂ | Et | B9 | resin |
| 7-504 | N=CH—NMe₂ | Et | B10 | resin |
| 7-505 | N=CH—NMe₂ | Et | B11 | |
| 7-506 | N=CH—NMe₂ | Et | B12 | |
| 7-507 | N=CH—NMe₂ | Et | B13 | |
| 7-508 | N=CH—NMe₂ | c-Pr | B1 | resin |
| 7-509 | N=CH—NMe₂ | c-Pr | B2 | resin |
| 7-510 | N=CH—NMe₂ | c-Pr | B3 | |
| 7-511 | N=CH—NMe₂ | c-Pr | B4 | |
| 7-512 | N=CH—NMe₂ | c-Pr | B5 | |
| 7-513 | N=CH—NMe₂ | c-Pr | B6 | |
| 7-514 | N=CH—NMe₂ | c-Pr | B7 | |
| 7-515 | N=CH—NMe₂ | c-Pr | B8 | resin |
| 7-516 | N=CH—NMe₂ | c-Pr | B9 | resin |
| 7-517 | N=CH—NMe₂ | c-Pr | B10 | resin |
| 7-518 | N=CH—NMe₂ | c-Pr | B11 | |
| 7-519 | N=CH—NMe₂ | c-Pr | B12 | |
| 7-520 | N=CH—NMe₂ | c-Pr | B13 | |
| 7-521 | N=CH—NMe₂ | CHFCH₃ | B1 | resin |
| 7-522 | N=CH—NMe₂ | CHFCH₃ | B2 | resin |
| 7-523 | N=CH—NMe₂ | CHFCH₃ | B3 | |
| 7-524 | N=CH—NMe₂ | CHFCH₃ | B4 | |
| 7-525 | N=CH—NMe₂ | CHFCH₃ | B5 | |
| 7-526 | N=CH—NMe₂ | CHFCH₃ | B6 | |
| 7-527 | N=CH—NMe₂ | CHFCH₃ | B7 | |
| 7-528 | N=CH—NMe₂ | CHFCH₃ | B8 | resin |
| 7-529 | N=CH—NMe₂ | CHFCH₃ | B9 | resin |
| 7-530 | N=CH—NMe₂ | CHFCH₃ | B10 | resin |
| 7-531 | N=CH—NMe₂ | CHFCH₃ | B11 | |
| 7-532 | N=CH—NMe₂ | CHFCH₃ | B12 | |
| 7-533 | N=CH—NMe₂ | CHFCH₃ | B13 | |
| 7-534 | N=CH—NMe₂ | CHFC₂H₅ | B1 | resin |
| 7-535 | N=CH—NMe₂ | CHFC₂H₅ | B2 | resin |
| 7-536 | N=CH—NMe₂ | CHFC₂H₅ | B3 | |
| 7-537 | N=CH—NMe₂ | CHFC₂H₅ | B4 | |
| 7-538 | N=CH—NMe₂ | CHFC₂H₅ | B5 | |
| 7-539 | N=CH—NMe₂ | CHFC₂H₅ | B6 | |
| 7-540 | N=CH—NMe₂ | CHFC₂H₅ | B7 | |
| 7-541 | N=CH—NMe₂ | CHFC₂H₅ | B8 | resin |
| 7-542 | N=CH—NMe₂ | CHFC₂H₅ | B9 | resin |

TABLE 7-continued

Compounds of the formula (I-B),

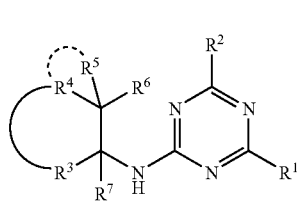

(I-B)

where, in the table which follows,
the symbol B* represents the group of the formula

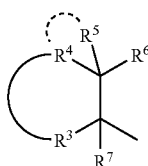

(B*)

(abbreviations B1 to B13 inter alia,
see table of abbreviations before table 1):

| No. | R¹ | R² | B* | phys. data |
|---|---|---|---|---|
| 7-543 | N=CH—NMe₂ | CHFC₂H₅ | B10 | resin |
| 7-544 | N=CH—NMe₂ | CHFC₂H₅ | B11 | |
| 7-545 | N=CH—NMe₂ | CHFC₂H₅ | B12 | |
| 7-546 | N=CH—NMe₂ | CHFC₂H₅ | B13 | |
| 7-547 | N=CH—NMe₂ | CF(CH₃)₂ | B1 | resin |
| 7-548 | N=CH—NMe₂ | CF(CH₃)₂ | B2 | resin |
| 7-549 | N=CH—NMe₂ | CF(CH₃)₂ | B3 | |
| 7-550 | N=CH—NMe₂ | CF(CH₃)₂ | B4 | |
| 7-551 | N=CH—NMe₂ | CF(CH₃)₂ | B5 | |
| 7-552 | N=CH—NMe₂ | CF(CH₃)₂ | B6 | |
| 7-553 | N=CH—NMe₂ | CF(CH₃)₂ | B7 | |
| 7-554 | N=CH—NMe₂ | CF(CH₃)₂ | B8 | resin |
| 7-555 | N=CH—NMe₂ | CF(CH₃)₂ | B9 | resin |
| 7-556 | N=CH—NMe₂ | CF(CH₃)₂ | B10 | resin |
| 7-557 | N=CH—NMe₂ | CF(CH₃)₂ | B11 | |
| 7-558 | N=CH—NMe₂ | CF(CH₃)₂ | B12 | |
| 7-559 | N=CH—NMe₂ | CF(CH₃)₂ | B13 | |
| 7-560 | N=CH—NMe₂ | 1-F-c-Pr | B1 | resin |
| 7-561 | N=CH—NMe₂ | 1-F-c-Pr | B2 | resin |
| 7-562 | N=CH—NMe₂ | 1-F-c-Pr | B3 | |
| 7-563 | N=CH—NMe₂ | 1-F-c-Pr | B4 | |
| 7-564 | N=CH—NMe₂ | 1-F-c-Pr | B5 | |
| 7-565 | N=CH—NMe₂ | 1-F-c-Pr | B6 | |
| 7-566 | N=CH—NMe₂ | 1-F-c-Pr | B7 | |
| 7-567 | N=CH—NMe₂ | 1-F-c-Pr | B8 | resin |
| 7-568 | N=CH—NMe₂ | 1-F-c-Pr | B9 | resin |
| 7-569 | N=CH—NMe₂ | 1-F-c-Pr | B10 | resin |
| 7-570 | N=CH—NMe₂ | 1-F-c-Pr | B11 | |
| 7-571 | N=CH—NMe₂ | 1-F-c-Pr | B12 | |
| 7-572 | N=CH—NMe₂ | 1-F-c-Pr | B13 | |
| 7-573 | N=CH—NMe₂ | CHF2 | B1 | resin |
| 7-574 | N=CH—NMe₂ | CHF2 | B2 | resin |
| 7-575 | N=CH—NMe₂ | CHF2 | B3 | |
| 7-576 | N=CH—NMe₂ | CHF2 | B4 | |
| 7-577 | N=CH—NMe₂ | CHF2 | B5 | |
| 7-578 | N=CH—NMe₂ | CHF2 | B6 | |
| 7-579 | N=CH—NMe₂ | CHF2 | B7 | |
| 7-580 | N=CH—NMe₂ | CHF2 | B8 | resin |
| 7-581 | N=CH—NMe₂ | CHF2 | B9 | resin |
| 7-582 | N=CH—NMe₂ | CHF2 | B10 | resin |
| 7-583 | N=CH—NMe₂ | CHF2 | B11 | |
| 7-584 | N=CH—NMe₂ | CHF2 | B12 | |
| 7-585 | N=CH—NMe₂ | CHF2 | B13 | |
| 7-586 | N=CH-morph | H | B1 | resin |
| 7-587 | N=CH-morph | H | B2 | resin |
| 7-588 | N=CH-morph | H | B3 | |
| 7-589 | N=CH-morph | H | B4 | |
| 7-590 | N=CH-morph | H | B5 | |
| 7-591 | N=CH-morph | H | B6 | |
| 7-592 | N=CH-morph | H | B7 | |
| 7-593 | N=CH-morph | H | B8 | resin |
| 7-594 | N=CH-morph | H | B9 | resin |
| 7-595 | N=CH-morph | H | B10 | resin |
| 7-596 | N=CH-morph | H | B11 | |
| 7-597 | N=CH-morph | H | B12 | |
| 7-598 | N=CH-morph | H | B13 | |
| 7-599 | N=CH-morph | Me | B1 | resin |
| 7-600 | N=CH-morph | Me | B2 | resin |
| 7-601 | N=CH-morph | Me | B3 | |
| 7-602 | N=CH-morph | Me | B4 | |
| 7-603 | N=CH-morph | Me | B5 | |
| 7-604 | N=CH-morph | Me | B6 | |
| 7-605 | N=CH-morph | Me | B7 | |
| 7-606 | N=CH-morph | Me | B8 | resin |
| 7-607 | N=CH-morph | Me | B9 | resin |
| 7-608 | N=CH-morph | Me | B10 | resin |
| 7-609 | N=CH-morph | Me | B11 | |
| 7-610 | N=CH-morph | Me | B12 | |
| 7-611 | N=CH-morph | Me | B13 | |
| 7-612 | N=CH-morph | Et | B1 | resin |
| 7-613 | N=CH-morph | Et | B2 | resin |
| 7-614 | N=CH-morph | Et | B3 | |
| 7-615 | N=CH-morph | Et | B4 | |
| 7-616 | N=CH-morph | Et | B5 | |
| 7-617 | N=CH-morph | Et | B6 | |
| 7-618 | N=CH-morph | Et | B7 | |
| 7-619 | N=CH-morph | Et | B8 | resin |
| 7-620 | N=CH-morph | Et | B9 | resin |
| 7-621 | N=CH-morph | Et | B10 | resin |
| 7-622 | N=CH-morph | Et | B11 | |
| 7-623 | N=CH-morph | Et | B12 | |
| 7-624 | N=CH-morph | Et | B13 | |
| 7-625 | N=CH-morph | c-Pr | B1 | resin |
| 7-626 | N=CH-morph | c-Pr | B2 | resin |
| 7-627 | N=CH-morph | c-Pr | B3 | |
| 7-628 | N=CH-morph | c-Pr | B4 | |
| 7-629 | N=CH-morph | c-Pr | B5 | |
| 7-630 | N=CH-morph | c-Pr | B6 | |
| 7-631 | N=CH-morph | c-Pr | B7 | |
| 7-632 | N=CH-morph | c-Pr | B8 | resin |
| 7-633 | N=CH-morph | c-Pr | B9 | resin |
| 7-634 | N=CH-morph | c-Pr | B10 | resin |
| 7-635 | N=CH-morph | c-Pr | B11 | |
| 7-636 | N=CH-morph | c-Pr | B12 | |
| 7-637 | N=CH-morph | c-Pr | B13 | |
| 7-638 | N=CH-morph | CHFCH₃ | B1 | resin |
| 7-639 | N=CH-morph | CHFCH₃ | B2 | resin |
| 7-640 | N=CH-morph | CHFCH₃ | B3 | |
| 7-641 | N=CH-morph | CHFCH₃ | B4 | |
| 7-642 | N=CH-morph | CHFCH₃ | B5 | |
| 7-643 | N=CH-morph | CHFCH₃ | B6 | |
| 7-644 | N=CH-morph | CHFCH₃ | B7 | |
| 7-645 | N=CH-morph | CHFCH₃ | B8 | resin |
| 7-646 | N=CH-morph | CHFCH₃ | B9 | resin |
| 7-647 | N=CH-morph | CHFCH₃ | B10 | resin |
| 7-648 | N=CH-morph | CHFCH₃ | B11 | |

TABLE 7-continued

Compounds of the formula (I-B),

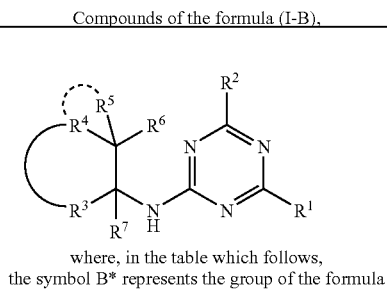
(I-B)

where, in the table which follows,
the symbol B* represents the group of the formula

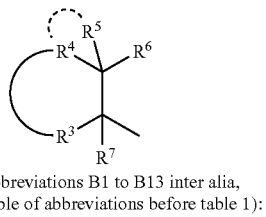
(B*)

(abbreviations B1 to B13 inter alia,
see table of abbreviations before table 1):

| No. | R$^1$ | R$^2$ | B* | phys. data |
|---|---|---|---|---|
| 7-649 | N=CH-morph | CHFCH$_3$ | B12 | |
| 7-650 | N=CH-morph | CHFCH$_3$ | B13 | |
| 7-651 | N=CH-morph | CHFC$_2$H$_5$ | B1 | resin |
| 7-652 | N=CH-morph | CHFC$_2$H$_5$ | B2 | resin |
| 7-653 | N=CH-morph | CHFC$_2$H$_5$ | B3 | |
| 7-654 | N=CH-morph | CHFC$_2$H$_5$ | B4 | |
| 7-655 | N=CH-morph | CHFC$_2$H$_5$ | B5 | |
| 7-656 | N=CH-morph | CHFC$_2$H$_5$ | B6 | |
| 7-657 | N=CH-morph | CHFC$_2$H$_5$ | B7 | |
| 7-658 | N=CH-morph | CHFC$_2$H$_5$ | B8 | resin |
| 7-659 | N=CH-morph | CHFC$_2$H$_5$ | B9 | resin |
| 7-660 | N=CH-morph | CHFC$_2$H$_5$ | B10 | resin |
| 7-661 | N=CH-morph | CHFC$_2$H$_5$ | B11 | |
| 7-662 | N=CH-morph | CHFC$_2$H$_5$ | B12 | |
| 7-663 | N=CH-morph | CHFC$_2$H$_5$ | B13 | |
| 7-664 | N=CH-morph | CF(CH$_3$)$_2$ | B1 | resin |
| 7-665 | N=CH-morph | CF(CH$_3$)$_2$ | B2 | resin |
| 7-666 | N=CH-morph | CF(CH$_3$)$_2$ | B3 | |
| 7-667 | N=CH-morph | CF(CH$_3$)$_2$ | B4 | |
| 7-668 | N=CH-morph | CF(CH$_3$)$_2$ | B5 | |
| 7-669 | N=CH-morph | CF(CH$_3$)$_2$ | B6 | |
| 7-670 | N=CH-morph | CF(CH$_3$)$_2$ | B7 | |
| 7-671 | N=CH-morph | CF(CH$_3$)$_2$ | B8 | resin |
| 7-672 | N=CH-morph | CF(CH$_3$)$_2$ | B9 | resin |
| 7-673 | N=CH-morph | CF(CH$_3$)$_2$ | B10 | resin |
| 7-674 | N=CH-morph | CF(CH$_3$)$_2$ | B11 | |
| 7-675 | N=CH-morph | CF(CH$_3$)$_2$ | B12 | |
| 7-676 | N=CH-morph | CF(CH$_3$)$_2$ | B13 | |
| 7-677 | N=CH-morph | 1-F-c-Pr | B1 | resin |
| 7-678 | N=CH-morph | 1-F-c-Pr | B2 | resin |
| 7-679 | N=CH-morph | 1-F-c-Pr | B3 | |
| 7-680 | N=CH-morph | 1-F-c-Pr | B4 | |
| 7-681 | N=CH-morph | 1-F-c-Pr | B5 | |
| 7-682 | N=CH-morph | 1-F-c-Pr | B6 | |
| 7-683 | N=CH-morph | 1-F-c-Pr | B7 | |
| 7-684 | N=CH-morph | 1-F-c-Pr | B8 | resin |
| 7-685 | N=CH-morph | 1-F-c-Pr | B9 | resin |
| 7-686 | N=CH-morph | 1-F-c-Pr | B10 | resin |
| 7-687 | N=CH-morph | 1-F-c-Pr | B11 | |
| 7-688 | N=CH-morph | 1-F-c-Pr | B12 | |
| 7-689 | N=CH-morph | 1-F-c-Pr | B13 | |
| 7-690 | N=CH-morph | CHF2 | B1 | resin |
| 7-691 | N=CH-morph | CHF2 | B2 | resin |
| 7-692 | N=CH-morph | CHF2 | B3 | |
| 7-693 | N=CH-morph | CHF2 | B4 | |
| 7-694 | N=CH-morph | CHF2 | B5 | |
| 7-695 | N=CH-morph | CHF2 | B6 | |
| 7-696 | N=CH-morph | CHF2 | B7 | |
| 7-697 | N=CH-morph | CHF2 | B8 | resin |
| 7-698 | N=CH-morph | CHF2 | B9 | resin |
| 7-699 | N=CH-morph | CHF2 | B10 | resin |
| 7-700 | N=CH-morph | CHF2 | B11 | |
| 7-701 | N=CH-morph | CHF2 | B12 | |
| 7-702 | N=CH-morph | CHF2 | B13 | |

Explanations for table 7:
"NMR" of the example compounds was in each case measured as a $^1$H NMR spectrum at 400 MHz (CDCl$_3$) ($^1$H nuclear resonance data). Characteristic chemical shifts δ (ppm) for example compounds are listed below:
Ex. No.  δ (ppm) =
7-79:    4.35 (m, 1 H), 1.90-0.80 (m, 12 H), 0.50-0.20 (m, 2H)

(B) FORMULATION EXAMPLES a) A dusting product is obtained by mixing 10 parts by weight of a compound of the formula (I) and 90 parts by weight of talc as an inert substance and comminuting them in a hammer mill.

b) A readily water-dispersible wettable powder is obtained by mixing 25 parts by weight of a compound of the formula (I), 64 parts by weight of kaolin-containing quartz as an inert substance, 10 parts by weight of potassium lignosulfonate and one part by weight of sodium oleylmethyltaurate as a wetting agent and dispersant, and grinding them in a pin mill.

c) A readily water-dispersible dispersion concentrate is obtained by mixing 20 parts by weight of a compound of the formula (I) with 6 parts by weight of alkylphenol polyglycol Ether®Triton X 207), 3 parts by weight of isotridecanol polyglycol ether (8 EO) and 71 parts by weight of paraffinic mineral oil (boiling range, for example, from approx. 255 to more than 277° C.) and grinding them in a frictional ball mill to a fineness of below 5 microns.

d) An emulsifiable concentrate is obtained from 15 parts by weight of a compound of the formula (I), 75 parts by weight of cyclohexanone as a solvent and 10 parts by weight of ethoxylated nonylphenol as an emulsifier.

e) A water-dispersible granule is obtained by mixing
   75 parts by weight of a compound of the formula (I),
   10 " of calcium lignosulfonate,
   5 " of sodium laurylsulfate,
   3 " of polyvinyl alcohol and
   7 " of kaolin,
grinding them in a pin mill and granulating the powder in a fluidized bed by spraying on water as a granulating liquid.

f) A water-dispersible granule is also obtained by homogenizing and precomminuting 25 parts by weight of a compound of the formula (I),
5 " of sodium 2,2'-dinaphthylmethane-6,6'-disulfonate
2 " of sodium oleylmethyltaurate,
1 part by weight of polyvinyl alcohol,
17 parts by weight of calcium carbonate and
50 " of water in a colloid mill, then grinding them on a bead mill and atomizing and drying the suspension thus obtained in a spray tower by means of a one-substance nozzle.

(C) BIOLOGICAL EXAMPLES

1. Pre-Emergence Herbicidal Action

Seeds or rhizome pieces of mono- and dicotyledonous weed plants were placed in sandy loam in plastic pots and covered with soil. The inventive compounds, which have been formulated in the form of wettable powders or emulsion concentrates, were then applied to the surface of the covering soil as an aqueous suspension or emulsion in different dosages with an application rate of from 600 to 800 l/ha of water (converted).

After the treatment, the pots were placed in a greenhouse and kept under good growth conditions for the weeds. The plant or emergence damage is scored visually after the emergence of the test plants after an experiment time of from 3 to 4 weeks in comparison to untreated controls. As the test results showed, the inventive compounds exhibited good herbicidal pre-emergence activity against a wide spectrum of broadleaf and gramineous weeds. For example, the examples no. 1-19, 1-98, 1-317, 1-335, 1-420, 1-475, 1-493, 1-499, 1-572, 1-651, 2-199, 5-201, 6-199 and 7-79 of tables 1 to 7 exhibited very good herbicidal action in the text against harmful plants such as *Stellaria media, Lolium multiflorum, Amaranthus retroflexus, Sinapis alba, Avena sativa* and *Setaria viridis* in the pre-emergence method at an application rate of 500 g or less of active substance per hectare.

2. Post-Emergence Herbicidal Action

Seeds or rhizome pieces of mono- and dicotyledonous weeds were placed in sandy loam in plastic pots, covered with soil and grown in a greenhouse under good growth conditions. Three weeks after the sowing, the test plants were treated at the three-leaf stage. The inventive compounds formulated as spray powders or as emulsion concentrates were sprayed onto the green plant parts in various dosages with an application rate of from 600 to 800 l/ha of water (converted). After the test plants had been left to stand in the greenhouse under optimal growth conditions for approx. 3 to 4 weeks, the action of the preparations was scored visually in comparison to untreated controls. The inventive compositions also had good post-emergence herbicidal activity against a wide spectrum of economically important gramineous and broadleaf weeds. For example, examples no. 1-19, 1-256, 1-317, 1-335, 1-414, 1-420, 1-475, 1-493, 1-572, 1-651, 2-199, 5-201, 6-199 and 7-79 of tables 1 to 7 exhibited very good herbicidal action in the test against harmful plants such as *Sinapis alba, Echinochloa crus-galli, Lolium multiflorum, Stellaria media, Cyperus iria, Amaranthus retroflexus, Setaria viridis, Avena sativa, Lamium purpureum, Matricaria inodora, Papaver rhoeas, Veronica persica, Viola trocolor, Kochia* spp and *Chenopodium album* in the post-emergence method at an application rate of 500 g and less of active substance per hectare.

3. Herbicidal Action in Plantation Crops

In a field experiment, plantation crops were grown in trial plots under natural conditions, in the course of which natural growth of harmful plants occurred. Thereafter, the plots were treated with the inventive compounds by spraying the harmful plants with an aqueous dispersion of the particular compound. About three weeks after the application of the treatment carried out in this way, the trial plots were scored with regard to harmful plant growth and damage, and the plantation crops were scored visually in comparison to control plots.

The inventive compounds had very good herbicidal action against the harmful plants, while plantation crops such as oil palms, coconut palms, rubber trees, citrus trees, pineapples, cotton, coffee trees had no recognizable phytotoxic damage.

Having thus described in detail various embodiments of the present invention, it is to be understood that the invention defined by the above paragraphs is not to be limited to particular details set forth in the above description as many apparent variations thereof are possible without departing from the spirit or scope of the present invention.

What is claimed is:
1. A compound of the formula (I) or salt thereof, in which

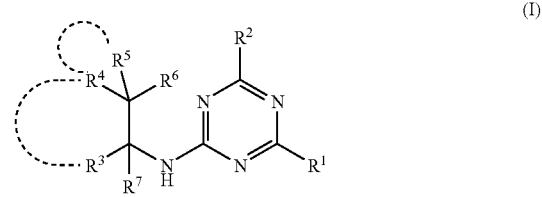

(I)

$R^1$ is a radical of the formula —$NH_2$, —$NH(B^1-D^1)$, or —$N(B^1-D^1)(B^2-D^2)$, in each of which $B^1$, $B^2$, $D^1$ and $D^2$ are each as defined below, or a group of the formula

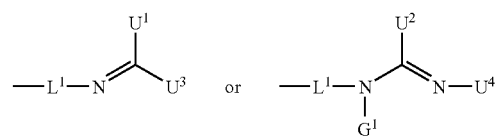

where
$L^1$ is a direct bond, —O—, —S— or a group of the formula —$NG^2$-,
$U^1$, $U^2$ are each independently a group of the formula $G^3$, $OG^4$, $SG^5$, $NG^6G^7$, $NG^8NG^9G^{10}$, $NG^{11}OG^{12}$ or $NG^{11}SG^{12}$,
$U^3$ is a group of the formula $G^{13}$, $OG^{14}$, $SG^{15}$, $NG^{16}G^{17}$, $NG^{18}NG^{19}G^{20}$ $NG^{21}OG^{22}$ or $NG^{23}SG^{24}$
$U^4$ is a group of the formula $G^{25}$, $OG^{26}$, $SG^{27}$ or $NG^{28}G^{29}$,
where the $G^1$ to $G^{29}$ radicals are each independently hydrogen, aryl which is unsubstituted or substituted and has from 6 to 30 carbon atoms including substituents, or ($C_3$-$C_9$)cycloalkyl which is unsubstituted or substituted and has from 3 to 30 carbon atoms including substituents, or heterocyclyl which is substituted or unsubstituted and has from 2 to 30 carbon atoms including substituents, or
($C_1$-$C_6$)alkyl, ($C_2$-$C_6$)alkenyl or ($C_2$-$C_6$)alkynyl,
where each of the 3 latter radicals is unsubstituted or substituted by one or more radicals from the group consisting of halogen, hydroxyl, cyano, nitro, thiocyanato, $(C_1-C_4)$alkoxy, $(C_1-C_4)$haloalkoxy, $(C_2-C_4)$alkenyloxy, $(C_2-C_4)$haloalkenyloxy, $(C_1-C_4)$alkylthio, $(C_1-C_4)$haloalkylthio, acyl, $(C_3-C_9)$cycloalkyl, which is unsubstituted or substituted, phenyl which is unsubstituted or substituted, and heterocyclyl which is unsubstituted or substituted, and has from 1 to 30 carbon atoms including substituents, or the $U^1$ and $U^3$ or $U^2$ and $U^4$ or $U^2$ and $G^1$ or $U^4$ and $G^1$ radicals, in pairs with the atoms connecting them, are each a carbocyclic or heterocyclic ring having from 4 to 7 ring atoms, where the ring is unsubstituted or substituted, and has up to 30 carbon atoms including substituents, $B^1$ and $B^2$ are each independently a divalent group of the formula —C(=Z*)-, —C(=Z*)-Z**-, —C(=Z*)-NH— or —C(=Z*)-NR*-, where Z* is an oxygen or sulfur atom, Z** is an oxygen or sulfur atom and R* is $(C_1-C_6)$alkyl, aryl, aryl$(C_1-C_6)$alkyl, $(C_3-C_9)$cycloalkyl or $(C_3-C_9)$cycloalkyl$(C_1-C_6)$alkyl, where each of the 5 latter radicals is unsubstituted or substituted and has up to 30 carbon atoms including substituents, $D^1$ and $D^2$ are each independently hydrogen, $(C_1-C_6)$alkyl, aryl, aryl$(C_1-C_6)$alkyl, $(C_3-C_9)$cycloalkyl or $(C_3-C_9)$cycloalkyl$(C_1-C_6)$alkyl, where each of the 5 latter radicals is unsubstituted or substituted and has up to 30 carbon atoms including substituents, $R^2$ is hydrogen, $(C_1-C_6)$alkyl, $(C_2-C_6)$alkenyl or $(C_2-C_6)$alkynyl where each of the three latter groups is unsubstituted or substituted by one or more of the radicals from the group which consists of halogen, hydroxyl, cyano, $(C_1-C_6)$alkoxy, $(C_1-C_6)$alkylthio, $(C_1-C_6)$haloalkoxy, $(C_1-C_4)$alkoxy-$(C_1-C_4)$alkoxy and optionally halogen-, cyano-, $(C_1-C_4)$alkyl- or $(C_1-C_4)$haloalkyl-substituted $(C_3-C_6)$cycloalkyl, or is $(C_3-C_6)$cycloalkyl which is unsubstituted or substituted by one or more radicals from the group consisting of halogen, cyano, $(C_1-C_4)$alkyl and $(C_1-C_4)$haloalkyl, $R^3$ is cyclopropyl or cyclobutyl, where each of the latter two radicals is unsubstituted or substituted by one or more radicals from the group consisting of halogen, $(C_1-C_4)$alkyl, $(C_1-C_4)$haloalkyl, $(C_2-C_4)$alkenyl, $(C_2-C_4)$alkynyl, $(C_1-C_4)$alkoxy, $(C_1-C_4)$haloalkoxy and $(C_1-C_4)$alkylthio, where the cyclic $R^3$ radical, by its carbon atom in the 2 position, (a) may be connected to the divalent $R^4$ group=methylene and may thus form, with the molecular moiety $R^3$-C—C-$R^4$, a bicycle composed of a five-membered ring and the three- or four-membered ring of $R^3$, or (b) may be bonded directly or via a methylene group to the carbon atom in the 2 position of the cyclic $CR^4R^5$ radical and thus form a tricycle with the molecular moiety $R^3$—C—$CR^4R^5$, and $R^4$ and $R^5$ are each independently $(C_1-C_6)$alkyl, $(C_2-C_6)$alkenyl or $(C_2-C_6)$alkynyl, where each of the latter three radicals is unsubstituted or substituted by one or more radicals from the group consisting of halogen, $(C_1-C_4)$alkoxy, $(C_1-C_4)$haloalkoxy and $(C_1-C_4)$alkylthio, or cyclopropyl which is unsubstituted or substituted by one or more radicals from the group consisting of halogen, $(C_1-C_4)$alkyl, $(C_1-C_4)$haloalkyl, $(C_2-C_4)$alkenyl, $(C_2-C_4)$alkynyl, $(C_1-C_4)$alkoxy, $(C_1-C_4)$haloalkoxy and $(C_1-C_4)$alkylthio, or $R^4$ and $R^5$, together with the carbon atom bonded to them, are a 3- to 9-membered carbocyclic ring which is unsubstituted or substituted by one or more radicals from the group consisting of halogen, $(C_1-C_4)$alkyl, $(C_1-C_4)$haloalkyl, $(C_1-C_4)$alkoxy-$(C_1-C_4)$alkyl, $(C_1-C_4)$alkoxy, $(C_1-C_4)$haloalkoxy and $(C_1-C_4)$alkylthio, where a cyclic $CR^4R^5$ radical, by its carbon atom in the 2 position, may be bonded to the carbon atom in the 2 position of the cycle of the $R^3$ group directly or via a methylene group and may thus form a tricycle with the molecular moiety $R^3$—C—$CR^4R^5$, or $R^4$ is a divalent group of the formula —$CH_2$— which is bonded to the carbon atom in the 2 position of the cyclic $R^3$ radical and may thus form, with the molecular moiety $R^3$-C—C-$R^4$, a bicycle composed of a five-membered ring and the three- or four-membered ring of $R^3$, and $R^6$ is hydrogen or $(C_1-C_4)$alkyl which is unsubstituted or substituted by one or more radicals from the group consisting of halogen, $(C_1-C_4)$alkoxy, $(C_1-C_4)$haloalkoxy and $(C_1-C_4)$alkylthio, and $R^7$ is hydrogen, methyl, ethyl or cyclopropyl which is unsubstituted or substituted by one or more radicals from the group consisting of halogen, $(C_1-C_4)$alkyl, $(C_1-C_4)$haloalkyl, $(C_1-C_4)$alkoxy, $(C_1-C_4)$haloalkoxy and $(C_1-C_4)$alkylthio.

2. A compound of the formula (I) or salts thereof as claimed in claim 1, wherein $R^1$ is a radical of the formula —$NH_2$, —NH($B^1$-$D^1$), or —N($B^1$-$D^1$)($B^2$-$D^2$), in each of which $B^1$, $B^2$, $D^1$ and $D^2$ are as defined below, or a group of the formula $$-L^1-N=\overset{U^1}{\underset{}{C}}-U^3 \quad \text{or} \quad -L^1-N=\overset{U^2}{\underset{G^1}{C}}-N-U^4$$

where $L^1$ is a direct bond, —O—, —S— or a group of the formula —$NG^2$-, preferably a direct bond, $U^1$, $U^2$ are each independently a group of the formula $G^3$, $OG^4$, $SG^5$, $NG^6G^7$, $NG^8NG^9G^{10}$, $NG^{11}OG^{12}$ or $NG^{11}SG^{12}$, $U^3$ is a group of the formula $G^{13}$, $OG^{14}$ $SG^{15}$ $NG^{16}G^{17}$, $NG^{18}NG^{19}G^{20}$ $NG^{21}OG^{22}$ or $NG^{23}SG^{24}$, $U^4$ is a group of the formula $G^{25}$, $OG^{26}$, $SG^{27}$ or $NG^{28}G^{29}$, where the $G^1$ to $G^{29}$ radicals are each independently hydrogen or phenyl which is unsubstituted or substituted and has from 6 to 30 carbon atoms including substituents, or $(C_3-C_8)$cycloalkyl which is unsubstituted or substituted and has from 3 to 30 carbon atoms including substituents, or heterocyclyl which is substituted or unsubstituted and has from 2 to 30 carbon atoms including substituents, or $(C_1-C_6)$alkyl, $(C_2-C_6)$alkenyl or $(C_2-C_6)$alkynyl, where each of the 3 latter radicals is unsubstituted or substituted by one or more radicals from the group of halogen, hydroxyl, cyano, nitro, thiocyanato, $(C_1-C_4)$alkoxy, $(C_1-C_4)$haloalkoxy, $(C_2-C_4)$alkenyloxy, $(C_2-C_4)$haloalkenyloxy, $(C_1-C_4)$alkylthio, $(C_1-C_4)$alkylsulfinyl, $(C_1-C_4)$alkylsulfonyl, $(C_1-C_4)$haloalkylthio, $(C_1-C_4)$haloalkylsulfinyl, $(C_1-C_4)$haloalkylsulfonyl, $(C_3-C_9)$cycloalkyl which is unsubstituted or substituted, phenyl which is unsubstituted or substituted, and heterocyclyl which is unsubstituted or substituted, and radicals of the formulae R'-C(=Z')-, R'-C(=Z')-Z-, R'-Z-C(=Z')-, R'R"N—C(=Z')-, R'-Z-C(=Z')-O—, R'R"N—C(=Z')-Z-, R'-Z-C(=Z')-NR"— and R'R"N—C(=Z')-NR'"—, in which R', R" and R'" are each independently $(C_1-C_6)$alkyl, phenyl, phenyl$(C_1-C_6)$alkyl, $(C_3$-

$C_9$)cycloalkyl or ($C_3$-$C_9$)cyclo-alkyl($C_1$-$C_6$) alkyl, where each of the 5 latter radicals is unsubstituted or substituted, and in which Z and Z' are each independently an oxygen or sulfur atom, or the $U^1$ and $U^3$ or $U^2$ and $U^4$ or $U^2$ and $G^1$ or $U^4$ and $G^1$ radicals, in pairs with the atoms connecting them, are each a carbocyclic or heterocyclic ring having from 4 to 7 ring atoms, where the ring is unsubstituted or substituted, $B^1$ and $B^2$ are each independently a divalent group of the formula —C(=Z*)-, —C(=Z*)-Z**-, —C(=Z*)-NH— or —C(=Z*)-NR*-, where Z* is an oxygen or sulfur atom, Z** is an oxygen or sulfur atom and R* is ($C_1$-$C_6$)alkyl, phenyl, phenyl($C_1$-$C_6$)alkyl, ($C_3$-$C_9$)cycloalkyl or ($C_3$-$C_9$)cycloalkyl($C_1$-$C_6$)alkyl, where each of the 5 latter radicals is unsubstituted or substituted and has up to 20 carbon atoms, including substituents, $D^1$ and $D^2$ are each independently hydrogen, ($C_1$-$C_6$) alkyl, phenyl, phenyl($C_1$-$C_6$)alkyl, ($C_3$-$C_9$)cycloalkyl or ($C_3$-$C_9$)cycloalkyl($C_1$-$C_6$)alkyl, where each of the 5 latter radicals is unsubstituted or substituted and has up to 20 carbon atoms, including substituents.

3. A compound of the formula (I) or salts thereof as claimed in claim 1, wherein $R^1$ is amino, acylamino having from 1 to 6 carbon atoms, di($C_1$-$C_4$)alkylamino-($C_1$-$C_4$)alkylideneamino or N-heterocyclylamino-($C_1$-$C_4$)alkylideneamino, where the N-heterocycle is a saturated heterocyclic ring having from 1 to 3 ring heteroatoms from the group of N, O and S and at least one nitrogen atom as a ring heteroatom which is bonded to the alkylidene group.

4. A compound of the formula (I) or salts thereof as claimed in claim 1, wherein $R^2$ is hydrogen, ($C_1$-$C_6$)alkyl, ($C_2$-$C_6$)alkenyl or ($C_2$-$C_6$)alkynyl, where each of the three latter groups is unsubstituted or substituted by one or more radicals from the group which consists of halogen, ($C_1$-$C_4$)alkoxy, ($C_1$-$C_4$)alkylthio, ($C_1$-$C_4$)haloalkoxy, ($C_1$-$C_2$)alkoxy($C_1$-$C_2$)alkoxy and optionally halogen- or ($C_1$-$C_4$)alkyl-substituted ($C_3$-$C_6$)cycloalkyl, or is ($C_3$-$C_6$)cycloalkyl which is unsubstituted or substituted by one or more radicals from the group consisting of halogen and ($C_1$-$C_4$)alkyl, $R^3$ is cyclopropyl or cyclobutyl, where each of the two latter radicals is unsubstituted or substituted by one or more radicals from the group consisting of halogen, ($C_1$-$C_4$)alkyl, ($C_2$-$C_4$)alkenyl and ($C_2$-$C_4$)alkynyl, $R^4$ and $R^5$ are each independently ($C_1$-$C_4$)alkyl, ($C_2$-$C_4$)alkenyl or ($C_2$-$C_4$)alkynyl, where each of the latter three radicals is unsubstituted or substituted by one or more radicals from the group consisting of halogen, ($C_1$-$C_4$)alkoxy, ($C_1$-$C_4$)haloalkoxy and ($C_1$-$C_4$)alkylthio, or cyclopropyl which is unsubstituted or substituted by one or more radicals from the group consisting of halogen and ($C_1$-$C_4$)alkyl, or $R^4$ and $R^5$, together with the carbon atom bonded to them, is a 3- to 6-membered carbocyclic ring which is unsubstituted or substituted by one or more radicals from the group consisting of halogen and ($C_1$-$C_4$)alkyl, $R^6$ is hydrogen or ($C_1$-$C_4$)alkyl which is unsubstituted or substituted by one or more radicals from the group consisting of halogen, ($C_1$-$C_4$)alkoxy, ($C_1$-$C_4$)haloalkoxy and ($C_1$-$C_4$)alkylthio, $R^7$ is hydrogen, methyl, ethyl or cyclopropyl which is unsubstituted or substituted by one or more radicals from the group consisting of halogen, ($C_1$-$C_4$)alkyl and ($C_1$-$C_4$)haloalkyl.

5. A compound of the formula (I) or salts thereof as claimed in claim 1, which are compounds of the formula (I-A) and salts thereof

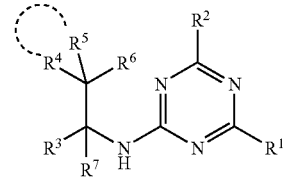

(I-A)

in which $R^1$ to $R^7$ are each as defined in formula (I), where the $R^4$ and $R^5$ groups may be connected in a cyclic system, but the $R^3$ and $R^4$ groups are not connected in a cyclic system.

6. A process for preparing compounds of the formula (I) or salts thereof as claimed in claim 1, which comprises a) reacting a compound of the formula (II)

$R^2$-Fu  (II)

in which Fu is a functional group from the group of carboxylic ester, carboxylic orthoester, carbonyl chloride, carboxamide, carboxylic anhydride and trichloromethyl with a compound of the formula (III) or an acid addition salt thereof

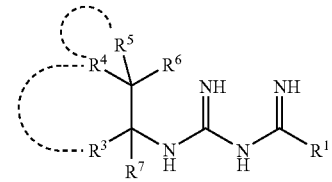

(III)

or b) reacting a compound of the formula (IV)

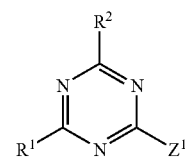

(IV)

in which $Z^1$ is an exchangeable radical or a leaving group, for example chlorine, trichloromethyl, ($C_1$-$C_4$) alkylsulfonyl, unsubstituted or substituted phenyl-($C_1$-$C_4$)alkylsulfonyl or ($C_1$-$C_4$)alkylphenylsulfonyl with an amine of the formula (V) or an acid addition salt thereof

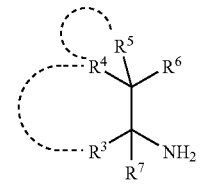

(V)

or c) derivatizing a compound of the formula (I') or salt thereof

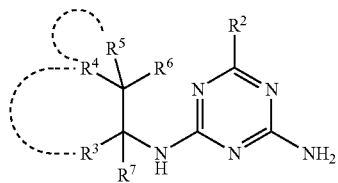
(I')

on the amino group to give the compound of the formula (I), where, in the formulae (II), (III), (IV), (V) and (I'), the $R^1$, $R^2$, $R^3$, $R^4$, $R^5$, $R^6$ and $R^7$ are each as defined in formula (I).

7. A herbicidal or crop growth-regulating composition, which comprises one or more compounds of the formula (I) or salts thereof as claimed in claim 1 and formulation assistants customary in crop protection.

8. A method for controlling harmful plants or for regulating the growth of plants, which comprises applying an effective amount of one or more compounds of the formula (I) or salts thereof as claimed in claim 1 to the plants, plant seeds or the area under cultivation.

9. The method as claimed in claim 8, wherein the compounds of the formula (I) or salts thereof are applied to control harmful plants in crops of useful or ornamental plants.

10. The method as claimed in claim 9, wherein the crop plants are transgenic crop plants.

11. The method as claimed in claim 9, wherein the crop plants are selected from plantation crops.

* * * * *